(12) United States Patent
Furet et al.

(10) Patent No.: US 8,674,099 B2
(45) Date of Patent: *Mar. 18, 2014

(54) QUINOXALINE CARBOXAMIDE DERIVATIVES AS PROTEIN TYROSINE KINASE INHIBITORS

(75) Inventors: Pascal Furet, Thann (FR); Diana Graus Porta, Basel (CH); Vito Guagnano, Basel (CH)

(73) Assignee: Novartis AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 13/587,032

(22) Filed: Aug. 16, 2012

(65) Prior Publication Data

US 2012/0309766 A1 Dec. 6, 2012

Related U.S. Application Data

(63) Continuation of application No. 12/470,191, filed on May 21, 2009, now Pat. No. 8,273,882.

(30) Foreign Application Priority Data

May 23, 2008 (EP) ..................... 08156846

(51) Int. Cl.
C07D 401/00 (2006.01)
(52) U.S. Cl.
USPC ......... 544/353; 544/404; 546/304; 548/335.5
(58) Field of Classification Search
USPC .............. 544/353, 404; 546/304; 548/335.5
See application file for complete search history.

(56) References Cited

U.S. PATENT DOCUMENTS

| | | | |
|---|---|---|---|
| 7,037,929 B1 | 5/2006 | Pevarello | |
| 2007/0066646 A1 | 3/2007 | Clauzel et al. | |
| 2007/0213355 A1 | 9/2007 | Capraro et al. | |
| 2010/0168062 A1 | 7/2010 | Gerspacher et al. | |

FOREIGN PATENT DOCUMENTS

| | | |
|---|---|---|
| WO | 02/068394 A1 | 9/2002 |
| WO | WO 02/089738 A2 | 11/2002 |
| WO | WO 03/007955 A2 | 1/2003 |
| WO | WO 03/024446 A2 | 3/2003 |
| WO | WO 03/030902 A1 | 4/2003 |
| WO | WO 2004/098494 A2 | 11/2004 |
| WO | 2005/054238 A1 | 6/2005 |
| WO | WO 2005/056547 A2 | 6/2005 |
| WO | WO 2005/077920 A1 | 8/2005 |
| WO | WO 2005-087742 A1 | 9/2005 |
| WO | 2005/115986 A1 | 12/2005 |
| WO | 2007/035157 A1 | 3/2007 |
| WO | 2007/117607 A2 | 10/2007 |
| WO | 2008/148867 A2 | 12/2008 |
| WO | 2009/069044 A1 | 6/2009 |
| WO | 2009/141398 A1 | 11/2009 |
| WO | 2009/143153 A1 | 11/2009 |
| WO | 2009/143313 A1 | 11/2009 |
| WO | 2009/143317 A1 | 11/2009 |
| WO | WO 2009/141386 * | 11/2009 |
| WO | 2010/068311 A1 | 6/2010 |

OTHER PUBLICATIONS

Hackam, et al. JAMA, 296(14), 2006, 1731-1732.*
Jordan, V. C. Nature Reviews: Drug Discovery, 2, 2003, 205.*
Turner and Grose, "Fibroblast growth factor signalling: from development to cancer," Nature Reviews 10:116-129 (Feb. 2010).
Supuran et al., "Protein Tyrosine Kinase Inhibitors as Anticancer Agents", Expert Opin. Ther. Patents, 2004 vol. 14 No. 1 pp. 35-53.

* cited by examiner

Primary Examiner — Douglas M Willis
(74) Attorney, Agent, or Firm — Laura K. Madden

(57) ABSTRACT

The invention relates to compounds of formula (I)

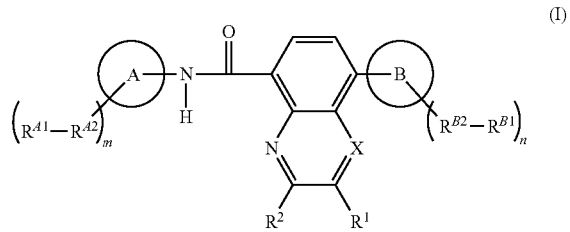

wherein the substituents are as defined in the specification, in free form or in the form of a pharmaceutically acceptable salt, solvate, ester, N-oxide thereof; processes for the preparation thereof; to pharmaceuticals containing such compounds, in particular for the use in one or more Protein tyrosine kinase mediated diseases.

7 Claims, No Drawings

QUINOXALINE CARBOXAMIDE DERIVATIVES AS PROTEIN TYROSINE KINASE INHIBITORS

This application is a continuation of U.S. application Ser. No. 12/470,191, filed on 21 May 2009, now U.S. Pat. No. 8,273,882 which claims priority to EP Application Serial No. 08156846.1 filed 23 May 2008, the contents of which are incorporated herein by reference in their entirety.

FIELD OF THE INVENTION

The invention relates to quinoline/quinoxaline-carboxamide derivatives of the formula (I) given below (including its salts, solvates, esters, N-oxides); processes for the preparation thereof; pharmaceutical compositions comprising a compound of the formula (I), optionally in the presence of a combination partner; the application of a compound of formula (I) in a process for the treatment of the human or animal body, (in particular with regard to a proliferative disease); the use of a compound of formula (I) for manufacturing a medicament for the treatment of such diseases.

BACKGROUND OF THE INVENTION

Protein kinases (PKs) are enzymes which catalyze the phosphorylation of specific serine, threonine or tyrosine residues in cellular proteins. These post-translational modifications of substrate proteins act as molecular switch regulating cell proliferation, activation and/or differentiation. Aberrant or excessive PK activity has been observed in many disease states including benign and malignant proliferative disorders. In many cases, it has been possible to treat diseases in vitro and in many cases in vivo, such as proliferative disorders, by making use of PK inhibitors. The kinases fall largely into two groups, those specific for phosphorylating serine and threonine, and those specific for phosphorylating tyrosine. In addition, some kinases, referred to as "dual specificity" kinases, are able to phosphorylate tyrosine as well as serine/threonine residues.

WO2006/000420 (in particular p. 1-8) discloses details on PKs, their mode of action and relation to disorders or conditions to be treated. This document also discloses heteroaryl aryl ureas, useful for the treatment of protein kinase dependent diseases. Further, WO03/023004 and WO02/102972 disclose disorders resulting from FGFR3 mutations. Further, WO05/118580 generically discloses quinoline derivatives useful as HIV inhibitors. In these documents and the references cited therein, where protein kinases are involved, the modulation of an aberrant activity (especially the inhibition of an activity of such a kinase) can be expected reasonably to be useful in the diseases mentioned in this document.

Although considered active, the molecules disclosed in the above-referenced documents; they show certain disadvantages. There is thus an unmet need for improved (e.g. highly affine and/or selective) molecules capable of blocking aberrant constitutive receptor protein tyrosine kinase activity, in particular FGFR activity, thereby addressing the clinical manifestations associated with the above-mentioned mutations, and modulating various biological functions. In view of the large number of protein kinase inhibitors and the multitude of proliferative and other PK-related diseases, there is an ever-existing need to provide novel classes of compounds that are useful as PK inhibitors and thus in the treatment of these Protein Tyrosine Kinase (PTK) related diseases. Particularly required are new classes of pharmaceutically advantageous PK inhibiting compounds.

DETAILED DESCRIPTION OF THE INVENTION

Thus, in a first aspect, the invention relates to compounds of the formula (I),

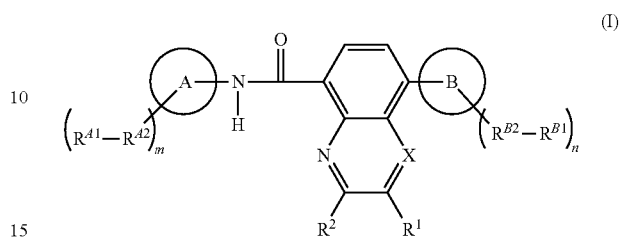

wherein
X represents N or CH;
R$^1$ represents
  hydrogen,
  halogen,
  alkyl,
  alkyl substituted with saturated heterocyclyl which is unsubstituted or substituted by alkyl,
  amino,
  mono-substituted amino wherein the substituent is selected from the group consisting of alkyl, aminoalkyl, alkylaminoalkyl, dialkylaminoalkyl,
  di-substituted amino wherein the substituents are selected from the group consisting of alkyl, aminoalkyl, alkylaminoalkyl, dialkylaminoalkyl,
  alkoxy,
  substituted alkoxy wherein the substituents are selected from the group consisting of halo and alkoxy;
R$^2$ represents
  hydrogen,
  halogen,
  alkyl,
  alkyl substituted with saturated heterocyclyl which is unsubstituted or substituted by alkyl,
  amino,
  mono-substituted amino wherein the substituent is selected from the group consisting of alkyl, aminoalkyl, alkylaminoalkyl, dialkylaminoalkyl,
  di-substituted amino wherein the substituents are selected from the group consisting of alkyl, aminoalkyl, alkylaminoalkyl, dialkylaminoalkyl,
  alkoxy,
  substituted alkoxy wherein the substituents are selected from the group consisting of halo and alkoxy;
A represents aryl or heteroaryl;
B represents aryl or heteroaryl;
R$^{A1}$ represents hydrogen or a substituent different from hydrogen;
R$^{A2}$ represents a direct bond or an alkanediyl;
R$^{B1}$ represents hydrogen or a substituent different from hydrogen;
R$^{B2}$ represents a direct bond or aminocarbonyl;
m represents an integer selected from 0 to 3;
n represents an integer selected from 0 to 5;
or a salt, solvate, ester, N-oxide thereof.

The invention may be more fully appreciated by reference to the following description, including the following glossary of terms and the concluding examples. As used herein, the terms "including", "containing" and "comprising" are used herein in their open, non-limiting sense.

Any formula given herein is intended to represent compounds having structures depicted by the structural formula as well as certain variations or forms. In particular, compounds of any formula given herein may have asymmetric centers and therefore exist in different enantiomeric forms. If at least one asymmetrical carbon atom is present in a compound of the formula (I), such a compound may exist in optically active form or in the form of a mixture of optical isomers, e.g. in the form of a racemic mixture. All optical isomers and their mixtures, including the racemic mixtures, are part of the present invention. Thus, any given formula given herein is intended to represent a racemate, one or more enantiomeric forms, one or more diastereomeric forms, and mixtures thereof. Furthermore, certain structures may exist as geometric isomers (i.e. cis and trans isomers), as tautomers, or as atropisomers. Additionally, any formula given herein is intended to represent hydrates, solvates, and polymorphs of such compounds, and mixtures thereof.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as $^2H$, $^3H$, $^{11}C$, $^{13}C$, $^{14}C$, $^{15}N$, $^{18}F$, $^{31}P$, $^{32}P$, $^{35}S$, $^{36}Cl$, $^{125}I$ respectively. Various isotopically labeled compounds of the present invention, for example those into which radioactive isotopes such as $^3H$, $^{13}C$, and $^{14}C$ are incorporated. Such isotopically labelled compounds are useful in metabolic studies (preferably with $^{14}C$), reaction kinetic studies (with, for example $^2H$ or $^3H$), detection or imaging techniques such as positron emission tomography (PET) or single-photon emission computed tomography (SPECT) including drug or substrate tissue distribution assays, or in radioactive treatment of patients. In particular, an $^{18}F$ or labeled compound may be particularly preferred for PET or SPECT studies. Further, substitution with heavier isotopes such as deuterium (i.e., $^2H$) may afford certain therapeutic advantages resulting from greater metabolic stability, for example increased in vivo half-life or reduced dosage requirements. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

When referring to any formula given herein, the selection of a particular moiety from a list of possible species for a specified variable is not intended to define the moiety for the variable appearing elsewhere. In other words, where a variable appears more than once, the choice of the species from a specified list is independent of the choice of the species for the same variable elsewhere in the formula (where one or more up to all more general expressions in embodiments characterized as preferred above or below can be replaced with a more specific definition, thus leading to a more preferred embodiment of the invention, respectively).

It goes without saying that substituents are only at positions where they are chemically possible, the person skilled in the art being able to decide (either experimentally or theoretically) without inappropriate effort which substitutions are possible and which are not. For example, amino or hydroxy groups with free hydrogen may be unstable if bound to carbon atoms with unsaturated (e.g. olefinic) bonds. Additionally, it will of course be understood that the substituents as listed above may themselves be substituted by any substituent, subject to the aforementioned restriction to appropriate substitutions as recognised by the skilled man.

Where the plural form (e.g. compounds, salts) is used, this includes the singular (e.g. a single compound, a single salt). "A compound" does not exclude that (e.g. in a pharmaceutical formulation) more than one compound of the formula (I) (or a salt thereof) is present.

The acid addition salt of compounds of formula (I) are preferably pharmaceutically acceptable salts. Such salts are known in the field.

The following general definitions shall apply in this specification, unless otherwise specified:

Halogen (or halo) denotes fluorine, bromine, chlorine or iodine, in particular fluorine, chlorine. Halogen-substituted groups and moieties, such as alkyl substituted by halogen (halogenalkyl) can be mono-, poly- or per-halogenated.

Heteroatoms are atoms other than Carbon and Hydrogen, preferably nitrogen (N), oxygen (O) or sulfur (S).

The prefix "lower" or "$C_1$-$C_7$" denotes a radical having up to and including a maximum of 7, especially up to and including a maximum of 4 carbon atoms, the radicals in question being either linear or branched with single or multiple branching.

"Alkyl" refers to a straight-chain or branched-chain alkyl group, preferably represents a straight-chain or branched-chain $C_{1-12}$alkyl, particularly preferably represents a straight-chain or branched-chain $C_{1-7}$alkyl; for example, methyl, ethyl, n- or iso-propyl, n-, iso-, sec- or tert-butyl, n-pentyl, n-hexyl, n-heptyl, n-octyl, n-nonyl, n-decyl, n-undecyl, n-dodecyl, with particular preference given to methyl, ethyl, n-propyl, iso-propyl and n-butyl and iso-butyl. Alkyl may be unsubstituted or substituted. Exemplary substituents include, but are not limited to hydroxyl, alkoxy, halogen and amino. An example of a substituted alkyl is trifluoromethyl. Cycloalkyl may also be a substituent to alkyl. An example of such a case is the moiety (alkyl)-cyclopropyl or alkanediyl-cyclopropyl, e.g. —$CH_2$-cyclopropyl. $C_1$-$C_7$-alkyl is preferably alkyl with from and including 1 up to and including 7, preferably from and including 1 to and including 4, and is linear or branched; preferably, lower alkyl is butyl, such as n-butyl, sec-butyl, isobutyl, tert-butyl, propyl, such as n-propyl or isopropyl, ethyl or preferably methyl.

Each alkyl part of other groups like "alkoxy", "alkoxyalkyl", "alkoxycarbonyl", "alkoxycarbonylalkyl", "alkylsulfonyl", "alkylsulfinyl", "alkylamino", "halogenalkyl" shall have the same meaning as described in the above-mentioned definition of "alkyl".

"Alkanediyl" refers to a straight-chain or branched-chain alkanediyl group. It preferably represents a straight-chain or branched-chain $C_{1-12}$ alkanediyl, particularly preferably represents a straight-chain or branched-chain $C_{1-6}$ alkanediyl; for example, methandiyl (—$CH_2$—), 1,2-ethanediyl (—$CH_2$—$CH_2$—), 1,1-ethanediyl ((—CH($CH_3$)—), 1,1-, 1,2-, 1,3-propanediyl and 1,1-, 1,2-, 1,3-, 1,4-butanediyl, with particular preference given to methandiyl, 1,1-ethanediyl, 1,2-ethanediyl, 1,3-propanediyl, 1,4-butanediyl. Alkanediyl may be substituted or unsubstituted as defined for alkyl, preferably unsubstituted.

"Cycloalkyl" refers to a saturated or partially saturated, monocyclic, fused polycyclic, or spiro polycyclic, carbocycle having from 3 to 12 ring atoms per carbocycle. Illustrative examples of cycloalkyl groups include the following moieties: cyclopropyl, cyclobutyl, cyclpentyl and cylclohexyl. Cycloalkyl may be unsubstituted or substituted; exemplary substituents are provided in the definition for alkyl.

"Aryl" refers to an aromatic homocyclic ring system with 6 or more carbon atoms; aryl is preferably an aromatic moiety with 6 to 14 ring carbon atoms, more preferably with 6 to 10 ring carbon atoms, such as phenyl or naphthyl, preferably phenyl. Aryl may be unsubstituted or substituted by one or more, preferably up to three, more preferably up to two substituents independently selected from the group consisting of unsubstituted or substituted heterocyclyl as described below, especially pyrrolidinyl, such as pyrrolidino, oxopyrrolidinyl, such as oxo-pyrrolidino, $C_1$-$C_7$-alkyl-pyrrolidinyl, 2,5-di-($C_1$-$C_7$alkyl)pyrrolidinyl, such as 2,5-di-($C_1$-$C_7$alkyl)-pyrrolidino, tetrahydrofuranyl, thiophenyl, $C_1$-$C_7$-alkylpyrazolidinyl, pyridinyl, piperidino, piperidino substituted by amino or N-mono- or N,N-di-[lower alkyl, phenyl, $C_1$-$C_7$-alkanoyl and/or phenyl-lower alkyl)-amino, unsubstituted or N-lower alkyl substituted piperidinyl bound via a ring carbon atom, piperazino, lower alkylpiperazino, morpholino, thiomorpholino, S-oxo-thiomorpholino or S,S-dioxothiomorpholino; amino-$C_1$-$C_7$-alkyl, N—$C_1$-$C_7$-alkanoylamino-$C_1$-$C_7$-alkyl, N—$C_1$-$C_7$-alkanesulfonyl-amino-$C_1$-$C_7$-alkyl, carbamoyl-$C_1$-$C_7$-alkyl, [N-mono- or N,N-di-($C_1$-$C_7$-alkyl)-carbamoyl]$C_1$-$C_7$-alkyl, $C_1$-$C_7$-alkanesulfinyl-$C_1$-$C_7$-alkyl, $C_1$-$C_7$-alkanesulfonyl-$C_1$-$C_7$-alkyl, phenyl, naphthyl, mono- to tri-[$C_1$-$C_7$-alkyl, halo and/or cyano]-phenyl or mono- to tri-[$C_1$-$C_7$-alkyl, halo and/or cyano]-naphthyl; $C_3$-$C_8$-cycloalkyl, mono- to tri-[$C_1$-$C_7$-alkyl and/or hydroxy]-$C_3$-$C_8$-cycloalkyl; halo, hydroxy, lower alkoxy, lower-alkoxy-lower alkoxy, (lower-alkoxy)-lower alkoxy-lower alkoxy, halo-$C_1$-$C_7$-alkoxy, phenoxy, naphthyloxy, phenyl- or naphthyl-lower alkoxy; amino-$C_1$-$C_7$-alkoxy, lower-alkanoyloxy, benzoyloxy, naphthoyloxy, formyl (CHO), amino, N-mono- or N,N-di-($C_1$-$C_7$-alkyl)-amino, $C_1$-$C_7$-alkanoylamino, $C_1$-$C_7$-alkanesulfonylamino, carboxy, lower alkoxy carbonyl, e.g.; phenyl- or naphthyl-lower alkoxycarbonyl, such as benzyloxycarbonyl; $C_1$-$C_7$-alkanoyl, such as acetyl, benzoyl, naphthoyl, carbamoyl, N-mono- or N,N-disubstituted carbamoyl, such as N-mono- or N,N-di-substituted carbamoyl wherein the substitutents are selected from lower alkyl, (lower-alkoxy)-lower alkyl and hydroxy-lower alkyl; amidino, guanidino, ureido, mercapto, lower alkylthio, phenyl- or naphthylthio, phenyl- or naphthyl-lower alkylthio, lower alkyl-phenylthio, lower alkyl-naphthylthio, halogen-lower alkylmercapto, sulfo (—$SO_3H$), lower alkanesulfonyl, phenyl- or naphthyl-sulfonyl, phenyl- or naphthyl-lower alkylsulfonyl, alkylphenylsulfonyl, halogen-lower alkylsulfonyl, such as trifluoromethanesulfonyl; sulfonamido, benzosulfonamido, azido, azido-$C_1$-$C_7$-alkyl, especially azidomethyl, $C_1$-$C_7$-alkanesulfonyl, sulfamoyl, N-mono- or N,N-di-($C_1$-$C_7$-alkyl)-sulfamoyl, morpholinosulfonyl, thiomorpholinosulfonyl, cyano and nitro; where each phenyl or naphthyl (also in phenoxy or naphthoxy) mentioned above as substituent or part of a substituent of substituted alkyl (or also of substituted aryl, heterocyclyl etc. mentioned herein) is itself unsubstituted or substituted by one or more, e.g. up to three, preferably 1 or 2, substituents independently selected from halo, halo-lower alkyl, such as trifluoromethyl, hydroxy, lower alkoxy, azido, amino, N-mono- or N,N-di-(lower alkyl and/or $C_1$-$C_7$-alkanoyl)-amino, nitro, carboxy, lower-alkoxy-carbonyl, carbamoyl, cyano and/or sulfamoyl.

"Heterocyclyl" refers to a heterocyclic radical that is unsaturated (=carrying the highest possible number of conjugated double bonds in the ring(s)), saturated or partially saturated and is preferably a monocyclic or in a broader aspect of the invention bicyclic, tricyclic or spirocyclic ring; and has 3 to 24, more preferably 4 to 16, most preferably 5 to 10 and most preferably 5 or 6 ring atoms; the bonding ring preferably having 4 to 12, especially 5 to 7 ring atoms. The heterocyclic radical (heterocyclyl) may be unsubstituted or substituted by one or more, especially 1 to 3, substituents independently selected from the group consisting of the substituents defined above for substituted alkyl and/or from one or more of the following substituents: oxo (=O), thio (=S), imino(=NH), imino-lower alkyl. Further, heterocyclyl is especially a heterocyclyl radical selected from the group consisting of oxiranyl, azetidine, azirinyl, aziridinyl, 1,2-oxathiolanyl, thienyl (=thiophenyl), furanyl, tetrahydrofuryl, pyranyl, thiopyranyl, thianthrenyl, isobenzofuranyl, benzofuranyl, chromenyl, 2H-pyrrolyl, pyrrolyl, pyrrolinyl, pyrrolidinyl, imidazolyl, imidazolidinyl, benzimidazolyl, pyrazolyl, pyrazinyl, pyrazolidinyl, thiazolyl, isothiazolyl, dithiazolyl, oxazolyl, isoxazolyl, pyridyl, pyrazinyl, pyrimidinyl, piperidinyl, piperazinyl, pyridazinyl, morpholinyl, thiomorpholinyl, (S-oxo or S,S-dioxo)-thiomorpholinyl, indolizinyl, azepanyl, diazepanyl, especially 1,4-diazepanyl, isoindolyl, 3H-indolyl, indolyl, benzimidazolyl, cumaryl, indazolyl, triazolyl, tetrazolyl, purinyl, 4H-quinolizinyl, isoquinolyl, quinolyl, tetrahydroquinolyl, tetrahydroisoquinolyl, decahydroquinolyl, octahydroisoquinolyl, benzofuranyl, dibenzofuranyl, benzothiophenyl, dibenzothiophenyl, phthalazinyl, naphthyridinyl, quinoxalyl, quinazolinyl, quinazolinyl, cinnolinyl, pteridinyl, carbazolyl, beta-carbolinyl, phenanthridinyl, acridinyl, perimidinyl, phenanthrolinyl, furazanyl, phenazinyl, phenothiazinyl, phenoxazinyl, chromenyl, isochromanyl, chromanyl, benzo[1,3]dioxol-5-yl and 2,3-dihydrobenzo[1,4]dioxin-6-yl, each of these radicals being unsubstituted or substituted by one or more, preferably up to three, substituents selected from those mentioned above for substituted aryl and/or from one or more of the following substituents: oxo (=O), thio (=S), imino(=NH), imino-lower alkyl.

"Heteroaryl" refers to a specific subgroup of heterocyclyl, namely such unsaturated heterocyclic groups that are also aromatic. Such heteroaryl may be substituted with substituents as identified above for heterocyclyl. Further, heteroaryl may be a charged moiety, such as in pyridine-N-oxide. Due to tautomerism, e.g. keto-enol-tautomerism, heteroaryl may also be drawn as a partly unsaturated heterocyclyl (e.g. 2-hydroxypyridine). For example, heteroaryl includes pyridyl, pyrimidinyl, pyridazinyl, 1,3,5-triazolyl, 1,2,3-triazolyl, 1,2,4-triazolyl, quinolinyl, isoquinolinyl, quinoxalinyl, acridinyl, purinyl, pteridinyl, pyrrolyl, pyrazolyl, imidazolyl, 1,2,3-triazolyl, 1,2,4-triazolyl, indolyl, indazolyl, benzopyranyl, benzothiopyranyl, benzo[1,3]dioxole, benzo-imidazolyl, tetrazolyl, furanyl, benzofuranyl, oxazolyl, isoxazolyl, thienyl, thiazolyl, isothiazolyl, etc.

"Arylalkyl" refers to an aryl group bound to the molecule via an alkyl group, such as a methyl or ethyl group, preferably phenethyl or benzyl, in particular benzyl. Similarly, cycloalkylalkyl and heterocyclyl represents a cycloalkyl group bound to the molecule via an alkyl group or a heterocyclyl group bound to the molecule via an alkyl group. In each instance, aryl, heterocyclyl, cycloalkyl and alkyl may be substituted as defined above.

"Treatment" includes prophylactic (preventive) and therapeutic treatment as well as the delay of progression of a disease or disorder.

"FGFR kinase mediated diseases" (especially FGFR3 kinase mediated diseases) are such diseases, disorders or conditions (collectively "diseases") that respond in a beneficial way, e.g. amelioration of one or more symptoms, delay of the onset of a disease, up to temporary or complete cure from a disease, to the inhibition of a protein tyrosine kinase, especially inhibition of a FGFR (such as FGFR3) kinase. Among the diseases to be treated by FGFR inhibition, especially proliferative diseases such as cancer diseases, solid tumors like breast cancer, bladder cancer, endometrial cancer, hepatocellular cancer, glioblastoma, or multiple myeloma, EMS myeloid proliferative disorders, may be mentioned.

"Salts" (which, what is meant by "or salts thereof" or "or a salt thereof", can be present alone or in mixture with free compound of the formula (I) are preferably pharmaceutically acceptable salts. Such salts are formed, for example, as acid addition salts, preferably with organic or inorganic acids, from compounds of formula (I) with a basic nitrogen atom, especially the pharmaceutically acceptable salts. Suitable inorganic acids are, for example, halogen acids, such as hydrochloric acid, sulfuric acid, or phosphoric acid. Suitable organic acids are, e.g., carboxylic acids or sulfonic acids, such as fumaric acid or methansulfonic acid. For isolation or purification purposes it is also possible to use pharmaceutically unacceptable salts, for example picrates or perchlorates. For therapeutic use, only pharmaceutically acceptable salts or free compounds are employed (where applicable in the form of pharmaceutical preparations), and these are therefore preferred. In view of the close relationship between the novel compounds in free form and those in the form of their salts, including those salts that can be used as intermediates, for example in the purification or identification of the novel compounds, any reference to the free compounds hereinbefore and hereinafter is to be understood as referring also to the corresponding salts, as appropriate and expedient.

Combination refers to either a fixed combination in one dosage unit form, or a kit of parts for the combined administration where a compound of the formula (I) and a combination partner (e.g. an other drug as explained below, also referred to as "therapeutic agent" or "co-agent") may be administered independently at the same time or separately within time intervals, especially where these time intervals allow that the combination partners show a cooperative, e.g. synergistic effect. The terms "co-administration" or "combined administration" or the like as utilized herein are meant to encompass administration of the selected combination partner to a single subject in need thereof (e.g. a patient), and are intended to include treatment regimens in which the agents are not necessarily administered by the same route of administration or at the same time. The term "pharmaceutical combination" as used herein means a product that results from the mixing or combining of more than one active ingredient and includes both fixed and non-fixed combinations of the active ingredients. The term "fixed combination" means that the active ingredients, e.g. a compound of formula (I) and a combination partner, are both administered to a patient simultaneously in the form of a single entity or dosage. The term "non-fixed combination" means that the active ingredients, e.g. a compound of formula (I) and a combination partner, are both administered to a patient as separate entities either simultaneously, concurrently or sequentially with no specific time limits, wherein such administration provides therapeutically effective levels of the two compounds in the body of the patient. The latter also applies to cocktail therapy, e.g. the administration of three or more active ingredients.

In preferred embodiments, which are preferred independently, collectively or in any combination or sub-combination, the invention relates to a compound of the formula (I), in free base form or in acid addition salt form, wherein the substituents are as defined herein.

In another embodiment, the invention relates to a compound of formula IA

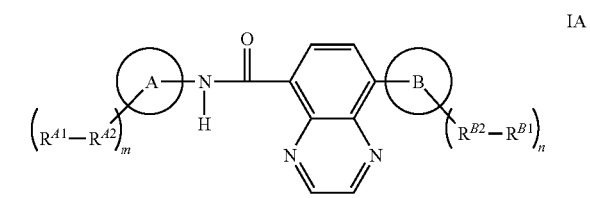

IA wherein the substituents are as defined for a compound of formula I.

In a further embodiment, the invention relates to a compound of formula IB

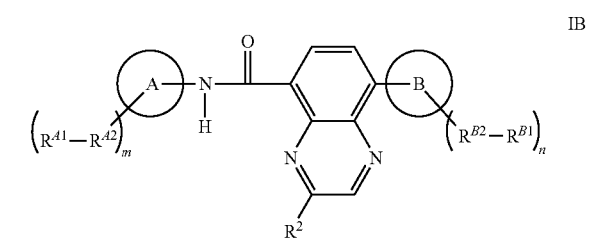

IB wherein the substituents are as defined for a compound of formula I.

In a further embodiment, the invention relates to a compound of formula IC

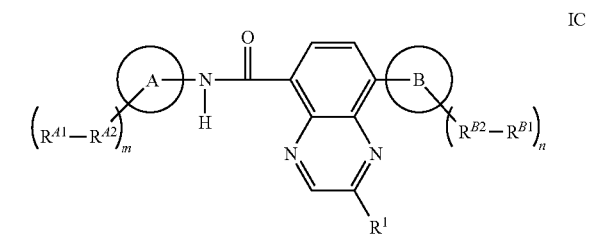

IC wherein the substituents are as defined for a compound of formula I.

In a further embodiment, the invention relates to a compound of formula ID

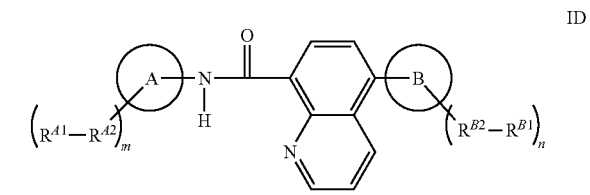

ID wherein the substituents are as defined for a compound of formula I.

In a further embodiment, the invention relates to a compound of formula IE

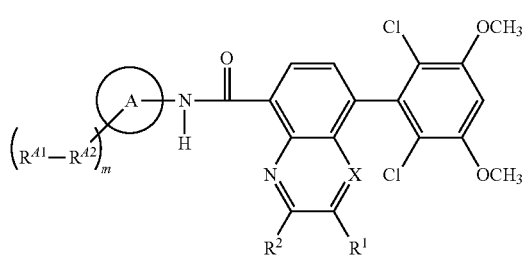

wherein the substituents are as defined for a compound of formula I.

In a further embodiment, the invention relates to a compound of formula IF

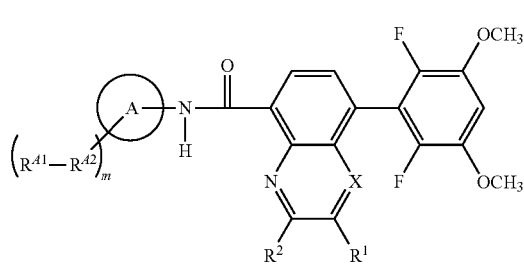

wherein the substituents are as defined for a compound of formula I.

In a further embodiment, the invention relates to a compound of formula IG

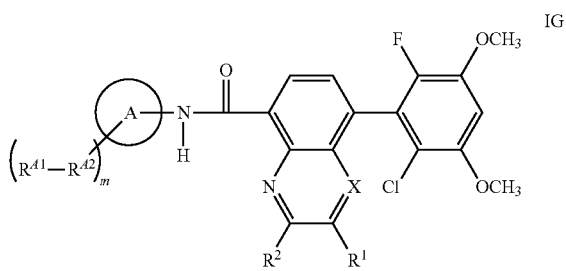

wherein the substituents are as defined for a compound of formula I.

In a further embodiment, the invention relates to a compound of formula IH

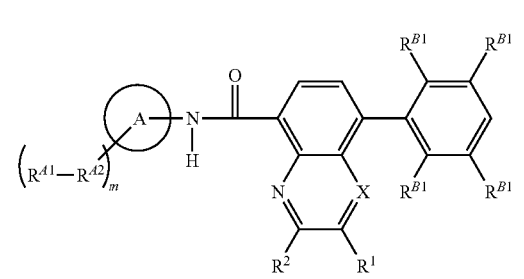

wherein the substituents are as defined for a compound of formula I.

The below mentioned preferences for the substituents may apply in any combination or sub-combination to the compounds of formulae IA to IH.

$R^1$ preferably represents
hydrogen,
halogen,
substituted $C_{1-12}$alkyl wherein the substitutents are selected from the group of saturated, mono-, bi-, tri- or spirocyclic heterocyclyl having 5 to 10 ring atoms and which heterocyclyl is unsubstituted or substituted by $C_{1-12}$alkyl,
amino,
mono-substituted amino wherein the substituent is selected from the group consisting of $C_{1-12}$alkyl, amino $C_{1-12}$alkyl,
di-substituted amino wherein the substituents are selected from the group consisting of $C_{1-12}$alkyl, amino $C_{1-12}$alkyl,
$C_{1-12}$alkoxy,
halo-$C_{1-12}$alkoxy.

$R^1$ particular preferably represents
hydrogen,
fluoro,
chloro,
$C_{1-4}$alkyl,
substituted $C_{1-4}$alkyl wherein the substitutents are selected from the group of saturated, monocyclic heterocyclyl having 5 to 6 ring atoms and which heterocyclyl is unsubstituted or substituted by $C_{1-4}$alkyl,
amino,
mono-substituted amino wherein the substituent is selected from the group consisting of $C_{1-4}$alkyl, amino-$C_{1-4}$alkyl, $C_{1-4}$alkyl-amino-$C_{1-4}$alkyl, di-$C_{1-4}$alkyl-amino $C_{1-4}$alkyl,
di-substituted amino wherein the substituents are selected from the group consisting of $C_{1-4}$alkyl, amino-$C_{1-4}$alkyl, $C_{1-4}$alkyl-amino-$C_{1-4}$alkyl, di-$C_{1-4}$alkyl-amino $C_{1-4}$alkyl,
$C_{1-4}$alkoxy,
fluoro-$C_{1-4}$alkoxy,
chloro-$C_{1-4}$alkoxy.

$R^1$ very particular preferably represents hydrogen, (2-dimethylamino-ethyl)-methyl-amino, 4-ethyl-piperazin-1-yl-methyl, methyl; with particular preference given to hydrogen.

$R^2$ preferably represents
hydrogen,
halogen,
substituted $C_{1-12}$alkyl wherein the substitutents are selected from the group of saturated, mono-, bi-, tri- or spirocyclic heterocyclyl having 5 to 10 ring atoms and which heterocyclyl is unsubstituted or substituted by $C_{1-12}$alkyl,
amino,
mono-substituted amino wherein the substituent is selected from the group consisting of $C_{1-12}$alkyl, amino $C_{1-12}$alkyl,
di-substituted amino wherein the substituents are selected from the group consisting of $C_{1-12}$alkyl, amino $C_{1-12}$alkyl,
$C_{1-12}$alkoxy,
halo-$C_{1-12}$alkoxy.

$R^2$ particular preferably represents
hydrogen,
fluoro,
chloro,
$Cl_{1-4}$alkyl, substituted $C_{1-4}$alkyl wherein the substitutents are selected from the group of saturated, monocyclic heterocyclyl having 5 to 6 ring atoms and which heterocyclyl is unsubstituted or substituted by $C_{1-4}$alkyl),
amino,
mono-substituted amino wherein the substituent is selected from the group consisting of $C_{1-4}$alkyl, amino-$C_{1-4}$alkyl, $C_{1-4}$alkyl-amino-$C_{1-4}$alkyl, di-$C_{1-4}$alkyl-amino $C_{1-4}$alkyl,
di-substituted amino wherein the substituents are selected from the group consisting of $C_{1-4}$alkyl, amino-$C_{1-4}$alkyl, $C_{1-4}$alkyl-amino-$C_{1-4}$alkyl, di-$C_{1-4}$alkyl-amino $C_{1-4}$alkyl,
$C_{1-4}$alkoxy,
fluoro-$C_{1-4}$alkoxy,
chloro-$C_{1-4}$alkoxy.
$R^2$ very particular preferably represents hydrogen, (2-dimethylamino-ethyl)-methyl-amino, 4-ethyl-piperazin-1-yl-methyl, methyl; with particular preference given to hydrogen.
A preferably represents an aromatic moiety with 6 to 14 ring carbon atoms or a heteroaromatic moiety with 5-13 ring; whereby such aromatic or heteroaromatic moiety is unsubstituted or substituted by one or more substituents —$R^{A1}$-$R^{A2}$ as defined herein.
A particular preferably represents an aromatic moiety selected from the group consisting of phenyl, naphtyl or a heteroaromatic moiety with 5 to 6 ring atoms and whereby at least one of the heteroatoms is nitrogen, each aromatic or heteroaromatic moiety is unsubstituted or substituted by one or more substituents —$R^{A1}$-$R^{A2}$ as defined herein.
A very particular preferably represents optionally substituted aryl or heteroaryl wherein said aryl or heteroaryl is selected from the group consisting of phenyl, pyridyl (such as pyrid-2-yl, pyrid-3-yl), pyrimidyl (such as pyramid-5-yl), pyrolyl (such as pyrol-3-yl), imidazolyl (such as imidazo-2-yl or imidazo-4-yl), pyrazolyl (such as pyradzo-3-yl), triazolyl (such as triazo-3-yl) and wherein said aryl or heteroaryl is unsubstituted or substituted by one or more substituents —$R^{A1}$-$R^{A2}$ as defined herein.
B preferably represents an aromatic moiety with 6 to 14 ring carbon atoms or a heteroaromatic moiety with 5-13 ring atoms; whereby such aromatic or heteroaromatic moiety is unsubstituted or substituted by one or more substituents —$R^{B1}$-$R^{B2}$ as defined below.
B particular preferably represents an aromatic moiety selected from the group consisting of phenyl, naphtyl or a heteroaromatic moiety with 5 to 10 ring atoms and whereby at least one of the heteroatoms is nitrogen or sulfur, each aromatic or heteroaromatic moiety is unsubstituted or substituted by one or more substituents —$R^{B1}$-$R^{B2}$ as defined herein.
B very particular preferably represents optionally substituted aryl or heteroaryl wherein said aryl or heteroaryl is selected from the group consisting of phenyl, naphtyl (such as alpha-naphtyl), pyridyl (such as pyrid-3-yl), pyridyl-N-oxide (such as pyrid-3-yl-N-oxide), chinolinyl, isochinolinyl (such as isochinolin-4-yl, isochinolin-5-yl), thiophenyl (such as thiophen-3-yl), thionaphthenyl (such as thionaphthen-3-yl) and wherein said aryl or heteroaryl is unsubstituted or substituted by one or more substituents —$R^{B1}$-$R^{B2}$ as defined herein.
$R^{A1}$ preferably represents hydrogen; or formyl, $C_{1-7}$alkylcarbonyl, $C_{1-7}$alkoxycarbonyl, aminocarbonyl, N—$C_{1-7}$alkylaminocarbonyl, N,N-di-$C_{1-7}$alkylaminocarbonyl; benzyl; or hydroxy, $C_{1-7}$alkoxy, amino-$C_{1-7}$alkoxy, $C_{1-7}$alkoxy, N,N-di-$C_{1-7}$alkylamino-$C_{1-7}$alkoxy; heterocyclyl-$C_{1-7}$alkoxy whereby said heterocyclyl has 3 to 10 ring atoms, at least one ring atom is nitrogen, is bound via nitrogen, is optionally substituted by $C_{1-7}$alkyl and/or hydroxy; or a group —$NR^{A3}R^{A4}$ or a group —C(O)—$NR^{A3}R^{A4}$.
$R^{A1}$ particular preferably represents hydrogen; or formyl, $C_{1-4}$alkylcarbonyl, $C_{1-4}$alkoxycarbonyl, aminocarbonyl, N,N-di-$C_{1-4}$alkylaminocarbonyl; benzyl; or hydroxy, $C_{1-4}$alkoxy, N,N-di-$C_{1-4}$alkylamino-$C_{1-4}$alkoxy; heterocyclyl-$C_{1-4}$alkoxy whereby said heterocyclyl has 5 to 6 ring atoms, at least one ring atom is nitrogen, is bound via nitrogen, is optionally substituted by $C_{1-4}$alkyl; or a group —$NR^{A3}R^{A4}$.
$R^{A1}$ very particular preferably represents hydrogen; or methoxycarbonyl, tert.butoxycarbonyl, aminocarbonyl; or a group —$NR^{A3}R^{A4}$; or hydroxy, N,N-dimethylaminoethoxy, N,N-dimethylaminomethoxy; heterocyclyl-$C_{1-4}$alkoxy whereby said heterocyclyl is bound via nitrogen and selected from the group consisiting of pyrrolidinyl, piperidinyl, N-methylpiperazinyl, N-ethyl-piperazinyl, N-isopropyl-piperazinyl or morpholinyl.
$R^{A2}$ preferably represents a direct bond or a straight-chain or branched-chain $C_{1-12}$ alkanediyl.
$R^{A2}$ particular preferably represents a direct bond or a straight-chain or branched-chain $C_{1-6}$ alkanediyl.
$R^{A2}$ very particular preferably represents a direct bond, methandiyl, 1,2-ethanediyl, 1,1-ethanediyl, 1,1-, 1,2-, 1,3-propanediyl and 1,1-, 1,2-, 1,3-, 1,4-butanediyl, with particular preference given to direct bond, methandiyl, 1,2-ethanediyl.
$R^{A3}$ and $R^{A4}$ preferably represent independent from each other hydrogen, $C_{1-7}$alkyl, hydroxy-$C_{1-7}$alkyl, halogen-$C_{1-7}$alkyl, cyano-$C_{1-7}$alkyl, amino-$C_{1-7}$alkyl, N—$C_{1-7}$alkylamino-$C_{1-7}$-alkyl, N,N-di-$C_{1-7}$alkylamin-$C_{1-7}$alkyl, aminocarbonyl-$C_{1-7}$alkyl, N—$C_{1-7}$alkylaminocarbonyl-$C_{1-7}$-alkyl, N,N-di-$C_{1-7}$alkylaminocarbonyl-$C_{1-7}$-alkyl, a saturated, partly saturated or unsaturated hetereocycle which has 3 to 10 ring atoms, and which is optionally substituted by 1 to 3 substituents selected from the group consisting of $C_{1-7}$alkyl, hydroxyl, oxo, hydroxy-$C_{1-7}$alkyl, benzyl, methoxybenzyl, amino, $C_{1-7}$alkylamino, N,N-di-$C_{1-7}$alkylamino or
$R^{A3}$ and $R^{A4}$ preferably represent together with the nitrogen to which they are bound a saturated, partly saturated or unsaturated hetereocycle which has 3 to 10 ring atoms, and which is optionally substituted by 1 to 3 substituents selected from the group consisting of $C_{1-7}$alkyl, cyano, halogen, hydroxyl, oxo, hydroxy-$C_{1-7}$alkyl, $C_{1-7}$alkylcarbonyl, benzyl, methoxybenzyl, amino, $C_{1-7}$alkylamino, N,N-di-$C_{1-7}$alkylamino.
$R^{A3}$ and $R^{A4}$ particular preferably represent independent from each other methyl, ethyl, n- or iso-propyl, n-, iso-, sec- or tert-butyl, hydroxymethyl, 2-hydroxyethyl, amino-methyl or -ethyl, dimethylaminomethyl or -ethyl, aminocarbonyl-methyl or -ethyl, N,N-dimethylaminocarbonyl-methyl or -ethyl, N,N-diethylaminocarbonyl-methyl or -ethyl or
$R^{A3}$ and $R^{A4}$ particular preferably represent together with the nitrogen to which they are bound a saturated, partly saturated or unsaturated hetereocycle selected from the group consisting of azetidine, pyrrolidinyl, piperidinyl, piperazinyl, morpholinyl, thiomorpholinyl, and which is optionally substituted by 1 substituent selected from the group consisting of methyl, ethyl, n- or iso-propyl, n-, iso-, sec- or tert-butyl, cyano, halogen, hydroxy, oxo, hydroxyethyl, benzyl, methoxybenzyl, N,N-dimethylamino, N,N-diethylamino.
$R^{B1}$ preferably represents halo, a straight-chain or branched-chain unsubstituted $C_{1-7}$alkyl, a straight-chain or branched-chain unsubstituted $C_{1-7}$alkoxy, straight-chain or branched-chain halo-$C_{1-7}$alkyl.

$R^{B1}$ particular preferably represents methyl, ethyl, n- or isopropyl, n-, iso-, sec- or tert-butyl, n-pentyl, n-hexyl, n-heptyl, methyoxy, ethyoxy, n- or iso-propoxy, n-, iso-, sec- or tert-butoxy, n-pentoxy, n-hexoxy, n-heptoxy, fluormethyl, chlormethyl, trifluoromethyl, fluoro, chloro, bromo.

$R^{B1}$ very particular preferably represents methyl, methoxy, trifluormethyl, fluoro, chloro.

$R^{B2}$ preferably represents a direct bond.

m preferably represents 0, 1, 2, 3 or 4.

m particular preferably represents 0, 1 or 4.

n preferably represents 0, 1 or 2 n particular preferably represents 0 or 1.

In a further embodiment when ring B represents phenyl and n represents 2, the substituents $R^{B2}$-$R^{B1}$ are preferably in the ortho-positions.

In a further embodiment when ring B represents phenyl and n represents 4, the substituents $R^{B2}$-$R^{B1}$ are preferably in the ortho and meta-positions.

The invention further relates to pharmaceutically acceptable prodrugs of a compound of formula (I).

The invention further relates to pharmaceutically acceptable metabolites of a compound of formula (I).

The invention further relates to protected derivatives of a compound of formula (I).

The invention relates especially to the compounds of the formula (I) given in the Examples, as well as the methods of manufacture described therein.

The invention also provides, in a second aspect, pharmacological uses of compounds of formula (I). The compounds of formula (I) have valuable pharmacological properties, as described hereinbefore and hereinafter. They inhibit various protein kinases, such as tyrosine kinases, for example VEGFR$^2$ (KDR), PDGFR, cKIT, LCK, cAbl, RET and FGFR kinases, especially FGFR1, FGFR2, FGFR3, FGFR4.

In Vitro Experiments

The efficacy of the compounds of formula (I) as inhibitors of protein kinase activity can be demonstrated according to known procedures; in particular according to the assays described in the experimental part below. Generally, the activity of a protein kinase is assayed in the presence or absence of inhibitor by measuring the phosphorylation of a synthetic substrate by purified N-terminally His- or GST-tagged kinase domains, in the presence of selected concentrations of ATP and using the appropriate assay technology: Time-Resolved Fluorescence Resonance Energy Transfer (TR-FRET) (LanthaScreen™) or microfluidic Caliper system.

In Vivo Experiments

There are also experiments to demonstrate the antitumor activity of compounds of the formula (I) in vivo according to methods known in the field (e.g. as described herein).

The in vivo antitumor activity is tested, for example, using bladder carcinoma cell lines, such as the human urinary bladder transitional cell carcinoma RT112 cell line (DSMZ ACC #418).

Tumors are obtained after subcutaneous injection of the respective cells (minimum 1×10$^6$ cells in 100 ml phosphate buffered physiological saline) into the carrier mice or rat. The treatment is started, as soon as the tumor has reached an average size of 100 mm$^3$. Tumor growth is determined three times weekly and 24 h after the last treatment by measurement of the perpendicular diameter. In case of tumors, tumor volumes are determined according to the Formula L×D×p/6 (see Evans, B. D., Smith, I. E., Shorthouse, A. J. and Millar, J. J., Brit. J. Cancer, 45: 466-468, 1982). The antitumor activity is expressed as T/C % (average increase of the tumor volume of treated animals divided by the average increase of tumor volume in control animals multiplied by 100). Tumor regression (%) represents the smallest mean tumor volume compared to the mean tumor volume at the beginning of the treatment. Each animal in which the tumor reaches a diameter of more than 1.5 to 2 cm$^3$ is sacrificed.

Clinical Studies

The pharmacological activity of a compound of formula (I) may, for example, be demonstrated in a clinical study or in a test procedure according to methods generally accepted in the field; e.g. as essentially described hereinafter.

Suitable clinical studies are, for example, open label non-randomized, dose escalation studies in patients with one of the tumor diseases mentioned above. The beneficial effects on proliferative diseases can be determined directly through the results of these studies or by changes in the study design which are known as such to a person skilled in the art. The efficacy of the treatment can be determined in such studies, e.g., in case of tumors after 18 or 24 weeks by radiologic evaluation of the tumors every 6 weeks, in case of a leukemia e.g. by determination of the count of aberrant white blood cells, and by staining mononuclear cells and/or by means of determining minimum residual disease (MRD) e.g. by FACS-LPC MRD or PCR.

Alternatively, a placebo-controlled, double blind study can be used in order to prove the benefits of the compounds of the formula (I) mentioned herein.

An exemplary (though not limiting) schedule for administration of a compound of formula (I) is daily administration, with preferably 1 to 3 daily dosages for a longer time, possibly until the disease is cured or, if only palliative treatment is achieved, for as long as required; alternatively, treatment e.g. for 5 days, and/or administration at days 1, 4 and 9, with eventual repetition after a certain time without treatment is possible. Alternatively, treatment several times a day (e.g. 2 to 5 times) or treatment by continuous administration (e.g. infusion), e.g. at the time points indicated in the last sentence, are possible. Generally, administration is orally or parenterally, preferably orally. The test compounds are preferably diluted in water or in sterile 0.9% saline.

Diseases:

On the basis of these tests and studies, a compound of formula (I) according to the invention shows therapeutic efficacy especially against disorders dependent on protein tyrosine kinase ("protein tyrosine kinase dependent diseases") such as FGFR, VEGFR2 (KDR), PDGF-R, cKIT, LCK, cABL, RET, especially proliferative diseases mediated FGFR kinase activity. The compounds of formula (I), that inhibit the protein tyrosine kinase activities mentioned, especially tyrosine protein kinases mentioned above and below, can therefore be used in the treatment of protein kinase dependent diseases. Thus, a compound of formula (I) is in particular useful in the treatment of diseases identified below.

FGFR dependent diseases include a wide variety of disorders or conditions known to the person skilled in the art.

A first group of FGFR dependents diseases relates to a benign or malignant proliferative disease, e.g. a cancer, e.g. tumors and/or metastasis (wherever located). In a preferred embodiment, the proliferative disease is a cancer. The proliferative diseases include, without being limited to, cancers of the bladder, cervix, or oral squamous cell carcinomas (in particular with mutated FGFR3 and/or elevated FGFR3 expression), multiple myeloma (in particular with t(4,14) chromosomal translocation), breast cancers (in particular with gene amplification and/or protein overexpression of FGFR1, FGFR2 or FGFR4), endometrial cancer (in particular with FGFR2 mutations), hepatocellular cancer (in particular with elevated expression of FGFR3 or FGFR4 or FGF ligands), any cancer type with an amplification of the 11q13 amplicon, which contains the FGF3, FGF4 and FGF19 loci, for example breast cancer, hepatocellular cancer, EMS myeloproliferative disorders (in particular with abnormal FGFR1 fusion proteins), lymphomas (in particular with abnormal FGFR3 fusion proteins), glioblastomas (in particular with FGFR1 abnormal expression or mutations), gastric carcinomas (in particular with FGFR2 mutations or overexpression or FGFR3 mutations), pancreatic carcinomas (in particular with abnormal FGFR1 or FGFR4 expression), prostate carcinomas (in particular with abnormal expression of FGFR1, FGFR4, or FGF ligands); pituitary tumors (in particular with abnormal FGFR4), any cancer that requires angiogenesis.

A second group of FGFR dependents diseases relates to non-cancer disorders. Such non-cancer disorders include, without being limited to, benign skin tumors (in particular with FGFR3 activating mutations), skeletal disorders (in particular resulting from mutations in FGFRs) including achondroplasia, hypochondroplasia, severe achondroplasia with developmental delay and acanthosis nigricans (SADDAN), thanatophoric dysplasia (TD), muenke coronal craniosynostosis, crouzon syndrome with acanthosis nigricans, both familial and sporadic forms of Pfeiffer syndrome; disorders related to alterations of phosphate homeostasis, for example autosomal dominant hypophosphatemic rickets (ADHR, in particular related to FGF23 missense mutations), x-linked hypophosphatemic rickets (XLH; an x-linked dominant disorder related to inactivating mutations in the PHEX gene), tumor-induced osteomalacia (TIO, an acquired disorder of isolated phosphate), or fibrous dysplasia of the bone (FD).

A third group of FGFR dependent diseases relates to inflammatory or autoimmune diseases. The inhibition of FGFR activity has been found to represent a means for treating T cell mediated inflammatory or autoimmune diseases, as for example in treatment of T-cell mediated inflammatory or autoimmune diseases including but not limited to rheumatoid arthritis (RA), collagen II arthritis, multiple sclerosis (MS), systemic lupus erythematosus (SLE), psoriasis, juvenile onset diabetes, Sjogren's disease, thyroid disease, sarcoidosis, autoimmune uveitis, inflammatory bowel disease (Crohn's and ulcerative colitis), celiac disease and myasthenia gravis.

A fourth group of FGFR dependent diseases relates tot the group consisting of obesity, diabetes and/or diseases related thereto. Methods of antagonizing FGFRs, especially FGFR1 or FGFR4, have also been described to be useful in the treatment of obesity, diabetes and/or diseases related thereto, such as metabolic syndrome, cardiovascular diseases, hypertension, aberrant cholesterol and triglyceride levels, dermatological disorders e.g. infections, varicose veins, Acanthosis nigricans, eczema, exercise intolerance, diabetes type 2, insulin resistance, hypercholesterolemia, cholelithiasis, orthopedic injury, thromboembolic disease, coronary or vascular restriction (e.g. atherosclerosis), daytime sleepiness, sleep apnoea, end stage renal disease, gallbladder disease, gout, heat disorders, impaired immune response, impaired respiratory function, infections following wounds, infertility, liver disease, lower back pain, obstetric and gynecological complications, pancreatitis, stroke, surgical complications, urinary stress incontinence and/or gastrointestinal disorders.

Further, enhanced (especially bronchial) expression of FGFRs, especially FGFR1, has been reported to be associated with Chronic Obstructive Pulmonary Disease (COPD).

Further, acidic Fibroblast Growth Factor (especially FGF-1) and FGFR1 have also been described to be involved in aberrant signaling in retinoblastoma, leading to proliferation upon binding of FGF-1.

Non-FGFR protein kinase dependent diseases include VEGFR2 (KDR), PDGF, cKIT, LCK, cABL and RET dependent diseases and are especially proliferative diseases, preferably benign or especially malignant tumours (for example carcinoma of the kidneys, liver, adrenal glands, bladder, breast, stomach, ovaries, colon, rectum, prostate, pancreas, lungs, vagina or thyroid, sarcoma, glioblastomas and numerous tumours of the neck and head, as well as leukemias). They are able to bring about the regression of tumours and to prevent the formation of tumour metastases and the growth of (also micro)-metastases. In addition they can be used in epidermal hyperproliferation (e.g. psoriasis), in prostate hyperplasia, and in the treatment of neoplasias, especially of epithelial character, for example mammary carcinoma. It is also possible to use the compounds of formula (I) in the treatment of diseases of the immune system insofar as several or, especially, individual tyrosine protein kinases are involved; furthermore, the compounds of formula (I) can be used also in the treatment of diseases of the central or peripheral nervous system where signal transmission by at least one tyrosine protein kinase, especially selected from those mentioned specifically, is involved.

VEGFR2 (KDR) dependent diseases include a wide variety of disorders or conditions known to the person skilled in the art. Vascular endothelial growth factor receptor-2 (VEGFR2; KDR) is expressed on the primary vascular endothelium and is essential for normal vascular development. Angiogenesis, or the sprouting of new blood vessels, is also a central process in the growth of solid tumors. For many cancers, the extent of vascularization of a tumor is a negative prognostic indicator signifying aggressive disease and increased potential for metastasis. Recent efforts to understand the molecular basis of tumor-associated angiogenesis have identified several potential therapeutic targets, including the receptor tyrosine kinases for the angiogenic factor vascular endothelial growth factor (VEGF). The compounds of formula (I) as inhibitors of VEGF-receptor tyrosine kinase activity, may primarily inhibit the growth of blood vessels and are thus, for example, effective against a number of diseases associated with deregulated angiogenesis, especially diseases caused by ocular neovascularisation, especially retinopathies, such as diabetic retinopathy or age-related macula degeneration, psoriasis, haemangioblastoma, such as haemangioma, mesangial cell proliferative disorders, such as chronic or acute renal diseases, e.g. diabetic nephropathy, malignant nephrosclerosis, thrombotic microangiopathy syndromes or transplant rejection, or especially inflammatory renal disease, such as glomerulonephritis, especially mesangioproliferative glomerulonephritis, haemolytic-uraemic syndrome, diabetic nephropathy, hypertensive nephrosclerosis, atheroma, arterial restenosis, autoimmune diseases, diabetes, endometriosis, chronic asthma, and especially neoplastic diseases, for example so-called solid tumors (especially cancers of the gastrointestinal tract, the pancreas, breast, stomach, cervix, bladder, kidney, prostate, ovaries, endometrium, lung, brain, melanoma, Kaposi's sarcoma, squamous cell carcinoma of head and neck, malignant pleural mesothelioma, lymphoma or multiple myeloma) and liquid tumors (e.g. leukemias), especially those expressing KDR, are especially important. A compound of formula (I) inhibits the growth of tumours and is especially suited to preventing the metastatic spread of tumors and the growth of micrometastases. These diseases are thus also Protein kinase dependent diseases.

PDGF dependent diseases include a wide variety of disorders or conditions known to the person skilled in the art. Compounds of the formula (I), in view of their activity as PDGF receptor inhibitors, are also especially appropriate in the treatment of proliferate diseases, especially glioblastoma, small lung cancer, atherosclerosis, thrombosis, psoriasis, scleroderma or fibrosis.

cKIT dependent diseases include a wide variety of disorders or conditions known to the person skilled in the art. It is known that such kinases are frequently aberrantly expressed in common human cancers such as breast cancer, head and neck cancers, gastrointestinal cancer such as colon, rectal or stomach cancer, leukemia, and ovarian, bronchial, lung or pancreatic cancer. KIT kinase expression has been documented in a wide variety of human malignancies such as mastocytosis/mast cell leukemia, gastrointestinal stromal tumors (GIST), small cell lung carcinoma (SCLC), sinonasal natural killer/T-cell lymphoma, testicular cancer (seminoma), thyroid carcinoma, malignant melanoma, ovarian carcinoma, adenoid cystic carcinoma, acute myelogenous leukemia (AML), breast carcinoma, pediatric T-cell acute lymphoblastic leukemia, angiosarcoma, anaplastic large cell lymphoma, endometrial carcinoma, and prostate carcinoma. The kinase activity of KIT has been implicated in the pathophysiology of several of these—and additional tumors—including breast carcinoma, SCLC, GIST, germ cell tumors, mast cell leukemia, neuroblastoma, AML, melanoma and ovarian carcinoma. Further, C-kit is a receptor tyrosine kinase expressed on the surface of mast cells, to which stem cell factor (SCF) is a ligand. Aberrant c-kit signaling is a mediator of certain autoimmune diseases. Binding of SCF to the c-kit receptor mediates various functions of the mast cell. As an important mediator of mast cell function, c-kit plays a role in pathologies associated with mast cells (MC). C-kit functions through mast cell generation, which plays an important role in triggering autoimmune diseases.

LCK dependent diseases include a wide variety of disorders or conditions known to the person skilled in the art. LCK is a cytoplastic tyrosine kinase of the Src family expressed in T cells and natural killer cells. It is generally accepted that Lck activity is important for signaling mediated by the T cell receptor and leads to normal T cell development and activation. Thus, compounds of formula (I) are a useful immunosuppressive for the treatment of autoimmune and inflammatory disorders and/or organ transplant rejection (in particular T cell mediated).

cABL dependent diseases include a wide variety of disorders or conditions known to the person skilled in the art. In CML, a reciprocally balanced chromosomal translocation in hematopoietic stem cells (HSCs) produces the BCR-ABL hybrid gene. The latter encodes the oncogenic Bcr-Abl fusion protein. Whereas ABL encodes a tightly regulated protein tyrosine kinase, which plays a fundamental role in regulating cell proliferation, adherence and apoptosis, the BCR-ABL fusion gene encodes as constitutively activated kinase, which trans-forms HSCs to produce a phenotype exhibiting deregulated clonal proliferation, reduced capacity to adhere to the bone marrow stroma and a reduces apoptotic response to mutagenic stimuli, which enable it to accumulate progressively more malignant transformations. Compounds of the formula (I), in view of their activity as Abl protein tyrosune kinase inhibitors, are also especially appropriate in the treatment of leukemias, e.g. CML or acute lymphoblastic leukemia (ALL).

RET dependent diseases include a wide variety of disorders or conditions known to the person skilled in the art. In humans, activating RET mutations are found in the inherited cancer syndrome multiple endocrine neoplasia 2 and in sporadic medullary and papillary thyroid carcinomas. The specific type and location of RET mutations are strongly correlated with the disease phenotype and also have diagnostic and prognostic value. Further, RET-associated thyroid tumors encompass malignancies of the parafollicular C.cells and of follicular epithelial cells, of which the most common are papillary thyroid carcinomas. In addition, RET mutations cause the early onset cancer syndrome multiple endocrine neoloasia type 2 associated with several endocrine tumors including MTX, PC and parathyroid hyperplasia.

The invention also provides, in a third aspect, a combination of a compound of formula (I) and one or more further therapeutic agents. A compound of formula (I) can be administered alone or in combination with one or more other therapeutic agents, possible combination therapy taking the form of fixed combinations or the administration of a compound of the invention and one or more other therapeutic agents being staggered or given independently of one another, or the combined administration of fixed combinations and one or more other therapeutic agents. A compound of formula (I) can besides or in addition be administered especially for tumor therapy in combination with chemotherapy, radiotherapy, immunotherapy, surgical intervention, or a combination of these. Long-term therapy is equally possible as is adjuvant therapy in the context of other treatment strategies, as described above. Other possible treatments are therapy to maintain the patient's status after tumor regression, or even chemopreventive therapy, for example in patients at risk.

Thus, a compound of the formula (I) may be used to advantage in combination with other antiproliferative compounds. Such antiproliferative compounds include, but are not limited to aromatase inhibitors; antiestrogens; topoisomerase I inhibitors; topoisomerase II inhibitors; microtubule active compounds; alkylating compounds; histone deacetylase inhibitors; compounds which induce cell differentiation processes; cyclooxygenase inhibitors; MMP inhibitors; mTOR inhibitors; antineoplastic antimetabolites; platin compounds; compounds targeting/decreasing a protein or lipid kinase activity and further anti-angiogenic compounds; compounds which target, decrease or inhibit the activity of a protein or lipid phosphatase; gonadorelin agonists; anti-androgens; methionine aminopeptidase inhibitors; bisphosphonates; biological response modifiers; antiproliferative antibodies; heparanase inhibitors; inhibitors of Ras oncogenic isoforms; telomerase inhibitors; proteasome inhibitors; compounds used in the treatment of hematologic malignancies; compounds which target, decrease or inhibit the activity of Flt-3; Hsp90 inhibitors such as 17-AAG (17-allylaminogeldanamycin, NSC330507), 17-DMAG (17-dimethylaminoethylamino-17-demethoxy-geldanamycin, NSC707545), IPI-504, CNF1010, CNF2024, CNF1010 from Conforma Therapeutics; temozolomide (TEMODAL®); kinesin spindle protein inhibitors, such as SB715992 or SB743921 from GlaxoSmithKline, or pentamidine/chlorpromazine from CombinatoRx; MEK inhibitors such as ARRY142886 from Array PioPharma, AZD6244 from AstraZeneca, PD181461 from Pfizer, leucovorin, EDG binders, antileukemia compounds, ribonucleotide reductase inhibitors, S-adenosylmethionine decarboxylase inhibitors, antiproliferative antibodies or other chemotherapeutic compounds. Further, alternatively or in addition they may be used in combination with other tumor treatment approaches, including surgery, ionizing radiation, photodynamic therapy, implants, e.g. with corticosteroids, hormones, or they may be used as radiosensitizers. Also, in anti-inflammatory and/or antiproliferative treatment, combination with anti-inflammatory drugs is included. Combination is also possible with antihistamine drug substances, bronchodilatatory drugs, NSAID or antagonists of chemokine receptors.

The term "aromatase inhibitor" as used herein relates to a compound which inhibits the estrogen production, i.e. the conversion of the substrates androstenedione and testosterone to estrone and estradiol, respectively. The term includes, but is not limited to steroids, especially atamestane, exemestane and formestane and, in particular, non-steroids, especially aminoglutethimide, roglethimide, pyridoglutethimide, trilostane, testolactone, ketokonazole, vorozole, fadrozole, anastrozole and letrozole. Exemestane can be administered, e.g., in the form as it is marketed, e.g. under the trademark AROMASIN. Formestane can be administered, e.g., in the form as it is marketed, e.g. under the trademark LENTARON. Fadrozole can be administered, e.g., in the form as it is marketed, e.g. under the trademark AFEMA. Anastrozole can be administered, e.g., in the form as it is marketed, e.g. under the trademark ARIMIDEX. Letrozole can be administered, e.g., in the form as it is marketed, e.g. under the trademark FEMARA or FEMAR. Aminoglutethimide can be administered, e.g., in the form as it is marketed, e.g. under the trademark ORIMETEN. A combination of the invention comprising a chemotherapeutic agent which is an aromatase inhibitor is particularly useful for the treatment of hormone receptor positive tumors, e.g. breast tumors.

The term "antiestrogen" as used herein relates to a compound which antagonizes the effect of estrogens at the estrogen receptor level. The term includes, but is not limited to tamoxifen, fulvestrant, raloxifene and raloxifene hydrochloride. Tamoxifen can be administered, e.g., in the form as it is marketed, e.g. under the trademark NOLVADEX. Raloxifene hydrochloride can be administered, e.g., in the form as it is marketed, e.g. under the trademark EVISTA. Fulvestrant can be formulated as disclosed in U.S. Pat. No. 4,659,516 or it can be administered, e.g., in the form as it is marketed, e.g. under the trademark FASLODEX. A combination of the invention comprising a chemotherapeutic agent which is an antiestrogen is particularly useful for the treatment of estrogen receptor positive tumors, e.g. breast tumors.

The term "anti-androgen" as used herein relates to any substance which is capable of inhibiting the biological effects of androgenic hormones and includes, but is not limited to, bicalutamide (CASODEX), which can be formulated, e.g. as disclosed in U.S. Pat. No. 4,636,505. The term "gonadorelin agonist" as used herein includes, but is not limited to abarelix, goserelin and goserelin acetate. Goserelin is disclosed in U.S. Pat. No. 4,100,274 and can be administered, e.g., in the form as it is marketed, e.g. under the trademark ZOLADEX. Abarelix can be formulated, e.g. as disclosed in U.S. Pat. No. 5,843,901.

The term "topoisomerase I inhibitor" as used herein includes, but is not limited to topotecan, gimatecan, irinotecan, camptothecian and its analogues, 9-nitrocamptothecin and the macromolecular camptothecin conjugate PNU-166148 (compound A1 in WO99/17804). Irinotecan can be administered, e.g. in the form as it is marketed, e.g. under the trademark CAMPTOSAR. Topotecan can be administered, e.g., in the form as it is marketed, e.g. under the trademark HYCAMTIN.

The term "topoisomerase II inhibitor" as used herein includes, but is not limited to the anthracyclines such as doxorubicin (including liposomal formulation, e.g. CAELYX), daunorubicin, epirubicin, idarubicin and nemorubicin, the anthraquinones mitoxantrone and losoxantrone, and the podophillotoxines etoposide and teniposide. Etoposide can be administered, e.g. in the form as it is marketed, e.g. under the trademark ETOPOPHOS. Teniposide can be administered, e.g. in the form as it is marketed, e.g. under the trademark VM 26-BRISTOL. Doxorubicin can be administered, e.g. in the form as it is marketed, e.g. under the trademark ADRIBLASTIN or ADRIAMYCIN. Epirubicin can be administered, e.g. in the form as it is marketed, e.g. under the trademark FARMORUBICIN. Idarubicin can be administered, e.g. in the form as it is marketed, e.g. under the trademark ZAVEDOS. Mitoxantrone can be administered, e.g. in the form as it is marketed, e.g. under the trademark NOVANTRON.

The term "microtubule active compound" relates to microtubule stabilizing, microtubule destabilizing compounds and microtublin polymerization inhibitors including, but not limited to taxanes, e.g. paclitaxel and docetaxel, vinca alkaloids, e.g., vinblastine, especially vinblastine sulfate, vincristine especially vincristine sulfate, and vinorelbine, discodermolides, cochicine and epothilones and derivatives thereof, e.g. epothilone B or D or derivatives thereof.

Paclitaxel may be administered e.g. in the form as it is marketed, e.g. TAXOL. Docetaxel can be administered, e.g., in the form as it is marketed, e.g. under the trademark TAXOTERE. Vinblastine sulfate can be administered, e.g., in the form as it is marketed, e.g. under the trademark VINBLASTIN R.P. Vincristine sulfate can be administered, e.g., in the form as it is marketed, e.g. under the trademark FARMISTIN. Discodermolide can be obtained, e.g., as disclosed in U.S. Pat. No. 5,010,099. Also included are Epothilone derivatives which are disclosed in WO98/10121, U.S. Pat. No. 6,194,181, WO98/25929, WO98/08849, WO99/43653, WO98/22461 and WO00/31247. Especially preferred are Epothilone A and/or B.

The term "alkylating compound" as used herein includes, but is not limited to, cyclophosphamide, ifosfamide, melphalan or nitrosourea (BCNU or Gliadel). Cyclophosphamide can be administered, e.g., in the form as it is marketed, e.g. under the trademark CYCLOSTIN. Ifosfamide can be administered, e.g., in the form as it is marketed, e.g. under the trademark HOLOXAN.

The term "histone deacetylase inhibitors" or "HDAC inhibitors" relates to compounds which inhibit the histone deacetylase and which possess antiproliferative activity. This includes compounds disclosed in WO02/22577, especially N-hydroxy-3-[4-[[(2-hydroxyethyl)[2-(1H-indol-3-yl) ethyl]-amino]methyl]phenyl]-2E-2-propenamide, N-hydroxy-3-[4-[[[2-(2-methyl-1H-indol-3-yl)-ethyl]-amino] methyl]phenyl]-2E-2-propenamide and pharmaceutically acceptable salts thereof. It further especially includes Suberoylanilide hydroxamic acid (SAHA).

The term "antineoplastic antimetabolite" includes, but is not limited to, 5-Fluorouracil or 5-FU, capecitabine, gemcitabine, DNA demethylating compounds, such as 5-azacytidine and decitabine, methotrexate and edatrexate, and folic acid antagonists such as pemetrexed. Capecitabine can be administered, e.g., in the form as it is marketed, e.g. under the trademark XELODA. Gemcitabine can be administered, e.g., in the form as it is marketed, e.g. under the trademark GEMZAR.

The term "platin compound" as used herein includes, but is not limited to, carboplatin, cis-platin, cisplatinum and oxaliplatin. Carboplatin can be administered, e.g., in the form as it is marketed, e.g. under the trademark CARBOPLAT. Oxaliplatin can be administered, e.g., in the form as it is marketed, e.g. under the trademark ELOXATIN.

The term "compounds targeting/decreasing a protein or lipid kinase activity"; or a "protein or lipid phosphatase activity"; or "further anti-angiogenic compounds" as used herein includes, but is not limited to, protein tyrosine kinase and/or serine and/or threonine kinase inhibitors or lipid kinase inhibitors, e.g., a) compounds targeting, decreasing or inhibiting the activity of the platelet-derived growth factor-receptors (PDGFR), such as compounds which target, decrease or inhibit the activity of PDGFR, especially compounds which inhibit the PDGF receptor, e.g. a N-phenyl-2-pyrimidine-amine derivative, e.g. imatinib, SU101, SU6668 and GFB-111;

b) compounds targeting, decreasing or inhibiting the activity of the fibroblast growth factor-receptors (FGFR);

c) compounds targeting, decreasing or inhibiting the activity of the insulin-like growth factor receptor I (IGF-1R), such as compounds which target, decrease or inhibit the activity of IGF-1R, especially compounds which inhibit the kinase activity of IGF-1 receptor, such as those compounds disclosed in WO02/092599, or antibodies that target the extracellular domain of IGF-1 receptor or its growth factors;

d) compounds targeting, decreasing or inhibiting the activity of the Trk receptor tyrosine kinase family, or ephrin B4 inhibitors;

e) compounds targeting, decreasing or inhibiting the activity of the Axl receptor tyrosine kinase family;

f) compounds targeting, decreasing or inhibiting the activity of the Ret receptor tyrosine kinase;

g) compounds targeting, decreasing or inhibiting the activity of the Kit/SCFR receptor tyrosine kinase, e.g. imatinib;

h) compounds targeting, decreasing or inhibiting the activity of the C-kit receptor tyrosine kinases—(part of the PDGFR family), such as compounds which target, decrease or inhibit the activity of the c-Kit receptor tyrosine kinase family, especially compounds which inhibit the c-Kit receptor, e.g. imatinib;

i) compounds targeting, decreasing or inhibiting the activity of members of the c-Abl family, their gene-fusion products (e.g. BCR-Abl kinase) and mutants, such as compounds which target decrease or inhibit the activity of c-Abl family members and their gene fusion products, e.g. a N-phenyl-2-pyrimidine-amine derivative, e.g. imatinib or nilotinib (AMN107); PD180970; AG957; NSC 680410; PD173955 from ParkeDavis; or dasatinib (BMS-354825)

j) compounds targeting, decreasing or inhibiting the activity of members of the protein kinase C (PKC) and Raf family of serine/threonine kinases, members of the MEK, SRC, JAK, FAK, PDK1, PKB/Akt, and Ras/MAPK family members, and/or members of the cyclin-dependent kinase family (CDK) and are especially those staurosporine derivatives disclosed in U.S. Pat. No. 5,093,330, e.g. midostaurin; examples of further compounds include e.g. UCN-01, safingol, BAY 43-9006, Bryostatin 1, Perifosine; Ilmofosine; RO 318220 and RO 320432; GO 6976; Isis 3521; LY333531/LY379196; isochinoline compounds such as those disclosed in WO00/09495; FTIs; PD184352 or QAN697 (a P13K inhibitor) or AT7519 (CDK inhibitor);

k) compounds targeting, decreasing or inhibiting the activity of protein-tyrosine kinase inhibitors, such as compounds which target, decrease or inhibit the activity of protein-tyrosine kinase inhibitors include imatinib mesylate (GLEEVEC) or tyrphostin. A tyrphostin is preferably a low molecular weight (Mr<1500) compound, or a pharmaceutically acceptable salt thereof, especially a compound selected from the benzylidenemalonitrile class or the S-arylbenzenemalonirile or bisubstrate quinoline class of compounds, more especially any compound selected from the group consisting of Tyrphostin A23/RG-50810; AG 99; Tyrphostin AG 213; Tyrphostin AG 1748; Tyrphostin AG 490; Tyrphostin B44; Tyrphostin B44 (+) enantiomer; Tyrphostin AG 555; AG 494; Tyrphostin AG 556, AG957 and adaphostin (4-{[(2,5-dihydroxyphenyl)methyl]amino}-benzoic acid adamantyl ester; NSC 680410, adaphostin);

l) compounds targeting, decreasing or inhibiting the activity of the epidermal growth factor family of receptor tyrosine kinases (EGFR, ErbB2, ErbB3, ErbB4 as homo- or heterodimers) and their mutants, such as compounds which target, decrease or inhibit the activity of the epidermal growth factor receptor family are especially compounds, proteins or antibodies which inhibit members of the EGF receptor tyrosine kinase family, e.g. EGF receptor, ErbB2, ErbB3 and ErbB4 or bind to EGF or EGF related ligands, and are in particular those compounds, proteins or monoclonal antibodies generically and specifically disclosed in WO97/02266, e.g. the compound of ex. 39, or in EP 0 564 409, WO99/03854, EP 0520722, EP 0 566 226, EP 0 787 722, EP 0 837 063, U.S. Pat. No. 5,747,498, WO98/10767, WO97/30034, WO97/49688, WO97/38983 and, especially, WO96/30347 (e.g. compound known as CP 358774), WO96/33980 (e.g. compound ZD 1839) and WO95/03283 (e.g. compound ZM105180); e.g. trastuzumab (Herceptin™), cetuximab (Erbitux™), Iressa, Tarceva, OSI-774, CI-1033, EKB-569, GW-2016, E1.1, E2.4, E2.5, E6.2, E6.4, E2.11, E6.3 or E7.6.3, and 7H-pyrrolo-[2,3-d]pyrimidine derivatives which are disclosed in WO03/013541; and m) compounds targeting, decreasing or inhibiting the activity of the c-Met receptor, such as compounds which target, decrease or inhibit the activity of c-Met, especially compounds which inhibit the kinase activity of c-Met receptor, or antibodies that target the extracellular domain of c-Met or bind to HGF.

Further anti-angiogenic compounds include compounds having another mechanism for their activity, e.g. unrelated to protein or lipid kinase inhibition e.g. thalidomide (THALOMID) and TNP-470.

The term "Compounds which target, decrease or inhibit the activity of a protein or lipid phosphatase" includes, but is not limited to inhibitors of phosphatase 1, phosphatase 2A, or CDC25, e.g. okadaic acid or a derivative thereof.

The term "Compounds which induce cell differentiation processes" includes, but is not limited to e.g. retinoic acid, α- γ- or δ-tocopherol or α- γ- or δ-tocotrienol.

The term "cyclooxygenase inhibitor" as used herein includes, but is not limited to, e.g. Cox-2 inhibitors, 5-alkyl substituted 2-arylaminophenylacetic acid and derivatives, such as celecoxib (CELEBREX), rofecoxib (VIOXX), etoricoxib, valdecoxib or a 5-alkyl-2-arylaminophenylacetic acid, e.g. 5-methyl-2-(2'-chloro-6'-fluoroanilino)phenyl acetic acid, lumiracoxib.

The term "bisphosphonates" as used herein includes, but is not limited to, etridonic, clodronic, tiludronic, pamidronic, alendronic, ibandronic, risedronic and zoledronic acid. "Etridonic acid" can be administered, e.g., in the form as it is marketed, e.g. under the trademark DIDRONEL. "Clodronic acid" can be administered, e.g., in the form as it is marketed, e.g. under the trademark BONEFOS. "Tiludronic acid" can be administered, e.g., in the form as it is marketed, e.g. under the trademark SKELID. "Pamidronic acid" can be administered, e.g. in the form as it is marketed, e.g. under the trademark AREDIA™. "Alendronic acid" can be administered, e.g., in the form as it is marketed, e.g. under the trademark FOSAMAX. "Ibandronic acid" can be administered, e.g., in the form as it is marketed, e.g. under the trademark BONDRANAT. "Risedronic acid" can be administered, e.g., in the form as it is marketed, e.g. under the trademark ACTONEL. "Zoledronic acid" can be administered, e.g. in the form as it is marketed, e.g. under the trademark ZOMETA.

The term "mTOR inhibitors" relates to compounds which inhibit the mammalian target of rapamycin (mTOR) and which possess antiproliferative activity such as sirolimus (Rapamune®), everolimus (Certican™), CCI-779 and ABT578.

The term "heparanase inhibitor" as used herein refers to compounds which target, decrease or inhibit heparin sulfate degradation. The term includes, but is not limited to, PI-88. The term "biological response modifier" as used herein refers to a lymphokine or interferons, e.g. interferon γ.

The term "inhibitor of Ras oncogenic isoforms", e.g. H-Ras, K-Ras, or N-Ras, as used herein refers to compounds which target, decrease or inhibit the oncogenic activity of Ras e.g. a "farnesyl transferase inhibitor" e.g. L-744832, DK8G557 or R115777 (Zarnestra). The term "telomerase inhibitor" as used herein refers to compounds which target, decrease or inhibit the activity of telomerase. Compounds which target, decrease or inhibit the activity of telomerase are especially compounds which inhibit the telomerase receptor, e.g. telomestatin.

The term "methionine aminopeptidase inhibitor" as used herein refers to compounds which target, decrease or inhibit the activity of methionine aminopeptidase. Compounds which target, decrease or inhibit the activity of methionine aminopeptidase are e.g. bengamide or a derivative thereof.

The term "proteasome inhibitor" as used herein refers to compounds which target, decrease or inhibit the activity of the proteasome. Compounds which target, decrease or inhibit the activity of the proteasome include e.g. Bortezomid (Velcade™) and MLN 341.

The term "matrix metalloproteinase inhibitor" or ("MMP" inhibitor) as used herein includes, but is not limited to, collagen peptidomimetic and nonpeptidomimetic inhibitors, tetracycline derivatives, e.g. hydroxamate peptidomimetic inhibitor batimastat and its orally bioavailable analogue marimastat (BB-2516), prinomastat (AG3340), metastat (NSC 683551) BMS-279251, BAY 12-9566, TAA211, MMI270B or AAJ996.

The term "compounds used in the treatment of hematologic malignancies" as used herein includes, but is not limited to, FMS-like tyrosine kinase inhibitors e.g. compounds targeting, decreasing or inhibiting the activity of FMS-like tyrosine kinase receptors (Flt-3R); interferon, 1-b-D-arabinofuransylcytosine (ara-c) and bisulfan; and ALK inhibitors e.g. compounds which target, decrease or inhibit anaplastic lymphoma kinase.

Compounds which target, decrease or inhibit the activity of FMS-like tyrosine kinase receptors (Flt-3R) are especially compounds, proteins or antibodies which inhibit members of the Flt-3R receptor kinase family, e.g. PKC412, midostaurin, a staurosporine derivative, SU11248 and MLN518.

The term "HSP90 inhibitors" as used herein includes, but is not limited to, compounds targeting, decreasing or inhibiting the intrinsic ATPase activity of HSP90; degrading, targeting, decreasing or inhibiting the HSP90 client proteins via the ubiquitin proteosome pathway. Compounds targeting, decreasing or inhibiting the intrinsic ATPase activity of HSP90 are especially compounds, proteins or antibodies which inhibit the ATPase activity of HSP90 e.g., 17-allylamino, 17-demethoxygeldanamycin (17AAG), a geldanamycin derivative; other geldanamycin related compounds; radicicol and HDAC inhibitors.

The term "antiproliferative antibodies" as used herein includes, but is not limited to, trastuzumab (Herceptin™), Trastuzumab-DM1, erbitux, bevacizumab (Avastin™), rituximab (Rituxan®), PRO64553 (anti-CD40) and 2C4 Antibody. By antibodies is meant e.g. intact monoclonal antibodies, polyclonal antibodies, multispecific antibodies formed from at least 2 intact antibodies, and antibodies fragments so long as they exhibit the desired biological activity.

For the treatment of acute myeloid leukemia (AML), compounds of formula (I) can be used in combination with standard leukemia therapies, especially in combination with therapies used for the treatment of AML. In particular, compounds of formula (I) can be administered in combination with, e.g., farnesyl transferase inhibitors and/or other drugs useful for the treatment of AML, such as Daunorubicin, Adriamycin, Ara-C, VP-16, Teniposide, Mitoxantrone, Idarubicin, Carboplatinum and PKC412.

The term "antileukemic compounds" includes, for example, Ara-C, a pyrimidine analog, which is the 2"-alpha-hydroxy ribose (arabinoside) derivative of deoxycytidine. Also included is the purine analog of hypoxanthine, 6-mercaptopurine (6-MP) and fludarabine phosphate. Compounds which target, decrease or inhibit activity of histone deacetylase (HDAC) inhibitors such as sodium butyrate and suberoylanilide hydroxamic acid (SAHA) inhibit the activity of the enzymes known as histone deacetylases. Specific HDAC inhibitors include MS275, SAHA, FK228 (formerly FR901228), Trichostatin A and compounds disclosed in U.S. Pat. No. 6,552,065, in particular, N-hydroxy-3-[4-[[[2-(2-methyl-1H-indol-3-yl)-ethyl]-amino]methyl]phenyl]-2E-2-propenamide, or a pharmaceutically acceptable salt thereof and N-hydroxy-3-[4-[(2-hydroxyethyl){2-(1H-indol-3-yl) ethyl]-amino]methyl]phenyl]-2E-2-propenamide, or a pharmaceutically acceptable salt thereof, especially the lactate salt.

"Somatostatin receptor antagonists" as used herein refers to compounds which target, treat or inhibit the somatostatin receptor such as octreotide, and SOM230.

"Tumor cell damaging approaches" refer to approaches such as ionizing radiation. The term "ionizing radiation" referred to above and hereinafter means ionizing radiation that occurs as either electromagnetic rays (such as X-rays and gamma rays) or particles (such as alpha and beta particles). Ionizing radiation is provided in, but not limited to, radiation therapy and is known in the art. See Hellman, Principles of Radiation Therapy, Cancer, in *Principles and Practice of Oncology*, Devita et al., Eds., 4$^{th}$ Edition, Vol. 1, pp. 248-275 (1993).

The term "EDG binders" as used herein refers a class of immunosuppressants that modulates lymphocyte recirculation, such as FTY720.

The term "ribonucleotide reductase inhibitors" includes, but is not limited to to pyrimidine or purine nucleoside analogs including, but not limited to, fludarabine and/or cytosine arabinoside (ara-C), 6-thioguanine, 5-fluorouracil, cladribine, 6-mercaptopurine (especially in combination with ara-C against ALL) and/or pentostatin. Ribonucleotide reductase inhibitors are especially hydroxyurea or 2-hydroxy-1H-isoindole-1,3-dione derivatives, such as PL-1, PL-2, PL-3, PL-4, PL-5, PL-6, PL-7 or PL-8 mentioned in Nandy et al., *Acta Oncologica*, Vol. 33, No. 8, pp. 953-961 (1994).

The term "S-adenosylmethionine decarboxylase inhibitors" as used herein includes, but is not limited to the compounds disclosed in U.S. Pat. No. 5,461,076.

Also included are in particular those compounds, proteins or monoclonal antibodies of VEGF disclosed in WO98/35958, e.g. 1-(4-chloroanilino)-4-(4-pyridylmethyl)phthalazine or a pharmaceutically acceptable salt thereof, e.g. the succinate, or in WO00/09495, WO00/27820, WO00/59509, WO98/11223, WO00/27819 and EP 0 769 947; those as described by Prewett et al, *Cancer Res*, Vol. 59, pp. 5209-5218 (1999); Yuan et al., *Proc Natl Acad Sci USA*, Vol. 93, pp. 14765-14770 (1996); Zhu et al., *Cancer Res*, Vol. 58, pp. 3209-3214 (1998); and Mordenti et al., *Toxicol Pathol*, Vol. 27, No. 1, pp. 14-21 (1999); in WO00/37502 and WO94/10202; ANGIOSTATIN, described by O'Reilly et al., *Cell*, Vol. 79, pp. 315-328 (1994); ENDOSTATIN, described by O'Reilly et al., *Cell*, Vol. 88, pp. 277-285 (1997); anthranilic acid amides; ZD4190; ZD6474; SU5416; SU6668; bevacizumab; or anti-VEGF antibodies or anti-VEGF receptor antibodies, e.g. rhuMAb and RHUFab, VEGF aptamer e.g. Macugon; FLT-4 inhibitors, FLT-3 inhibitors, VEGFR-2 IgG1 antibody, Angiozyme (RPI 4610) and Bevacizumab (Avastin™).

"Photodynamic therapy" as used herein refers to therapy which uses certain chemicals known as photosensitizing compounds to treat or prevent cancers. Examples of photodynamic therapy include treatment with compounds, such as e.g. VISUDYNE and porfimer sodium.

"Angiostatic steroids" as used herein refers to compounds which block or inhibit angiogenesis, such as, e.g., anecortave, triamcinolone, hydrocortisone, 11-α-epihydrocotisol, cortexolone, 17α-hydroxyprogesterone, corticosterone, desoxycorticosterone, testosterone, estrone and dexamethasone.

"Implants containing corticosteroids" as used herein includes, but is not limited to compounds, such as e.g. fluocinolone, dexamethasone.

"Other chemotherapeutic compounds" include, but are not limited to, plant alkaloids, hormonal compounds and antagonists; biological response modifiers, preferably lymphokines or interferons; antisense oligonucleotides or oligonucleotide derivatives; shRNA or siRNA; or miscellaneous compounds or compounds with other or unknown mechanism of action.

The compounds of the invention are also useful as co-therapeutic compounds for use in combination with other drug substances such as anti-inflammatory, bronchodilatory or antihistamine drug substances, particularly in the treatment of inflammatory diseases such as those mentioned hereinbefore, for example as potentiators of therapeutic activity of such drugs or as a means of reducing required dosaging or potential side effects of such drugs. A compound of the invention may be mixed with the other drug substance in a fixed pharmaceutical composition or it may be administered separately, before, simultaneously with or after the other drug substance. Accordingly the invention includes a combination of a compound of the invention as hereinbefore described with an anti-inflammator or antihistamine drug substance, said compound of the invention and said drug substance being in the same or different pharmaceutical composition.

Suitable anti-inflammatory drugs include steroids, in particular glucocorticosteroids such as budesonide, beclamethasone dipropionate, fluticasone propionate, ciclesonide or mometasone furoate, or steroids described in WO02/88167, WO02/12266, WO02/100879, WO02/00679 (especially those of Examples 3, 11, 14, 17, 19, 26, 34, 37, 39, 51, 60, 67, 72, 73, 90, 99 and 101), WO03/035668, WO03/048181, WO03/062259, WO03/064445, WO03/072592, non-steroidal glucocorticoid receptor agonists such as those described in WO00/00531, WO02/10143, WO03/082280, WO03/082787, WO03/104195, WO04/005229; LTB4 antagonists such LY293111, CGS025019C, CP-195543, SC-53228, BIIL 284, ONO 4057, SB 209247 and those described in U.S. Pat. No. 5,451,700; LTD4 antagonists such as montelukast and zafirlukast; PDE4 inhibitors such cilomilast (Ariflo® GlaxoSmithKline), Roflumilast (Byk Gulden), V-11294A (Napp), BAY19-8004 (Bayer), SCH-351591 (Schering-Plough), Arofylline (Almirall Prodesfarma), PD189659/PD168787 (Parke-Davis), AWD-12-281 (Asta Medica), CDC-801 (Celgene), SelCID™ CC-10004 (Celgene), VM554/UM565 (Vernalis), T-440 (Tanabe), KW-4490 (Kyowa Hakko Kogyo), and those disclosed in WO92/19594, WO93/19749, WO93/19750, WO93/19751, WO98/18796, WO99/16766, WO01/13953, WO03/104204, WO03/104205, WO03/39544, WO04/000814, WO04/000839, WO04/005258, WO04/018450, WO04/018451, WO04/018457, WO04/018465, WO04/018431, WO04/018449, WO04/018450, WO04/018451, WO04/018457, WO04/018465, WO04/019944, WO04/019945, WO04/045607 and WO04/037805; A2a agonists such as those disclosed in EP 409595A2, EP 1052264, EP 1241176, WO94/17090, WO96/02543, WO96/02553, WO98/28319, WO99/24449, WO99/24450, WO99/24451, WO99/38877, WO99/41267, WO99/67263, WO99/67264, WO99/67265, WO99/67266, WO00/23457, WO00/77018, WO00/78774, WO01/23399, WO01/27130, WO01/27131, WO01/60835, WO01/94368, WO02/00676, WO02/22630, WO02/96462, WO03/086408, WO04/039762, WO04/039766, WO04/045618 and WO04/046083; A2b antagonists such as those described in WO02/42298; and beta-2 adrenoceptor agonists such as albuterol (salbutamol), metaproterenol, terbutaline, salmeterol fenoterol, procaterol, and especially, formoterol and pharmaceutically acceptable salts thereof, and compounds (in free or salt or solvate form) of formula (I) of WO0075114, preferably compounds of the Examples thereof, especially a compound of formula

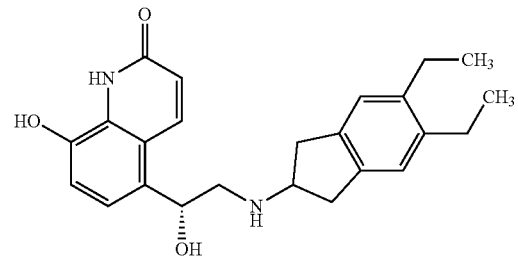 [SMILES: CCc1cc2c(cc1CC)CC(NC[C@H](O)c1ccc(O)c3[nH]c(=O)ccc13)C2]

and pharmaceutically acceptable salts thereof, as well as compounds (in free or salt or solvate form) of formula (I) of WO04/16601, and also compounds of WO04/033412. Suitable bronchodilatory drugs include anticholinergic or antimuscarinic compounds, in particular ipratropium bromide, oxitropium bromide, tiotropium salts and CHF 4226 (Chiesi), and glycopyrrolate, but also those described in WO01/04118, WO02/51841, WO02/53564, WO03/00840, WO03/87094, WO04/05285, WO02/00652, WO03/53966, EP 424021, U.S. Pat. No. 5,171,744, U.S. Pat. No. 3,714,357, WO03/33495 and WO04/018422.

Suitable antihistamine drug substances include cetirizine hydrochloride, acetaminophen, clemastine fumarate, promethazine, loratidine, desloratidine, diphenhydramine and fexofenadine hydrochloride, activastine, astemizole, azelastine, ebastine, epinastine, mizolastine and tefenadine as well as those disclosed in WO03/099807, WO04/026841 and JP 2004107299.

Other useful combinations of compounds of the invention with anti-inflammatory drugs are those with antagonists of chemokine receptors, e.g. CCR-1, CCR-2, CCR-3, CCR-4, CCR-5, CCR-6, CCR-7, CCR-8, CCR-9 and CCR10, CXCR1, CXCR2, CXCR3, CXCR4, CXCR5, particularly CCR-5 antagonists such as Schering-Plough antagonists SC-351125, SCH-55700 and SCH-D, Takeda antagonists such as N-[[4-[[[6,7-dihydro-2-(4-methylphenyl)-5H-benzocyclohepten-8-yl]carbonyl]amino]phenyl]methyl]tetrahydro-N,N-dimethyl-2H-pyran-4-amin-ium chloride (TAK-770), and CCR-5 antagonists described in U.S. Pat. No. 6,166,037 (particularly claims 18 and 19), WO00/66558 (particularly claim 8), WO00/66559 (particularly claim 9), WO04/018425 and WO04/026873.

Therapeutic agents for possible combination are especially one or more antiproliferative, cytostatic or cytotoxic compounds, for example one or several agents selected from the group which includes, but is not limited to, an inhibitor of polyamine biosynthesis, an inhibitor of a protein kinase, especially of a serine/threonine protein kinase, such as protein kinase C, or of a tyrosine protein kinase, such as the EGF receptor tyrosine kinase, e.g. Iressa®, the VEGF receptor tyrosine kinase, e.g. PTK787 or Avastin®, or the PDGF receptor tyrosine kinase, e.g. STI571 (Glivec®), a cytokine, a negative growth regulator, such as TGF-β or IFN-β, an aromatase inhibitor, e.g. letrozole (Femara®) or anastrozole, an inhibitor of the interaction of an SH2 domain with a phosphorylated protein, antiestrogens, topoisomerase I inhibitors, such as irinotecan, topoisomerase II inhibitors, microtubule active agents, e.g. paclitaxel or an epothilone, alkylating agents, antiproliferative antimetabolites, such as gemcitabine or capecitabine, platin compounds, such as carboplatin or cis-platin, bisphosphonates, e.g. AREDIA® or ZOMETA®, and monoclonal antibodies, e.g. against HER2, such as trastuzumab.

The structure of the active agents identified by code nos., generic or trade names may be taken from the actual edition of the standard compendium "The Merck Index" or from databases, e.g. Patents International (e.g. IMS World Publications).

The above-mentioned compounds, which can be used in combination with a compound of the formula (I), can be prepared and administered as described in the art, such as in the documents cited above.

Thus, the invention relates in a further aspect to a combination comprising a therapeutically effective amount of a compound of formula (I) in free form or in pharmaceutically acceptable salt form and a second drug substance, for simultaneous or sequential administration.

The invention also provides, in a further aspect, a pharmaceutical preparation (composition), comprising a compound of formula (I) as defined herein, or a pharmaceutically acceptable salt of such a compound, or a hydrate or solvate thereof, and at least one pharmaceutically acceptable carrier and/or diluents and optionally one or more further drug substances.

The compounds of the invention may be administered by any conventional route, in particular parenterally, for example in the form of injectable solutions or suspensions, enterally, e.g. orally, for example in the form of tablets or capsules, topically, e.g. in the form of lotions, gels, ointments or creams, or in a nasal or a suppository form. Topical administration is e.g. to the skin. A further form of topical administration is to the eye. Pharmaceutical compositions comprising a compound of the invention in association with at least one pharmaceutical acceptable carrier or diluent may be manufactured in conventional manner by mixing with a pharmaceutically acceptable carrier or diluent.

The invention relates also to pharmaceutical compositions comprising an effective amount, especially an amount effective in the treatment of one of the above-mentioned diseases (=disorders), of a compound of formula (I) or a pharmaceutically acceptable salt thereof together with one or more pharmaceutically acceptable carriers that are suitable for topical, enteral, for example oral or rectal, or parenteral administration and that may be inorganic or organic, solid or liquid.

There can be used for oral administration especially tablets or gelatin capsules that comprise the active ingredient together with diluents, for example lactose, dextrose, mannitol, and/or glycerol, and/or lubricants and/or polyethylene glycol. Tablets may also comprise binders, for example magnesium aluminum silicate, starches, such as corn, wheat or rice starch, gelatin, methylcellulose, sodium carboxymethylcellulose and/or polyvinylpyrrolidone, and, if desired, disintegrators, for example starches, agar, alginic acid or a salt thereof, such as sodium alginate, and/or effervescent mixtures, or adsorbents, dyes, flavorings and sweeteners. It is also possible to use the pharmacologically active compounds of the present invention in the form of parenterally administrable compositions or in the form of infusion solutions. The pharmaceutical compositions may be sterilized and/or may comprise excipients, for example preservatives, stabilisers, wetting compounds and/or emulsifiers, solubilisers, salts for regulating the osmotic pressure and/or buffers. The present pharmaceutical compositions, which may, if desired, comprise other pharmacologically active substances are prepared in a manner known per se, for example by means of conventional mixing, granulating, confectionning, dissolving or lyophilising processes, and comprise approximately from 1% to 99%, especially from approx. 1% to approx. 20%, active ingredient(s).

The dosage of the active ingredient to be applied to a warm-blooded animal depends upon a variety of factors including type, species, age, weight, sex and medical condition of the patient; the severity of the condition to be treated; the route of administration; the renal and hepatic function of the patient; and the particular compound employed. A physician, clinician or veterinarian of ordinary skill can readily determine and prescribe the effective amount of the drug required to prevent, counter or arrest the progress of the condition. Optimal precision in achieving concentration of drug within the range that yields efficacy without toxicity requires a regimen based on the kinetics of the drug's availability to target sites. This involves a consideration of the distribution, equilibrium, and elimination of a drug. The dose of a compound of the formula (I) or a pharmaceutically acceptable salt thereof to be administered to warm-blooded animals, for example humans of approximately 70 kg body weight, is preferably from approximately 3 mg to approximately 5 g, more preferably from approximately 10 mg to approximately 1.5 g per person per day, divided preferably into 1 to 3 single doses which may, for example, be of the same size. Usually, children receive half of the adult dose.

In a further aspect, the invention relates to a compound of formula (I) or a pharmaceutically acceptable salt, as a medicament/for use as a medicament, in particular for the treatment of one or more Protein tyrosine kinase mediated diseases.

In a further aspect, the invention relates to the use of a compound of formula (I) or a pharmaceutically acceptable salt, as active ingredient in a medicament, in particular for the treatment of one or more Protein tyrosine kinase mediated diseases.

In a further aspect, the invention relates to the use of a compound of formula (I) or a pharmaceutically acceptable salt, as medicament, in particular for the treatment of one or more Protein tyrosine kinase mediated diseases.

In a further aspect, the invention relates to the use of a compound of formula (I) or a pharmaceutically acceptable salt, for the manufacture of a medicament for the treatment of one or more Protein tyrosine kinase mediated diseases.

In a further aspect, the invention relates to a compound of formula (I) or a pharmaceutically acceptable salt of such a compound, for use in a method for the treatment of a subject in need thereof, especially for the treatment of a Protein tyrosine kinase mediated disease, most especially in a patient requiring such treatment.

In a further aspect, the invention relates to a method for the treatment of a disease which responds to an inhibition of a FGFR (such as FGFR3) kinase, which comprises administering a compound of formula (I) or a pharmaceutically acceptable salt thereof, wherein the radicals and symbols have the meanings as defined above, especially in a quantity effective against said disease, to a warm-blooded animal requiring such treatment.

In a further aspect, the invention relates to a pharmaceutical composition comprising a compound of formula (I) as active ingredient in association with at least one pharmaceutical carrier or diluent. Such compositions may be manufactured in conventional manner. In a further aspect, the invention relates to a method of treatment of one or more Protein tyrosine kinase mediated diseases, in a subject in need of such treatment, which comprises administering to such subject a therapeutically effective amount of compound of formula I.

In a further aspect, the invention relates to pharmaceutical compositions comprising: (a) an effective amount of compound of formula (I) and pharmaceutically acceptable salts, pharmaceutically acceptable prodrugs, and pharmaceutically active metabolites thereof; and (b) one or more pharmaceutically acceptable excipients and/or diluents.

In a further aspect, the invention relates to a pharmaceutical composition for treatment of a disease, e.g. of solid or liquid tumours in warm-blooded animals, including humans, comprising a dose effective in the treatment of said disease of a compound of the formula (I) as described above or a pharmaceutically acceptable salt of such a compound together with a pharmaceutically acceptable carrier (=carrier material).

The invention also provides, in a further aspect, methods of manufacturing a compound of formula (I) and intermediates and their methods of manufacturing; such intermediates are useful for the manufacturing of a compound of formula (I). A compound of the formula (I) may be prepared by processes that, though not applied hitherto for the new compounds of the present invention where they thus form new processes, are known per se, the following scheme illustrates methods for such preparation.

Preferably, a process for the manufacture of a compound of the formula (I) comprises either Method A) reacting a carboxylic acid of the formula (II),

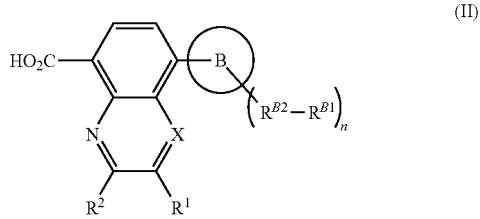

(II)

wherein the substituents are as defined for a compound of the formula (I) with an amine of the formula (III)

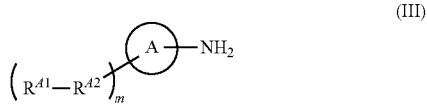

(III)

optionally in the prensence of a diluent (such as a polar organic solvent), optionally in the presence of a reaction aid (such as DMAP or TBTU), optionally in the presence of a base (such as an amine) to obtain a compound of formula I; or Method B) reacting a compound of formula (X)

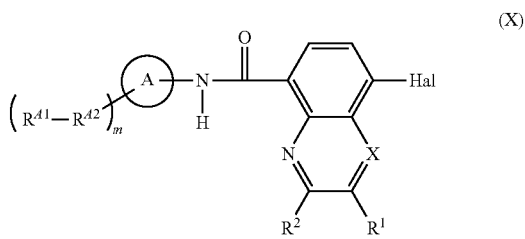

(X)

wherein the substituents are as defined for a compound of the formula (I) and Hal represents halo (in particular bromo) with a boron compound of the formula (V)

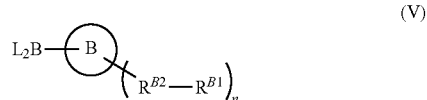

(V)

wherein the substituents are as defined for a compound of the formula (I) and $L_2B$ represents represents a boronic acid residue or an ester thereof (such as $(HO)_2B$—) or 4,4,5,5-tetramethyl-[1,3,2]dioxaborolan-2-yl-), optionally in the presence of a diluent (such as an apolar organic solvent), optionally in the presence of a catalyst (such as a homogeneous Pd-catalyst), optionally in the presence of an reaction aid (such as an inorganic base) to obtain a compound of formula I;

and, if desired, converting a compound of the formula (I) obtained according to method A) or method B) into a different compound of the formula (I), and/or converting an obtainable salt of a compound of the formula (I) into a different salt thereof, and/or converting an obtainable free compound of the formula (I) into a salt thereof, and/or separating an obtainable isomer of a compound of the formula (I) from one or more different obtainable isomers of the formula I.

Method A) is particularly useful for manufacturing of compounds wherein X represents N (such as formula (I-A), (I-B), (I-C); while method B) is particular useful for manufacturing of compounds wherein X represents CH (such as formula (I-D)).

Reaction Conditions

Where temperatures are given hereinbefore or hereinafter, "about" has to be added, as minor deviations from the numeric values given, e.g. variations of ±10%, are tolerable. All reactions may take place in the presence of one or more diluents and/or solvents. Protective gases, such as argon, may be used. The starting materials may be used in equimolar amounts; alternatively, a compound may be used in excess, e.g. to function as a solvent or to shift equilibrium or to generally accelerate reaction rates. Reaction aids, such as acids, bases or catalysts may be added in suitable amounts, as known in the field, required by a reaction and in line with generally known procedures.

Intermediates and final products can be worked up and/or purified according to standard methods, e.g. using chromatographic methods, distribution methods, (re-) crystallization, and the like. Intermediates may be directly used in the further reaction step or may be subject to one or more work up and/or purification steps. Additionally, intermediates may be subject to further derivatization/functionalization, as the case may be. For example, substitution of an aryl/heteroaryl ring may take place to introduce additional substituents (such as chloro, fluoro).

Starting materials may be used as commercially available, and/or subject to one or more work up and/or purification steps and/or produced in situ.

Amide Forming Reaction

Such reactions are generally known in the field. The reaction typically takes place in the presence of an activating agent (such as TBTU or others) which may be added in a slight excess and in the presence of a tert. amine and in the presence of one or more diluents (such as polar aprotic diluents). Typically, the reaction takes place at r.t., reaction times may vary, good conversion rates are typically obtained after 18 hours. Further details may be found in the examples.

Suzuki-Coupling

This reaction is, inter alia, useful for manufacturing of compounds of formula (I) according to method B) as described above. Reaction conditions, starting materials and catalysts for a Suzuki(-Miyaura) reaction are generally known in the field. This reaction typically takes place by palladium-catalyzed crosscoupling of organoboranes (e.g. of formula (V) or a reactive derivative thereof, with a halogen derivative (e.g. of the formula (IV) or (X)). The reaction may be typically performed in analogy to the procedure described by K. Jones, M. Keenan, and F. Hibbert [Synlett, 1996, (6), 509-510].

Protecting Groups

Protected derivatives of the compounds of the invention can be made by means known to those of ordinary skill in the art. Protecting groups are such groups that are typically no longer present in the final compounds once they are removed, while groups that remain as substituents are not protecting groups in the sense used here which are groups that are added at a starting material or intermediate stage and removed to obtain a final compound. Also in the case of conversions of a compound of the formula (I) into a different compound of the formula (I), protecting groups may be introduced and removed, if useful or required.

The protecting groups may already be present in precursors and should protect the functional groups concerned against unwanted secondary reactions, such as acylations, etherifications, esterifications, oxidations, solvolysis, and similar reactions. It is a characteristic of protecting groups that they lend themselves readily, i.e. without undesired secondary reactions, to removal, typically by acetolysis, protonolysis, solvolysis, reduction, photolysis or also by enzyme activity, for example under conditions analogous to physiological conditions, and that they are not present in the end-products. The specialist knows, or can easily establish, which protecting groups are suitable with the reactions mentioned above and below.

The protection of such functional groups by such protecting groups, the protecting groups themselves, and their removal reactions are described for example in standard reference works, such as J. F. W. McOmie, "Protective Groups in Organic Chemistry", Plenum Press, London and New York 1973, in T. W. Greene, "Protective Groups in Organic Synthesis", Third edition, Wiley, New York 1999, in "The Peptides"; Volume 3 (editors: E. Gross and J. Meienhofer), Academic Press, London and New York 1981, in "Methoden der organischen Chemie" (*Methods of organic chemistry*), Houben Weyl, 4th edition, Volume 15/I, Georg Thieme Verlag, Stuttgart 1974, in H.-D. Jakubke and H. Jescheit, "Aminosäuren, Peptide, Proteine" (*Amino acids, peptides, proteins*), Verlag Chemie, Weinheim, Deerfield Beach, and Basel 1982, and in Jochen Lehmann, "Chemie der Kohlenhydrate: Monosaccharide and Derivate" (*Chemistry of carbohydrates: monosaccharides and derivatives*), Georg Thieme Verlag, Stuttgart 1974.

Optional Reactions and Conversions

A compound of the formula (I) may be converted into a different compound of the formula (I). The following description provides a non-limiting overview of particular relevant optional reactions and conversions:

Benzyl groups: For example, in a compound of the formula (I) having a benzyl which is optionally substituted (e.g. methoxybenzyl), said benzyl moiety may be removed by hydrogenation, e.g. in the presence of a noble metal catalyst, such as palladium on coal, in an appropriate solvent, such as an alcohol, e.g. methanol, at appropriate temperatures, e.g. from 0 to 50° C., in the case of removal from the piperazine nitrogen in the additional presence of an acid, e.g. HCl, to yield the corresponding compound wherein instead of the benzyl moiety a hydrogen is present.

N-oxides: A compound of formula (I) can be converted to a corresponding N-oxide. The reaction is typically carried out with a suitable oxidizing agent, preferably a peroxide, for example m-chloroperbenzoic acid, in a suitable solvent, e.g. halogenated hydrocarbon, typically chloroform or dichloromethane, or in a lower alkanecarboxylic acid, typically acetic acid, preferably at a temperature between 0° C. and the boiling temperature of the reaction mixture, especially at about room temperature. Compounds of formula (I) in unoxidized form can typically be prepared from N-oxides of compounds of formula (I) by treating with a reducing agent (e.g., sulfur, sulfur dioxide, triphenyl phosphine, lithium borohydride, sodium borohydride, phosphorus trichloride, tribromide, or the like) in a suitable inert organic solvent (e.g. acetonitrile, ethanol, aqueous dioxane, or the like) at 0 to 80° C.

Salts of compounds of formula (I) having at least one salt-forming group may be prepared in a manner known per se. For example, an acid addition salt of compounds of formula (I) with basic groups (e.g. basic nitrogen) can be typically obtained in customary manner, e.g. by treating a compound of the formula (I) with an acid or a suitable anion exchange reagent. A salt of a compound of formula (I) having acid groups may be typically formed by treating the compound with a metal compound, such as an alkali metal salt of a suitable organic carboxylic acid, e.g. the sodium salt of 2-ethylhexanoic acid, with an organic alkali metal or alkaline earth metal compound, such as the corresponding hydroxide, carbonate or hydrogen carbonate, such as sodium or potassium hydroxide, carbonate or hydrogen carbonate, with a corresponding calcium compound or with ammonia or a suitable organic amine, stoichiometric amounts or only a small excess of the salt-forming agent preferably being used. Internal salts of compounds of formula (I) containing acid and basic salt-forming groups, e.g. a free carboxy group and a free amino group, may be formed, e.g. by the neutralization of salts, such as acid addition salts, to the isoelectric point, e.g. with weak bases, or by treatment with ion exchangers. A salt of a compound of the formula (I) can be typically converted in customary manner into the free compound; a metal or ammonium salt can be converted, for example, by treatment with a suitable acid, and an acid addition salt, for example, by treatment with a suitable basic agent into a different salt. In both cases, suitable ion exchangers may be used.

Prodrug derivatives of the compounds of the invention can be prepared by methods known to those of ordinary skill in the art (e.g., for further details see Saulnier et al., (1994), Bio-organic and Medicinal Chemistry Letters, Vol. 4, p. 1985). For example, appropriate prodrugs can be typically prepared by reacting a non-derivatized compound of the invention with a suitable carbamylating agent (e.g., 1,1-acyloxyalkylcarbanochloridate, para-nitrophenyl carbonate, or the like).

Solvates: Compounds of the present invention can be conveniently prepared, or formed during the process of the invention, as solvates (e.g., hydrates). Hydrates of compounds of the present invention can be conveniently prepared by recrystallization from an aqueous/organic solvent mixture, using organic solvents such as dioxin, tetrahydrofuran or methanol.

For example, in a compound of the formula (I) wherein a substituent carries an amino or amino-$C_1$-$C_7$-alkyl substituent, the amino can be converted into acylamino, e.g. $C_1$-$C_7$-alkanoylamino or $C_1$-$C_7$-alkanesulfonylamino, typically by reaction with a corresponding $C_1$-$C_7$-alkanoylhalogenide or $C_1$-$C_7$-alkanesulfonylhalogenide, e.g. a corresponding chloride, in the presence of a tertiary nitrogen base, such as triethylamine or pyridine, in the absence or presence of an appropriate solvent, such a methylene chloride, for example at temperatures in the range from −20 to 50° C., e.g. at about room temperature.

In a compound of the formula (I) wherein a substituent carries a cyano substituent, the cyano may be converted to an aminomethyl group, e.g. by hydrogenation in the presence of an appropriate metal catalyst, such as Raney Nickel or Raney Cobalt, in an appropriate solvent, e.g. a lower alkanol, such as methanol and/or ethanol, for example at temperatures in the range from −20 to 50° C., e.g. at about room temperature.

In a compound of the formula (I) wherein a substituent carries a carboxyl group (—COOH), the latter can be converted into an amide group, e.g. an N—$C_1$-$C_7$-alkyl-carbamoyl group, typically by reaction with the corresponding amine, e.g. in the presence of a coupling agent, that forms a preferred reactive derivative of the carboxyl group in situ, for example dicyclohexylcarbodiimide/1-hydroxybenzotriazole (DCC/HOBT); bis(2-oxo-3-oxazolidinyl)phosphinic chloride (BOPCI); O-(1,2-dihydro-2-oxo-1-pyridyl)-N,N,N',N'-tetramethyl-uronium tetrafluoroborate (TPTU); O-benzotriazol-1-yl)-N,N,N',N'-tetramethyluronium tetrafluoroborate (TBTU); (benzotriazol-1-yloxy)-tripyrrolidinophosphonium-hexafluoro-phosphate (PyBOP), O-(1H-6-chlorobenzotriazole-1-yl)-1,1,3,3-tetramethyluronium hexafluorophosphate, 1-(3-dimethylaminopropyl)-3-ethylcarbodiimide hydrochloride/hydroxybenzotriazole or/1-hydroxy-7-azabenzotriazole (EDC/HOBT or EDC/HOAt) or HOAt alone, or with (1-chloro-2-methyl-propenyl)-dimethylamine. For review of some other possible coupling agents, see e.g. Klauser; Bodansky, *Synthesis* (1972), 453-463. The reaction mixture is preferably stirred at a temperature of between approximately −20 and 50° C., especially between 0° C. and 30° C., e.g. at room temperature.

Salts of a compound of formula (I) with a salt-forming group may be prepared in a manner known per se. Acid addition salts of compounds of formula (I) may thus be obtained by treatment with an acid or with a suitable anion exchange reagent. A salt with two acid molecules (for example a dihalogenide of a compound of formula I) may also be converted into a salt with one acid molecule per compound (for example a monohalogenide); this may be typically done by heating to a melt, or for example by heating as a solid under a high vacuum at elevated temperature, for example from 130 to 170° C., one molecule of the acid being expelled per molecule of a compound of formula I. Salts can usually be converted to free compounds, e.g. by treating with suitable basic compounds, for example with alkali metal carbonates, alkali metal hydrogencarbonates, or alkali metal hydroxides, typically $K_2CO_3$ or sodium NaOH.

Stereoisomeric mixtures, e.g. mixtures of diastereomers, can be separated into their corresponding isomers in a manner known per se by means of suitable separation methods. Diastereomeric mixtures for example may be separated into their individual diastereomers by means of fractionated crystallization, chromatography, solvent distribution, and similar procedures. This separation may take place either at the level of a starting compound or in a compound of formula (I) itself. Enantiomers may be separated through the formation of diastereomeric salts, for example by salt formation with an enantiomer-pure chiral acid, or by means of chromatography, for example by HPLC, using chromatographic substrates with chiral ligands. A more detailed description of the techniques applicable to the resolution of stereoisomers of compounds from their racemic mixture can be found in J. Jacques, A. Collet, S. H. Wilen, "Enantiomers, Racemates and Resolutions", Wiley, 1981.

It should be emphasized that reactions analogous to the conversions mentioned in this chapter may also take place at the level of appropriate intermediates (and are thus useful in the preparation of corresponding starting materials).

Insofar as the production of the starting materials is not particularly described, the compounds are known or can be prepared analogously to methods known in the art or as disclosed in the Examples hereinafter.

One of skill in the art will appreciate that the above transformations are only representative of methods for preparation of the compounds of the present invention, and that other well known methods can similarly be used.

Starting Materials:

The starting materials of the formulae II, III, IV and V, as well as other starting materials mentioned herein, e.g. below, can be prepared according to or in analogy to methods that are known in the art, are known in the art and/or are commercially available. Novel starting materials, as well as processes for the preparation thereof, are likewise an embodiment of the present invention. In the preferred embodiments, such starting materials are used and the reaction chosen are selected so as to enable the preferred compounds to be obtained. Wherein the starting materials and intermediates $R^1$, $R^2$, $R^{A1}$, $R^{A2}$, $R^{B1}$, $R^{B1}$, X, ring A, ring B, m and n are used ("the substituents of formula (I)"), these symbols preferably have the meanings given for a compound of the formula (I), if not indicated otherwise.

In the starting materials (including intermediates), which may also be used and/or obtained as salts where appropriate and expedient, the substituents are preferably as defined for a compound of the formula I.

Compounds of the formula (II) are known or may be prepared by processes that, though not applied hitherto for the compounds of the formula (II) where they thus form new processes, are known per se, the following scheme illustrates methods for such preparation. A process for the manufacture of a compound of the formula (II) comprises method A), step 1: reacting first a compound of formula (IV)

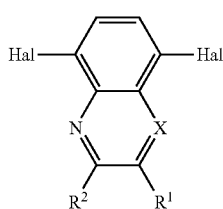

(IV)

wherein the substituents are as defined for a compound of the formula (I) and Hal represents halo (in particular bromo) with a boron compound of the formula (V)

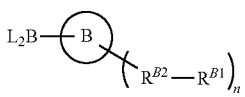

(V)

wherein the substituents are as defined for a compound of the formula (I) and $L_2B$ represents represents a boronic acid residue or an ester thereof (such as $(HO)_2B—$) or 4,4,5,5-tetramethyl-[1,3,2]dioxaborolan-2-yl-), optionally in the presence of a diluent (such as an apolar organic solvent), optionally in the presence of a catalyst (such as a homogeneous Pd-catalyst), optionally in the presence of an reaction aid (such as an inorganic base);
step 2: converting the thus obtained compound, optionally after purification or isolation, with CuCN, optionally in the presence of a polar organic solvent (such as NMP) into the corresponding cyano derivative;
step 3: hydrolysing the thus obtained compound, optionally after purification or isolation, optionally in the presence of an polar organic solvent, to obtain a compound of formula (II);
or, method B), hydrolizing an ester of formula (IIX)

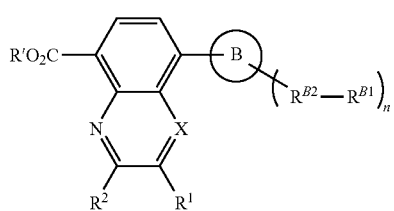

(IIX)

wherein the substituents are as defined for a compound of the formula (I) and R' represents lower alkyl (in particular ethyl) under basic conditions, optionally in the prsende of a diluent, to obtain a compound of formula (II);
and, if desired, converting a compound of the formula (II) obtained into a different compound of the formula (II), and/or converting an obtainable salt of a compound of the formula (II) into a different salt thereof, and/or converting an obtainable free compound of the formula (II) into a salt thereof, and/or separating an obtainable isomer of a compound of the formula (II) from one or more different obtainable isomers of the formula (II).

The subsequent conversion of a compound of formula (II) into another compound of formula (II) is further illustrated by the following scheme.

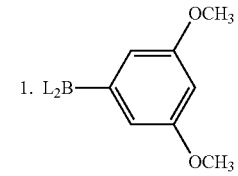

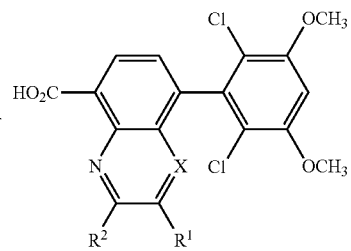

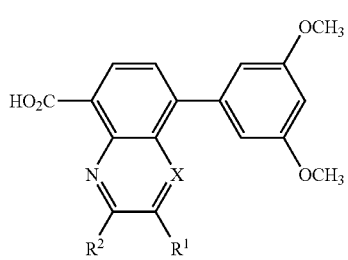

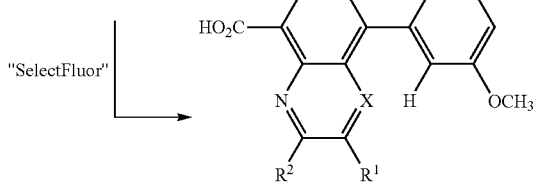

In this scheme, the substituents have the meaning as defined herein. Thus, compounds of formula (II), in particular wherein ring B represents phenyl, a halogenation step may take place once a compound of formula (II) is formed. Such subsequent reaction step (halogenation step) is particular suitable if a substituent $—R^{B2}-R^{B1}$ (such as fluoro or chloro) is to be introduced in one or both of the ortho-position(s) of ring B. Thus, the invention relates also to a process of manufacturing a compound of formula (II) wherein a Suzuki-coupling reaction as described above is followed by a substitution reaction, in particular a halogenation reaction of ring B.

Compounds of the formula (III) are known or may be prepared by processes that, though not applied hitherto for the compounds of the formula (III) where they thus form new processes, are known per se, the following scheme illustrates methods for such preparation. A process for the manufacture of a compound of the formula (III) comprises the step of reducing a compound of formula (IX)

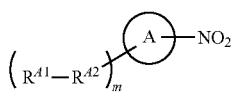 (IX)

wherein the substituents are as defined for a compound of the formula (I) with a reducing agent, optionally in the presence of a diluent and, if desired, converting a compound of the formula (III) obtained into a different compound of the formula (III), and/or converting an obtainable salt of a compound of the formula (III) into a different salt thereof, and/or converting an obtainable free compound of the formula (III) into a salt thereof, and/or separating an obtainable isomer of a compound of the formula (III) from one or more different obtainable isomers of the formula (III).

Compounds of the formula (IV) are known or may be prepared by processes that, though not applied hitherto for the compounds of the formula (IV) where they thus form new processes, are known per se, the following scheme illustrates methods for such preparation. A process for the manufacture of a compound of the formula (IV) wherein X represents N, comprises the step of reacting a compound of formula (VI)

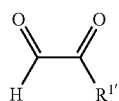 (VI)

wherein $R^{1'}$ represents either $R^1$ or $R^2$ as defined for a compound of the formula (I) and with a compound of formula (VII),

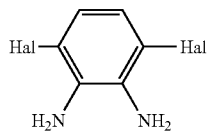 (VII)

wherein Hal represents halo, in particular bromo, optionally in the presence of a diluent and, if desired, converting a compound of the formula (IV) obtained into a different compound of the formula (IV), and/or converting an obtainable salt of a compound of the formula (IV) into a different salt thereof, and/or converting an obtainable free compound of the formula (IV) into a salt thereof, and/or separating an obtainable isomer of a compound of the formula (IV) from one or more different obtainable isomers of the formula (IV).

Compounds of the formula (V) are known or may be prepared by processes that, though not applied hitherto for the compounds of the formula (V) where they thus form new processes, are known per se, the following scheme illustrates methods for such preparation.

A process for the manufacture of a compound of the formula (V) comprises the step of reacting a compound of formula (XIII)

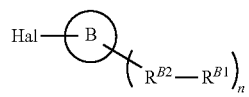 (XIII)

wherein the substituents are as defined for a compound of the formula (I) and hal represents halogen, in particular bromo, first with a lithiation agent (such as butyllitium), optionally in the presence of a diluent, followed by reaction with a boronic acid or derivative thereof (such as trimethylboranate or bis-pinacolate-diboron)

and, if desired, converting a compound of the formula (V) obtained into a different compound of the formula (V), and/or converting an obtainable salt of a compound of the formula (V) into a different salt thereof, and/or converting an obtainable free compound of the formula (V) into a salt thereof, and/or separating an obtainable isomer of a compound of the formula (V) from one or more different obtainable isomers of the formula (V).

Compounds of the formula (X) are known or may be prepared by processes that, though not applied hitherto for the compounds of the formula (X) where they thus form new processes, are known per se, the following scheme illustrates methods for such preparation. A process for the manufacture of a compound of the formula (X) comprises the step of reacting a compound of formula (XI)

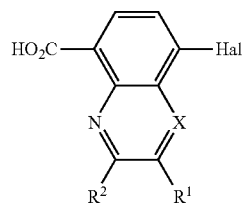 (XI)

wherein the substituents are as defined for a compound of the formula (I) (in particular wherein X represents CH) and hal represents halo (in particular bromo) with an amine of formula (III)

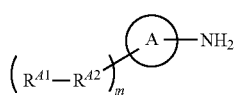 (III)

wherein the substituents are as defined for a compound of the formula (I), optionally in the presence of a diluent (such as a polor organic solvent), optionally in the presence of a reaction aid (such as DMAP or TBTU), optionally in the presence of a base (such as an amine) to obtain a compound of formula (X)

and, if desired, converting a compound of the formula (X) obtained into a different compound of the formula (X), and/or converting an obtainable salt of a compound of the formula (X) into a different salt thereof, and/or converting an obtainable free compound of the formula (X) into a salt thereof, and/or separating an obtainable isomer of a compound of the formula (X) from one or more different obtainable isomers of the formula (X).

This process is particular useful for compounds of formula (X), weherein X represents CH.

Compounds of the formula (XI) are known or may be prepared by processes that, though not applied hitherto for the compounds of the formula (XI) where they thus form new processes, are known per se, the following scheme illustrates methods for such preparation. A process for the manufacture of a compound of the formula (XI) comprises the step of oxidizing a compound of formula (XII)

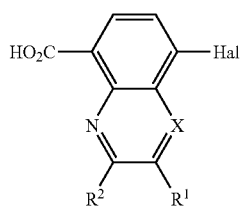

wherein the substituents are as defined for a compound of the formula (I) (in particular wherein X represents CH) and hal represents halo (in particular bromo) with an oxidizing agent (such as $KMnO_4$) optionally in a diluent
and, if desired, converting a compound of the formula (XI) obtained into a different compound of the formula (XI), and/or converting an obtainable salt of a compound of the formula (XI) into a different salt thereof, and/or converting an obtainable free compound of the formula (XI) into a salt thereof, and/or separating an obtainable isomer of the formula (XI) from one or more different obtainable isomers of the formula (XI).

This process is particular useful for compounds of formula (X), weherein X represents CH.

The following examples illustrate the invention without limiting the scope thereof.

Temperatures are measured in degrees Celsius. Unless otherwise indicated, the reactions take place at rt. Microwave Apparatus: Emrys Optimizer (Biotage)

Analytical HPLC conditions are as follows:
System 1: Linear gradient 20-100% solvent A in 5 min+1.5 min 100% solvent A; detection at 215 nm, flow rate 1 mL/min at 30° C. Column: Nucleosil 100-3 C18 (70×4.0 mm). Solvent A=$CH_3CN$+0.1% TFA; Solvent B=$H_2O$+0.1% TFA.
System 2: 40% Solvent A for 5 min and then linear gradient 40-100% solvent A in 5 min+5 min 100% solvent A, flow rate 0.8 mL/min. Column: C18 XDB (250×4.6 mm). Solvent A=$CH_3CN$; Solvent B=20 mM $NH_4OAc$ in $H_2O$.
System 3: Linear gradient 30-100% solvent A in 4 min+2 min 100% solvent A; flow rate 0.8 mL/min. Column: Hypersil C18 (250×4.6 mm). Solvent A=$CH_3CN$; Solvent B=$H_2O$+0.1% TFA.

The following Abbreviations and Acronyms are used:

| | |
|---|---|
| AcOH | acetic acid |
| $Boc_2O$ | tert-butoxycarbonyl anhydride |
| bp | boiling point |
| brine | saturated solution of NaCl in water |
| $CH_3CN$ | acetonitrile |
| $Cs_2CO_3$ | cesium carbonate |
| CuCN | copper (I) cyanide |
| DCM | dichloromethane |
| conc. | concentrated |
| DIEA | diisopropylethylamine |
| DMAP | 4-(dimethylamino) pyridine |
| DME | 1,2-dimethoxyethane |
| DMF | dimethyl formamide |
| DMP | 1,3-dimethyl-3,4,5,6-tetrahydro-2-(1H)-pyrimidinone |
| DMSO | dimethylsulfoxide |
| equiv | equivalent(s) |
| $Et_2O$ | diethyl ether |
| EtOAc | ethyl acetate |
| EtOH | ethanol |
| h | hour(s) |
| Hex | hexane |
| HCl | hydrochloric acid |
| $H_2O$ | water |
| HPLC | high pressure liquid chromatography |
| KOH | potassium hydroxyde |
| L | liter(s) |
| $LiAlH_4$ | lithium aluminum hydride |
| LiOH | lithium hydroxyde |
| mCPBA | m-cloroperbenzoic acid |
| Me | methyl |
| MeOH | methanol |
| mL | milliliter(s) |
| min | minute(s) |
| m.p. | melting point |
| MPLC | medium pressure liquid chromatography |
| MS | mass spectrum |
| $NaBH_4$ | sodium borohydride |
| $Na_2CO_3$ | sodium carbonate |
| NaH | sodium hydride |
| $NaHCO_3$ | sodium bicarbonate |
| NaOH | sodium hydroxyde |
| $Na_2SO_4$ | sodium sulfate |
| NBS | N-bromosuccinimide |
| $NH_4OAc$ | ammonium acetate |
| NMP | 1-methyl-2-pyrrolidone |
| NMR | Nuclear Magnetic Resonance |
| $PdCl_2$(dppf) | [1,1'-bis(diphenylphosphino) ferrocene]dichloro-palladium(II) |
| $Pd(PPh_3)_4$ | tetrakis(triphenylphosphine) palladium(0) |
| $Pd(PhCN)_2Cl_2$ | Bis(benzonitrile)palladium(II)chloride |
| Ph | phenyl |
| PPTS | p-toluensulfonic acid |
| $R_f$ | ratio of fronts (TLC) |
| rt | room temperature |
| SelectFluor | 1-chloromethyl-4-fluoro-1,4-diazobicyclo[2.2.2]octane bis(tetrafluoroborate) |
| TBTU | O-(Benzotriazol-1-yl)-N,N,N',N'-tetramethyluronium tetrafluoroborate |
| TFA | $CF_3COOH$ |
| THF | tetrahydrofuran |
| TLC | thin layer chromatography |
| $t_R$ | time of retention |
| wt. | weight |

For convenience, the following synthetic schemes are provided, wherein scheme 1 relates to examples 1-81 scheme 2 relates to examples 82-84 scheme 3 relates to examples 85-87 scheme 4 relates to examples 88-96 scheme 5 relates to examples 174-178 schemes 6 and 7 relate to examples 179-187

Scheme 1
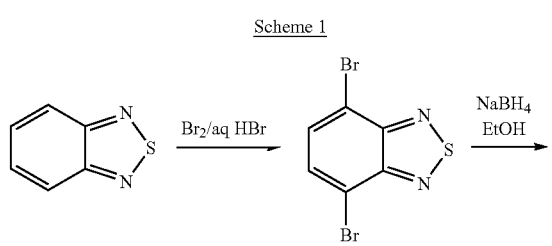
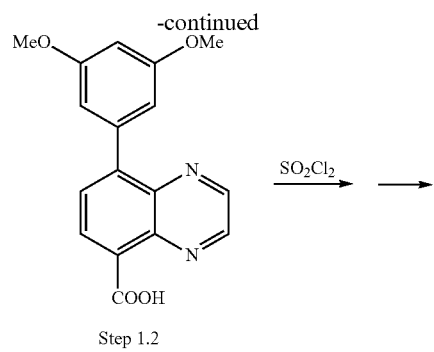
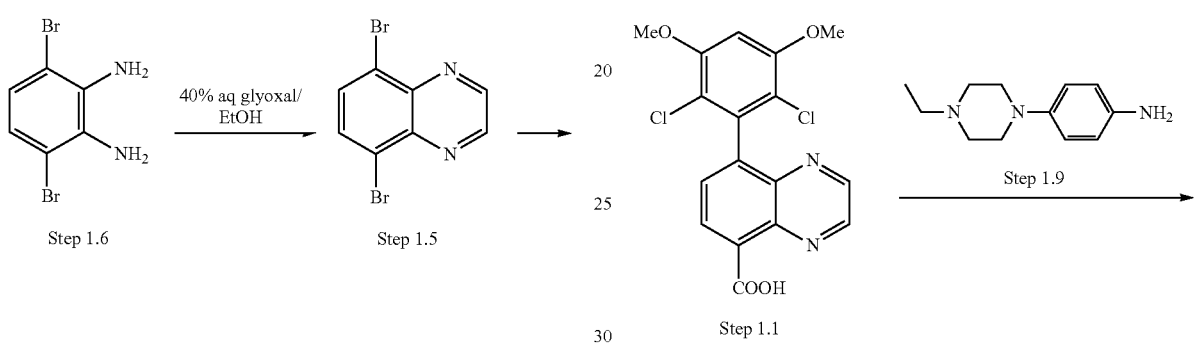
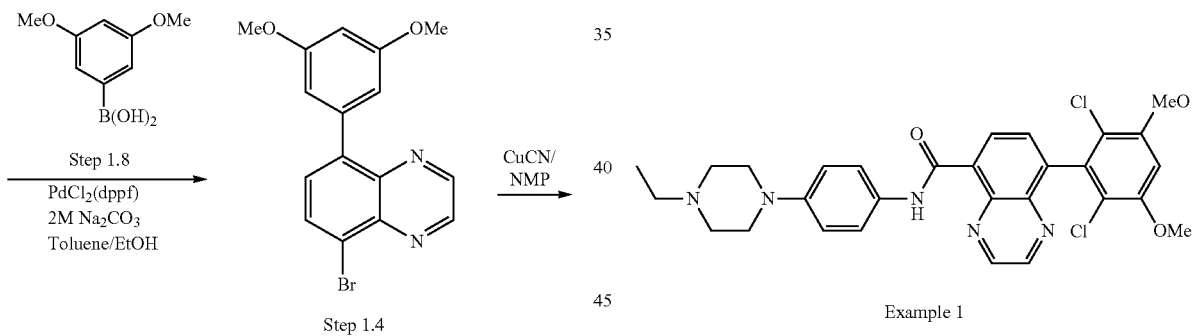
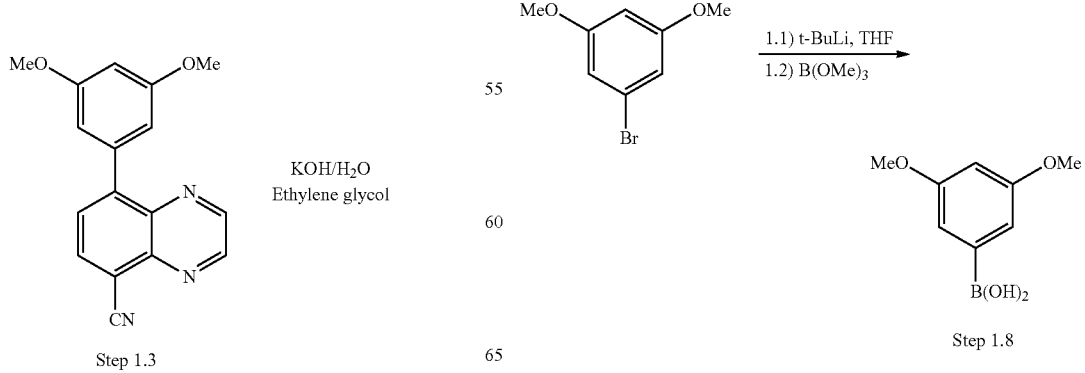

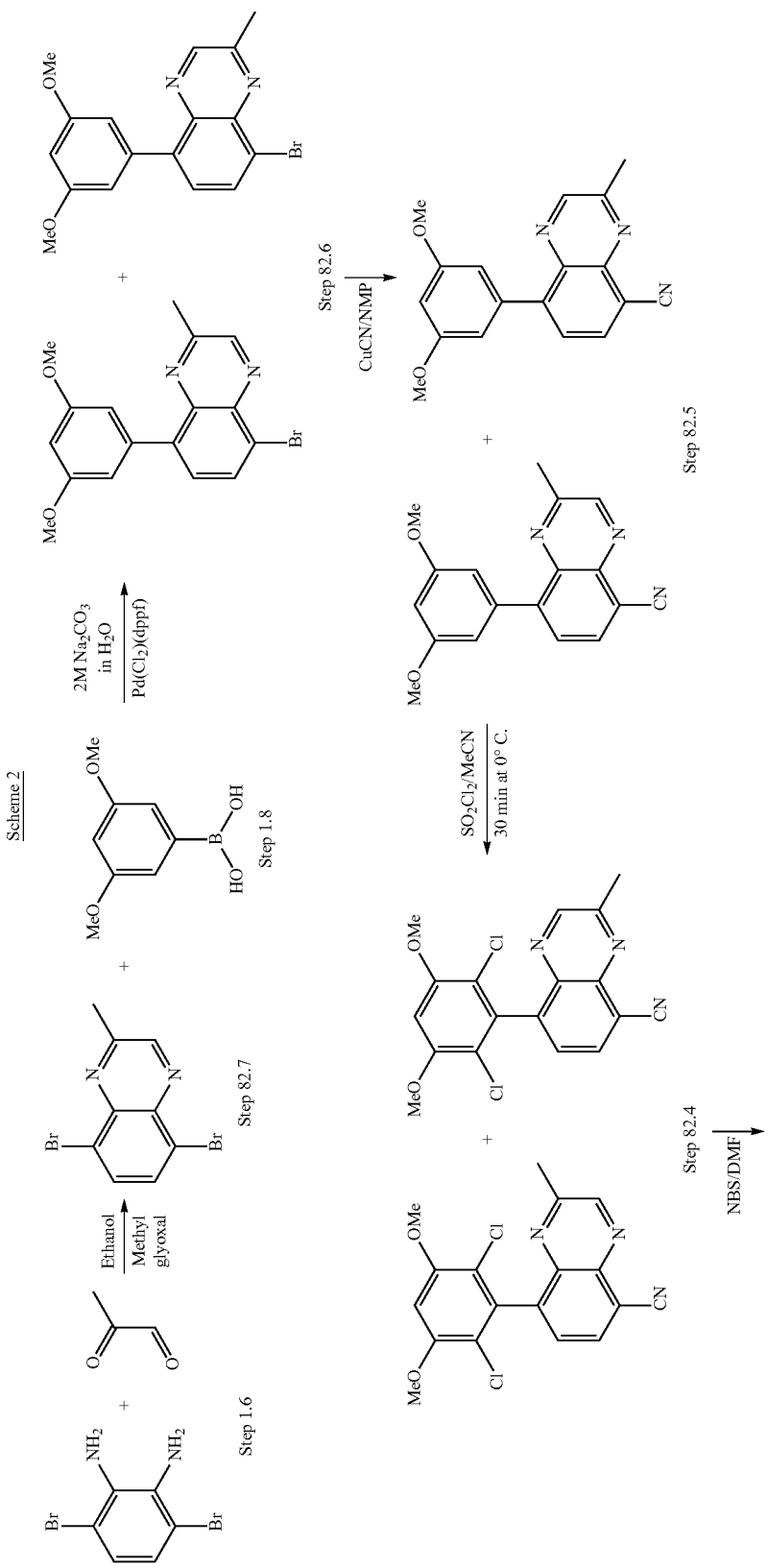

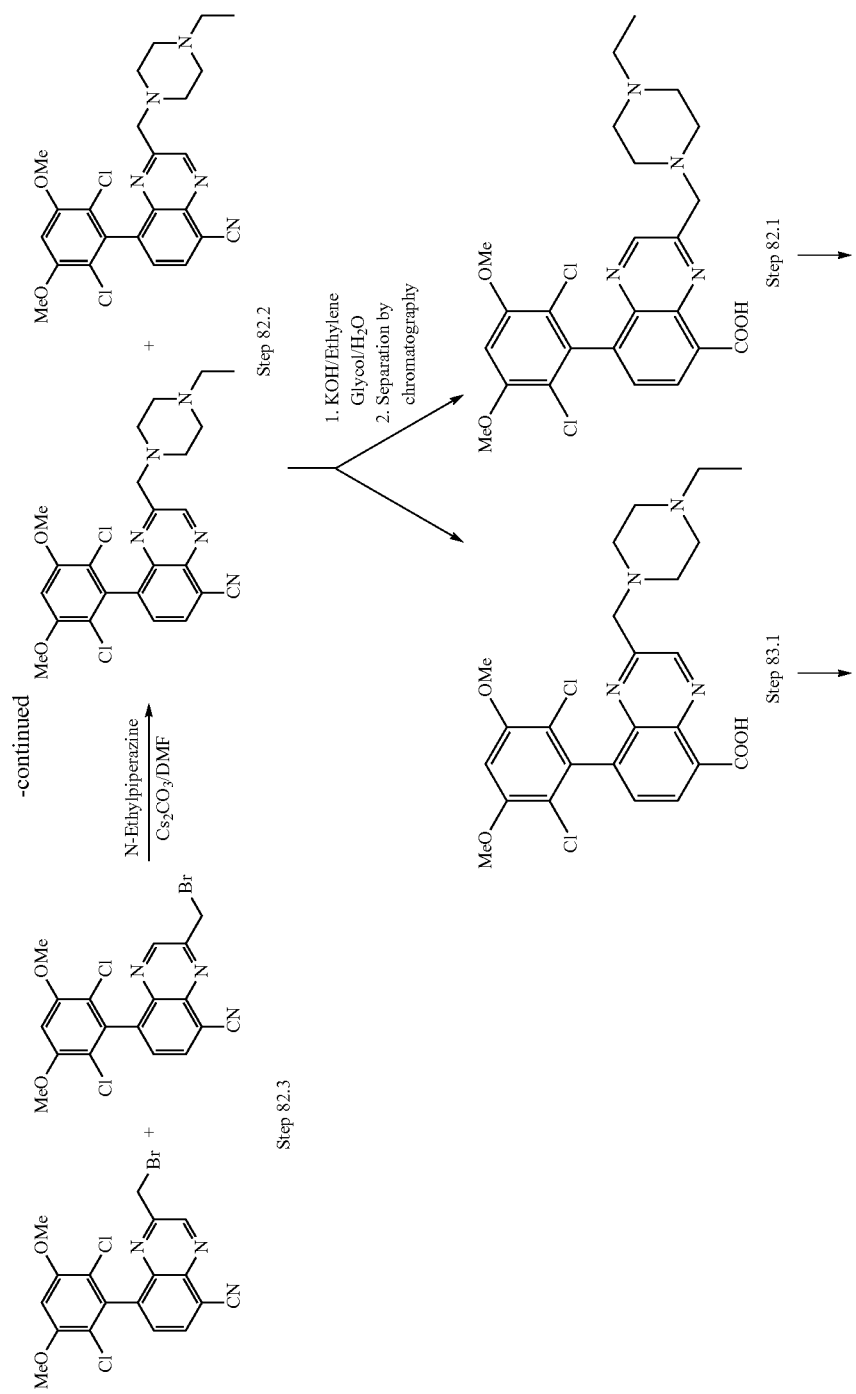

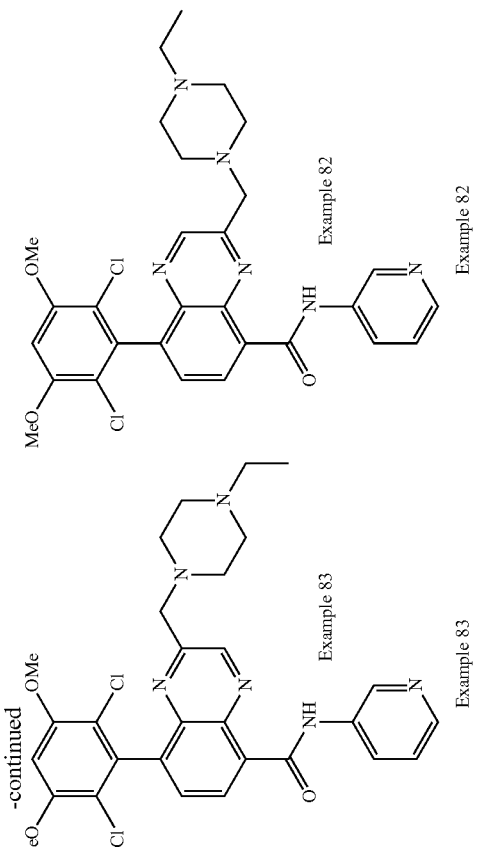
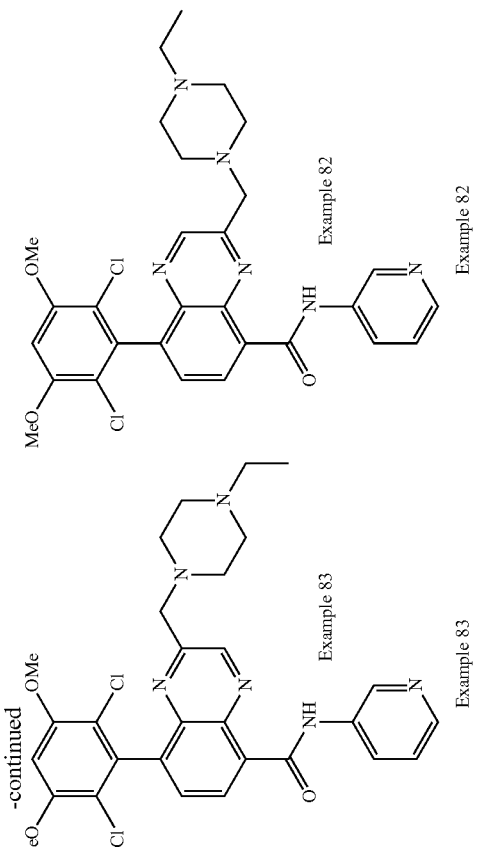

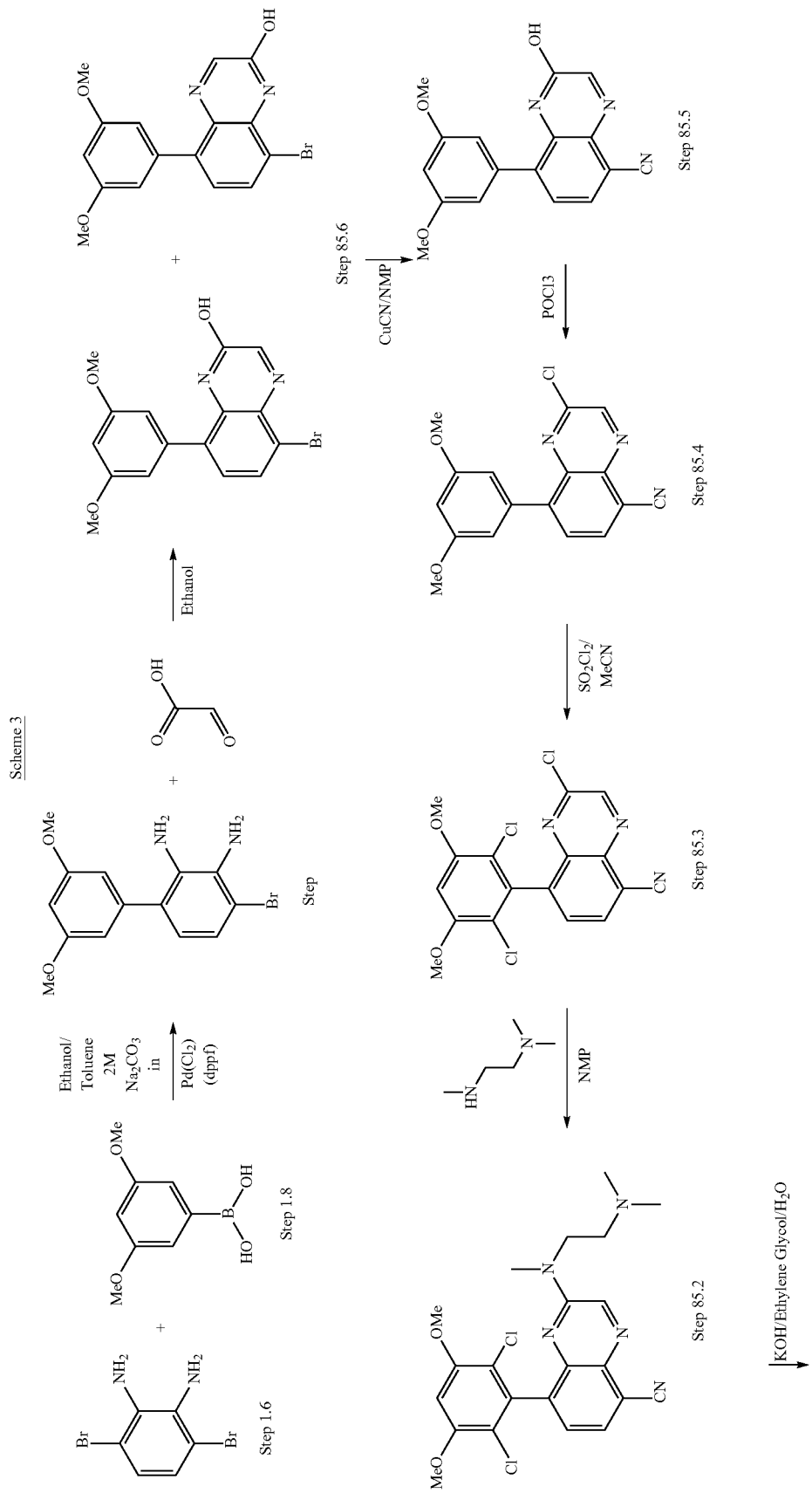
Scheme 3

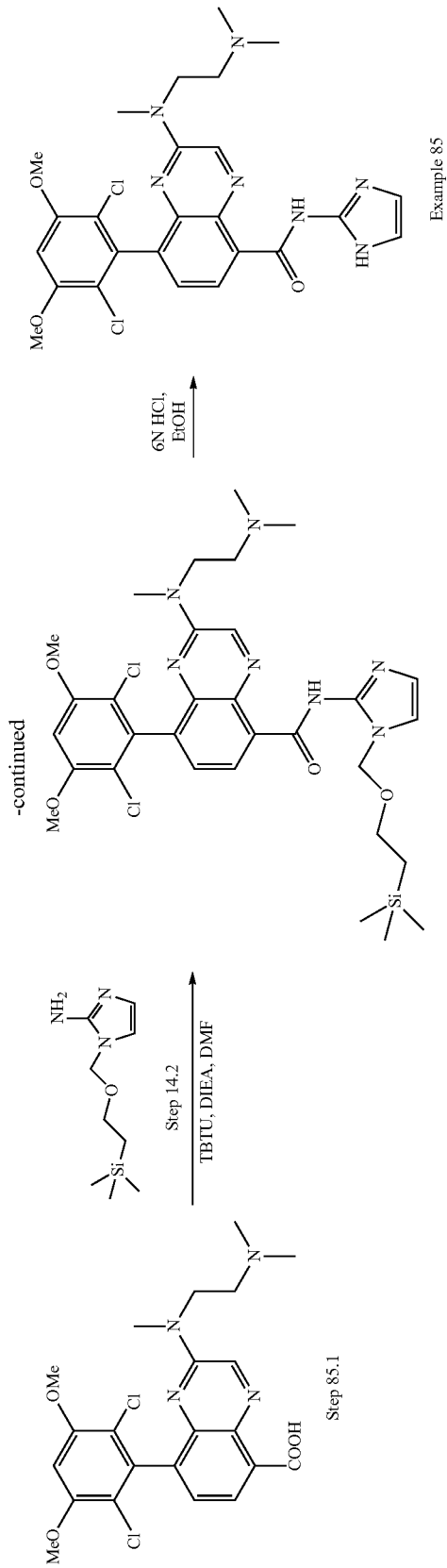

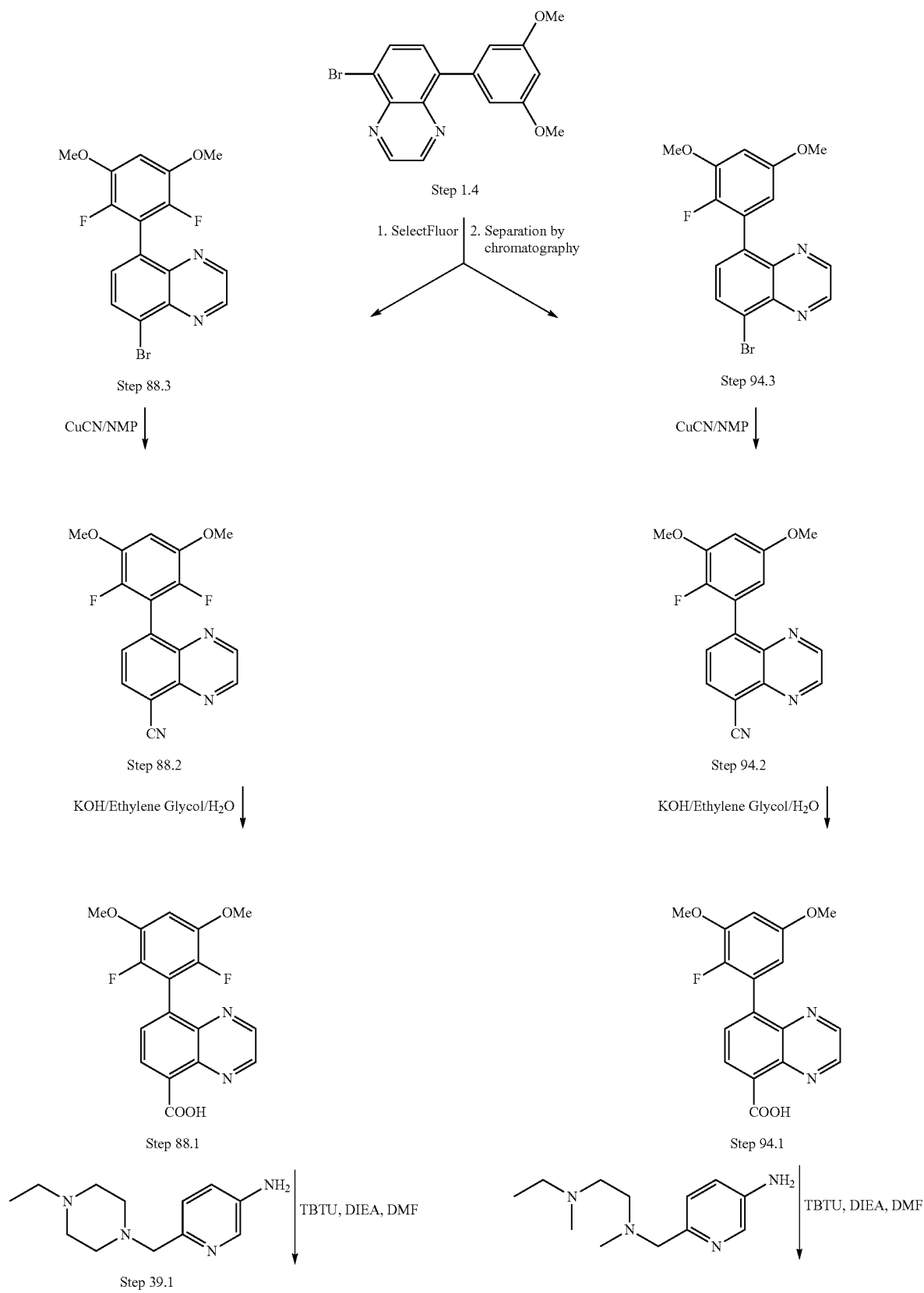

-continued
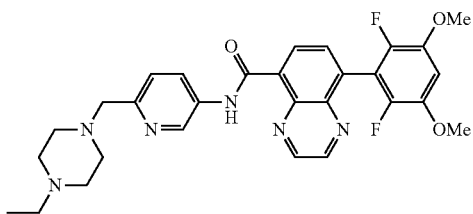
Example 88
Example 88
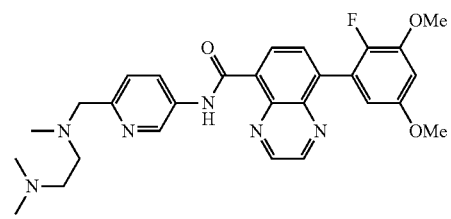
Example 94
Example 94
Scheme 5
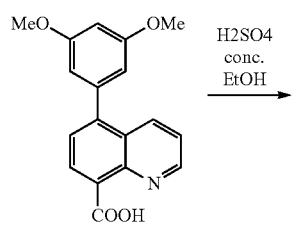 →(H2SO4 conc. EtOH)→ 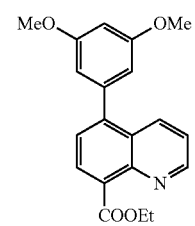 →(1. SelectFluor  2. Separation by chromatography)→ 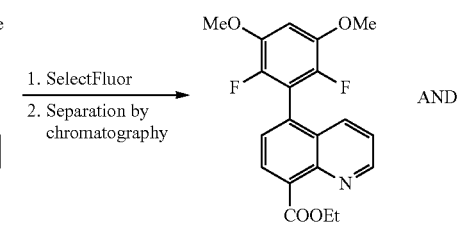 AND 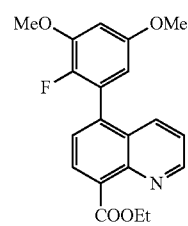
Step 157.2    Step 176.2    Step 176.1    Step 178.3
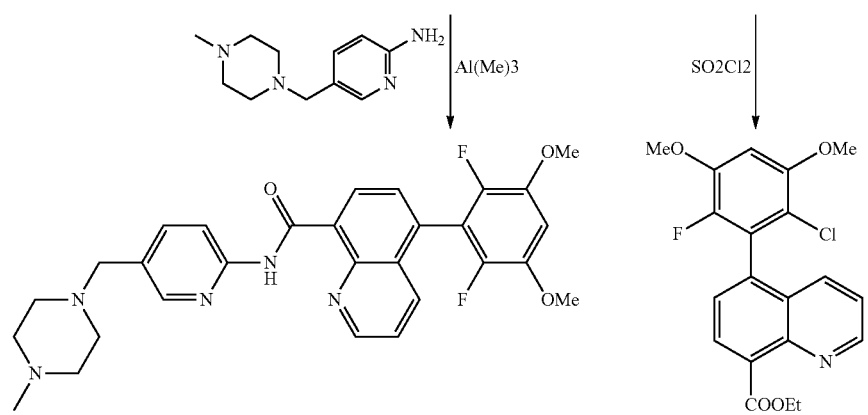
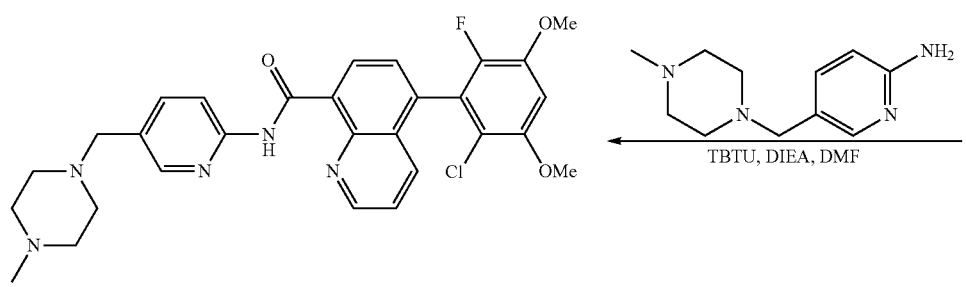 ←(TBTU, DIEA, DMF)— 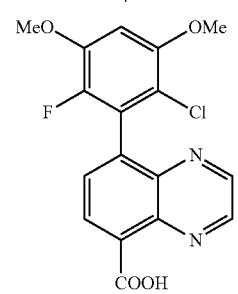
Example 178

Scheme 6
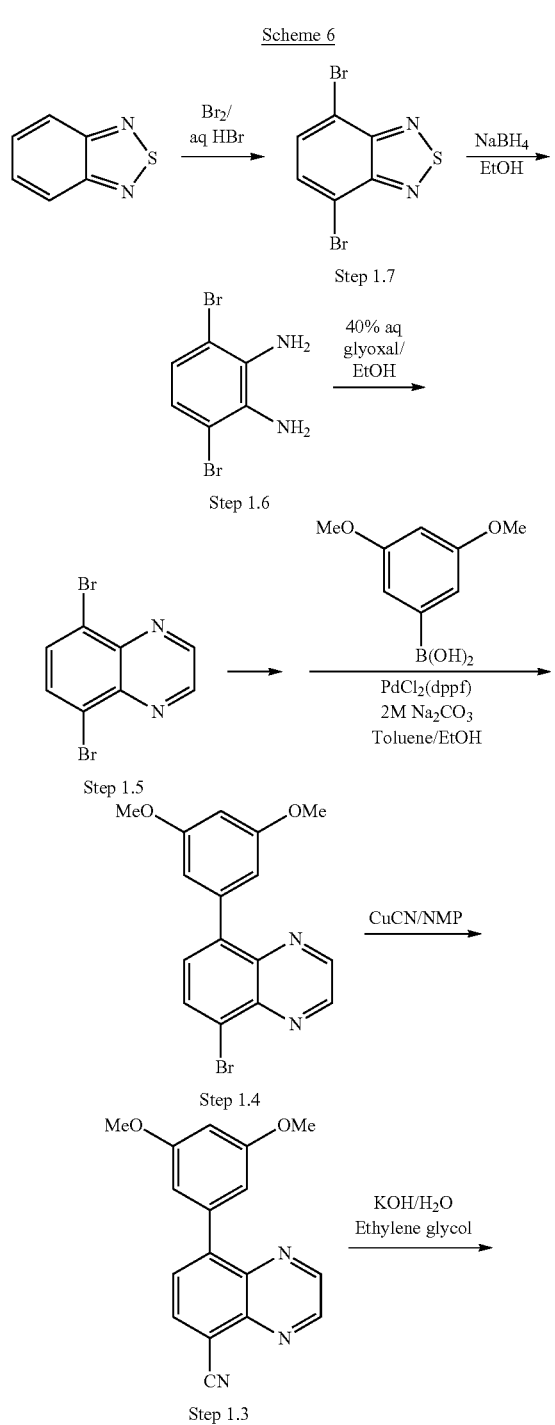
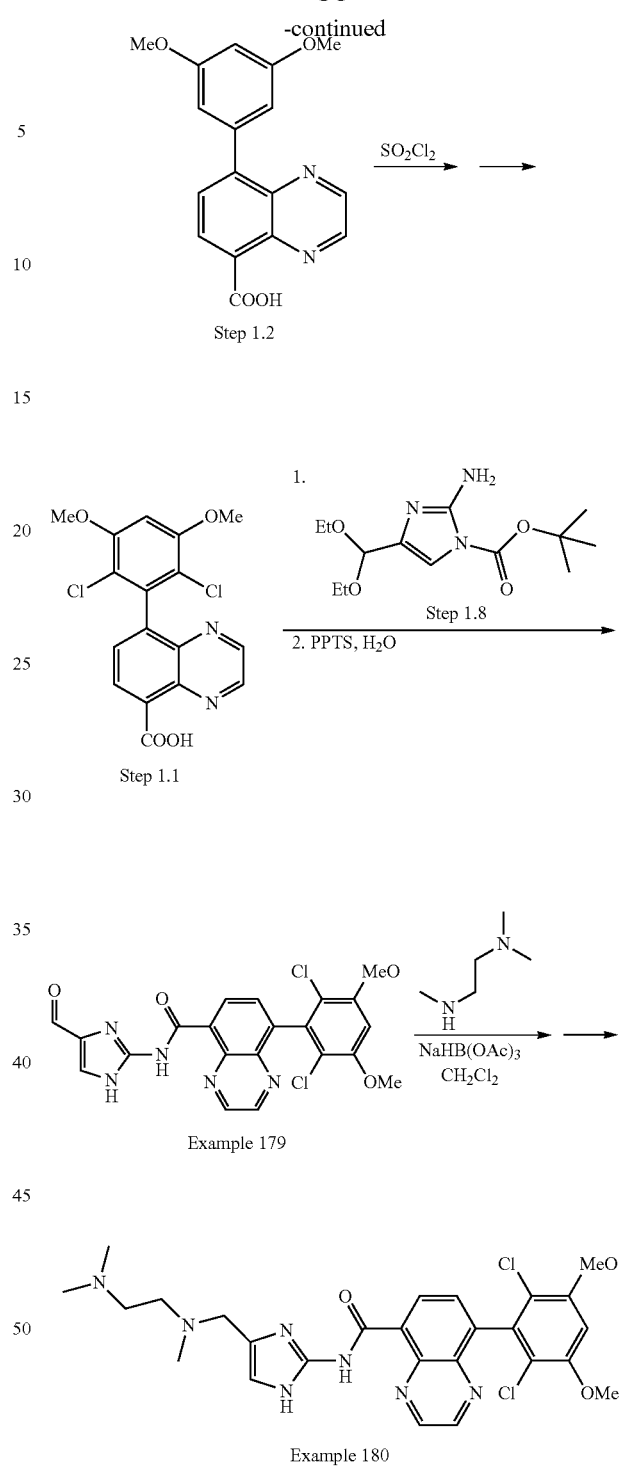
Scheme 7
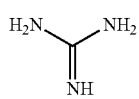

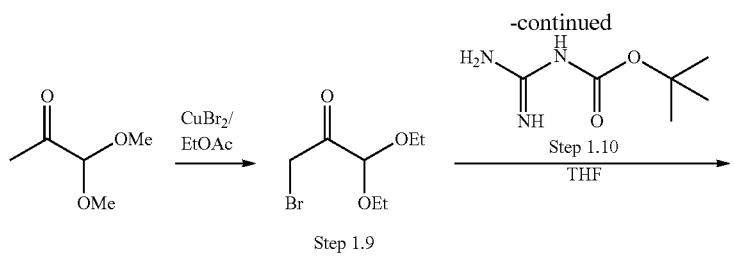
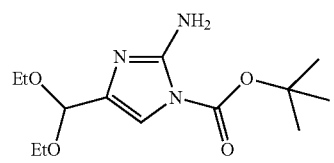

Step 1.9  Step 1.10 THF  Step 1.8

EXAMPLE 1

8-(2,6-Dichloro-3,5-dimethoxy-phenyl)-quinoxaline-5-carboxylic acid [4-(4-ethyl-piperazin-1-yl)-phenyl]-amide

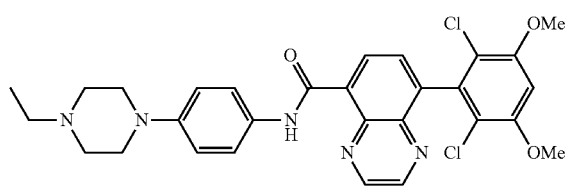 [SMILES: CCN1CCN(c2ccc(NC(=O)c3ccc(-c4c(Cl)c(OC)cc(OC)c4Cl)c4nccnc34)cc2)CC1]

A mixture of propylphosphonic anhydride (50% in DMF, 0.31 mL, 0.53 mmol, 2 equiv), 8-(2,6-dichloro-3,5-dimethoxy-phenyl)-quinoxaline-5-carboxylic acid (100 mg, 0.26 mmol) (Step 1.1), 4-(4-ethylpiperazin-1-yl)-aniline (Step 1.9) (65 mg, 0.32 mmol, 1.2 equiv), DMAP (2 mg), and Et$_3$N (0.37 mL, 2.65 mmol, 10 equiv) in DMF (2.0 mL), was stirred for 18 h at rt, under an argon atmosphere. The reaction mixture was diluted with EtOAc and H$_2$O. The aqueous layer was separated and extracted with EtOAc. The combined organic phase was washed with brine, dried (Na$_2$SO$_4$), filtered and concentrated. The residue was purified by trituration in Et$_2$O to afford the title compound as a yellow solid: ES-MS: 565.9 [M+H]$^+$; t$_R$=4.26 min (System 1).

Step 1.1: 8-(2,6-Dichloro-3,5-dimethoxy-phenyl)-quinoxaline-5-carboxylic acid

Sulfuryl chloride (1.7 mL, 21.3 mmol, 2 equiv) was added dropwise to a cold (5° C.) suspension of 8-(3,5-dimethoxyphenyl)-quinoxaline-5-carboxylic acid (Step 1.2) (3.3 g, 10.6 mmol) in CH$_3$CN (30 mL). The reaction mixture was stirred at 5° C. for 2 h, quenched by addition of H$_2$O, and concentrated. Trituration of the residue in H$_2$O provided 4.0 g of the title compound as a white solid: ESI-MS: 378.9 [M+H]$^+$; t$_R$=4.54 min (System 1).

Step 1.2: 8-(3,5-Dimethoxy-phenyl)-quinoxaline-5-carboxylic acid

KOH (6.0 g, 107 mmol, 10 equiv) was added to 8-(3,5-dimethoxy-phenyl)-quinoxaline-5-carbonitrile (Step 1.3) (3.12 g, 10.7 mmol) in ethylene glycol (30 mL). The reaction mixture was stirred at 150° C. for 3 h (a solution was obtained), allowed to cool to rt, diluted with Et$_2$O/H$_2$O, and extracted with Et$_2$O. The aqueous phase was acidified to pH 5 by addition of HCl. Vacuum filtration of the resulting suspension afforded 3.3 g of the title compound as a yellow solid: ESI-MS: 311.0 [M+H]$^+$; t$_R$=4.34 min (System 1).

Step 1.3: 8-(3,5-Dimethoxy-phenyl)-quinoxaline-5-carbonitrile

A mixture of 5-bromo-8-(3,5-dimethoxy-phenyl)-quinoxaline (Step 1.4) (4.54 g, 13.2 mmol) and CuCN (1.54 g, 17.1 mmol, 1.3 equiv) in NMP (50 mL) was stirred for 2 h at 180° C., under an argon atmosphere. The reaction mixture was allowed to cool to rt, diluted with EtOAc (10% aqueous solution of ethylenediamine) (150 mL), and filtered to afford 1.19 g (batch 1) of the title compound as a yellow solid. The filtrate was extracted with DCM. The organic phase was washed with H$_2$O and brine, dried (Na$_2$SO$_4$), filtered and concentrated. The residue was triturated in EtOAc to provide 2.31 g (batch 2) of the title compound: ESI-MS: 292.1 [M+H]$^+$; t$_R$=4.53 min (System 1).

Step 1.4: 5-Bromo-8-(3,5-dimethoxy-phenyl)-quinoxaline

A mixture of 3,5-dimethoxyphenylboronic acid (Step 1.8) (3.38 g, 18.6 mmol) in EtOH (15 mL) was added dropwise to a mixture of 5,8-dibromo-quinoxaline (Step 1.5) (10.7 g, 37.1 mmol, 2 equiv), PdCl$_2$(dppf) (530 mg, 0.7 mmol, 0.03 equiv), Na$_2$CO$_3$ (2 M solution in H$_2$O, 37 mL, 74.3 mmol, 4 equiv) in toluene (100 mL) at 105° C., under an argon atmosphere. The reaction mixture was stirred at 105° C. for 2 h, allowed to cool to rt, diluted with EtOAc and H$_2$O, filtered through a pad of celite and extracted with EtOAc. The organic phase was washed with H$_2$O and brine, dried (Na$_2$SO$_4$), filtered and concentrated in vacuo. The crude product was purified by trituration in DCM, followed by silica gel column chromatography (Hex/EtOAc, 4:1) to afford 4.54 g of the title compound as a yellow solid: ES-MS: 345.0 [M+H]$^+$; t$_R$=5.13 min (System 1); R$_f$=0.17 (Hex/EtOAc, 4:1).

Step 1.5: 5,8-Dibromo-quinoxaline

A 40% aqueous solution of glyoxal (8.8 M, 6.3 mL, 55.1 mmol, 1.3 equiv) was added to a suspension of 3,6-dibromobenzene-1,2-diamine (Step 1.6) (11.3 g, 42.4 mmol) in EtOH (280 mL). The reaction mixture was heated to reflux for 3 h and allowed to cool to rt overnight. Vacuum filtration of the reaction mixture afforded 9.7 g of the title compound as a yellow solid: APCI-MS: 286.2/288.1/290.1 [M−1]$^−$; t$_R$=4.40 min (System 1).

Step 1.6: 3,6-Dibromo-benzene-1,2-diamine

NaBH$_4$ (26 g, 680 mmol, 10 equiv) was added portionwise (2 h) to a vigorously stirred suspension of 4,7-dibromo-benzo[1,2,5]thiadiazole (Step 1.7) (20 g, 68.0 mmol) in EtOH (400 mL), under a nitrogen atmosphere and keeping the internal temperature below 15° C. The reaction mixture was allowed to warm to 30° C., stirred for 1 h, cooled to 5° C., quenched by addition of H$_2$O (50 mL), and concentrated. The residue was diluted with Et₂O/H₂O. The resulting suspension was filtered and the filtrate extracted with Et₂O. The organic phase was washed with H₂O and brine, dried (Na₂SO₄), filtered and concentrated. The residue was triturated in hexane to provide 12 g of the title compound as a white solid: ESI-MS: 262.9/264.9/266.9 [M–H]⁻; $t_R$=4.20 min (System 1).

Step 1.7: 4,7-Dibromo-benzo[1,2,5]thiadiazole

Bromine (18.6 mL, 265 mmol, 1.2 equiv) was added to a refluxing solution of 1,2,5-benzothiazole (30 g, 220 mmol) in HBr (48% in H₂O, 150 mL). The reaction mixture was stirred for 4 h at reflux and allowed to cool to rt. The resulting solid was collected by vacuum filtration, washed with H₂O, dried under vacuum, and triturated in MeOH to afford 63 g of the title compound as an off-white solid: ¹H NMR (400 MHz, DMSO-d6) δ(ppm): 8.00 (s, 2H); $t_R$=5.05 min (System 1).

Step 1.8: 3,5-dimethoxyphenylboronic acid t-BuLi (1.7 M in pentatne, 63 mL, 106 mmol, 2.1 equiv) was added dropwise to a cold (–78° C.) solution of 3,5-dimethoxy-bromobenzene (11 g, 50.7 mmol) in THF (400 mL), under an argon atmosphere. The yellow mixture si stirred for 45 min at –78° C. Trimethyl borate (20 mL, 179 mmol, 3.5 equiv) was then added. The colorless reaction mixture was allowed to warm to 0° C., quenched by addition of a saturated solution of NH₄Cl (5 mL), and concentrated. The residue was diluted with EtOAc/NH₄Cl (saturated aqueous solution), and extracted with EtOAc. The organic phase was dried (Na₂SO₄), filtered and concentrated. The residue was triturated in Et₂O to provide 6.8 g of the title compound as a white solid: ESI-MS: 183.1 [M+H]⁺; $t_R$=2.70 min (System 1).

Step 1.9: 4-(4-Ethylpiperazin-1-yl)-aniline

A suspension of 1-ethyl-4-(4-nitro-phenyl)-piperazine (Step 1.10) (6.2 g, 26.35 mmol) and Raney nickel (2 g) in MeOH (120 mL) was stirred for 7 h at rt, under a hydrogen atmosphere. The reaction mixture was filtered through a pad of celite and concentrated to afford 5.3 g of the title compound as a violet solid: ESI-MS: 206.1 [M+H]⁺; TLC: $R_f$=0.15 (DCM/MeOH+1% NH₃$^{aq}$, 9:1).

Step 1.10: 1-Ethyl-4-(4-nitro-phenyl)-piperazine

A mixture of 1-bromo-4-nitrobenzene (6 g, 29.7 mmol) and 1-ethylpiperazine (7.6 mL, 59.4 mmol, 2 equiv) was heated to 80° C. for 15 h. After cooling to rt, the reaction mixture was diluted with H₂O and DCM/MeOH (9:1, v/v). The aqueous layer was separated and extracted with DCM/MeOH, 9:1. The organic phase was washed with brine, dried (sodium sulfate), filtered and concentrated. Purification of the residue by silica gel column chromatography (DCM/MeOH+1% NH₃$^{aq}$, 9:1) afforded 6.2 g of the title compound as a yellow solid: ESI-MS: 236.0 [M+H]⁺; $t_R$=2.35 min (purity: 100%, system 1); TLC: $R_f$=0.50 (DCM/MeOH+1% NH₃$^{aq}$, 9:1).

EXAMPLE 2

8-(2,6-Dichloro-3,5-dimethoxy-phenyl)-quinoxaline-5-carboxylic acid [3-(4-ethyl-piperazin-1-yl)-phenyl]-amide

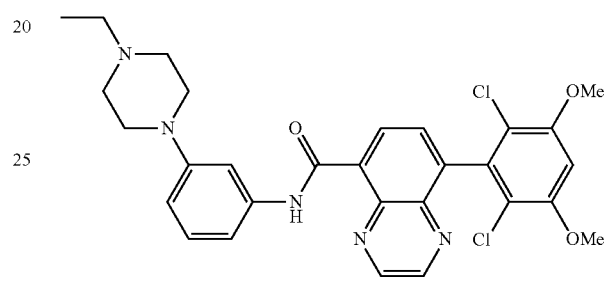

The title compound was prepared in analogy to the procedure described in Example 1 but using 3-(4-ethylpiperazin-1-yl)-aniline (Step 2.1). Purification of the crude product by silica gel column chromatography (DCM/MeOH/NH₃$^{aq}$, 96.5:2.5:1) afforded 147 mg of the title compound as a yellow solid: ESI-MS: 565.9/567.9 [M+H]⁺; $t_R$=4.35 min (System 1); TLC: $R_f$=0.30 (DCM/MeOH/NH₃$^{aq}$, 96.5:2.5:1).

Step 2.1: 3-(4-Ethylpiperazin-1-yl)-aniline

The title compound was prepared in analogy to the procedure described in Step 1.9 but using 1-ethyl-4-(3-nitro-phenyl)-piperazine (Step 2.2). Title compound: ESI-MS: 206.2 [M+H]⁺; $t_R$=2.49 min (System 1).

Step 2.2: 1-Ethyl-4-(3-nitro-phenyl)-piperazine

A mixture of 2-fluoro-4-nitrobenzene (3.2 mL, 29.7 mmol) and 1-ethylpiperazine (7.6 mL, 59.4 mmol, 2 equiv) was heated to reflux for 117 h. After cooling to rt, the reaction mixture was diluted with H₂O and DCM/MeOH, 9:1. The aqueous layer was separated and extracted with DCM/MeOH, 9:1. The organic phase was washed with brine, dried (Na₂SO₄), filtered and concentrated. Purification of the residue by silica gel column chromatography (DCM/MeOH, 1:0→95:5) afforded 6 g of the title compound as a brown oil: ESI-MS: 236.0 [M+H]⁺; t_R=2.49 min (System 1); TLC: R_f=0.26 (DCM/MeOH, 95:5).

EXAMPLE 3

8-(2,6-Dichloro-3,5-dimethoxy-phenyl)-quinoxaline-5-carboxylic acid (4-carbamoyl-phenyl)-amide

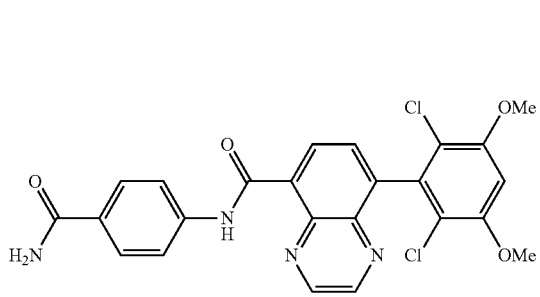 [SMILES: COc1cc(OC)c(Cl)c(-c2ccc(C(=O)Nc3ccc(C(N)=O)cc3)c3nccnc23)c1Cl]

The title compound was prepared in analogy to the procedure described in Example 1 but using 4-aminobenzamide. Purification of the crude product by silica gel column chromatography (DCM/MeOH, 95:5), followed by trituration in EtOAc, afforded the title compound as a white solid: ESI-MS: 496.9/498.9 [M+H]⁺; t_R=4.72 min (System 1); TLC: R_f=0.17 (DCM/MeOH, 96:5).

EXAMPLE 4

8-(2,6-Dichloro-3,5-dimethoxy-phenyl)-quinoxaline-5-carboxylic acid (4-morpholin-4-yl-phenyl)-amide

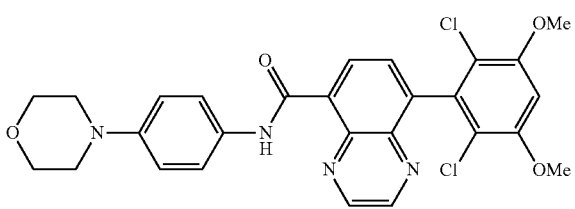 [SMILES: COc1cc(OC)c(Cl)c(-c2ccc(C(=O)Nc3ccc(N4CCOCC4)cc3)c3nccnc23)c1Cl]

The title compound was prepared in analogy to the procedure described in Example 1 but using N-(4-aminophenyl)-morpholine. Purification of the crude product by silica gel column chromatography (DCM/MeOH, 97.5:2.5) afforded the title compound as a red solid: ESI-MS: 538.9/540.9 [M+H]⁺; t_R=4.61 min (System 1); TLC: R_f=0.15 (DCM/MeOH, 97.5:2.5).

EXAMPLE 5

8-(2,6-Dichloro-3,5-dimethoxy-phenyl)-quinoxaline-5-carboxylic acid [4-(2-dimethylamino-ethoxy)-phenyl]-amide

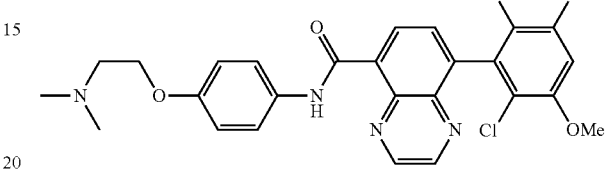

The title compound was prepared in analogy to the procedure described in Example 1 but using 4-(2-dimethylamino-ethoxy)-phenylamine (Step 5.1). Purification of the crude product by silica gel column chromatography (DCM/MeOH/NH₃^aq, 96.5:2.5:1) afforded the title compound as a red solid: ESI-MS: 540.8/542.7 [M+H]⁺; t_R=4.19 min (System 1); TLC: R_f=0.41 (DCM/MeOH/NH₃^aq, 96.5:2.5:1).

Step 5.1: 4-(2-Dimethylamino-ethoxy)-phenylamine

1-Chloro-2-dimethylaminoethane hydrochloride (2 g, 21.9 mmol, 1.2 equiv) was added in one portion to a mixture of 4-aminophenol (2 g, 18.3 mmol) and finely powdered sodium hydroxide (1.8 g, 45.8 mmol, 2.5 equiv) in DMF (27 mL), under an argon atmosphere. The reaction mixture was stirred for 17 h at rt. The resulting dark suspension was filtered. The filtrate was diluted with DCM (200 ml) and washed with brine (2×50 mL). The organic phase was dried (Na₂SO₄), filtered and concentrated. Purification of the residue by silica gel column chromatography (DCM/MeOH, 7:3) provided 3 g of the title compound as a brown solid: API-MS: 181.2 [M+H]⁺; TLC: R_f=0.18 (DCM/MeOH, 7:3).

EXAMPLE 6

8-(2,6-Dichloro-3,5-dimethoxy-phenyl)-quinoxaline-5-carboxylic acid (5-carbamoyl-pyridin-2-yl)-amide

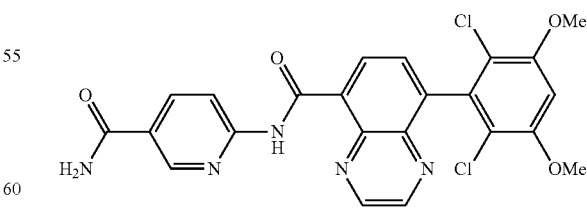

The title compound was prepared in analogy to the procedure described in Example 1 but using 6-aminonicotinamide. Purification of the crude product by silica gel column chromatography (DCM/MeOH, 97.5:2.5), followed by trituration in EtOAc, afforded the title compound as a yellow solid:

ESI-MS: 497.9/499.9 [M+H]⁺; $t_R$=4.59 min (System 1); TLC: $R_f$=0.12 (DCM/MeOH, 97.5:2.5).

EXAMPLE 7

8-(2,6-Dichloro-3,5-dimethoxy-phenyl)-quinoxaline-5-carboxylic acid (4-hydroxy-phenyl)-amide

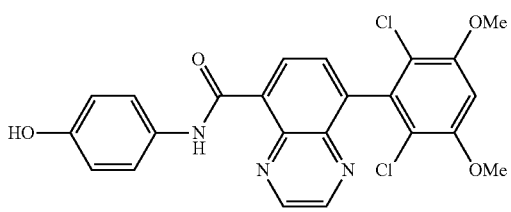 [SMILES: COc1cc(OC)c(Cl)c(-c2ccc(C(=O)Nc3ccc(O)cc3)c3nccnc23)c1Cl]

The title compound was prepared in analogy to the procedure described in Example 1 but using 4-aminophenol. Purification of the crude product by silica gel column chromatography (DCM/MeOH, 95:5), followed by trituration in DCM, afforded the title compound as a yellow solid: ESI-MS: 469.9/471.9 [M+H]⁺; $t_R$=4.71 min (System 1); TLC: $R_f$=0.44 (DCM/MeOH, 95:5).

EXAMPLE 8

8-(2,6-Dichloro-3,5-dimethoxy-phenyl)-quinoxaline-5-carboxylic acid (4-piperazin-1-yl-phenyl)-amide

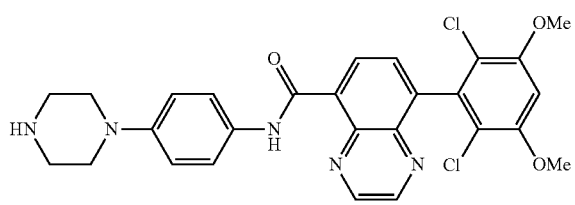 [SMILES: COc1cc(OC)c(Cl)c(-c2ccc(C(=O)Nc3ccc(N4CCNCC4)cc3)c3nccnc23)c1Cl]

A mixture of 4-(4-{[8-(2,6-dichloro-3,5-dimethoxy-phenyl)-quinoxaline-5-carbonyl]-amino}-phenyl)-piperazine-1-carboxylic acid tert-butyl ester (Step 8.1) (137 mg, 0.22 mmol) and a 4 N solution of HCl in dioxane (5 mL) was stirred for 1 h at rt. The reaction mixture was diluted with DCM and H₂O. The aqueous layer was separated and extracted with DCM. The organic phase was washed with H₂O and brine, dried (Na₂SO₄), filtered and concentrated. The residue was triturated in Et₂O to afford 95 mg of the title compound as a red solid: ESI-MS: 537.9/539.9 [M+H]⁺; $t_R$=4.01 min (System 1).

Step 8.1: 4-(4-{[8-(2,6-Dichloro-3,5-dimethoxy-phenyl)-quinoxaline-5-carbonyl]-amino}-phenyl)-piperazine-1-carboxylic acid tert-butyl ester The title compound was prepared in analogy to the procedure described in Example 1 but using 4-(4-amino-phenyl)-piperazine-1-carboxylic acid tert-butyl ester (Step 8.2). After workup with DCM and H₂O, trituration of the crude product in Et₂O afforded the title compound as a yellow solid: ES-MS: 637.9/639.9 [M+H]⁺; $t_R$=5.31 min (System 1).

Step 8.2: 4-(4-Amino-phenyl)-piperazine-1-carboxylic acid tert-butyl ester

A suspension of 4-(4-nitro-phenyl)-piperazine-1-carboxylic acid tert-butyl ester (Step 8.3) (1.26 g, 4.1 mmol) and palladium on carbon (200 mg) in MeOH (30 mL) was stirred for 30 min at rt, under a hydrogen atmosphere. The reaction mixture was filtered through a pad of celite and concentrated to afford 1.1 g of the title compound as a pink solid: ESI-MS: 278.2 [M+H]⁺; $t_R$=2.85 min (System 1).

Step 8.3: 4-(4-Nitro-phenyl)-piperazine-1-carboxylic acid tert-butyl ester

Di-tert-butyl-dicarbonate (1 M in THF, 5.8 mL, 5.8 mmol, 1.2 equiv) was added to a solution of 1-(4-nitro-phenyl)-piperazine (1 g, 4.8 mmol) and triethylamine (1.0 mL, 7.2 mmol, 1.5 equiv) in THF (20 mL). The reaction mixture was stirred for 15 min at rt, quenched by addition of H₂O (0.5 mL), and concentrated. The residue was diluted with EtOAc, washed with a saturated aqueous solution of NH₄Cl, H₂O and brine, dried (sodium sulfate), filtered and concentrated. Trituration of the crude product in Et₂O afforded 1.26 g of the title compound as a yellow solid: ES-MS: 308.1 [M+H]⁺; $t_R$=5.00 min (System 1).

EXAMPLE 9

8-(2,6-Dichloro-3,5-dimethoxy-phenyl)-quinoxaline-5-carboxylic acid [4-(4-methyl-piperazin-1-yl)-phenyl]-amide

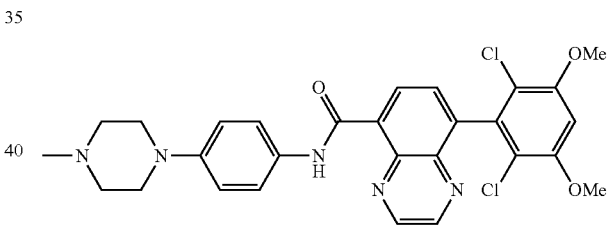

The title compound was prepared in analogy to the procedure described in Example 1 but using 4-(4-methylpiperazin-1-yl)-aniline (WO2006000420). Title compound: ESI-MS: 551.8/553.9 [M+H]⁺; $t_R$=4.17 min (System 1).

EXAMPLE 10

8-(2,6-Dichloro-3,5-dimethoxy-phenyl)-quinoxaline-5-carboxylic acid [4-(4-isopropyl-piperazin-1-yl)-phenyl]-amide

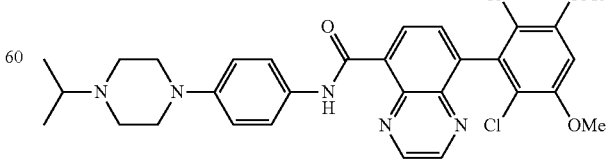

The title compound was prepared in analogy to the procedure described in Example 1 but using 4-(4-isopropylpiperazin-1-yl)-aniline (WO2006000420). Title compound: ESI-MS: 579.9/581.9 [M+H]⁺; $t_R$=4.37 min (System 1).

EXAMPLE 11

8-(2,6-Dichloro-3,5-dimethoxy-phenyl)-quinoxaline-5-carboxylic acid [4-(4-isopropyl-piperazin-1-ylmethyl)-phenyl]-amide

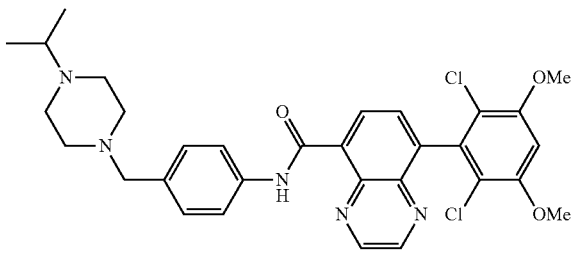 [SMILES: COc1cc(OC)c(Cl)c(-c2ccc(C(=O)Nc3ccc(CN4CCN(C(C)C)CC4)cc3)c3nccnc23)c1Cl]

The title compound was prepared in analogy to the procedure described in Example 1 but using 4-(4-isopropyl-piperazin-1-ylmethyl)-phenylamine (Step 11.1). Title compound: ESI-MS: 593.8/595.8 [M+H]⁺; $t_R$=3.73 min (System 1).

Step 11.1: 4-(4-Isopropyl-piperazin-1-ylmethyl)-phenylamine

A suspension of 1-isopropyl-4-(4-nitro-benzyl)-piperazine (Step 11.2) (5.7 g, 21.65 mmol) and Raney Nickel (2 g) in MeOH (100 mL) was stirred for 6 h at rt, under a hydrogen atmosphere. The reaction mixture was filtered through a pad of celite and concentrated to afford 4.9 g of the title compound as a white solid: ESI-MS: 234.2.

Step 11.2: 1-Isopropyl-4-(4-nitro-benzyl)-piperazine

A mixture of 4-nitrobenzylchloride (4.1 g, 23.90 mmol), N-isopropylpiperazine (3.6 g, 28.67 mmol, 1.2 equiv), potassium carbonate (6.5 g, 47.79 mmol, 2 equiv) and acetone (82 ml) was stirred for 16 h at reflux. The reaction mixture was allowed to cool, was then filtered and concentrated. The residue was purified by silica gel column chromatography (DCM/MeOH+1% NH₃$^{aq}$, 9:1) to afford 5.7 g of the title compound: ESI-MS: 264.1 [M+H]⁺; TLC: $t_R$=1.73 min (System 1); TLC: $R_f$=0.34 (DCM/MeOH+1% NH₃$^{aq}$, 9:1).

EXAMPLE 12

8-(2,6-Dichloro-3,5-dimethoxy-phenyl)-quinoxaline-5-carboxylic acid [4-(4-ethyl-piperazin-1-ylmethyl)-phenyl]-amide

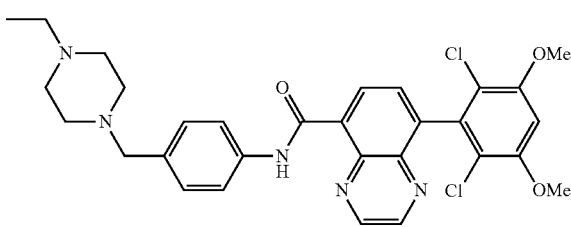

The title compound was prepared in analogy to the procedure described in Example 1 but using 4-(4-ethyl-piperazin-1-ylmethyl)-phenylamine. Title compound: ESI-MS: 579.8/581.8 [M+H]⁺; $t_R$=3.66 min (System 1).

Step 12.1: 4-(4-Ethyl-piperazin-1-ylmethyl)-phenylamine

The title compound was prepared in analogy to the procedure described in Step 11.1 but using 1-ethyl-4-(4-nitro-benzyl)-piperazine (Step 12.2): ESI-MS: 220.1 [M+H]⁺; TLC: $R_f$=0.08 (DCM/MeOH+1% NH₃$^{aq}$, 9:1).

Step 12.2: 1-Ethyl-4-(4-nitro-benzyl)-piperazine

The title compound was prepared in analogy to the procedure described in Step 11.2. The title compound: ESI-MS: 250.1 [M+H]⁺; TLC: $R_f$=0.31 (DCM/MeOH+1% NH₃$^{aq}$, 9:1).

EXAMPLE 13

8-(2,6-Dichloro-3,5-dimethoxy-phenyl)-quinoxaline-5-carboxylic acid [4-(2-pyrrolidin-1-yl-ethoxy)-phenyl]-amide

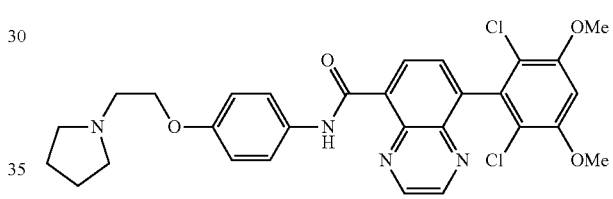

The title compound was prepared in analogy to the procedure described in Example 1 but using 4-(2-pyrrolidin-1-yl-ethoxy)-phenylamine (WO2005047273). The title compound: ESI-MS: 566.8/568.8 [M+H]⁺; $t_R$=4.37 min (System 1).

EXAMPLE 14

8-(2,6-Dichloro-3,5-dimethoxy-phenyl)-quinoxaline-5-carboxylic acid (1H-imidazol-2-yl)-amide

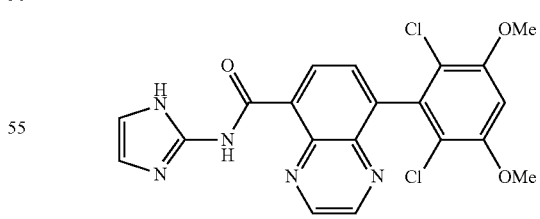

A mixture of 8-(2,6-dichloro-3,5-dimethoxy-phenyl)quinoxaline-5-carboxylic acid [1-(2-trimethylsilanyl-ethoxymethyl)-1H-imidazol-2-yl]-amide (Step 14.1) (0.527 g, 0.82 mmol), 5 N HCl (7 mL), and EtOH (4 mL) was stirred at 65° C. for 10 h. The reaction mixture was allowed to cool to rt, basified by addition of a saturated aqueous solution of Na₂CO₃, and extracted with DCM. The combined organic phase was washed with H₂O and brine, dried (Na₂SO₄), filtered and concentrated. The residue was purified by silica gel column chromatography (DCM/MeOH/NH₃$^{aq}$, 94:5:1) to afford 0.288 g of the title compound as a yellow solid: ESI-MS: 443.9/445.9 [M+H]⁺; $t_R$=3.74 min (System 1); TLC: $R_f$=0.30 (DCM/MeOH/NH₃$^{aq}$, 94:5:1).

Step 14.1: 8-(2,6-Dichloro-3,5-dimethoxy-phenyl)-quinoxaline-5-carboxylic acid [1-(2-trimethylsilanyl-ethoxymethyl)-1H-imidazol-2-yl]-amide A mixture of 8-(2,6-dichloro-3,5-dimethoxy-phenyl)quinoxaline-5-carboxylic acid (Step 1.1) (0.400 g, 1.06 mmol), 1-(2-trimethylsilanyl-ethoxymethyl)-1H-imidazol-2-ylamine (Step 14.2) (0.270 g, 1.27 mmol, 1.2 equiv), TBTU (408 mg, 1.27 mmol, 1.2 equiv), DIEA (0.74 mL, 4.23 mmol, 4.0 equiv) in DMF (5 mL) was stirred for 2 h at rt, diluted with EtOAc and H₂O, and extracted with EtOAc.washed with a saturated aqueous solution of NaHCO₃, H₂O, and brine. The organic phase was washed with H₂O and brine, dried (Na₂SO₄), filtered and concentrated. The residue was purified by silica gel column chromatography (DCM/MeOH, 95:5) to afford 0.518 g of the title compound as a yellow foam: ES-MS: 573.8/575.8 [M+H]⁺; $t_R$=5.03 min (System 1); $R_f$=0.19 (DCM₂/MeOH, 95:5).

Step 14.2: 1-(2-Trimethylsilanyl-ethoxymethyl)-1H-imidazol-2-ylamine

A suspension of 2-nitro-1-(2-trimethylsilanyl-ethoxymethyl)-1H-imidazole (Step 14.3) (1.84 g, 7.57 mmol) and palladium on carbon (200 mg) in MeOH (30 mL) was stirred for 40 min at rt, under a hydrogen atmosphere. The reaction mixture was filtered through a pad of celite and concentrated to afford 1.55 g of the title compound: ESI-MS: 214.1 [M+H]⁺; $t_R$=3.26 min (System 1).

Step 14.3: 2-Nitro-1-(2-trimethylsilanyl-ethoxymethyl)-1H-imidazole

A suspension of 2-nitroimidazole (0.885 g, 7.8 mmol) and sodium hydride (60% dispersion in mineral oil, 0.440 g, 11.0 mmol, 1.4 equiv) in THF (20 mL) was stirred for 1.5 h at 5° C., under an argon atmosphere. 2-(Trimethylsilyl)ethoxymethyl chloride (1.5 mL, 8.6 mmol, 1.1 equiv) was then added. The reaction mixture was stirred for 2.5 h at 5° C., quenched by addition of a saturated aqueous solution of NH₄Cl, and extracted with EtOAc. The combined organic phase was washed with H₂O and brine, dried (sodium sulfate), filtered and concentrated. The residue was purified by silica gel column chromatography (Hex/EtOAc, 3:1) to afford 1.76 g of the title compound as a yellow oil: ES-MS: 244.1 [M+H]⁺; $t_R$=4.63 min (System 1); TLC: $R_f$=0.19 (Hex/EtOAc, 3:1).

EXAMPLE 15

8-(2,6-Dichloro-3,5-dimethoxy-phenyl)-quinoxaline-5-carboxylic acid (2H-pyrazol-3-yl)-amide

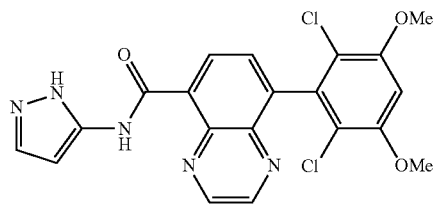 [SMILES: COc1cc(OC)c(Cl)c(-c2ccc(C(=O)Nc3ccn[nH]3)c3nccnc23)c1Cl]

The title compound was prepared in analogy to the procedures described in Example 14 but using 5-nitro-1H-pyrazole [Janssen, J. W. A. M.; Koeners, H. J.; Kruse, C. G.; Habraken, Clarisse L. Gorlaeus Lab., Univ. Leiden, Leiden, Neth. Journal of Organic Chemistry (1973), 38(10), 1777-82] instead of 2-nitroimidazole in Step 14.3. The title compound: ESI-MS: 443.9/445.9 [M+H]⁺; $t_R$=4.42 min (System 1); TLC: $R_f$=0.22 (DCM/MeOH/NH₃$^{aq}$, 94:5:1).

EXAMPLE 16

8-(2,6-Dichloro-3,5-dimethoxy-phenyl)-quinoxaline-5-carboxylic acid (3H-imidazol-4-yl)-amide

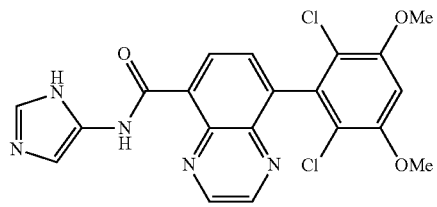 [SMILES: COc1cc(OC)c(Cl)c(-c2ccc(C(=O)Nc3cnc[nH]3)c3nccnc23)c1Cl]

The title compound was prepared in analogy to the procedures described in Example 14 but using 4-nitro-imidazole instead of 2-nitroimidazole in Step 14.3. The title compound: ESI-MS: 443.9/445.9 [M+H]⁺; $t_R$=3.66 min (System 1); TLC: $R_f$=0.14 (DCM/MeOH/NH₃$^{aq}$, 94:5:1).

EXAMPLE 17

8-(2,6-Dichloro-3,5-dimethoxy-phenyl)-quinoxaline-5-carboxylic acid (4H-[1,2,4]triazol-3-yl)-amide

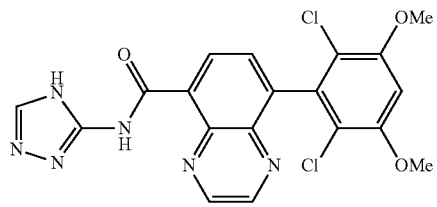 [SMILES: COc1cc(OC)c(Cl)c(-c2ccc(C(=O)Nc3nnc[nH]3)c3nccnc23)c1Cl]

The title compound was prepared in analogy to the procedures described in Example 14 but using 3-nitro-1,2,4-triazole instead of 2-nitroimidazole in Step 14.3. Trituration of the crude product in DCM afforded the title compound: ESI-MS: 444.9/446.9 [M+H]$^+$; $t_R$=4.24 min (System 1).

EXAMPLE 18

8-(2,6-Dichloro-3,5-dimethoxy-phenyl)-quinoxaline-5-carboxylic acid (4-diethylaminomethyl-1H-imidazol-2-yl)-amide

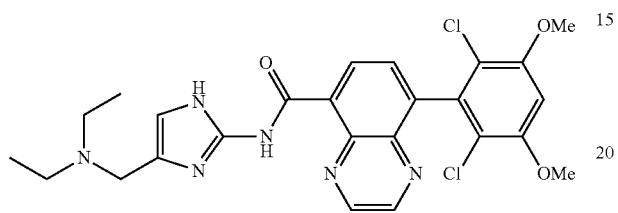

The title compound was prepared in analogy to the procedures described in Example 14 but using Raney nickel and MeOH/THF (1:1) instead of palladium on carbon and MeOH in Step 14.2, diethyl-(2-nitro-1H-imidazol-4-ylmethyl)-amine (Step 18.1) instead of 2-nitroimidazole in Step 14.3. The title compound: ESI-MS: 443.9/445.9 [M+H]$^+$; $t_R$=4.42 min (System 1); TLC: $R_f$=0.22 (DCM/MeOH/NH$_3^{aq}$, 94:5:1).

Step 18.1:
Diethyl-(2-nitro-1H-imidazol-4-ylmethyl)-amine

Formaldehyde (36% in H$_2$O, 1.0 mL, 13.3 mmol, 1.5 equiv) and diethyl amine (0.92 mL, 8.8 mmol) were added sequentially to a suspension of 2-nitro-imidazole (1 g, 8.8 mmol) in EtOH (20 mL). The resulting mixture was heated to reflux for 18 h, allowed to cool to rt, and concentrated. Trituration of the residue in Et$_2$O afforded an impure sample of the title compound which was used without further purification.

EXAMPLE 19

8-(2,6-Dichloro-3,5-dimethoxy-phenyl)-quinoxaline-5-carboxylic acid (4-pyrrolidin-1-ylmethyl-1H-imidazol-2-yl)-amide

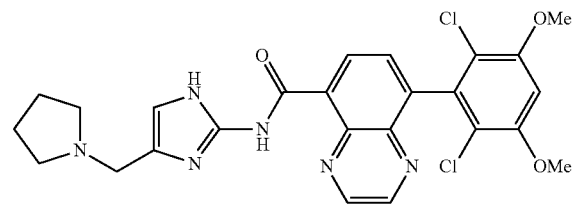

The title compound was prepared in analogy to the procedures described in Example 14 but using Raney nickel and MeOH/THF (1:1) instead of palladium on carbon and MeOH in Step 14.2, 2-nitro-4-pyrrolidin-1-ylmethyl-1H-imidazole (Step 19.1) instead of 2-nitroimidazole in Step 14.3. The title compound: ESI-MS: 526.9/528.9 [M+H]$^+$; $t_R$=3.48 min (System 1); TLC: $R_f$=0.30 (DCM/MeOH/NH$_3^{aq}$, 89:10:1).

Step 19.1:
2-Nitro-4-pyrrolidin-1-ylmethyl-1H-imidazole

The title compound was prepared in analogy to the procedure described in Step 18.1 but using pyrrolidine instead of diethyl amine, and it was obtained as an impure sample which was used without further purification.

EXAMPLE 20

8-(2,6-Dichloro-3,5-dimethoxy-phenyl)-quinoxaline-5-carboxylic acid [4-(4-methyl-piperazin-1-ylmethyl)-1H-imidazol-2-yl]-amide

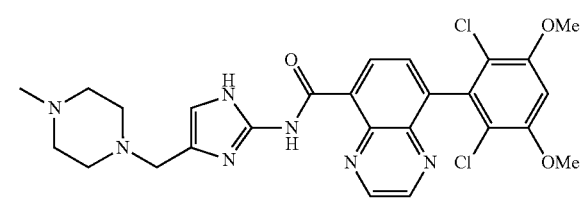 [SMILES: COc1cc(OC)c(Cl)c(-c2ccc(C(=O)Nc3nc(CN4CCN(C)CC4)c[nH]3)c3nccnc23)c1Cl]

The title compound was prepared in analogy to the procedures described in Example 14 but using Raney nickel and MeOH/THF (1:1) instead of palladium on carbon and MeOH in Step 14.2, 1-methyl-4-(2-nitro-1H-imidazol-4-ylmethyl)-piperazine (Step 20.1) instead of 2-nitroimidazole in Step 14.3. The title compound: ESI-MS: 555.8/557.8 [M+H]$^+$; $t_R$=3.22 min (System 1).

Step 20.1: 1-Methyl-4-(2-nitro-1H-imidazol-4-ylmethyl)-piperazine

The title compound was prepared in analogy to the procedure described in Step 18.1 but using 1-methylpiperazine instead of diethyl amine, and it was obtained as an impure sample which was used without further purification.

EXAMPLE 21

8-(2,6-Dichloro-3,5-dimethoxy-phenyl)-quinoxaline-5-carboxylic acid [4-(4-ethyl-piperazin-1-ylmethyl)-1H-imidazol-2-yl]-amide

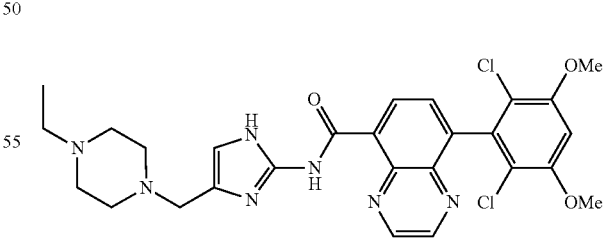

The title compound was prepared in analogy to the procedures described in Example 14 but using Raney nickel and MeOH/THF (1:1) instead of palladium on carbon and MeOH in Step 14.2, 1-ethyl-4-(2-nitro-1H-imidazol-4-ylmethyl)-piperazine (Step 21.1) instead of 2-nitroimidazole in Step 14.3. The title compound: ESI-MS: 569.8/571.8 [M+H]$^+$; $t_R$=3.29 min (System 1).

Step 21.1: 1-Ethyl-4-(2-nitro-1H-imidazol-4-ylm-ethyl)-piperazine

The title compound was prepared in analogy to the procedure described in Step 18.1 but using 1-ethylpiperazine instead of diethyl amine, and it was obtained as an impure sample which was used without further purification.

EXAMPLE 22

8-(2,6-Dichloro-3,5-dimethoxy-phenyl)-quinoxaline-5-carboxylic acid (4-dimethylaminomethyl-1H-imidazol-2-yl)-amide

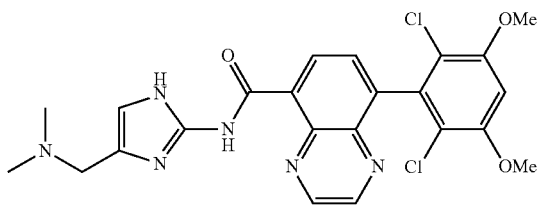

The title compound was prepared in analogy to the procedures described in Example 14 but using Raney nickel and MeOH/THF (1:1) instead of palladium on carbon and MeOH in Step 14.2, dimethyl-(2-nitro-1H-imidazol-4-ylmethyl)-amine (Step 22.2) instead of 2-nitroimidazole in Step 14.3. The title compound: ESI-MS: 500.9/502.8 $[M+H]^+$; $t_R$=3.35 min (System 1); TLC: $R_f$=0.40 (DCM/MeOH/NH$_3^{aq}$, 89:10:1).

Step 22.1: Dimethyl-(2-nitro-1H-imidazol-4-ylmethyl)-amine

The title compound was prepared in analogy to the procedure described in Step 18.1 but using dimethyl amine instead of diethyl amine, and it was obtained as an impure sample which was used without further purification.

EXAMPLE 23

8-(2,6-Dichloro-3,5-dimethoxy-phenyl)-quinoxaline-5-carboxylic acid (4-morpholin-4-ylmethyl-1H-imidazol-2-yl)-amide

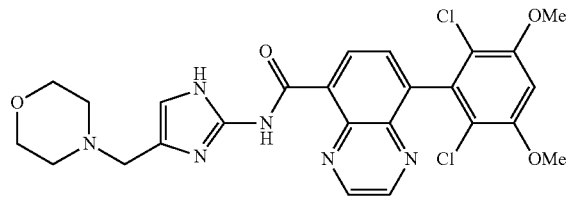 [SMILES: COc1cc(OC)c(Cl)c(-c2ccc(C(=O)Nc3nc(CN4CCOCC4)c[nH]3)c3nccnc23)c1Cl]

The title compound was prepared in analogy to the procedures described in Example 14 but using Raney nickel and MeOH/THF (1:1) instead of palladium on carbon and MeOH in Step 14.2, 4-(2-nitro-1H-imidazol-4-ylmethyl)-morpholine (Step 23.1) instead of 2-nitroimidazole in Step 14.3. The title compound: ESI-MS: 542.9/544.9 $[M+H]^+$; $t_R$=3.42 min (System 1); TLC: $R_f$=0.23 (DCM/MeOH/NH$_3^{aq}$, 89:10:1).

Step 23.1: 4-(2-Nitro-1H-imidazol-4-ylmethyl)-morpholine

The title compound was prepared in analogy to the procedure described in Step 18.1 but using morpholine instead of diethyl amine, and it was obtained as an impure sample which was used without further purification.

EXAMPLE 24

8-(2,6-Dichloro-3,5-dimethoxy-phenyl)-quinoxaline-5-carboxylic acid (6-oxo-1,6-dihydro-pyridin-3-yl)-amide

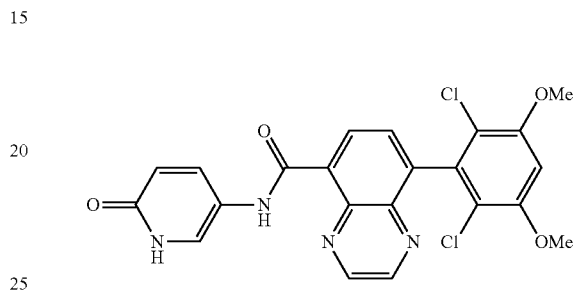

The title compound was prepared in analogy to the procedure described in Example 1 but using 5-amino-pyridin-2-ol (Step 24.1) and stirring the reaction mixture for 40 h at rt. Title compound: ESI-MS: 470.8/472.8 $[M+H]^+$; $t_R$=4.28 min (System 1); TLC: $R_f$=0.17 (DCM/MeOH, 95:5).

Step 24.1: 5-Amino-pyridin-2-ol

A suspension of 2-hydroxy-5-nitropyridine (5 g, 35.7 mmol) and palladium on carbon (500 mg) in MeOH (100 mL) was stirred for 1 h at rt, under a hydrogen atmosphere. The reaction mixture was filtered through a pad of celite and concentrated to afford 3.8 g of the title compound: ESI-MS: 110.8 $[M+H]^+$.

EXAMPLE 25

8-(2,6-Dichloro-3,5-dimethoxy-phenyl)-quinoxaline-5-carboxylic acid [5-(4-methyl-piperazine-1-carbonyl)-pyridin-2-yl]-amide

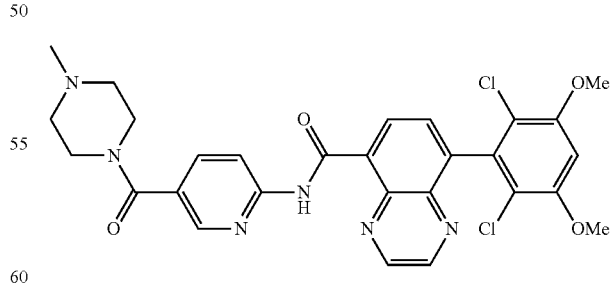

The title compound was prepared in analogy to the procedure described in Step 14.1 but using (6-amino-pyridin-3-yl)-(4-methyl-piperazin-1-yl)-methanone (Step 25.1) (2.4 equiv) and 2.4 equiv of TBTU. Title compound: ESI-MS: 580.8/582.8 $[M+H]^+$; $t_R$=3.86 min (System 1); TLC: $R_f$=0.29 (DCM/MeOH/NH$_3^{aq}$, 94:5:1).

Step 25.1: (6-Amino-pyridin-3-yl)-(4-methyl-piperazin-1-yl)-methanone

The title compound was prepared in analogy to the procedure described in Step 14.1 but using 6-amino-nicotinic acid and 1-methylpiperazine. The reaction mixture was stirred overnight at 0° C. DCM was used for dilution and extraction instead of EtOAc. The dried organic phase was concentrated to afford an impure sample of the title compound which was used without further purification.

EXAMPLE 26

8-(2,6-Dichloro-3,5-dimethoxy-phenyl)-quinoxaline-5-carboxylic acid [5-(4-ethyl-piperazin-1-ylmethyl)-pyridin-2-yl]-amide

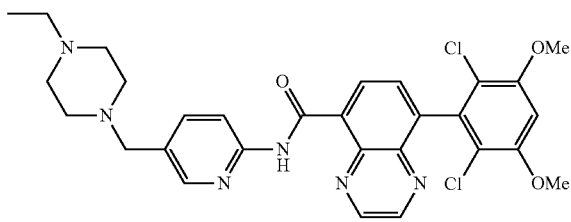

The title compound was prepared in analogy to the procedure described in Step 14.1 but using 2 equiv of 5-(4-ethyl-piperazin-1-ylmethyl)-pyridin-2-ylamine (Step 26.1) and stirring the reaction mixture for 20 h at rt. Title compound: ESI-MS: 580.8/582.8 [M+H]$^+$; $t_R$=3.63 min (System 1); TLC: $R_f$=0.31 (DCM/MeOH/NH$_3^{aq}$, 94:5:1).

Step 26.1: 5-(4-Ethyl-piperazin-1-ylmethyl)-pyridin-2-ylamine hydrochloride

A mixture of [5-(4-ethyl-piperazin-1-ylmethyl)-pyridin-2-yl]carbamic acid tert-butyl ester (Step 26.2) (0.75 g, 2.8 mmol) and a 4 N solution of HCl in dioxane (20 mL) was stirred for 72 h at rt and concentrated to afford 660 mg of the title compound as a white solid: ESI-MS: 221.1 [M+H]$^+$; $t_R$=0.80 min (System 1).

Step 26.2: [5-(4-Ethyl-piperazin-1-ylmethyl)-pyridin-2-yl]-carbamic acid tert-butyl ester A mixture of methanesulfonic acid 6-tert-butoxycarbonylamino-pyridin-3-ylmethyl ester (Step 26.3) (0.8 g, 2.6 mmol), N-ethylpiperazine (0.37 mL, 2.9 mmol, 1.1 equiv), cesium carbonate (1 g, 3.2 mmol, 1.2 equiv), and DMF (10 ml) was stirred for 2 h at rt, diluted with EtOAc and H$_2$O, and extracted with EtOAc. The organic phase was washed with H$_2$O and brine, dried (Na$_2$SO$_4$), filtered and concentrated to provide a yellow solid. Trituration in Et$_2$O afforded 0.75 g of the title compound as a white solid: ES-MS: 321.2 [M+H]$^+$.

Step 26.3: Methanesulfonic acid 6-tert-butoxycarbonylamino-pyridin-3-ylmethyl ester Methanesulfonic anhydride (0.854 g, 4.9 mmol, 1.1 equiv) was added portionwise to a cold (5° C.) mixture of (5-hydroxymethyl-pyridin-2-yl)-carbamic acid tert-butyl ester (Step 26.4) (1 g, 4.5 mmol) and triethylamine (0.75 mL, 5.4 mmol, 1.2 equiv) in DCM (20 mL), under an argon atmosphere. The reaction mixture was allowed to stir for 1 h at 5° C., diluted with EtOAc and H$_2$O, and extracted with EtOAc. The organic phase was washed with H$_2$O and brine, dried (Na$_2$SO$_4$), filtered and concentrated to provide 1.25 g of the title compound as a white solid: $t_R$=2.60 min (System 1).

Step 26.4: (5-Hydroxymethyl-pyridin-2-yl)-carbamic acid tert-butyl

Lithium aluminium hydride (1.6 g, 40.9 mmol, 1.1 equiv) was added portionwise to a cold (5° C.) solution of 6-tert-butoxycarbonylamino-nicotinic acid ethyl ester (Step 26.5) (9.9 g, 37.2 mmol) in THF (250 mL), under an argon atmosphere. The reaction mixture was stirred for 1 h at 5° C. and quenched by sequential addition of H$_2$O (4 mL), 15% NaOH aqueous solution (4 mL) and H$_2$O (12 mL). The resulting mixture was filtered through a pad of celite and concentrated. The residue was diluted with EtOAc and H$_2$O, and extracted with EtOAc. The organic phase was washed with H$_2$O and brine, dried (Na$_2$SO$_4$), filtered and concentrated. The residue was purified by trituration in Et$_2$O to provide 5 g of the title compound as a white solid: ESI-MS: 223.0 [M−H]$^-$; $t_R$=1.75 min (System 1).

Step 26.5: 6-tert-Butoxycarbonylamino-nicotinic acid ethyl ester

A solution of di-tert-butyl dicarbonate (1.7 g, 7.8 mmol, 1.3 equiv) in CH$_3$CN (20 mL) is added dropwise to a suspension of ethyl 6-aminonicotinate (1 g, 6.0 mmol) and DMAP (73 mg, 0.6 mmol, 0.1 equiv) in CH$_3$CN (10 mL) at rt. The reaction mixture was stirred for 4 h at rt and concentrated. The residue was diluted with EtOAc and H$_2$O, and extracted with EtOAc. The organic phase was washed with H$_2$O and brine, dried (Na$_2$SO$_4$), filtered and concentrated. The residue was purified by silica gel column chromatography (Hex/EtOAc, 4:1) to afford 1.18 g of the title compound as a white solid: ES-MS: 265.1 [M−H]$^-$; $t_R$=4.61 min (System 1); $R_f$=0.50 (Hex/EtOAc, 4:1).

EXAMPLE 27

8-(2,6-Dichloro-3,5-dimethoxy-phenyl)-quinoxaline-5-carboxylic acid (5-diethylaminomethyl-pyridin-2-yl)-amide

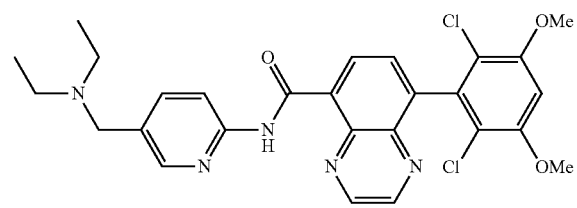 [SMILES: CCN(CC)Cc1ccc(NC(=O)c2ccc(-c3c(Cl)c(OC)cc(OC)c3Cl)c3nccnc23)nc1]

The title compound was prepared in analogy to the procedure described in Step 14.1 but using 5-diethylaminomethyl-pyridin-2-ylamine (prepared as described in Example 26 but using diethylamine in Step 26.2) and stirring the reaction mixture overnight at rt. Title compound: ESI-MS: 539.9/541.8 [M+H]$^+$; $t_R$=5.55 min (System 1); TLC: $R_f$=1.0 (DCM/MeOH/NH$_3^{aq}$, 89:10:1).

EXAMPLE 28

8-(2,6-Dichloro-3,5-dimethoxy-phenyl)-quinoxaline-5-carboxylic acid (5-dimethylaminomethyl-pyridin-2-yl)-amide

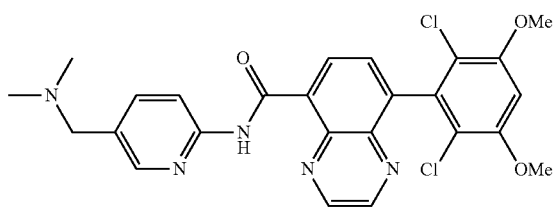 [SMILES: COc1cc(OC)c(Cl)c(-c2ccc(C(=O)Nc3ccc(CN(C)C)cn3)c3nccnc23)c1Cl]

The title compound was prepared in analogy to the procedure described in Step 14.1 but using 5-dimethylaminomethyl-pyridin-2-ylamine hydrochloride (prepared as described in Example 26 but using dimethylamine hydrochloride in Step 26.2) and stirring the reaction mixture for 20 h at rt. Title compound: ESI-MS: 511.9/513.9 [M+H]$^+$; $t_R$=3.96 min (System 1); TLC: $R_f$=0.56 (DCM/MeOH/NH$_3$$^{aq}$, 91:8:1).

EXAMPLE 29

8-(2,6-Dichloro-3,5-dimethoxy-phenyl)-quinoxaline-5-carboxylic acid (5-morpholin-4-ylmethyl-pyridin-2-yl)-amide

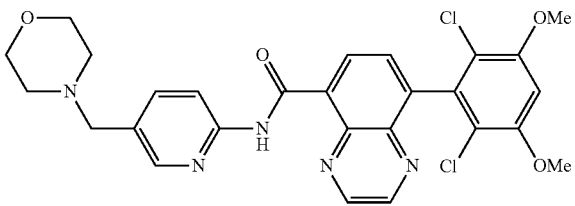

The title compound was prepared in analogy to the procedure described in Step 14.1 but using 5-morpholin-4-ylmethyl-pyridin-2-ylamine hydrochloride (prepared as described in Example 26 but using morpholine in Step 26.2) and stirring the reaction mixture for 18 h at rt. Title compound: ESI-MS: 553.9/555.8 [M+H]$^+$; $t_R$=3.98 min (System 1); TLC: $R_f$=0.61 (DCM/MeOH/NH$_3$$^{aq}$, 91:8:1).

EXAMPLE 30

8-(2,6-Dichloro-3,5-dimethoxy-phenyl)-quinoxaline-5-carboxylic acid (5-pyrrolidin-1-ylmethyl-pyridin-2-yl)-amide

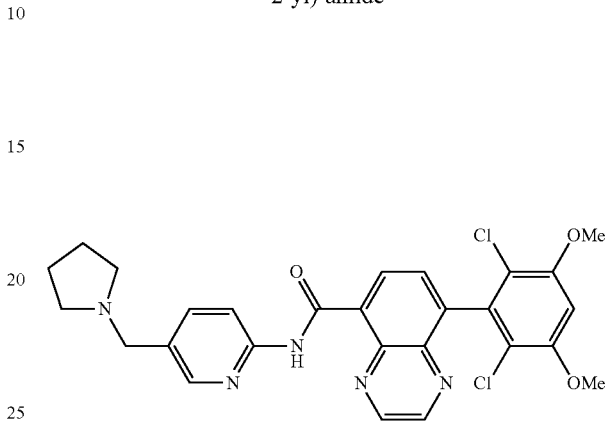

The title compound was prepared in analogy to the procedure described in Step 14.1 but using 5-pyrrolidin-1-ylmethyl-pyridin-2-ylamine hydrochloride (2 equiv, prepared as described in Example 26 but using pyrrolidine in Step 26.2) and stirring the reaction mixture for 21 h at rt. Title compound: ESI-MS: 537.9/539.9 [M+H]$^+$; $t_R$=4.16 min (System 1); TLC: $R_f$=0.50 (DCM/MeOH/NH$_3$$^{aq}$, 91:8:1).

EXAMPLE 31

8-(2,6-Dichloro-3,5-dimethoxy-phenyl)-quinoxaline-5-carboxylic acid [5-(4-methyl-piperazin-1-ylmethyl)-pyridin-2-yl]-amide

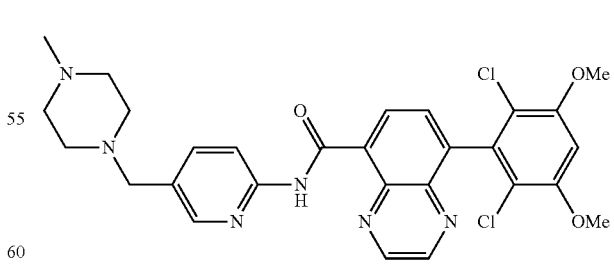

The title compound was prepared in analogy to the procedure described in Step 14.1 but using 5-(4-methyl-piperazin-1-ylmethyl)-pyridin-2-ylamine hydrochloride (prepared as described in Example 26 but using N-methylpiperazine in Step 26.2), 2.4 equiv of TBTU and stirring the reaction mixture for 22 h at rt. Title compound: ESI-MS: 566.8/568.8 [M+H]$^+$; $t_R$=3.62 min (System 1); TLC: $R_f$=0.41 (DCM/MeOH/NH$_3$$^{aq}$, 91:8:1).

EXAMPLE 32

8-(2,6-Dichloro-3,5-dimethoxy-phenyl)-quinoxaline-5-carboxylic acid (4,5-bis-dimethylaminomethyl-1H-imidazol-2-yl)-amide

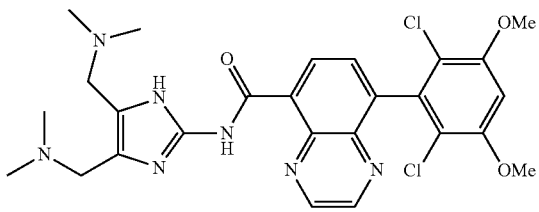 [SMILES: COc1cc(OC)c(Cl)c(-c2ccc(C(=O)Nc3nc(CN(C)C)c(CN(C)C)[nH]3)c3nccnc23)c1Cl]

A mixture of formaldehyde (36% in H$_2$O, 60 µL, 0.84 mmol, 9.3 equiv), dimethyl amine (40% in H$_2$O, 66 µL, 0.54 mmol, 6 equiv) and 8-(2,6-dichloro-3,5-dimethoxy-phenyl)-quinoxaline-5-carboxylic acid (1H-imidazol-2-yl)-amide (Example 14) (40 mg, 0.09 mmol) in n-butanol (2 mL) was heated to reflux for 1.5 h, allowed to cool to rt, and concentrated. The residue was diluted with DCM and an aqueous saturated solution of NaHCO$_3$. The layers were separated and the aqueous phase was extracted with DCM. The combined organic phase was washed with brine, dried (Na$_2$SO$_4$), filtered and concentrated. The residue was purified by silica gel column chromatography (DCM/MeOH/NH$_3$$^{aq}$, 91:8:1), followed by trituration in Et$_2$O, to afford 9 mg of the title compound as a yellow solid: ES-MS: 557.8/559.8 [M+H]$^+$; $t_R$=3.15 min (System 1); TLC: $R_f$=0.09 (DCM/MeOH/NH$_3$$^{aq}$, 91:8:1).

EXAMPLE 33

8-(2,6-Dichloro-3,5-dimethoxy-phenyl)-quinoxaline-5-carboxylic acid [6-(4-isopropyl-piperazin-1-yl)-pyridin-3-yl]-amide

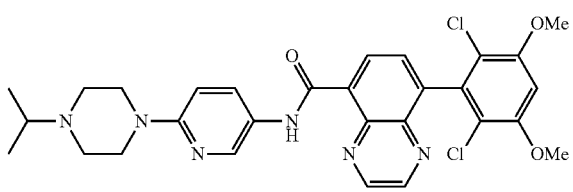

The title compound was prepared in analogy to the procedure described in Step 14.1 but using 6-(4-isopropyl-piperazin-1-yl)-pyridin-3-ylaniline (Step 33.1) and stirring the reaction mixture for 17 h at rt. Title compound: ESI-MS: 580.8/582.8 [M+H]$^+$; $t_R$=3.75 min (System 1); TLC: $R_f$=0.37 (DCM/MeOH/NH$_3$$^{aq}$, 94:5:1).

Step 33.1:
6-(4-Isopropyl-piperazin-1-yl)-pyridin-3-ylaniline

A mixture of 1-isopropyl-4-(4-nitro-phenyl)-piperazine (Step 33.2) (1.58 g, 6.32 mmol), iron (1.4 g, 25.3 mmol, 4 equiv), EtOH (20 mL), H$_2$O (5 mL) and AcOH (2.5 mL) was stirred for 2 h at 90° C. The reaction mixture was allowed to cool to rt, basified by addition of aqueous NH$_3$, filtered through a pad of celite. The filtrate was concentrated (to remove EtOH), extracted with EtOAc and DCM, saturated with NaCl and extracted with DCM. The organic phase was washed with brine, dried (Na$_2$SO$_4$), filtered and concentrated. Purification of the residue by silica gel column chromatography (DCM/MeOH/NH$_3$$^{aq}$, 91:8:1) afforded 1.1 g of the title compound as a purple solid: ESI-MS: 221.1 [M+H]$^+$; TLC: $R_f$=0.20 (DCM/MeOH/NH$_3$$^{aq}$, 91:8:1).

Step 33.2:
1-Isopropyl-4-(5-nitro-pyridin-2-yl)-piperazine

1-Isopropylpiperazine (1.8 mL, 12.7 mmol, 2 equiv) was added to a cold (5° C.) solution of 2-chloro-5-nitropyridine (1 g, 6.3 mmol,) in DCM (5 mL). The reaction mixture was allowed to warm to rt, stirred for 16 h, diluted with DCM and H$_2$O. The aqueous layer was separated and extracted with DCM. The organic phase was washed with brine, dried (Na$_2$SO$_4$), filtered and concentrated to provide 1.58 g of the title compound as a yellow solid: ESI-MS: 251.2 [M+H]$^+$; $t_R$=2.20 min.

EXAMPLE 34

8-(2,6-Dichloro-3,5-dimethoxy-phenyl)-quinoxaline-5-carboxylic acid [6-(4-ethyl-piperazin-1-yl)-pyridin-3-yl]-amide

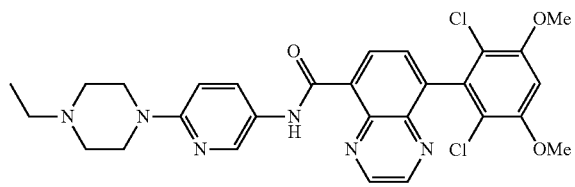 [SMILES: CCN1CCN(c2ccc(NC(=O)c3ccc(-c4c(Cl)c(OC)cc(OC)c4Cl)c4nccnc34)cn2)CC1]

The title compound was prepared in analogy to the procedure described in Step 14.1 but using 6-(4-ethylpiperazin-1-yl)-pyridin-3-ylaniline (prepared as described in Example 33 but using N-ethyl-piperazine in Step 33.2) and stirring the reaction mixture for 72 h at rt. Title compound: ESI-MS: 566.8/568.8 [M+H]$^+$; $t_R$=3.66 min (System 1); TLC: $R_f$=0.37 (DCM/MeOH/NH$_3$$^{aq}$, 94:5:1).

EXAMPLE 35

8-(2,6-Dichloro-3,5-dimethoxy-phenyl)-quinoxaline-5-carboxylic acid [2-(4-isopropyl-piperazin-1-yl)-pyrimidin-5-yl]-amide

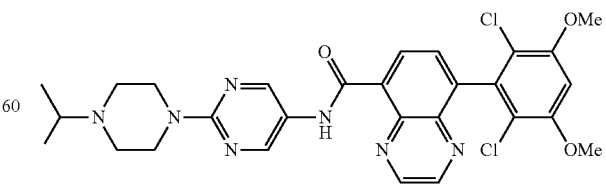

The title compound was prepared in analogy to the procedure described in Step 14.1 but using 2-(4-isopropyl-piperazin-1-yl)-pyrimidin-5-ylamine (Step 35.1) and stirring the reaction mixture for 72 h at rt. Title compound: ESI-MS: 581.7/583.7 [M+H]$^+$; $t_R$=4.18 min (System 1); TLC: $R_f$=0.62 (DCM/MeOH/NH$_3$$^{aq}$, 94:5:1).

Step 35.1:
2-(4-Isopropyl-piperazin-1-yl)-pyrimidin-5-ylamine

The title compound was prepared in analogy to the procedure described in Step 33.1 but using 2-(4-isopropyl-piperazin-1-yl)-5-nitro-pyrimidine (Step 35.2) and stirring the reaction mixture for 1.5 h. The title compound: ESI-MS: 222.1 [M+H]$^+$; TLC: $R_f$=0.13 (DCM/MeOH/NH$_3$$^{aq}$, 94:5:1).

Step 35.2:
2-(4-Isopropyl-piperazin-1-yl)-5-nitro-pyrimidine

1-Isopropylpiperazine (1.8 mL, 12.7 mmol, 2 equiv) was added to a cold (5° C.) solution of 2-chloro-5-nitropyrimidine (1 g, 6.3 mmol,) in DCM (5 mL). The reaction mixture was stirred for 20 min at 5° C. and then diluted with DCM and H$_2$O. The aqueous layer was separated and extracted with DCM. The organic phase was washed with brine, dried (Na$_2$SO$_4$), filtered and concentrated to provide 1.41 g of the title compound as a beige solid: ESI-MS: 252.2 [M+H]$^+$; $t_R$=1.89 min.

EXAMPLE 36

8-(2,6-Dichloro-3,5-dimethoxy-phenyl)-quinoxaline-5-carboxylic acid [2-(4-ethyl-piperazin-1-yl)-pyrimidin-5-yl]-amide

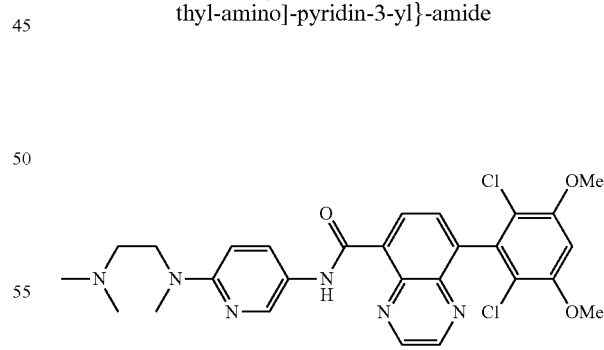

The title compound was prepared in analogy to the procedure described in Step 14.1 but using 2-(4-ethyl-piperazin-1-yl)-pyrimidin-5-ylamine (prepared as described in Example 35 but using N-ethyl-piperazine in Step 35.2) and stirring the reaction mixture for 72 h at rt. Title compound: ESI-MS: 567.9/569.9 [M+H]$^+$; $t_R$=4.11 min (System 1); TLC: $R_f$=0.56 (DCM/MeOH/NH$_3$$^{aq}$, 94:5:1).

EXAMPLE 37

8-(2,6-Dichloro-3,5-dimethoxy-phenyl)-quinoxaline-5-carboxylic acid {6-[methyl-(1-methyl-piperidin-4-yl)-amino]-pyridin-3-yl}-amide

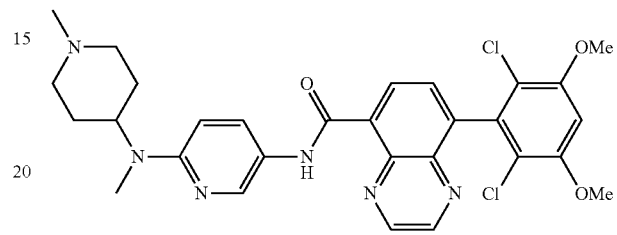

The title compound was prepared in analogy to the procedure described in Step 14.1 but using N-methyl-N-(1-methyl-piperidin-4-yl)benzene-1,4-diamine [prepared as described in Example 33 but using methyl-(1-methyl-piperidin-4-yl)-amine in Step 33.2 and stirring the corresponding reaction mixture for 15 h at rt] and stirring the reaction mixture for 3 days at rt. Title compound: ESI-MS: 581.0/583.2 [M+H]$^+$; $t_R$=3.46 min (System 1); TLC: $R_f$=0.18 (DCM/MeOH/NH$_3$$^{aq}$, 94:5:1).

EXAMPLE 38

8-(2,6-Dichloro-3,5-dimethoxy-phenyl)-quinoxaline-5-carboxylic acid {6-[(2-dimethylamino-ethyl)-methyl-amino]-pyridin-3-yl}-amide The title compound was prepared in analogy to the procedure described in Step 14.1 but using 5-amino-2-[N-(2-dimethylamino-ethyl)-N-methyl]-pyridine (prepared as described in Example 33 but using N,N,N'-trimethyl-ethane-1,2-diamine in Step 33.2 and stirring the corresponding reaction mixture for 15 h at rt) and stirring the reaction mixture for 3 days at rt. Title compound: ESI-MS: 554.8/557.0 [M+H]⁺; $t_R$=3.58 min (System 1).

EXAMPLE 39

8-(2,6-Dichloro-3,5-dimethoxy-phenyl)-quinoxaline-5-carboxylic acid [6-(4-methyl-piperazin-1-ylmethyl)-pyridin-3-yl]-amide

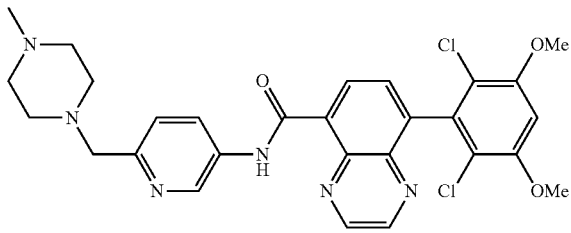

The title compound was prepared in analogy to the procedure described in Step 14.1 but using 6-(4-methyl-piperazin-1-ylmethyl)-pyridin-3-ylamine (Step 39.1), and stirring the reaction mixture for 3 h at rt. The crude product was purified by trituration with Et₂O. Title compound: ESI-MS: 566.9/569.1 [M+H]⁺; $t_R$=3.44 min (System 1).

Step 39.1: 6-(4-Methyl-piperazin-1-ylmethyl)-pyridin-3-ylamine

A suspension of 1-methyl-4-(5-nitro-pyridin-2-ylmethyl)-piperazine (Step 39.2) (0.529 g, 2.24 mmol) and Raney nickel (0.1 g) in MeOH (10 mL) was stirred for 1 h at rt, under a hydrogen atmosphere. The reaction mixture was filtered through a pad of celite and concentrated to afford 0.448 g of the title compound as an off-white solid: ESI-MS: 207.2 [M+H]⁺.

Step 39.2: 1-Methyl-4-(5-nitro-pyridin-2-ylmethyl)-piperazine

Sodium triacetoxyborohydride (1.4 g, 6.6 mmol, 2 equiv) was added portionwise to a cold (5° C.) solution of 5-nitro-pyridine-2-carbaldehyde (Step 39.3) (0.5 g, 3.3 mmol) and N-methyl-piperazine (0.4 mL, 3.6 mmol, 1.1 equiv) in DCM (10 mL). The reaction mixture was allowed to warm to rt, stirred for 16 h, diluted with DCM and saturated solution of NaHCO₃, and extracted with DCM. The organic phase was washed with H₂O and brine, dried (Na₂SO₄), filtered and concentrated. The residue was purified by silica gel column chromatography (DCM/MeOH/NH₃$^{aq}$, 91:8:1) to provide 0.532 g of the title compound as a yellow solid: ESI-MS: 237.2 [M+H]⁺; TLC: $R_f$=0.31 (DCM/MeOH/NH₃$^{aq}$, 91:8:1).

Step 39.3: 5-Nitro-pyridine-2-carbaldehyde

Diisobutylaluminium hydride (1 M in DCM, 44 mL, 44 mmol, 1.3 equiv) was added dropwise to a cold (−78° C.) solution of 5-nitro-pyridine-2-carboxylic acid ethyl ester (step 39.4) (6.56 g, 33.5 mmol) in DCM (130 mL), under an argon atmosphere. The reaction mixture was allowed to warm to 5° C., quenched by addition of an aqueous solution of potassium sodium tartrate, diluted with DCM and H₂O, stirred for 16 h at rt, and filtered through a pad of celite. The filtrate was extracted several times with DCM. The organic phase was washed with H₂O and brine, dried (Na₂SO₄), filtered and concentrated. The residue was purified by by silica gel column chromatography (EtOAc/Hex, 1:1) to provide 2.54 g of the title compound as a beige solid: ESI-MS: 151.1 [M−H]⁻.

Step 39.4: 5-Nitro-pyridine-2-carboxylic acid ethyl ester

A mixture of 5-nitro-pyridine-2-carboxylic acid (Step 39.5) (5.74 g, 34.2 mmol), H₂SO₄ (1 mL) and EtOH (50 mL) was stirred for 1.5 h at reflux. The residue was diluted with EtOAc and saturated solution of NaHCO₃. The aqueous layer was separated and extracted with EtOAc. The organic phase was washed with H₂O and brine, dried (Na₂SO₄), filtered and concentrated to afford 6.1 g of the title compound as a white solid: ES-MS: 197.1 [M+H]⁺; $t_R$=3.22 min (System 1).

Step 39.5: 5-Nitro-pyridine-2-carboxylic acid

A mixture of 2-bromo-5-nitro-pyridine (5.8 g, 28.6 mmol) and CuCN (3.3 g, 37.1 mmol, 1.3 equiv) in DMF (50 mL) was stirred at reflux for 15 min, under an argon atmosphere. The reaction mixture was allowed to cool to rt, diluted with Et₂O and H₂O. The aqueous layer was separated and extracted with Et₂O. The organic phase was washed with brine, dried (Na₂SO₄), filtered and concentrated. The residue was treated with 6N HCl (50 mL) for 1.5 h at reflux. The mixture was poured onto H₂O (200 mL). The resulting white solid was collected by vacuum filtration and dried to provide 3.1 g of the title compound: ESI-MS: 167.0 [M−H]⁻; $t_R$=1.59 min.

EXAMPLE 40

8-(2,6-Dichloro-3,5-dimethoxy-phenyl)-quinoxaline-5-carboxylic acid [6-(4-ethyl-piperazin-1-ylmethyl)-pyridin-3-yl]-amide

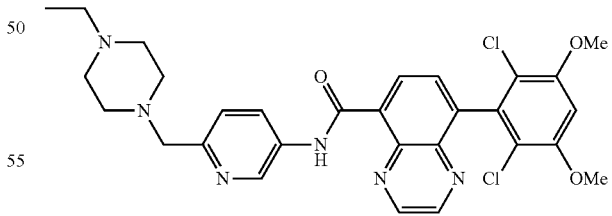

The title compound was prepared in analogy to the procedure described in Step 14.1 but using 6-(4-ethyl-piperazin-1-ylmethyl)-pyridin-3-ylamine (prepared as described in Example 39 but using N-ethyl-piperazine in Step 39.2), and stirring the reaction mixture for 16 h at rt. The crude product was purified by trituration with Et₂O. Title compound: ESI-MS: 580.9/583.1 [M+H]⁺; $t_R$=3.53 min (System 1).

EXAMPLE 41

8-(2,6-Dichloro-3,5-dimethoxy-phenyl)-quinoxaline-5-carboxylic acid (6-pyrrolidin-1-ylmethyl-pyridin-3-yl)-amide

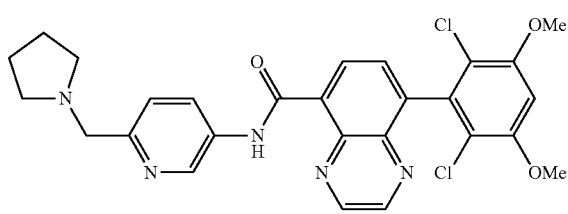

The title compound was prepared in analogy to the procedure described in Step 14.1 but using 6-pyrrolidin-1-ylmethyl-pyridin-3-ylamine (prepared as described in Example 39 but using pyrrolidine in Step 39.2), and stirring the reaction mixture for 1 h at rt. Title compound: ESI-MS: 538.0/540.1 [M+H]⁺; $t_R$=4.22 min (System 1); TLC: $R_f$=0.35 (DCM/MeOH/NH₃^{aq}, 94:5:1).

EXAMPLE 42

8-(2,6-Dichloro-3,5-dimethoxy-phenyl)-quinoxaline-5-carboxylic acid (6-diethylaminomethyl-pyridin-3-yl)-amide

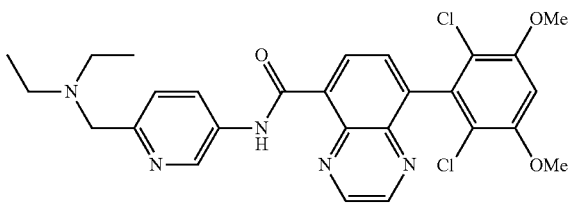 [SMILES: CCN(CC)Cc1ccc(NC(=O)c2ccc(-c3c(Cl)c(OC)cc(OC)c3Cl)c3nccnc23)cn1]

The title compound was prepared in analogy to the procedure described in Step 14.1 but using 6-diethylaminomethyl-pyridin-3-ylamine (prepared as described in Example 39 but using diethylamine in Step 39.2), and stirring the reaction mixture for 18 h at rt. The crude product was purified by trituration with Et₂O. Title compound: ESI-MS: 540.0/542.1 [M+H]⁺; $t_R$=4.30 min (System 1).

EXAMPLE 43

8-(2,6-Dichloro-3,5-dimethoxy-phenyl)-quinoxaline-5-carboxylic acid (6-morpholin-4-ylmethyl-pyridin-3-yl)-amide

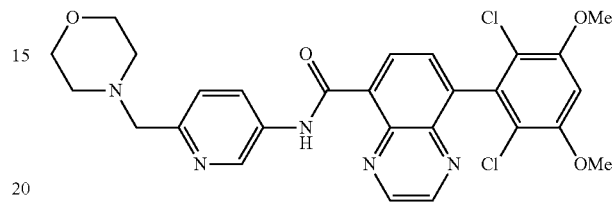

The title compound was prepared in analogy to the procedure described in Step 14.1 but using 6-morpholin-4-ylmethyl-pyridin-3-ylamine (prepared as described in Example 39 but using morpholine in Step 39.2), and stirring the reaction mixture for 18 h at rt. The crude product was purified by trituration with Et₂O. Title compound: ESI-MS: 553.9/556.1 [M+H]⁺; $t_R$=4.30 min (System 1).

EXAMPLE 44

8-(2-Fluoro-phenyl)-quinoxaline-5-carboxylic acid [4-(2-dimethylamino-ethoxy)-phenyl]-amide

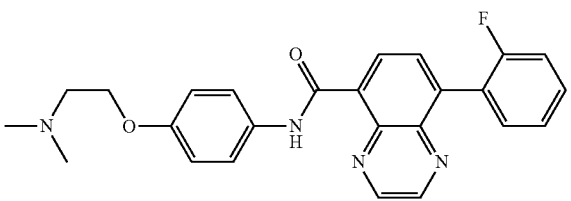 [SMILES: CN(C)CCOc1ccc(NC(=O)c2ccc(-c3ccccc3F)c3nccnc23)cc1]

The title compound was prepared in analogy to the procedure described in Step 14.1 but stirring the reaction mixture overnight and using 4-(2-dimethylamino-ethoxy)-phenylamine (Step 5.1) and 8-(2-fluoro-phenyl)-quinoxaline-5-carboxylic acid. The latter compound was prepared as described in Steps 1.2-1.7 but using 2-fluorophenylboronic acid in Step 1.4. Title compound: ESI-MS: 431.0 [M+H]+; $t_R$=3.93 min (System 1); TLC: $R_f$=0.29 (DCM/MeOH/ $NH_3{}^{aq}$, 96:3:1).

EXAMPLE 45

8-(2-Fluoro-phenyl)-quinoxaline-5-carboxylic acid (1H-imidazol-2-yl)-amide

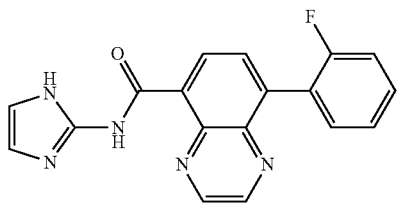 [SMILES: O=C(Nc1ncc[nH]1)c1ccc(-c2ccccc2F)c2nccnc12]

The title compound was prepared in analogy to the procedure described in Example 14 but using 8-(2-fluoro-phenyl)-quinoxaline-5-carboxylic acid (Example 44) in Step 14.1. Title compound: ESI-MS: 334.0 [M+H]+; $t_R$=3.39 min (System 1); TLC: $R_f$=0.54 (DCM/MeOH, 9:1).

EXAMPLE 46

8-Naphthalen-1-yl-quinoxaline-5-carboxylic acid [4-(4-methyl-piperazin-1-yl)-phenyl]-amide

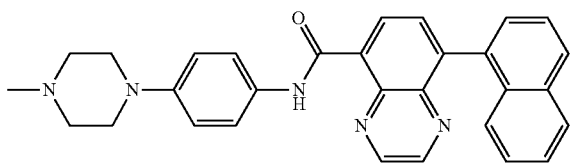 [SMILES: CN1CCN(c2ccc(NC(=O)c3ccc(-c4cccc5ccccc45)c4nccnc34)cc2)CC1]

The title compound was prepared in analogy to the procedure described in in Step 14.1 but stirring the reaction mixture overnight and using 4-(4-methylpiperazin-1-yl)-aniline (WO2006000420) and 8-naphthalen-1-yl-quinoxaline-5-carboxylic acid. The latter compound was synthesized as described in Steps 1.2-1.7 but using 1-naphtylboronic acid in Step 1.4. Title compound: ESI-MS: 474.0 [M+H]+; $t_R$=4.34 min (System 1); TLC: $R_f$=0.45 (DCM/MeOH/$NH_3{}^{aq}$, 94:5:1).

EXAMPLE 47

8-Naphthalen-1-yl-quinoxaline-5-carboxylic acid (5-diethylaminomethyl-pyridin-2-yl)-amide

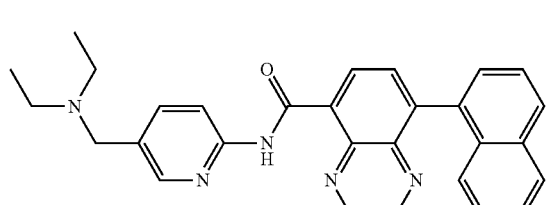

The title compound was prepared in analogy to the procedure described in Step 14.1 but stirring the reaction mixture overnight and using 5-diethylaminomethyl-pyridin-2-ylamine (Example 27) and 8-naphthalen-1-yl-quinoxaline-5-carboxylic acid (Example 46). Title compound: ESI-MS: 462.0 [M+H]+; $t_R$=4.35 min (System 1); TLC: $R_f$=0.72 (DCM/MeOH/$NH_3{}^{aq}$, 91:8:1).

EXAMPLE 48

8-Naphthalen-1-yl-quinoxaline-5-carboxylic acid [5-(4-methyl-piperazin-1-ylmethyl)-pyridin-2-yl]-amide

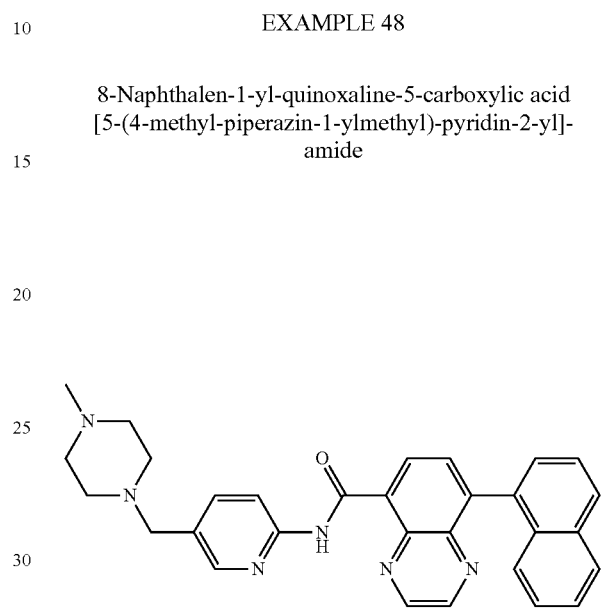

The title compound was prepared in analogy to the procedure described in Step 14.1 but stirring the reaction mixture for 72 h at rt and using 3 equiv of 5-(4-methyl-piperazin-1-ylmethyl)-pyridin-2-ylamine hydrochloride (Example 31), TBTU (2.4 equiv) and 8-naphthalen-1-yl-quinoxaline-5-carboxylic acid (Example 46). Title compound: ESI-MS: 489.1 [M+H]+; $t_R$=3.73 min (System 1); TLC: $R_f$=0.08 (DCM/MeOH, 9:1).

EXAMPLE 49

8-Naphthalen-1-yl-quinoxaline-5-carboxylic acid (1H-imidazol-2-yl)-amide

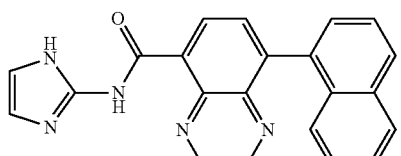

The title compound was prepared in analogy to the procedures described in Example 14 but using 8-naphthalen-1-yl-quinoxaline-5-carboxylic acid (Example 46). Title compound: ESI-MS: 366.1 [M+H]+; $t_R$=3.88 min (System 1); TLC: $R_f$=0.43 (DCM/MeOH, 9:1).

EXAMPLE 50

8-Naphthalen-1-yl-quinoxaline-5-carboxylic acid [6-(4-methyl-piperazin-1-yl)-pyridin-3-yl]-amide

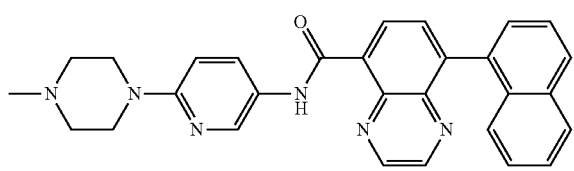 [SMILES: CN1CCN(c2ccc(NC(=O)c3ccc(-c4cccc5ccccc45)c4nccnc34)cn2)CC1]

The title compound was prepared in analogy to the procedure described in Step 14.1 but stirring the reaction mixture for 20 h at rt and using 6-(4-methylpiperazin-1-yl)-pyridin-3-ylamine (prepared as described in Example 33 but using N-methyl-piperazine in Step 33.2) and 8-naphthalen-1-yl-quinoxaline-5-carboxylic acid (Example 46). Title compound: ESI-MS: 475.0 [M+H]+; $t_R$=3.76 min (System 1).

EXAMPLE 51

8-Naphthalen-1-yl-quinoxaline-5-carboxylic acid [4-(4-methyl-piperazin-1-Ylmethyl)-1H-imidazol-2-yl]-amide

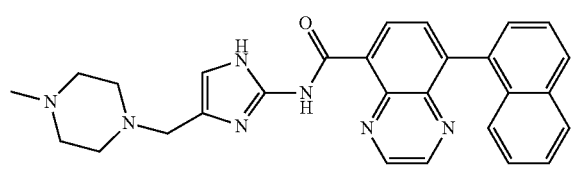 [SMILES: CN1CCN(Cc2c[nH]c(NC(=O)c3ccc(-c4cccc5ccccc45)c4nccnc34)n2)CC1]

The title compound was prepared in analogy to the procedures described in Example 14 but using 8-naphthalen-1-yl-quinoxaline-5-carboxylic acid (Example 46) in Step 14.1, Raney nickel and MeOH/THF (1:1) instead of palladium on carbon and MeOH in Step 14.2 and 1-methyl-4-(2-nitro-1H-imidazol-4-ylmethyl)-piperazine (Step 20.1) instead of 2-ni-troimidazole in Step 14.3. Title compound: ESI-MS: 478.1 [M+H]+; $t_R$=3.36 min (System 1); TLC: $R_f$=0.15 (DCM/MeOH, 9:1).

EXAMPLE 52

8-Isoquinolin-4-yl-quinoxaline-5-carboxylic acid [3-(4-ethyl-piperazin-1-yl)-phenyl]-amide

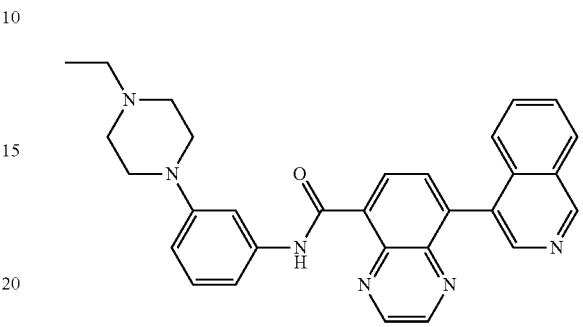

The title compound was prepared in analogy to the procedure described in Step 14.1 but using 3-(4-ethylpiperazin-1-yl)-aniline (Step 2.1) and 8-isoquinolin-4-yl-quinoxaline-5-carboxylic acid. The latter compound was synthesized as described in Steps 1.2-1.7 but using 4-isoquinolineboronic acid in Step 1.4. Title compound: ESI-MS: 489.2 [M+H]+; $t_R$=11.28 min (System 2).

EXAMPLE 53

8-Isoquinolin-4-yl-quinoxaline-5-carboxylic acid [4-(4-ethyl-piperazin-1-yl)-phenyl]-amide

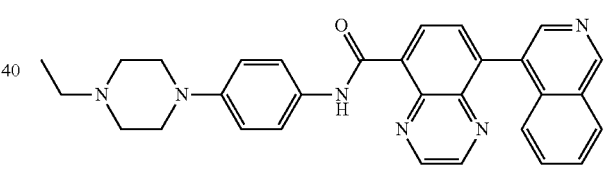

The title compound was prepared in analogy to the procedure described in Step 14.1 but using 4-(4-ethylpiperazin-1-yl)-aniline (Step 1.9) and 8-isoquinolin-4-yl-quinoxaline-5-carboxylic acid (Example 52). Title compound: ESI-MS: 489.1 [M+H]+; $t_R$=10.58 min (System 2).

EXAMPLE 54

8-Isoquinolin-4-yl-quinoxaline-5-carboxylic acid [4-(2-dimethylamino-ethoxy)-phenyl]-amide

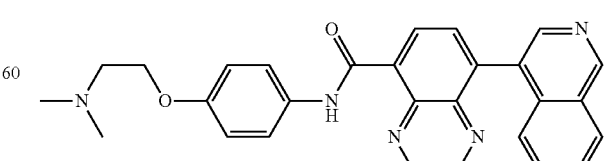

The title compound was prepared in analogy to the procedure described in Step 14.1 but using 4-(2-dimethylaminoethoxy)-phenylamine (Step 5.1) and 8-isoquinolin-4-yl-quinoxaline-5-car-boxylic acid (Example 52). Title compound: ESI-MS: 464.1 [M+H]⁺; $t_R$=8.23 min (System 2).

EXAMPLE 55

8-Isoquinolin-4-yl-quinoxaline-5-carboxylic acid (1H-imidazol-2-yl)-amide

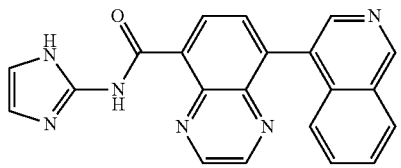 [SMILES: O=C(Nc1ncc[nH]1)c1ccc(-c2cncc3ccccc23)c2nccnc12]

The title compound was prepared in analogy to the procedures described in Example 14 but using 8-isoquinolin-4-yl-quinoxaline-5-carboxylic acid (Example 52) in Step 14.1. Title compound: ESI-MS: 367.0 [M+H]⁺; TLC: $R_f$=0.17 (DCM/MeOH, 95:5).

EXAMPLE 56

8-Isoquinolin-4-yl-quinoxaline-5-carboxylic acid [5-(4-methyl-piperazin-1-ylmethyl)-pyridin-2-yl]-amide

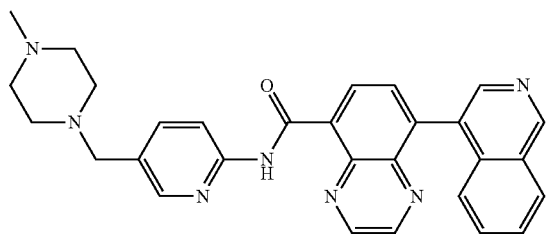 [SMILES: CN1CCN(Cc2ccc(NC(=O)c3ccc(-c4cncc5ccccc45)c4nccnc34)nc2)CC1]

The title compound was prepared in analogy to the procedure described in Step 14.1 but stirring the reaction mixture for 17 h at rt, using 2 equiv of 5-(4-methyl-piperazin-1-ylmethyl)-pyridin-2-ylamine hydrochloride (Example 31), TBTU (2 equiv) and 8-isoquinolin-4-yl-quinoxaline-5-carboxylic acid (Example 52). Title compound: ESI-MS: 490.0 [M+H]⁺; $t_R$=2.21 min (System 1); TLC: $R_f$=0.17 (DCM/MeOH, 9:1).

EXAMPLE 57

8-Isoquinolin-4-yl-quinoxaline-5-carboxylic acid [6-(4-methyl-piperazin-1-yl)-pyridin-3-yl]-amide

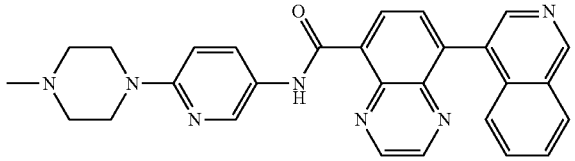 [SMILES: CN1CCN(c2ccc(NC(=O)c3ccc(-c4cncc5ccccc45)c4nccnc34)cn2)CC1]

The title compound was prepared in analogy to the procedure described in Step 14.1 but stirring the reaction mixture for 20 h at rt and using 6-(4-methylpiperazin-1-yl)-pyridin-3-ylamine (prepared as described in Example 33 but using N-methyl-piperazine in Step 33.2) and 8-isoquinolin-4-yl-quinoxaline-5-carboxylic acid (Example 52). Title compound: ESI-MS: 476.1 [M+H]⁺; $t_R$=1.98 min (System 1).

EXAMPLE 58

8-Isoquinolin-4-yl-quinoxaline-5-carboxylic acid [4-(4-methyl-piperazin-1-ylmethyl)-1H-imidazol-2-yl]-amide

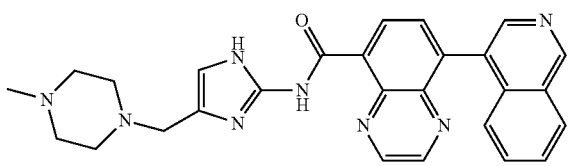 [SMILES: CN1CCN(Cc2c[nH]c(NC(=O)c3ccc(-c4cncc5ccccc45)c4nccnc34)n2)CC1]

The title compound was prepared in analogy to the procedures described in Example 14 but using 1-methyl-4-(2-nitro-1H-imidazol-4-ylmethyl)-piperazine (Step 20.1) instead of 2-nitroimidazole in Step 14.3, Raney nickel and MeOH/THF (1:1) instead of palladium on carbon and MeOH in Step 14.2, and 8-isoquinolin-4-yl-quinoxaline-5-carboxylic acid (Example 52) in Step 14.1. Title compound: ESI-MS: 479.0 [M+H]⁺; TLC: $R_f$=0.16 (DCM/MeOH, 9:1).

EXAMPLE 59

8-Benzo[b]thiophen-3-yl-quinoxaline-5-carboxylic acid [5-(4-methyl-piperazin-1-ylmethyl)-pyridin-2-yl]-amide

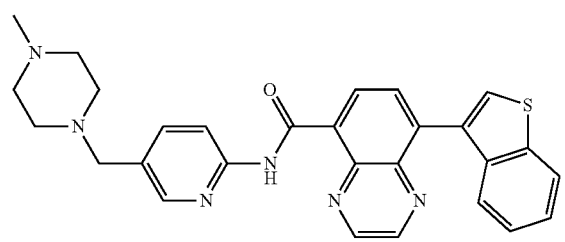 [SMILES: CN1CCN(Cc2ccc(NC(=O)c3ccc(-c4csc5ccccc45)c4nccnc34)nc2)CC1]

The title compound was prepared in analogy to the procedure described in Step 14.1 but stirring the reaction mixture at rt overnight and using 2 equiv of 5-(4-methyl-piperazin-1-ylmethyl)-pyridin-2-ylamine hydrochloride (Example 31), TBTU (2 equiv) and 8-benzo[b]thiophen-3-yl-quinoxaline-5-carboxylic acid. The carboxylic acid was synthesized as described in Steps 1.2-1.7 but using benzothiophene-3-boronic acid in Step 1.4. Title compound: ESI-MS: 494.9 [M+H]$^+$; $t_R$=3.77 min (System 1); TLC: $R_f$=0.17 (DCM/MeOH, 9:1).

EXAMPLE 60

8-Benzo[b]thiophen-3-yl-quinoxaline-5-carboxylic acid (1H-imidazol-2-yl)-amide

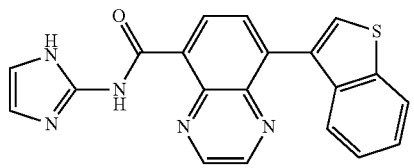 [SMILES: O=C(Nc1ncc[nH]1)c1ccc(-c2csc3ccccc23)c2nccnc12]

The title compound was prepared in analogy to the procedures described in Example 14 but using 8-benzo[b]thiophen-3-yl-quinoxaline-5-carboxylic acid (Example 59) in Step 14.1. Title compound: ESI-MS: 372.0 [M+H]$^+$; $t_R$=3.88 min (System 1); TLC: $R_f$=0.57 (DCM/MeOH, 9:1).

EXAMPLE 61

8-Benzo[b]thiophen-3-yl-quinoxaline-5-carboxylic acid [6-(4-methyl-piperazin-1-yl)-pyridin-3-yl]-amide

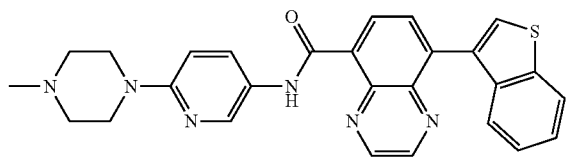 [SMILES: CN1CCN(c2ccc(NC(=O)c3ccc(-c4csc5ccccc45)c4nccnc34)cn2)CC1]

The title compound was prepared in analogy to the procedure described in Step 14.1 but stirring the reaction mixture for 20 h at rt, using 6-(4-methylpiperazin-1-yl)-pyridin-3-ylamine (prepared as described in Example 33 but using N-methyl-piperazine in Step 33.2) and 8-benzo[b]thiophen-3-yl-quinoxaline-5-carboxylic acid (Example 59). Title compound: ESI-MS: 481.0 [M+H]$^+$; $t_R$=3.81 min (System 1); TLC: $R_f$=0.40 (DCM/MeOH, 9:1).

EXAMPLE 62

8-Benzo[b]thiophen-3-yl-quinoxaline-5-carboxylic acid [4-(4-methyl-piperazin-1-ylmethyl)-1H-imidazol-2-yl]-amide

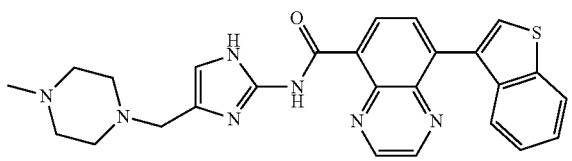 [SMILES: CN1CCN(Cc2c[nH]c(NC(=O)c3ccc(-c4csc5ccccc45)c4nccnc34)n2)CC1]

The title compound was prepared in analogy to the procedures described in Example 14 but stirring the reaction mixture for 20 h at 65° C., using 1-methyl-4-(2-nitro-1H-imidazol-4-ylmethyl)-piperazine (Step 20.1) instead of 2-nitroimidazole in Step 14.3, Raney nickel and MeOH/THF (1:1) instead of palladium on carbon and MeOH in Step 14.2, and 8-benzo[b]thiophen-3-yl-quinoxaline-5-carboxylic acid (Example 59) in Step 14.1. Title compound: ESI-MS: 484.0 [M+H]$^+$; $t_R$=3.36 min (System 1); TLC: $R_f$=0.10 (DCM/MeOH, 9:1).

EXAMPLE 63

8-(2-Chloro-5-methoxy-phenyl)-quinoxaline-5-carboxylic acid [3-(4-ethyl-piperazin-1-yl)-phenyl]-amide

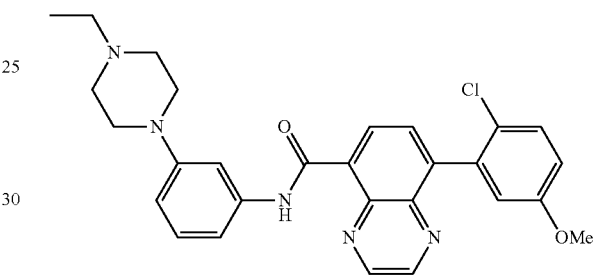

The title compound was prepared in analogy to the procedure described in Step 14.1 but using 3-(4-ethylpiperazin-1-yl)-aniline (Step 2.1) and 8-(2-chloro-5-methoxy-phenyl)-quinoxaline-5-carboxylic acid. The latter compound was synthesized as described in Steps 1.2-1.7 but using 2-chloro-4-methoxyphenylboronic acid in Step 1.4. Title compound: ESI-MS: 502.1 [M]$^+$; $t_R$=3.57 min (System 3).

EXAMPLE 64

8-(2-Chloro-5-methoxy-phenyl)-quinoxaline-5-carboxylic acid [4-(4-ethyl-piperazin-1-yl)-phenyl]-amide

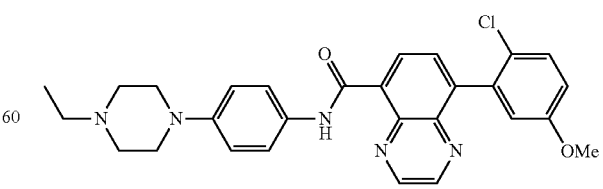

The title compound was prepared in analogy to the procedure described in Step 14.1 but using 4-(4-ethylpiperazin-1-yl)-aniline (Step 1.9) and 8-(2-chloro-5-methoxy-phenyl)- quinoxaline-5-carboxylic acid (Example 63). Title compound: ESI-MS: 502.1 [M]⁺; $t_R$=3.50 min (System 3).

EXAMPLE 65

8-(2-Chloro-5-methoxy-phenyl)-quinoxaline-5-carboxylic acid [4-(2-dimethylamino-ethoxy)-phenyl]-amide

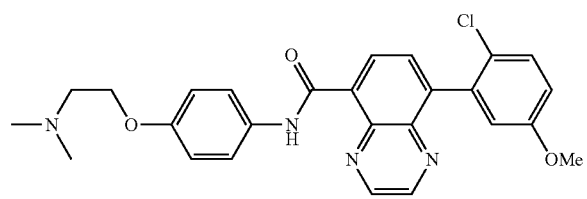 [SMILES: COc1ccc(Cl)c(-c2ccc(C(=O)Nc3ccc(OCCN(C)C)cc3)c3nccnc23)c1]

The title compound was prepared in analogy to the procedure described in Step 14.1 but using 4-(2-dimethylamino-ethoxy)-phenylamine (Step 5.1) and 8-(2-chloro-5-methoxy-phenyl)-quinoxaline-5-carboxylic acid (Example 63). Title compound: ESI-MS: 476.9 [M]⁺; $t_R$=3.43 min (System 3).

EXAMPLE 66

8-(2-Chloro-5-methoxy-phenyl)-quinoxaline-5-carboxylic acid (1H-imidazol-2-yl)-amide

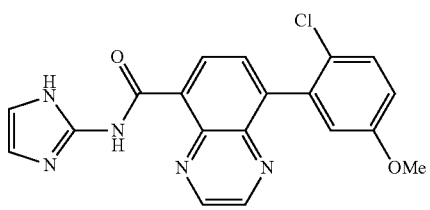 [SMILES: COc1ccc(Cl)c(-c2ccc(C(=O)Nc3ncc[nH]3)c3nccnc23)c1]

The title compound was prepared in analogy to the procedures described in Example 14 but using 8-(2-chloro-5-methoxy-phenyl)-quinoxaline-5-carboxylic acid (Example 63) in Step 14.1. Title compound: ESI-MS: 380.0 [M+H]⁺; $t_R$=3.61 min (System 1); TLC: $R_f$=0.36 (DCM/MeOH, 95:5).

EXAMPLE 67

8-(4-Methyl-thiophen-3-yl)-quinoxaline-5-carboxylic acid [5-(4-methyl-piperazin-1-ylmethyl)-pyridin-2-yl]-amide

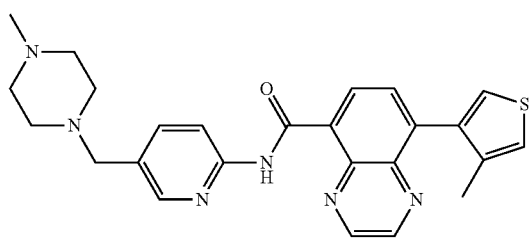 [SMILES: Cc1cscc1-c1ccc(C(=O)Nc2ccc(CN3CCN(C)CC3)cn2)c2nccnc12]

The title compound was prepared in analogy to the procedure described in Step 14.1 but stirring the reaction mixture at rt overnight, using 2 equiv of 5-(4-methyl-piperazin-1-ylmethyl)-pyridin-2-ylamine hydrochloride (Example 31), TBTU (2 equiv) and 8-(4-methyl-thiophen-3-yl)-quinoxaline-5-carboxylic acid. The carboxylic acid was synthesized as described in Steps 1.2-1.7 but using 4-methyl-3-thiopheneboronic acid in Step 1.4. Title compound: ESI-MS: 459.1 [M+H]⁺; $t_R$=3.41 min (System 1); TLC: $R_f$=0.25 (DCM/MeOH, 9:1).

EXAMPLE 68

8-(4-Methyl-thiophen-3-yl)-quinoxaline-5-carboxylic acid [6-(4-methyl-piperazin-1-yl)-pyridin-3-yl]-amide

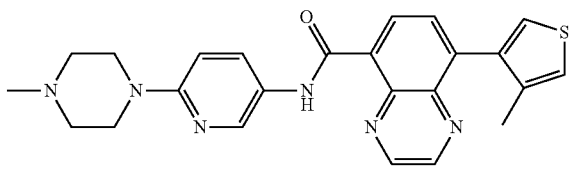 [SMILES: Cc1cscc1-c1ccc(C(=O)Nc2ccc(N3CCN(C)CC3)nc2)c2nccnc12]

The title compound was prepared in analogy to the procedure described in Step 14.1 but stirring the reaction mixture for 20 h at rt, using 6-(4-methylpiperazin-1-yl)-pyridin-3-ylamine (prepared as described in Example 33 but using N-methyl-piperazine in Step 33.2) and 8-(4-methyl-thiophen-3-yl)-quinoxaline-5-carboxylic acid (Example 67). Title compound: ESI-MS: 445.0 [M+H]⁺; $t_R$=3.42 min (System 1).

EXAMPLE 69

8-(4-Methyl-thiophen-3-O-quinoxaline-5-carboxylic acid [4-(4-methyl-piperazin-1-ylmethyl)-1H-imidazol-2-yl]-amide

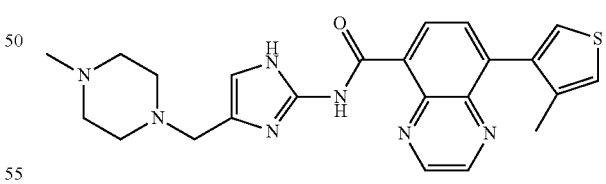

The title compound was prepared in analogy to the procedures described in Example 14 but stirring the reaction mixture for 16 h at 60° C., using 1-methyl-4-(2-nitro-1H-imidazol-4-ylmethyl)-piperazine (Step 20.1) instead of 2-nitroimidazole in Step 14.3, Raney nickel and MeOH/THF (1:1) instead of palladium on carbon and MeOH in Step 14.2, and 8-(4-methyl-thiophen-3-yl)-quinoxaline-5-carboxylic acid (Example 67) in Step 14.1. Title compound: ESI-MS: 448.0 [M+H]⁺; t_R=3.00 min (System 1); TLC: R_f=0.14 (DCM/MeOH, 9:1).

EXAMPLE 70

8-(4-Methyl-thiophen-3-yl)-quinoxaline-5-carboxylic acid (1H-imidazol-2-yl)-amide

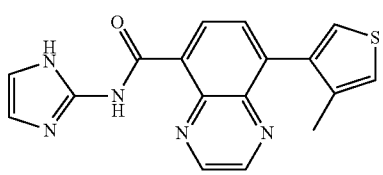 [SMILES: Cc1cscc1-c1ccc(C(=O)Nc2ncc[nH]2)c2nccnc12]

The title compound was prepared in analogy to the procedures described in Example 14 but using 8-(4-methyl-thiophen-3-yl)-quinoxaline-5-carboxylic acid (Example 67) in Step 14.1. Title compound: ESI-MS: 336.1 [M+H]⁺; t_R=3.47 min (System 1); TLC: R_f=0.66 (DCM/MeOH, 9:1).

EXAMPLE 71

8-(2,6-Dimethyl-phenyl)-quinoxaline-5-carboxylic acid [3-(4-ethyl-piperazin-1-yl)-phenyl]-amide

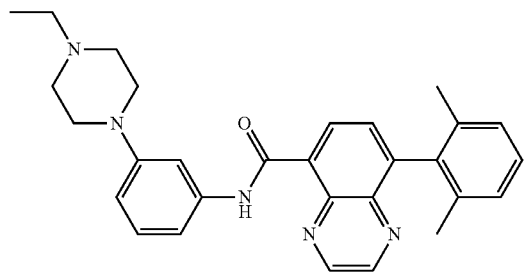 [SMILES: CCN1CCN(c2cccc(NC(=O)c3ccc(-c4c(C)cccc4C)c4nccnc34)c2)CC1]

The title compound was prepared in analogy to the procedure described in Step 14.1 but using 3-(4-ethylpiperazin-1-yl)-aniline (Step 2.1) and 8-(2,6-dimethyl-phenyl)-quinoxaline-5-carboxylic acid. The carboxylic acid was synthesized as described in Steps 1.2-1.7 but using 2,6-dimethylphenyl-boronic acid and Pd(PPh₃)₄ in Step 1.4. Title compound: ESI-MS: 466.2 [M+H]⁺; t_R=3.74 min (System 3).

EXAMPLE 72

8-(2,6-Dimethyl-phenyl)-quinoxaline-5-carboxylic acid [4-(4-ethyl-piperazin-1-yl)-phenyl]-amide

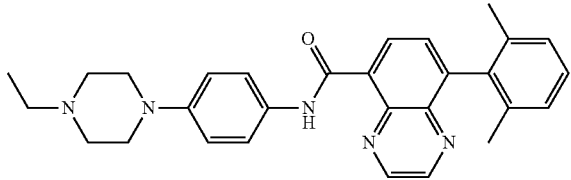 [SMILES: CCN1CCN(c2ccc(NC(=O)c3ccc(-c4c(C)cccc4C)c4nccnc34)cc2)CC1]

The title compound was prepared in analogy to the procedure described in Step 14.1 but using 4-(4-ethylpiperazin-1-yl)-aniline (Step 1.9) and 8-(2,6-dimethyl-phenyl)-quinoxaline-5-carbox-ylic acid (Example 71). Title compound: ESI-MS: 466.2 [M+H]⁺; t_R=3.67 min (System 3).

EXAMPLE 73

8-(2,6-Dimethyl-phenyl)-quinoxaline-5-carboxylic acid [4-(2-dimethylamino-ethoxy)-phenyl]-amide

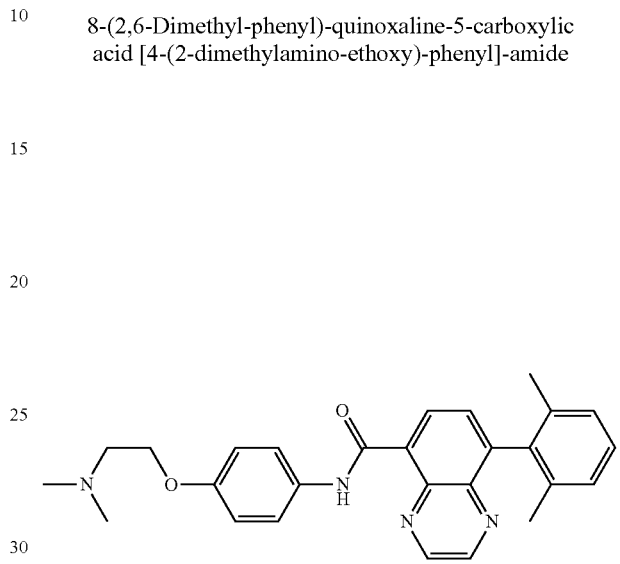

The title compound was prepared in analogy to the procedure described in Step 14.1 but using 4-(2-dimethylamino-ethoxy)-phenylamine (Step 5.1) and 8-(2,6-dimethyl-phenyl)-quinoxaline-5-carboxylic acid (Example 71). Title compound: ESI-MS: 441.1 [M+H]⁺; t_R=3.52 min (System 3).

EXAMPLE 74

8-(2,6-Dimethyl-phenyl)-quinoxaline-5-carboxylic acid (1H-imidazol-2-yl)-amide

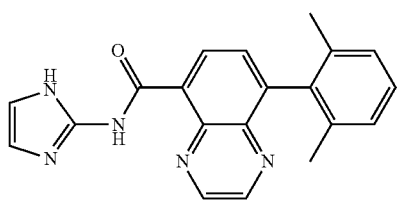 [SMILES: Cc1cccc(C)c1-c1ccc(C(=O)Nc2ncc[nH]2)c2nccnc12]

The title compound was prepared in analogy to the procedures described in Example 14 but using 8-(2,6-dimethyl-phenyl)-quinoxaline-5-carboxylic acid (Example 71) in Step 14.1. Title compound: ESI-MS: 344.1 [M+H]⁺; $t_R$=3.62 min (System 1); TLC: $R_f$=0.50 (DCM/MeOH, 95:5).

EXAMPLE 75

8-(2,6-Dimethyl-phenyl)-quinoxaline-5-carboxylic acid [5-(4-methyl-piperazin-1-ylmethyl-pyridin-2-yl]-amide

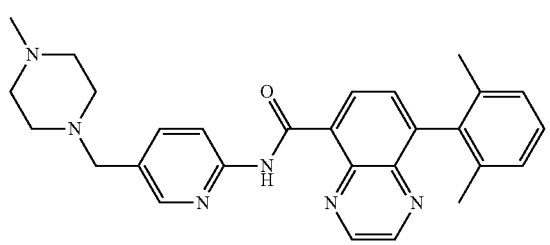 [SMILES: Cc1cccc(C)c1-c1ccc(C(=O)Nc2ccc(CN3CCN(C)CC3)cn2)c2nccnc12]

The title compound was prepared in analogy to the procedure described in Step 14.1 but stirring the reaction mixture for 2 days at rt, using 2 equiv of 5-(4-methyl-piperazin-1-ylmethyl)-pyridin-2-ylamine hydrochloride (Example 31), TBTU (2 equiv) and 8-(2,6-dimethyl-phenyl)-quinoxaline-5-carboxylic acid (Example 71). Title compound: ESI-MS: 467.1 [M+H]⁺; $t_R$=3.55 min (System 1); TLC: $R_f$=0.15 (DCM/MeOH, 9:1).

EXAMPLE 76

8-(2,6-Dimethyl-phenyl)-quinoxaline-5-carboxylic acid [6-(4-methyl-piperazin-1-yl)-pyridin-3-yl]-amide

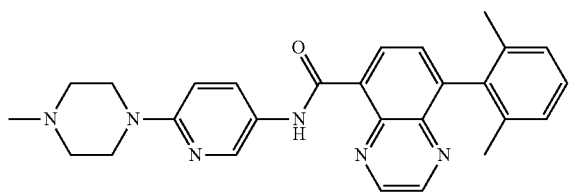 [SMILES: Cc1cccc(C)c1-c1ccc(C(=O)Nc2ccc(N3CCN(C)CC3)nc2)c2nccnc12]

The title compound was prepared in analogy to the procedure described in Step 14.1 but stirring the reaction mixture for 20 h at rt, using 6-(4-methylpiperazin-1-yl)-pyridin-3-ylamine (prepared as described in Example 33 but using N-methyl-piperazine in Step 33.2) and 8-(2,6-dimethyl-phenyl)-quinoxaline-5-carboxylic acid (Example 71). Title compound: ESI-MS: 453.1 [M+H]⁺; $t_R$=3.55 min (System 1).

EXAMPLE 77

8-(2,6-Dimethyl-phenyl)-quinoxaline-5-carboxylic acid [4-(4-methyl-piperazin-1-ylmethyl)-1H-imidazol-2-yl]-amide

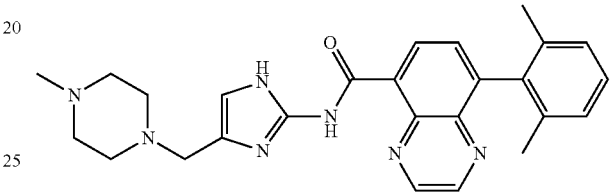

The title compound was prepared in analogy to the procedures described in Example 14 but stirring the reaction mixture for at 60° C. overnight, using 1-methyl-4-(2-nitro-1H-imidazol-4-ylmethyl)-piperazine (Step 20.1) instead of 2-nitroimidazole in Step 14.3 and 8-(2,6-dimethyl-phenyl)-quinoxaline-5-carboxylic acid (Example 71), and using Raney nickel and MeOH/THF (1:1) instead of palladium on carbon and MeOH in Step 14.2. Title compound: ESI-MS: 456.1 [M+H]⁺; $t_R$=3.18 min (System 1); TLC: $R_f$=0.15 (DCM/MeOH, 9:1).

EXAMPLE 78

8-(2,6-Dichloro-3,5-dimethoxy-phenyl)-quinoxaline-5-carboxylic acid pyridin-3-ylamide

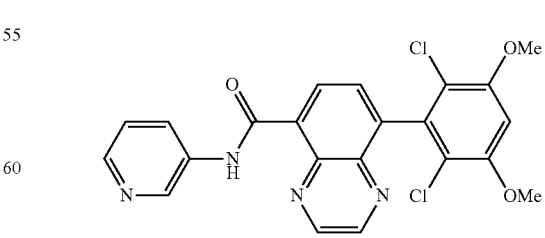

The title compound was prepared in analogy to the procedure described in Step 14.1 but using 3-aminopyridine and stirring the reaction mixture for 16 h at rt. Title compound:

ESI-MS: 455.0/456.9 [M+H]$^+$; $t_R$=3.76 min (System 1); TLC: $R_f$=0.35 (DCM/MeOH/NH$_3^{aq}$, 96:3:1).

EXAMPLE 79

8-(2,6-Dichloro-3,5-dimethoxy-phenyl)-quinoxaline-5-carboxylic acid pyridin-2-ylamide

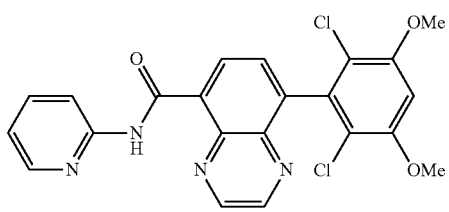 [SMILES: COc1cc(OC)c(Cl)c(-c2ccc(C(=O)Nc3ccccn3)c3nccnc23)c1Cl]

The title compound was prepared in analogy to the procedure described in Step 14.1 but using 2-aminopyridine (2 equiv), TBTU (4 equiv) and stirring the reaction mixture for 16 h at rt. Title compound: ESI-MS: 455.0/456.9 [M+H]$^+$; $t_R$=4.47 min (System 1); TLC: $R_f$=0.61 (DCM/MeOH/NH$_3^{aq}$, 96:3:1).

EXAMPLE 80

8-(2,6-Dichloro-3,5-dimethoxy-phenyl)-quinoxaline-5-carboxylic acid (5-methyl-pyridin-2-yl)-amide

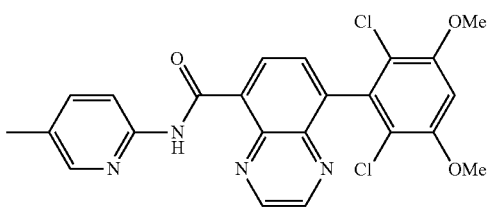 [SMILES: COc1cc(OC)c(Cl)c(-c2ccc(C(=O)Nc3ccc(C)cn3)c3nccnc23)c1Cl]

The title compound was prepared in analogy to the procedure described in Step 14.1 but using 2-amino-5-methylpyridine (2 equiv), TBTU (4 equiv) and stirring the reaction mixture for 4 days at rt. Title compound: ESI-MS: 469.0/470.9 [M+H]$^+$; $t_R$=4.48 min (System 1).

EXAMPLE 81

8-(2,6-Dichloro-3,5-dimethoxy-phenyl)-quinoxaline-5-carboxylic acid (5-{[(2-dimethylamino-ethyl)-methyl-amino]-methyl}-pyridin-2-yl)-amide

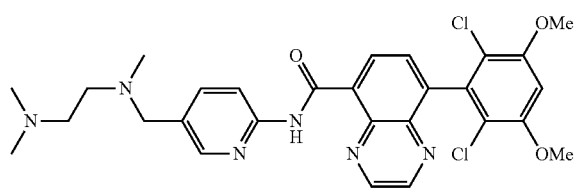 [SMILES: COc1cc(OC)c(Cl)c(-c2ccc(C(=O)Nc3ccc(CN(C)CCN(C)C)cn3)c3nccnc23)c1Cl]

The title compound was prepared in analogy to the procedure described in Step 14.1 but using N-(6-amino-pyridin-3-ylmethyl)-N,N',N'-trimethyl-ethane-1,2-diamine (prepared as described in Example 26 but using N,N,N'-trimethyl-ethane-1,2-diamine in Step 26.2) and stirring the reaction mixture for 4 days at rt. Title compound: ESI-MS: 569.0/571.2 [M+H]$^+$; $t_R$=3.44 min (System 1); TLC: $R_f$=0.19 (DCM/MeOH/NH$_3^{aq}$, 94:5:1).

EXAMPLE 82

8-(2,6-Dichloro-3,5-dimethoxy-phenyl)-3-(4-ethyl-piperazin-1-ylmethyl)-quinoxaline-5-carboxylic acid pyridin-3-ylamide

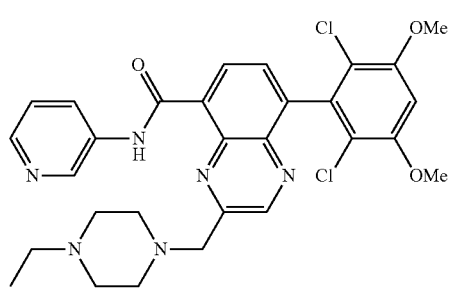 [SMILES: CCN1CCN(Cc2cnc3c(-c4c(Cl)c(OC)cc(OC)c4Cl)ccc(C(=O)Nc4cccnc4)c3n2)CC1]

The title compound was prepared in analogy to the procedure described in Step 14.1 but using 3-aminopyridine, 8-(2,6-dichloro-3,5-dimethoxy-phenyl)-3-(4-ethyl-piperazin-1-ylmethyl)-quinoxaline-5-carboxylic acid (Step 82.1) and stirring the reaction mixture for 12 h at rt. Title compound: ESI-MS: 581.0/583.2 [M+H]$^+$; $t_R$=3.24 min (System 1); TLC: $R_f$=0.38 (DCM/MeOH, 9:1).

Step 82.1: 8-(2,6-Dichloro-3,5-dimethoxy-phenyl)-3-(4-ethyl-piperazin-1-ylmethyl)-quinoxaline-5-carboxylic acid A solution of KOH (0.818 g, 14.6 mmol, 10 equiv) in H$_2$O (20 mL) was added to 710 mg (1.46 equiv) of a mixture of 8-(2,6-dichloro-3,5-dimethoxy-phenyl)-3-(4-ethyl-piperazin-1-ylmethyl)-quinoxaline-5-carbonitrile and 8-(2,6-dichloro-3,5-dimethoxy-phenyl)-2-(4-ethyl-piperazin-1-ylmethyl)-quinoxaline-5-carbonitrile (Step 82.2) (710 mg, 1.46 mmol) in ethylene glycol (20 mL). The reaction mixture was stirred at 150° C. for 3 h, allowed to cool to rt and washed with EtOAc (2×100 mL). The aqueous layer was acidified to pH 3-4 by addition of 1N HCl. The resulting suspension was filtered. The filtrate contains 8-(2,6-dichloro-3,5-dimethoxy-phenyl)-2-(4-ethyl-piperazin-1-ylmethyl)-quinoxaline-5-carboxylic acid (Step 83.1). The residue in the filter was triturated in 1N HCl (3 mL) and filtered. The filtrate was basified to pH 5 and extracted with DCM (2×100 mL). The organic layer was dried (Na$_2$SO$_4$), filtered and concentrated to afford 190 mg of the title compound as a white solid: ES-MS: 505.0/506.6 [M+H]$^+$; $t_R$=3.46 min (System 1).

Step 82.2: 8-(2,6-Dichloro-3,5-dimethoxy-phenyl)-3-(4-ethyl-piperazin-1-ylmethyl)-quinoxaline-5-carbonitrile and 8-(2,6-dichloro-3,5-dimethoxy-phenyl)-2-(4-ethyl-piperazin-1-ylmethyl)-quinoxaline-5-carbonitrile N-Ethylpiperazine (0.308 mL, 2.43 mmol, 1.1 equiv) was added to a mixture of 3-bromomethyl-8-(2,6-dichloro-3,5-dimethoxy-phenyl)-quinoxaline-5-carbonitrile and 2-bromomethyl-8-(2,6-dichloro-3,5-dimethoxy-phenyl)-quinoxaline-5-carbonitrile (Step 82.3) (1 g, 2.21 mmol) and Cs$_2$CO$_3$ (3.52 g, 20 mmol, 1.5 equiv) in DMF (50 mL). The reaction mixture was stirred for 10 min at rt, quenched by addition of a saturated aqueous solution of NaHCO$_3$ (150 mL) and extracted with EtOAc (2×300 mL). The organic phase was washed with a saturated aqueous solution of NaHCO$_3$ (150 mL), dried (Na$_2$SO$_4$), filtered and concentrated. The crude product was purified by silica gel column chromatography (DCM/MeOH, 1:0→95:5) to afford 0.71 g of a mixture of 8-(2,6-dichloro-3,5-dimethoxy-phenyl)-3-(4-ethyl-piperazin-1-ylmethyl)-quinoxaline-5-carbonitrile and 8-(2,6-dichloro-3,5-dimethoxy-phenyl)-2-(4-ethyl-piperazin-1-ylmethyl)-quinoxaline-5-carbonitrile Step 82.3: 3-Bromomethyl-8-(2,6-dichloro-3,5-dimethoxy-phenyl)-quinoxaline-5-carbonitrile and 2-bromomethyl-8-(2,6-dichloro-3,5-dimethoxy-phenyl)-quinoxaline-5-carbonitrile A mixture of 8-(2,6-dichloro-3,5-dimethoxy-phenyl)-3-methyl-quinoxaline-5-carbonitrile and 8-(2,6-dichloro-3,5-dimethoxy-phenyl)-2-methyl-quinoxaline-5-carbonitrile (Step 82.4) (4.93 g, 13.2 mmol) and NBS (3.52 g, 20 mmol, 1.5 equiv) in DMF (100 mL) was stirred at 80° C. for 3 h. Further NBS (2.35 g, 1 equiv) was added and the reaction mixture was stirred at 100° for 2 h, allowed to cool to rt, quenched by addition of a saturated aqueous solution of NaHCO$_3$ (250 mL) and extracted with EtOAc (2×300 mL). The organic phase was washed with a saturated aqueous solution of NaHCO$_3$ (150 mL), dried (Na$_2$SO$_4$), filtered and concentrated. The crude product was purified by silica gel column chromatography (Hex/EtOAc, 9:1→7:3) to afford 2.37 g of a mixture of 3-bromomethyl-8-(2,6-dichloro-3,5-dimethoxy-phenyl)-quinoxaline-5-carbonitrile and 2-bromomethyl-8-(2,6-dichloro-3,5-dimethoxy-phenyl)-quinoxaline-5-carbonitrile.

Step 82.4: 8-(2,6-Dichloro-3,5-dimethoxy-phenyl)-3-methyl-quinoxaline-5-carbonitrile and 8-(2,6-dichloro-3,5-dimethoxy-phenyl)-2-methyl-quinoxaline-5-carbonitrile Sulfuryl chloride (2.14 mL, 26.6 mmol, 1.8 equiv) was added dropwise to a cold (5° C.) suspension of 8-(3,5-dimethoxy-phenyl)-3-methyl-quinoxaline-5-carbonitrile and 8-(3,5-dimethoxy-phenyl)-2-methyl-quinoxaline-5-carbonitrile (Step 82.5) (4.51 g, 14.8 mmol) in CH$_3$CN (80 mL). The reaction mixture was stirred at 5° C. for 10 min, quenched by addition of a saturated aqueous solution of NaHCO$_3$ (250 mL) and extracted with EtOAc (2×300 mL). The organic phase was washed with a saturated aqueous solution of NaHCO$_3$ (150 mL), dried (Na$_2$SO$_4$), filtered and concentrated. The crude product was purified by silica gel column chromatography (Hex/EtOAc, 9:1→2:3) to afford 4.93 g of a mixture of 8-(2,6-dichloro-3,5-dimethoxy-phenyl)-3-methyl-quinoxaline-5-carbonitrile and 8-(2,6-dichloro-3,5-dimethoxy-phenyl)-2-methyl-quinoxaline-5-carbonitrile.

Step 82.5: 8-(3,5-Dimethoxy-phenyl)-3-methyl-quinoxaline-5-carbonitrile and 8-(3,5-dimethoxy-phenyl)-2-methyl-quinoxaline-5-carbonitrile A mixture of 8-bromo-5-(3,5-dimethoxy-phenyl)-2-methyl-quinoxaline and 5-bromo-8-(3,5-dimethoxy-phenyl)-2-methyl-quinoxaline (Step 82.6) (6.07 g, 16.9 mmol) and CuCN (1.98 g, 22 mmol, 1.3 equiv) in NMP (50 mL) was stirred for 5 h at 160° C., under an argon atmosphere. The reaction mixture was allowed to cool to rt, quenched by addition of a saturated aqueous solution of NaHCO$_3$ (250 mL) and extracted with EtOAc. The organic phase was washed with a saturated aqueous solution of NaHCO$_3$ (2×100 mL), dried (Na$_2$SO$_4$), filtered and concentrated. The crude product was purified by silica gel column chromatography (Hex/EtOAc, 9:1→2:3) to afford 4.51 g of a mixture of 8-(3,5-dimethoxy-phenyl)-3-methyl-quinoxaline-5-carbonitrile and 8-(3,5-dimethoxy-phenyl)-2-methyl-quinoxaline-5-carbonitrile.

Step 82.6: 8-Bromo-5-(3,5-dimethoxy-phenyl)-2-methyl-quinoxaline and 5-bromo-8-(3,5-dimethoxy-phenyl)-2-methyl-quinoxaline A mixture of 3,5-dimethoxyphenylboronic acid (Step 1.8) (4 g, 22 mmol) in EtOH (125 mL) was added dropwise to a mixture of 5,8-dibromo-2-methyl-quinoxaline (Step 82.7) (13.2 g, 43.8 mmol, 2 equiv), PdCl$_2$(dppf) (483 mg, 0.66 mmol, 0.03 equiv), Na$_2$CO$_3$ (2 M solution in H$_2$O, 44 mL, 88 mmol, 4 equiv) in toluene (250 mL) at 105° C., under an argon atmosphere. The reaction mixture was stirred at 105° C. for 4.5 h, allowed to cool to rt, quenched by addition of a saturated aqueous solution of NaHCO$_3$ and extracted with EtOAc. The organic phase was washed with a saturated aqueous solution of NaHCO$_3$, dried (Na$_2$SO$_4$), filtered and concentrated. The crude product was purified by silica gel column chromatography (Hex/EtOAc, 1:0→85:15) to afford 6.07 g of a mixture of 8-bromo-5-(3,5-dimethoxy-phenyl)-2-methyl-quinoxaline and 5-bromo-8-(3,5-dimethoxy-phenyl)-2-methyl-quinoxaline.

Step 82.7: 5,8-Dibromo-2-methyl-quinoxaline

A 40% aqueous solution of methylglyoxal (6.7 M, 6.3 mL, 112 mmol, 1.48 equiv) was added to a suspension of 3,6-dibromo-benzene-1,2-diamine (Step 1.6) (20 g, 75.5 mmol) in EtOH (400 mL). The reaction mixture was stirred for 2 h at rt and for 0.5 h at reflux, allowed to cool and filtered to afford 7.66 g of the title compound. The filtrate was concentrated and the residue triturated in EtOAc and filtered. The filtrate was concentrated and the residue was purified by silica gel column chromatography (Hex/EtOAc, 1:0→9:1) to provide additional 2.15 g of the title compound. The title compound: ESI-MS: 300.9/302.9/304.9 [M+H]$^+$; t$_R$=4.81 min (System 1); TLC: R$_f$=0.90 (Hex/EtOAc, 1:1).

EXAMPLE 83

8-(2,6-Dichloro-3,5-dimethoxy-phenyl)-2-(4-ethyl-piperazin-1-ylmethyl)-quinoxaline-5-carboxylic acid pyridin-3-ylamide

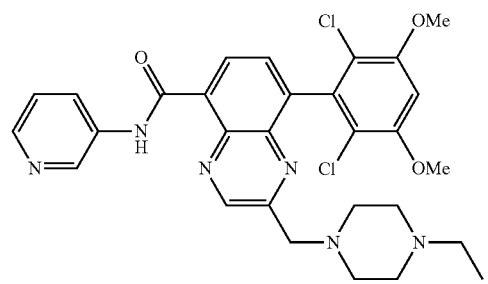 [SMILES: CCN1CCN(Cc2cnc3c(C(=O)Nc4cccnc4)ccc(-c4c(Cl)c(OC)cc(OC)c4Cl)c3n2)CC1]

The title compound was prepared in analogy to the procedure described in Step 14.1 but using 3-aminopyridine, 8-(2,6-dichloro-3,5-dimethoxy-phenyl)-2-(4-ethyl-piperazin-1-ylmethyl)-quinoxaline-5-carboxylic acid (Step 83.1) and stirring the reaction mixture for 2 days at rt. Title compound: ESI-MS: 581.0/583.2 [M+H]$^+$; $t_R$=3.04 min (System 1); TLC: $R_f$=0.33 (DCM/MeOH, 9:1).

Step 83.1: 8-(2,6-Dichloro-3,5-dimethoxy-phenyl)-2-(4-ethyl-piperazin-1-ylmethyl)-quinoxaline-5-carboxylic acid A solution of KOH (0.818 g, 14.6 mmol, 10 equiv) in H$_2$O (20 mL) was added to 710 mg (1.46 equiv) of the quinoxaline-5-carbonitriles mixture (Step 82.2) in ethylene glycol (20 mL). The reaction mixture was stirred at 150° C. for 3 h, allowed to cool to rt and washed with EtOAc (2×100 mL). The aqueous layer was acidified to pH 3-4 by addition of 1 N HCl. The resulting suspension was filtered. The filtrate was extracted with DCM (2×100 mL). The organic layer was dried (Na$_2$SO$_4$), filtered and concentrated. The residue was triturated in 1 N HCl (3 mL) and filtered. The filtrate was basified to pH 5 and extracted with DCM (2×100 mL). The organic layer was dried (Na$_2$SO$_4$), filtered and concentrated to afford 121 mg of the title compound as a white solid: ES-MS: 505.0/506.6 [M+H]$^+$; $t_R$=3.45 min (System 1).

EXAMPLE 84

8-(2,6-Dichloro-3,5-dimethoxy-phenyl)-2-(4-ethyl-piperazin-1-ylmethyl)-quinoxaline-5-carboxylic acid pyridin-2-ylamide

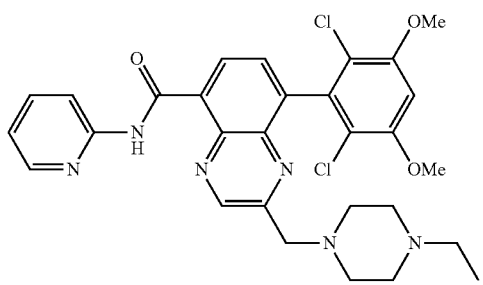 [SMILES: CCN1CCN(Cc2cnc3c(C(=O)Nc4ccccn4)ccc(-c4c(Cl)c(OC)cc(OC)c4Cl)c3n2)CC1]

The title compound was prepared in analogy to the procedure described in Step 14.1 but using 2-aminopyridine, 8-(2,6-dichloro-3,5-dimethoxy-phenyl)-2-(4-ethyl-piperazin-1-ylmethyl)-quinoxaline-5-carboxylic acid (Step 83.1) and stirring the reaction mixture for 2 days at rt. Title compound: ESI-MS: 581.0/583.2 [M+H]$^+$; $t_R$=3.62 min (System 1); TLC: $R_f$=0.45 (DCM/MeOH, 9:1).

EXAMPLE 85

8-(2,6-Dichloro-3,5-dimethoxy-phenyl)-2-[(2-dimethylamino-ethyl)-methyl-amino]-quinoxaline-5-carboxylic acid (1H-imidazol-2-yl)-amide

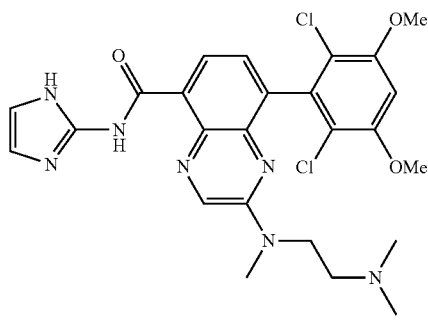 [SMILES: COc1cc(OC)c(Cl)c(-c2ccc(C(=O)Nc3ncc[nH]3)c3ncc(N(C)CCN(C)C)nc23)c1Cl]

The title compound was prepared in analogy to the procedures described in Example 14 but using 8-(2,6-dichloro-3,5-dimethoxy-phenyl)-2-[(2-dimethylamino-ethyl)-methyl-amino]-quinoxaline-5-carboxylic acid (Step 85.1) in Step 14.1. Title compound: ESI-MS: 544.0/545.9 [M+H]$^+$; $t_R$=3.13 min (System 1); TLC: $R_f$=0.21 (DCM/MeOH/NH$_3^{aq}$, 91:8:1).

Step 85.1: 8-(2,6-Dichloro-3,5-dimethoxy-phenyl)-2-[(2-dimethylamino-ethyl)-methyl-amino]-quinoxaline-5-carboxylic acid A solution of KOH (268 mg, 4.79 mmol, 10 equiv) in H$_2$O (2 mL) was added to 8-(2,6-dichloro-3,5-dimethoxy-phenyl)-2-[(2-dimethylamino-ethyl)-methyl-amino]-quinoxaline-5-carbonitrile (Step 85.2) (220 mg, 0.48 mmol) in ethylene glycol (2 mL). The reaction mixture was stirred at 150° C. for 48 h, allowed to cool to rt, diluted with Et$_2$O/H$_2$O, and extracted with Et$_2$O. The aqueous phase was acidified to pH 5 by addition of 6 N HCl. Vacuum filtration of the resulting suspension afforded 450 mg of the title compound as an impure yellow solid, which was used without further purification: ESI-MS: 479.0/480.9 [M+H]$^+$; $t_R$=3.75 min (System 1).

Step 85.2: 8-(2,6-Dichloro-3,5-dimethoxy-phenyl)-2-[(2-dimethylamino-ethyl)-methyl-amino]-quinoxaline-5-carbonitrile A mixture of 8-(2,6-dichloro-3,5-dimethoxy-phenyl)-2-[(2-dimethylamino-ethyl)-methyl-amino]-quinoxaline-5-carbonitrile (Step 85.3) (210 mg, 0.53 mmol) and N,N,N'-triethylethylene diamine (0.14 mL, 1.07 mmol, 2 equiv) in NMP (2 mL) was stirred at 120° C. for 5 min, allowed to cool, diluted with EtOAc/H$_2$O and extracted with EtOAc. The organic phase was washed with H$_2$O and brine, dried (Na$_2$SO$_4$), filtered and concentrated. The residue was triturated in Et$_2$O to provide 225 mg of the title compound as a yellow solid: ESI-MS: 460.1/461.9 [M+H]$^+$; $t_R$=3.97 min (System 1).

Step 85.3: 2-Chloro-8-(2,6-dichloro-3,5-dimethoxy-phenyl)-quinoxaline-5-carbonitrile Sulfuryl chloride (0.08 mL, 0.98 mmol, 2 equiv) was added dropwise to a cold (5° C.) suspension of 2-chloro-8-(3,5-dimethoxy-phenyl)-quinoxaline-5-carbonitrile (Step 85.4) (160 mg, 0.49 mmol) in CH$_3$CN (3 mL). The reaction mixture was stirred at 5° C. for 10 min, quenched by addition of H$_2$O, and concentrated. The residue was taken up in DCM, washed with a saturated aqueous solution of NaHCO$_3$, H$_2$O and brine, dried (Na$_2$SO$_4$), filtered and concentrated. Trituration of the residue in Et$_2$O provided 163 mg of the title compound as a white solid: ESI-MS: 394.0/395.6/396.3 [M+H]$^+$; $t_R$=5.13 min (System 1).

Step 85.4: 2-Chloro-8-(3,5-dimethoxy-phenyl)-quinoxaline-5-carbonitrile

A mixture of 8-(3,5-dimethoxy-phenyl)-2-hydroxy-quinoxaline-5-carbonitrile (Step 85.5) (100 mg, 0.33 mmol) and POCl$_3$ (1 mL) was stirred at 120° C. for 3 h, allowed to cool to rt and concentrated. The residue was diluted with DCM/NaHCO$_3$ saturated aqueous solution and extracted with DCM. The organic phase was washed with H$_2$O and brine, dried (Na$_2$SO$_4$), filtered and concentrated. The crude product was purified by silica gel column chromatography (Hex/EtOAc, 7:3) to afford 90 mg of the title compound as a yellow solid: ES-MS: 326.1 [M+H]$^+$; $t_R$=5.02 min (System 1); R$_f$=0.34 (Hex/EtOAc, 7:3).

Step 85.5: 8-(3,5-Dimethoxy-phenyl)-2-hydroxy-quinoxaline-5-carbonitrile

A mixture of 5-bromo-8-(3,5-dimethoxy-phenyl)-quinoxalin-2-ol and 8-bromo-5-(3,5-dimethoxy-phenyl)-quinoxalin-2-ol (Step 85.6) (609 mg, 1.7 mmol) (Step 1.4) and CuCN (183 mg, 2.0 mmol, 1.2 equiv) in NMP (5 mL) was stirred at 180° C. for 2 h. The reaction mixture was allowed to cool to rt, diluted with EtOAc/10% aqueous solution of ethylenediamine (25 mL) and extracted with EtOAc. The aqueous phase was acidified to pH 5 and extracted with EtOAc. The combined organic extracts were washed with H$_2$O and brine, dried (Na$_2$SO$_4$), filtered and concentrated. The residue was purified by silica gel column chromatography (Hex/EtOAc, 7:3) to afford 103 mg of the title compound as a yellow solid: ES-MS: 308.1 [M+H]$^+$; $t_R$=4.05 min (System 1); R$_f$=0.35 (Hex/EtOAc, 7:3).

Step 85.6: 5-Bromo-8-(3,5-dimethoxy-phenyl)-quinoxalin-2-ol and 8-bromo-5-(3,5-dimethoxy-phenyl)-quinoxalin-2-ol A mixture of 4-bromo-3',5'-dimethoxy-biphenyl-2,3-diamine (Step 85.7) (1 g, 3.1 mmol) and glyoxylite acid monohydrate (313 mg, 3.4 mmol, 1.1 equiv) in EtOH (20 mL) was stirred at reflux for 15 min, allowed to cool to rt. The resulting yellow solid was collected by vacuum filtration to provide 397 mg of the title mixture. The filtrate was concentrated and the residue was purified silica gel column chromatography (Hex/EtOAc, 1:1) to afford additional 225 mg of the title mixture.

Step 85.7: 4-Bromo-3',5'-dimethoxy-biphenyl-2,3-diamine

A mixture of 3,5-dimethoxyphenylboronic acid (15.1 g, 82.7 mmol, 1.1 equiv) (Step 1.8) in EtOH (50 mL) was added dropwise to a mixture of 3,6-dibromo-benzene-1,2-diamine (20 g, 75.2 mmol) (Step 1.6), PdCl$_2$(dppf) (6.1 g, 7.5 mmol, 0.1 equiv), Na$_2$CO$_3$ (2 M solution in H$_2$O, 150 mL, 300.8 mmol, 4 equiv) in toluene (300 mL) at 105° C., under an argon atmosphere. The reaction mixture was stirred at 105° C. for 3 h, allowed to cool to rt, diluted with EtOAc and H$_2$O and extracted with EtOAc. The organic phase was washed with H$_2$O and brine, dried (Na$_2$SO$_4$), filtered and concentrated. The crude product was purified by silica gel column chromatography (DCM) followed by trituration in EtOH to afford 9.2 g of the title compound as a white solid: ES-MS: 323.0/325.0 [M+H]$^+$; $t_R$=4.43 min (System 1); R$_f$=0.15 (DCM).

EXAMPLE 86

8-(2,6-Dichloro-3,5-dimethoxy-phenyl)-2-[(2-dimethylamino-ethyl)-methyl-amino]-quinoxaline-5-carboxylic acid pyridin-2-ylamide

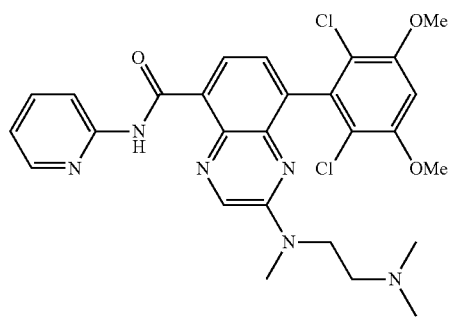 [SMILES: COc1cc(OC)c(Cl)c(-c2ccc(C(=O)Nc3ccccn3)c3ncc(N(C)CCN(C)C)nc23)c1Cl]

The title compound was prepared in analogy to the procedure described in Step 14.1 but using 8-(2,6-dichloro-3,5-dimethoxy-phenyl)-2-[(2-dimethylamino-ethyl)-methyl-amino]-quinoxaline-5-carboxylic acid (Step 85.1) and 2-aminopyridine. Title compound: ESI-MS: 555.0/557.2 [M+H]$^+$; $t_R$=3.61 min (System 1); TLC: R$_f$=0.42 (DCM/MeOH/NH$_3$$^{aq}$, 94:5:1).

EXAMPLE 87

8-(2,6-Dichloro-3,5-dimethoxy-phenyl)-2-[(2-dimethylamino-ethyl)-methyl-amino]-quinoxaline-5-carboxylic acid pyridin-3-ylamide

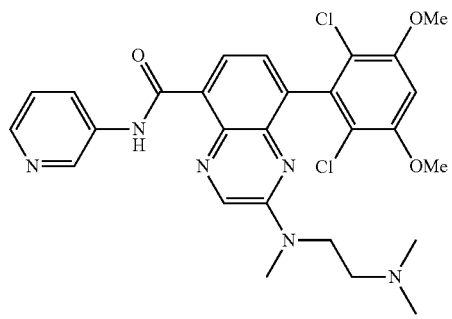 [SMILES: COc1cc(OC)c(Cl)c(-c2ccc(C(=O)Nc3cccnc3)c3ncc(N(C)CCN(C)C)nc23)c1Cl]

The title compound was prepared in analogy to the procedure described in Step 14.1 but using 8-(2,6-dichloro-3,5-dimethoxy-phenyl)-2-[(2-dimethylamino-ethyl)-methyl-amino]-quinoxaline-5-carboxylic acid (Step 85.1) and 3-aminopyridine. Title compound: ESI-MS: 555.0/557.2 [M+H]$^+$; $t_R$=3.16 min (System 1); TLC: $R_f$=0.20 (DCM/MeOH/NH$_3$$^{aq}$, 94:5:1).

EXAMPLE 88

8-(2,6-Difluoro-3,5-dimethoxy-phenyl)-quinoxaline-5-carboxylic acid [6-(4-ethyl-piperazin-1-ylmethyl)-pyridin-3-yl]-amide

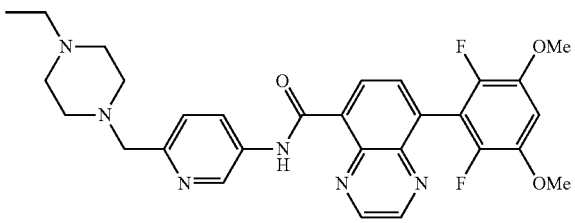

The title compound was prepared in analogy to the procedure described in Step 14.1 but using 8-(2,6-difluoro-3,5-dimethoxy-phenyl)-quinoxaline-5-carboxylic acid (Step 88.1), 6-(4-ethyl-piperazin-1-ylmethyl)-pyridin-3-ylamine (prepared as described in Example 39 but using N-ethyl-piperazine in Step 39.2), and stirring the reaction mixture for 3 h at rt. The crude product was purified by silica gel column chromatography (DCM/MeOH/NH$_3$$^{aq}$, 94:5:1). Title compound: ESI-MS: 549.1 [M+H]$^+$; $t_R$=3.22 min (System 1); TLC: $R_f$=0.13 (DCM/MeOH/NH$_3$$^{aq}$, 94:5:1).

Step 88.1: 8-(2,6-Difluoro-3,5-dimethoxy-phenyl)-quinoxaline-5-carboxylic acid A solution of KOH (2.4 g, 42.8 mmol, 10 equiv) in H$_2$O (10 mL) was added to 8-(2,6-difluoro-3,5-dimethoxy-phenyl)-quinoxaline-5-carbonitrile (Step 88.2) (1.4 g mg, 4.3 mmol) in ethylene glycol (20 mL). The reaction mixture was stirred at 150° C. for 4 h, allowed to cool to rt, diluted with Et$_2$O/H$_2$O, and extracted with Et$_2$O. The aqueous phase was acidified to pH 5 by addition of 6 N HCl. Vacuum filtration of the resulting suspension afforded 1.47 g of the title compound as a brown solid, which was used without further purification: ESI-MS: 347.1 [M+H]$^+$; $t_R$=4.22 min (System 1).

Step 88.2: 8-(2,6-Difluoro-3,5-dimethoxy-phenyl)-quinoxaline-5-carbonitrile

A mixture of 5-bromo-8-(2,6-difluoro-3,5-dimethoxy-phenyl)-quinoxaline (Step 88.3) (1.1 g, 2.9 mmol) (Step 88.3) and CuCN (312 mg, 3.4 mmol, 1.2 equiv) in NMP (10 mL) was stirred for 4 h at 150° C., under an argon atmosphere. The reaction mixture was allowed to cool to rt, diluted with DCM/ (10% aqueous solution of ethylenediamine) (100 mL) and extracted with DCM. The organic phase was washed with H$_2$O and brine, dried (Na$_2$SO$_4$), filtered and concentrated. The residue was triturated in EtOAc to provide 702 mg of the title compound as a beige solid: ESI-MS: 328.1 [M+H]$^+$; $t_R$=4.48 min (System 1).

Step 88.3: 5-Bromo-8-(2,6-difluoro-3,5-dimethoxy-phenyl)-quinoxaline

SelectFluor (20.5 g, 58 mmol, 2 equiv) was added portion-wise to a solution of 5-bromo-8-(3,5-dimethoxy-phenyl)-quinoxaline (Step 1.4) (10 g, 29 mmol) in CH$_3$CN (300 mL) at rt. The reaction mixture was stirred at rt for 0.5 h, quenched by addition of H$_2$O and concentrated to remove CH$_3$CN. The resulting mixture was diluted with EtOAc/H$_2$O and filtered to provide a white solid (batch 1). The filtrate was extracted with EtOAc. The organic phase was washed with H$_2$O and brine, dried (Na$_2$SO$_4$), filtered and concentrated to afford batch 2. The two batches were combined and purified by silica gel MPLC (Hex/EtOAc, 7:3) to afford a sample of 5-bromo-8-(2-fluoro-3,5-dimethoxy-phenyl)-quinoxaline (Step 94.3) and a sample of the title compound which was further purified by trituration in EtOAc to provide 2.28 g of a white solid. Title compound: ESI-MS: 381.0/382.9 [M+H]$^+$; $t_R$=4.92 min (System 1); TLC: $R_f$=0.26 (Hex/EtOAc, 7:3).

EXAMPLE 89

8-(2,6-Difluoro-3,5-dimethoxy-phenyl)-quinoxaline-5-carboxylic acid [6-(4-methyl-piperazin-1-ylmethyl)-pyridin-3-yl]-amide

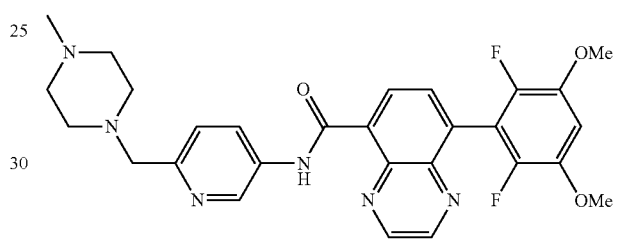

The title compound was prepared in analogy to the procedure described in Step 14.1 but using 8-(2,6-difluoro-3,5-dimethoxy-phenyl)-quinoxaline-5-carboxylic acid (Step 88.1), 6-(4-methyl-piperazin-1-ylmethyl)-pyridin-3-ylamine (Step 39.1), and stirring the reaction mixture for 16 h at rt. The crude product was purified by silica gel column chromatography (DCM/MeOH/NH$_3$$^{aq}$, 94:5:1) followed by trituration in Et$_2$O. Title compound: ESI-MS: 535.1 [M+H]$^+$; $t_R$=3.15 min (System 1); TLC: $R_f$=0.13 (DCM/MeOH/NH$_3$$^{aq}$, 94:5:1).

EXAMPLE 90

8-(2,6-Difluoro-3,5-dimethoxy-phenyl)-quinoxaline-5-carboxylic acid pyridin-3-ylamide

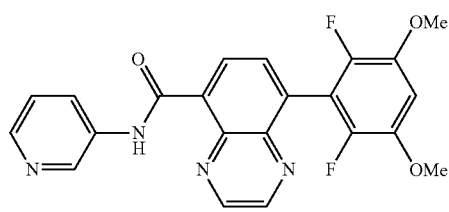 [SMILES: COc1cc(OC)c(F)c(-c2ccc(C(=O)Nc3cccnc3)c3nccnc23)c1F]

The title compound was prepared in analogy to the procedure described in Step 14.1 but using 8-(2,6-difluoro-3,5-dimethoxy-phenyl)-quinoxaline-5-carboxylic acid (Step 88.1), 3-aminopyridine, and stirring the reaction mixture for 72 h at rt. The crude product was purified by silica gel column chromatography (DCM/MeOH/NH$_3$$^{aq}$, 96:3:1) followed by trituration in Et₂O. Title compound: ESI-MS: 423.1 [M+H]⁺; $t_R$=3.53 min (System 1); TLC: $R_f$=0.56 (DCM/MeOH/NH₃$^{aq}$, 96:3:1).

EXAMPLE 91

8-(2,6-Difluoro-3,5-dimethoxy-phenyl)-quinoxaline-5-carboxylic acid pyridin-2-ylamide

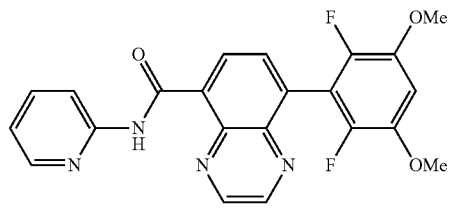 [SMILES: COc1cc(OC)c(F)c(-c2ccc(C(=O)Nc3ccccn3)c3nccnc23)c1F]

The title compound was prepared in analogy to the procedure described in Step 14.1 but using 8-(2,6-difluoro-3,5-dimethoxy-phenyl)-quinoxaline-5-carboxylic acid (Step 88.1), 2-aminopyridine, and stirring the reaction mixture for 72 h at rt. The crude product was purified by silica gel column chromatography (DCM/MeOH/NH₃$^{aq}$, 96:3:1), followed by trituration in Et₂O, a second silica gel column chromatography (Hex/EtOAc, 1:4) and an additional trituration in Et₂O. Title compound: ESI-MS: 423.1 [M+H]⁺; $t_R$=4.21 min (System 1); TLC: $R_f$=0.19 (Hex/EtOAc, 1:4).

EXAMPLE 92

8-(2,6-Difluoro-3,5-dimethoxy-phenyl)-quinoxaline-5-carboxylic acid [5-(4-ethyl-piperazin-1-ylmethyl)-pyridin-2-yl]-amide

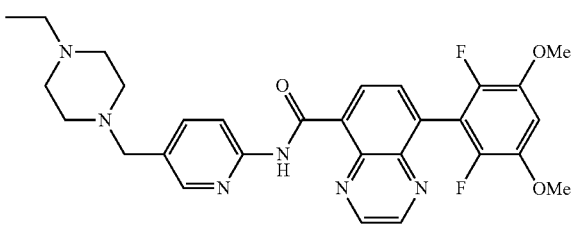 [SMILES: CCN1CCN(Cc2ccc(NC(=O)c3ccc(-c4c(F)c(OC)cc(OC)c4F)c4nccnc34)nc2)CC1]

The title compound was prepared in analogy to the procedure described in Step 14.1 but using 8-(2,6-difluoro-3,5-dimethoxy-phenyl)-quinoxaline-5-carboxylic acid (Step 88.1), 5-(4-ethyl-piperazin-1-ylmethyl)-pyridin-2-ylamine (Step 26.1), and stirring the reaction mixture for 48 h at rt and for 5 h at 50° C. after addition of further 1.2 equiv of TBTU. The crude product was purified by silica gel column chromatography (DCM/MeOH/NH₃$^{aq}$, 94:5:1). Title compound: ESI-MS: 549.1 [M+H]⁺; $t_R$=3.39 min (System 1); TLC: $R_f$=0.24 (DCM/MeOH/NH₃$^{aq}$, 94:5:1).

EXAMPLE 93

8-(2,6-Difluoro-3,5-dimethoxy-phenyl)-quinoxaline-5-carboxylic acid (4-pyrrolidin-1-ylmethyl-1H-imidazol-2-yl)-amide

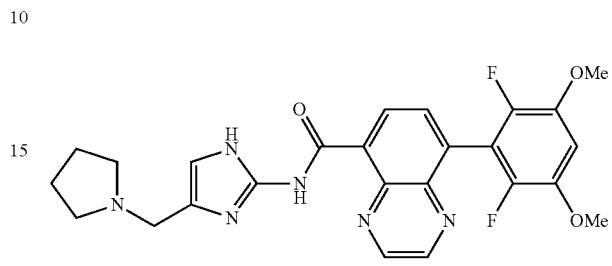

The title compound was prepared in analogy to the procedures described in Example 14 but stirring the reaction mixture for 6 h at 65° C. and using 8-(2,6-difluoro-3,5-dimethoxy-phenyl)-quinoxaline-5-carboxylic acid (Step 88.1). 2-Nitro-4-pyrrolidin-1-ylmethyl-1H-imidazole (Step 19.1) instead of 2-nitroimidazole was used in Step 14.3, and Raney nickel and MeOH/THF (1:1) instead of palladium on carbon and MeOH in Step 14.2. The title compound: ESI-MS: 495.0 [M+H]⁺; $t_R$=3.28 min (System 1); TLC: $R_f$=0.08 (DCM/MeOH/NH₃$^{aq}$, 94:5:1).

EXAMPLE 94

8-(2-Fluoro-3,5-dimethoxy-phenyl)-quinoxaline-5-carboxylic acid (5-{[(2-dimethylamino-ethyl)-methyl-amino]-methyl}-pyridin-2-yl)-amide

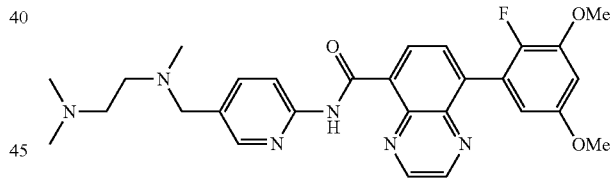

The title compound was prepared in analogy to the procedure described in Step 14.1 but using 8-(2-fluoro-3,5-dimethoxy-phenyl)quinoxaline-5-carboxylic acid (Step 94.1), N-(6-amino-pyridin-3-ylmethyl)-N,N',N'-trimethyl-ethane-1,2-diamine (prepared as described in Example 26 but using N,N,N'-trimethyl-ethane-1,2-diamine in Step 26.2) and stirring the reaction mixture for 18 h at rt. The crude product was purified by silica gel column chromatography (DCM/MeOH/NH₃$^{aq}$, 94:5:1). Title compound: ESI-MS: 519.2 [M+H]⁺; $t_R$=3.26 min (System 1); TLC: $R_f$=0.13 (DCM/MeOH/NH₃$^{aq}$, 94:5:1).

Step 94.1: 8-(2-Fluoro-3,5-dimethoxy-phenyl)-quinoxaline-5-carboxylic acid

A solution of KOH (2.95 g, 52.7 mmol, 10 equiv) in H₂O (20 mL) was added to 8-(2-fluoro-3,5-dimethoxy-phenyl)-quinoxaline-5-carbonitrile (Step 94.2) (1.63 g mg, 5.3 mmol) in ethylene glycol (20 mL). The reaction mixture was stirred at 150° C. for 5 h, allowed to cool to rt, diluted with Et₂O/

H₂O, and extracted with Et₂O. The aqueous phase was acidified to pH 3 by addition of HCl. The resulting yellow solid was collected by vacuum filtration to provide 1.71 g of the title compound: ESI-MS: 329.1 [M+H]⁺; $t_R$=4.18 min (System 1).

Step 94.2: 8-(2-Fluoro-3,5-dimethoxy-phenyl)-quinoxaline-5-carbonitrile

A mixture of 5-bromo-8-(2-fluoro-3,5-dimethoxy-phenyl)-quinoxaline (Step 94.3) (3.09 g, 8.5 mmol) and CuCN (918 mg, 10.2 mmol, 1.2 equiv) in NMP (30 mL) was stirred for 6.5 h at 160° C., under an argon atmosphere. The reaction mixture was allowed to cool to rt, diluted with DCM/(10% aqueous solution of ethylenediamine) (200 mL, v/v 1:1), filtered through celite and the filtrate extracted with DCM. The organic phase was washed with H₂O and brine, dried (Na₂SO₄), filtered and concentrated. The residue was triturated in DCM to provide 1.63 g of the title compound as a white solid: ESI-MS: 310.1 [M+H]⁺; $t_R$=4.41 min (System 1).

Step 94.3: 5-Bromo-8-(2-fluoro-3,5-dimethoxy-phenyl)-quinoxaline

SelectFluor (20.5 g, 58 mmol, 2 equiv) was added portionwise to a solution of 5-bromo-8-(3,5-dimethoxy-phenyl)-quinoxaline (Step 1.4) (10 g, 29 mmol) in CH₃CN (300 mL) at rt. The reaction mixture was stirred at rt for 0.5 h, quenched by addition of H₂O and concentrated to remove CH₃CN. The resulting mixture was diluted with EtOAc/H₂O and filtered to provide a white solid (batch 1). The filtrate was extracted with EtOAc. The organic phase was washed with H₂O and brine, dried (Na₂SO₄), filtered and concentrated to afford batch 2. The two batches were combined and purified by silica gel MPLC (Hex/EtOAc, 7:3) to afford a sample of 5-bromo-8-(2,6-difluoro-3,5-dimethoxy-phenyl)-quinoxaline (Step 88.3) and a sample of the title compound which was further purified by trituration in EtOAc to provide 2.42 g of a white solid. Title compound: ESI-MS: 364.9 [M+H]⁺; $t_R$=4.95 min (System 1); TLC: $R_f$=0.34 (Hex/EtOAc, 7:3).

EXAMPLE 95

8-(2-Fluoro-3,5-dimethoxy-phenyl)-quinoxaline-5-carboxylic acid [5-(4-ethyl-piperazin-1-ylmethyl)-pyridin-2-yl]-amide

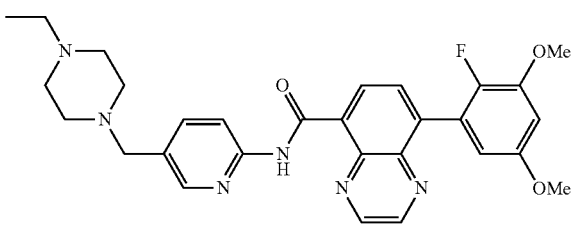

The title compound was prepared in analogy to the procedure described in Step 14.1 but using 8-(2-fluoro-3,5-dimethoxy-phenyl)quinoxaline-5-carboxylic acid (Step 94.1), 5-(4-ethyl-piperazin-1-ylmethyl)-pyridin-2-ylamine hydrochloride (Step 26.1) and stirring the reaction mixture for 6 days at rt. The crude product was purified by silica gel column chromatography (DCM/MeOH/NH₃$^{aq}$, 94:5:1). Title compound: ESI-MS: 531.2 [M+H]⁺; $t_R$=3.40 min (System 1); TLC: $R_f$=0.19 (DCM/MeOH/NH₃$^{aq}$, 94:5:1).

EXAMPLE 96

8-(2-Fluoro-3,5-dimethoxy-phenyl)-quinoxaline-5-carboxylic acid (4-pyrrolidin-1-ylmethyl-1H-imidazol-2-yl)-amide

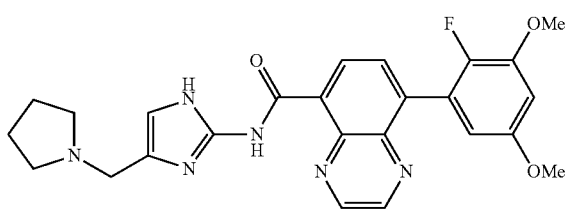 [SMILES: COc1cc(OC)c(F)c(-c2ccc(C(=O)Nc3nc(CN4CCCC4)c[nH]3)c3nccnc23)c1]

The title compound was prepared in analogy to the procedures described in Example 14 but stirring the reaction mixture for 6 h at 65° C. and using 8-(2-fluoro-3,5-dimethoxy-phenyl)-quinoxaline-5-carboxylic acid (Step 94.1). 2-Nitro-4-pyrrolidin-1-ylmethyl-1H-imidazole (Step 19.1) instead of 2-nitroimidazole was used in Step 14.3, and Raney nickel and MeOH/THF (1:1) instead of palladium on carbon and MeOH in Step 14.2. The title compound: ESI-MS: 477.2 [M+H]⁺; $t_R$=3.28 min (System 1); TLC: $R_f$=0.11 (DCM/MeOH/NH₃$^{aq}$, 94:5:1).

EXAMPLE 97

8-(3-Methoxy-2,5-dimethyl-phenyl)-quinoxaline-5-carboxylic acid [5-(4-ethyl-piperazin-1-ylmethyl)-pyridin-2-yl]-amide

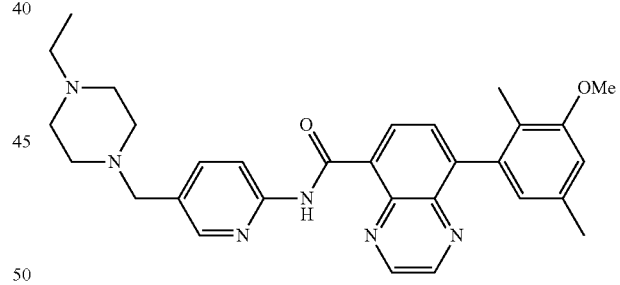

The title compound was prepared in analogy to the procedure described in Step 14.1 but using 8-(3-methoxy-2,5-dimethyl-phenyl)quinoxaline-5-carboxylic acid (Step 97.1), 5-(4-ethyl-piperazin-1-ylmethyl)-pyridin-2-ylamine hydrochloride (Step 26.1) and stirring the reaction mixture for 24 h at rt. The crude product was purified by silica gel column chromatography (DCM/MeOH/NH₃$^{aq}$, 94:5:1). Title compound: ESI-MS: 511.1 [M+H]⁺; $t_R$=3.75 min (System 1); TLC: $R_f$=0.29 (DCM/MeOH/NH₃$^{aq}$, 94:5:1).

Step 97.1: 8-(3-Methoxy-2,5-dimethyl-phenyl)-quinoxaline-5-carboxylic acid

The title compound was prepared in analogy to the procedures described in Steps 1.2-1.4 but with the following modifications. In Step 1.2, the reaction mixture was stirred at 150°

C. for 4 h. In Step 1.3, the reaction mixture was stirred at 160° C. for 5 h; DCM was used instead of EtOAc; the crude product was purified by silica gel column chromatography (Hex/EtOAC, 1:1). 3-Methoxy-2,5-dimethyl-phenyl boronic acid (Step 97.2) was used in Step 1.4. Title compound: ESI-MS: 309.2 [M+H]$^+$; $t_R$=4.71 min (System 1).

Step 97.2: 3-Methoxy-2,5-dimethyl-phenyl boronic acid

The title compound was prepared in analogy to the procedure described in Step 1.8 but using 1-bromo-3-methoxy-2,5-dimethyl-benzene (*Journal of Organic Chemistry* 1992, 57(10), 2774-83). The title compound was obtained as an impure sample and used without further purification.

EXAMPLE 98

8-(2-Chloro-5-methoxy-3,6-dimethyl-phenyl)-quinoxaline-5-carboxylic acid [5-(4-ethyl-piperazin-1-ylmethyl)-pyridin-2-yl]-amide

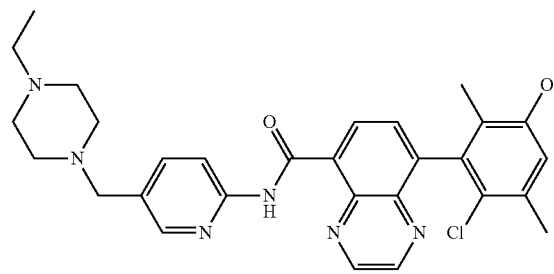 [SMILES: CCN1CCN(Cc2ccc(NC(=O)c3ccc(-c4cc(C)c[n+]([O-])c4C)c4nccnc34)nc2)CC1]

The title compound was prepared in analogy to the procedure described in Step 14.1 but using 8-(2-chloro-5-methoxy-3,6-dimethyl-phenyl)-quinoxaline-5-carboxylic acid (Step 98.1), 5-(4-ethyl-piperazin-1-ylmethyl)-pyridin-2-ylamine hydrochloride (Step 26.1) and stirring the reaction mixture for 20 h at rt. The crude product was purified by silica gel column chromatography (DCM/MeOH/NH$_3$$^{aq}$, 94:5:1). Title compound: ESI-MS: 545.0 [M+H]$^+$; $t_R$=3.91 min (System 1); TLC: R$_f$=0.23 (DCM/MeOH/NH$_3$$^{aq}$, 94:5:1).

Step 98.1: 8-(2-Chloro-5-methoxy-3,6-dimethyl-phenyl)-quinoxaline-5-carboxylic acid Sulfuryl chloride (29 µL, 0.37 mmol) in CH$_3$CN (1 mL) was added dropwise to a cold (−5° C.) suspension of 8-(3-methoxy-2,5-dimethyl-phenyl)-quinoxaline-5-carboxylic acid (Step 97.1) (113 mg, 0.37 mmol) in CH$_3$CN (4 mL). The reaction mixture was stirred for 10 min at −5° C., quenched by addition of H$_2$O (1 mL) and filtered to afford 42 mg of the title compound as a yellow solid. Title compound: ESI-MS: 343.0 [M+H]$^+$; $t_R$=4.90 min (System 1).

EXAMPLE 99

8-(2,5-Dimethyl-1-oxy-pyridin-3-yl)-quinoxaline-5-carboxylic acid [5-(4-ethyl-piperazin-1-ylmethyl)-pyridin-2-yl]-amide

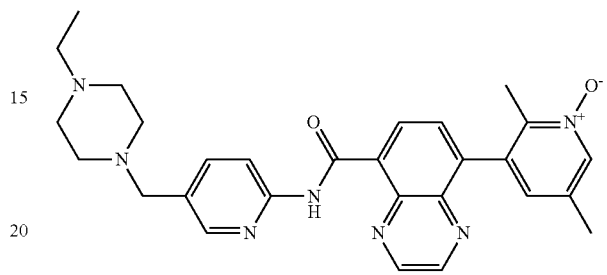

The title compound was prepared in analogy to the procedure described in Step 14.1 but using 8-(2,5-dimethyl-1-oxy-pyridin-3-yl)-quinoxaline-5-carboxylic acid (Step 99.1), 5-(4-ethyl-piperazin-1-ylmethyl)-pyridin-2-ylamine hydrochloride (Step 26.1) and stirring the reaction mixture for 24 h at rt. The crude product was purified by silica gel column chromatography (DCM/MeOH/NH$_3$$^{aq}$, 91.5:7.5:1), followed by trituration in Et$_2$O. Title compound: ESI-MS: 498.2 [M+H]$^+$; $t_R$=2.41 min (System 1); TLC: R$_f$=0.09 (DCM/MeOH/NH$_3$$^{aq}$, 91.5:7.5:1).

Step 99.1: 8-(2,5-Dimethyl-1-oxy-pyridin-3-yl)-quinoxaline-5-carboxylic acid

The title compound was prepared in analogy to the procedures described in Steps 1.2-1.3 but with the following modifications. In Step 1.2, 8-(2,5-dimethyl-1-oxy-pyridin-3-yl)-quinoxaline-5-carbonitrile (Step 99.2) was used; the reaction mixture was stirred at 150° C. for 1 h; the aqueous phase was acidified to pH 1 by addition of 6 N HCl and extracted with DCM; the organic phase was concentrated to afford the title compound. Title compound: ESI-MS: 296.1 [M+H]$^+$; $t_R$=2.51 min (System 1).

Step 99.2: 8-(2,5-Dimethyl-1-oxy-pyridin-3-yl)-quinoxaline-5-carbonitrile mCPBA (55% in H$_2$O, 215 mg, 0.68 mmol, 1.2 equiv) was added to a cold (5° C.) solution of 8-(2,5-dimethyl-pyridin-3-yl)-quinoxaline-5-carbonitrile (Step 99.3) (148 mg, 0.57 mmol) in DCM (3 mL). The reaction mixture was stirred at 5° C. for 20 min, diluted with DCM/saturated solution of NaHCO$_3$ and extracted with DCM. The organic phase was washed with H$_2$O and brine, dried (Na$_2$SO$_4$), filtered and concentrated to afford 106 mg of the title compound as a white solid. Title compound: ESI-MS: 277.2 [M+H]$^+$; $t_R$=2.84 min (System 1).

Step 99.3: 8-(2,5-Dimethyl-pyridin-3-yl)-quinoxaline-5-carbonitrile

A mixture of 5-bromo-8-(2,5-dimethyl-pyridin-3-yl)-quinoxaline (Step 99.4) (189 mg, 0.60 mmol) and CuCN (70 mg, 0.78 mmol, 1.3 equiv) in NMP (2 mL) was stirred for 6 h at 160° C., under an argon atmosphere. The reaction mixture was allowed to cool to rt, diluted with DCM/10% aqueous solution of ethylenediamine (25 mL), extracted with DCM. The organic phase was washed with H$_2$O and brine, dried (Na$_2$SO$_4$), filtered and concentrated. The residue was purified by silica gel column chromatography (DCM/MeOH/NH$_3^{aq}$, 94:5:1) to afford 150 mg of the title compound as a yellow solid. Title compound: ESI-MS: 261.2 [M+H]$^+$; t$_R$=1.92 min (System 1); TLC: R$_f$=0.68 (DCM/MeOH/NH$_3^{aq}$, 94:5:1).

Step 99.4:
5-Bromo-8-(2,5-dimethyl-pyridin-3-yl)-quinoxaline n-BuLi (1.6 M in hexanes, 6.7 mL, 10.8 mmol, 2.0 equiv) was added dropwise to a cold (−78° C.) solution of 3-bromo-2,5-dimethyl-pyridine (*Bulletin de la Societe Chimique de France*, 1972, (6), 2466-81) (1 g, 5.38 mmol) in Et$_2$O (20 mL), under an argon atmosphere. The reaction mixture was stirred for 1 h at −78° C. Triisopropyl borate (3.7 mL, 16.1 mmol, 3.0 equiv) was then added. The reaction mixture was allowed to warm to rt, quenched by addition of a saturated solution of NH$_4$Cl (1 mL), and concentrated. The residue was diluted with EtOAc/H$_2$O and the pH adjusted to 7. The aqueous layer was separated and extracted with EtOAc. The organic phase was dried (Na$_2$SO$_4$), filtered and concentrated to afford 170 mg of the title compound as a beige solid (batch 1). The aqueous layer was concentrated, the residue combined with batch 1 and dissolved in EtOH (5 mL). This solution was added to a mixture of 5,8-dibromo-quinoxaline (800 mg, 2.8 mmol) (Step 1.5), PdCl$_2$(dppf) (113 mg, 0.1 mmol, 0.05 equiv), Na$_2$CO$_3$ (2 M solution in H$_2$O, 5.6 mL, 11.1 mmol, 4 equiv) in toluene (30 mL) at 105° C., under an argon atmosphere. The reaction mixture was stirred at 105° C. for 4 h, allowed to cool to rt, diluted with EtOAc and H$_2$O, and extracted with EtOAc. The organic phase was washed with H$_2$O and brine, dried (Na$_2$SO$_4$), filtered and concentrated in vacuo. The crude product was purified by silica gel column chromatography (Hex/EtOAc, 1:4) to afford 250 mg of the title compound as a purple solid: ES-MS: 314.0/316.0 [M+H]$^+$; t$_R$=2.63 min (System 1); R$_f$=0.09 (Hex/EtOAc, 1:4).

EXAMPLE 100

8-(2,6-Dichloro-3,5-dimethoxy-phenyl)-quinoxaline-5-carboxylic acid [5-((R)-3-hydroxy-pyrrolidin-1-ylmethyl)-pyridin-2-yl]-amide

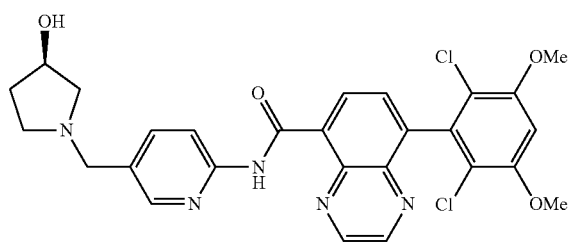 [SMILES: COc1cc(OC)c(Cl)c(-c2ccc(C(=O)Nc3ccc(CN4CC[C@@H](O)C4)cn3)c3nccnc23)c1Cl]

The title compound was prepared in analogy to the procedure described in Step 14.1 but using (R)-1-(6-amino-pyridin-3-ylmethyl)-pyrrolidin-3-ol (Step 100.1) and stirring the reaction mixture for 72 h at rt. The crude product was purified by silica gel column chromatography (DCM/NH$_3^{aq}$, 99:1→DCM/MeOH/NH$_3^{aq}$, 96:3:1). Title compound: ESI-MS: 554.0/556.2 [M+H]$^+$; t$_R$=3.77 min (System 1); TLC: R$_f$=0.29 (DCM/MeOH, 9:1).

Step 100.1: (R)-1-(6-Amino-pyridin-3-ylmethyl)-pyrrolidin-3-ol

A mixture of [5-((R)-3-hydroxy-pyrrolidin-1-ylmethyl)-pyridin-2-yl]carbamic acid tert-butyl ester (Step 100.2) (210 mg, 0.72 mmol), a 4 N solution of HCl in dioxane (2 mL), and MeOH (2 mL) was stirred for 16 h at rt and concentrated. The residue was purified by silica gel column chromatography (DCM/MeOH/NH$_3^{aq}$, 89:10:1) to afford 125 mg of the title compound as a yellow oil. Title compound: ESI-MS: 194.1 [M+H]$^+$; TLC: R$_f$=0.05 (DCM/MeOH, 9:1).

Step 100.2: [5-((R)-3-Hydroxy-pyrrolidin-1-ylmethyl)-pyridin-2-yl]-carbamic acid tert-butyl ester A mixture of (5-methyl-pyridin-2-yl)-carbamic acid tert-butyl ester (Step 100.3) (10.7 g, 51.4 mmol), NBS (10.1 g, 56.7 mmol, 1.1 equiv), AIBN (843 mg, 5.14 mmol, 0.1 equiv) in CCl$_4$ (500 mL) was stirred for 1 h at relfux. NBS (1.8 g, 10.1 mmol, 0.2 equiv) was added and the mixture was stirred at reflux for additional 30 min. The reaction mixture was filtered hot and the filtrate was concentrated. Trituration of the residue in CH$_3$CN afforded of 12.88 g of impure (5-bromomethyl-pyridin-2-yl)-carbamic acid tert-butyl ester (intermediate 100.2). (R)-3-Hydroxypyrrolidine (181 mg, 2.1 mmol, 1.2 equiv) was added to a mixture of intermediate 100.2 (500 mg, 1.75 mmol) and Cs$_2$CO$_3$ (684 mg, 2.1 mmol, 1.2 equiv) in DMF (5 ml). The reaction mixture was stirred for 24 h at rt, quenched by addition of a saturated aqueous solution of NaHCO$_3$ (150 mL) and extracted with EtOAc. The organic layer was washed with a saturated aqueous solution of NaHCO$_3$, dried (Na$_2$SO$_4$), filtered and concentrated. The residue was purified by silica gel column chromatography (DCM/NH$_3^{aq}$, 99:1→DCM/MeOH/NH$_3^{aq}$, 96:3:1) to afford 212 mg of the title compound as a white solid. Title compound: ESI-MS: 294.3 [M+H]$^+$; t$_R$=1.95 min (System 1); TLC: R$_f$=0.14 (DCM/MeOH, 9:1).

Step 100.3: (5-Methyl-pyridin-2-yl)-carbamic acid tert-butyl ester

A solution of di-tert-butyl dicarbonate (33.3 g, 153 mmol, 1.1 equiv) in DCM (50 mL) was added dropwise to a solution of 2-amino-5-methylpyridine (15 g, 139 mmol) and DMAP (1.7 g, 13.9 mmol, 0.1 equiv) in DCM (50 mL) at rt, under an argon atmosphere. The reaction mixture was stirred for 16 h at rt, quenched by addition of a saturated aqueous solution of NaHCO$_3$ (100 mL) and extracted with DCM. The organic phase was washed with a saturated aqueous solution of NaHCO$_3$, dried (Na$_2$SO$_4$), filtered and concentrated. The residue was purified by silica gel column chromatography (Hex/EtOAc, 9:1) to afford 11.73 g of the title compound as a white solid. Title compound: ESI-MS: 209.2 [M+H]+; $t_R$=2.40 min (System 1); TLC: $R_f$=0.86 (Hex/EtOAc, 1:1).

EXAMPLE 101

8-(2,6-Dichloro-3,5-dimethoxy-phenyl)-quinoxaline-5-carboxylic acid [5-((S)-3-hydroxy-pyrrolidin-1-ylmethyl)-pyridin-2-yl]-amide

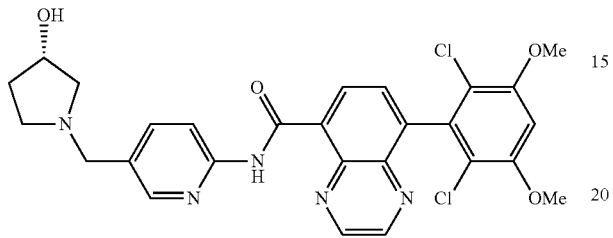

The title compound was prepared in analogy to the procedure described in Step 14.1 but using (S)-1-(6-amino-pyridin-3-ylmethyl)-pyrrolidin-3-ol (Step 101.1) and stirring the reaction mixture for 20 h at rt. The crude product was purified by silica gel column chromatography (DCM/NH$_3^{aq}$, 99:1→DCM/MeOH/NH$_3^{aq}$, 96:3:1). Title compound: ESI-MS: 553.9/556.2 [M+H]+; $t_R$=3.79 min (System 1); TLC: $R_f$=0.25 (DCM/MeOH, 9:1).

Step 101.1: (S)-1-(6-Amino-pyridin-3-ylmethyl)-pyrrolidin-3-ol

The title compound was prepared in analogy to the procedures described in Steps 100.1-100.2 but using (S)-3-hydroxypyrrolidine in Step 100.2: 194.2 [M+H]+; TLC: $R_f$=0.05 (DCM/MeOH, 9:1).

EXAMPLE 102

8-(2,6-Dichloro-3,5-dimethoxy-phenyl)-quinoxaline-5-carboxylic acid [5-(4-acetyl-piperazin-1-ylmethyl)-pyridin-2-yl]-amide

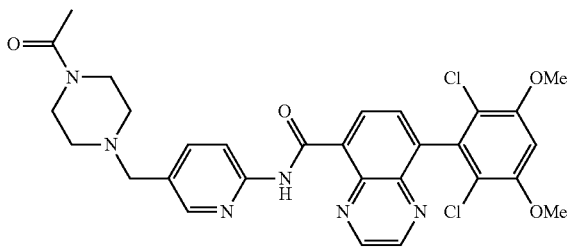 [SMILES: COc1cc(OC)c(Cl)c(-c2ccc(C(=O)Nc3ccc(CN4CCN(C(C)=O)CC4)cn3)c3nccnc23)c1Cl]

The title compound was prepared in analogy to the procedure described in Step 14.1 but using 1-[4-(6-amino-pyridin-3-ylmethyl)-piperazin-1-yl]-ethanone (Step 102.1) and stirring the reaction mixture for 20 h at rt. The crude product was purified by silica gel column chromatography (DCM/NH$_3^{aq}$, 99:1→DCM/MeOH/NH$_3^{aq}$, 98:1:1). Title compound: ESI-MS: 595.0/597.2 [M+H]+; $t_R$=3.82 min (System 1); TLC: $R_f$=0.42 (DCM/MeOH, 9:1).

Step 102.1: 1-[4-(6-Amino-pyridin-3-ylmethyl)-piperazin-1-yl]-ethanone

The title compound was prepared in analogy to the procedures described in Steps 100.1-100.2 but using 1-acetylpiperazine in Step 100.2: 235.3 [M+H]+; TLC: $R_f$=0.36 (DCM/MeOH, 9:1).

EXAMPLE 103

8-(2,6-Dichloro-3,5-dimethoxy-phenyl)-quinoxaline-5-carboxylic acid [5-(3-oxo-piperazin-1-ylmethyl)-pyridin-2-yl]-amide

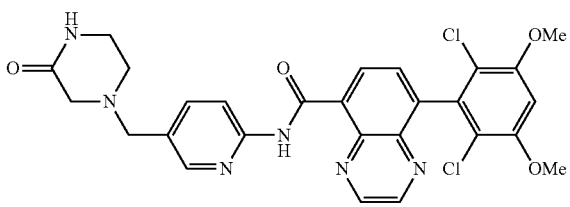 [SMILES: COc1cc(OC)c(Cl)c(-c2ccc(C(=O)Nc3ccc(CN4CCNC(=O)C4)cn3)c3nccnc23)c1Cl]

The title compound was prepared in analogy to the procedure described in Step 14.1 but using 4-(6-amino-pyridin-3-ylmethyl)-piperazin-2-one (Step 103.1) and stirring the reaction mixture for 72 h at rt. The crude product was purified by silica gel column chromatography (DCM/MeOH/NH$_3^{aq}$, 98:1:1) followed by trituration in Et$_2$O. Title compound: ESI-MS: 567.0/568.7 [M+H]+; $t_R$=3.68 min (System 1); TLC: $R_f$=0.27 (DCM/MeOH, 9:1).

Step 103.1: 4-(6-Amino-pyridin-3-ylmethyl)-piperazin-2-one

The title compound was prepared in analogy to the procedures described in Steps 100.1-100.2 but using piperazin-2-one in Step 100.2: 207.2 [M+H]+; TLC: $R_f$=0.14 (DCM/MeOH, 9:1).

EXAMPLE 104

8-(2,6-Dichloro-3,5-dimethoxy-phenyl)-quinoxaline-5-carboxylic acid [5-(1,1-dioxothiomorpholin-4-ylmethyl)-pyridin-2-yl]-amide

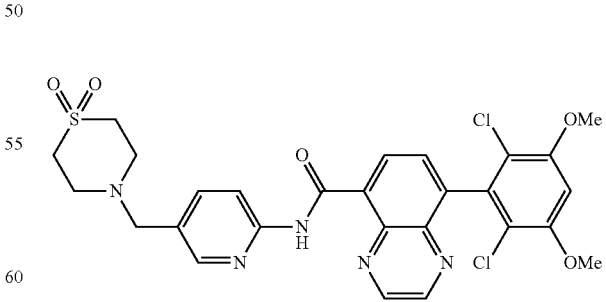

The title compound was prepared in analogy to the procedure described in Step 14.1 but using 5-(1,1-dioxothiomorpholin-4-ylmethyl)-pyridin-2-ylamine (Step 104.1) and stirring the reaction mixture for 72 h at rt. The crude product was purified by silica gel column chromatography (DCM/NH$_3^{aq}$, 99:1→DCM/MeOH/NH$_3^{aq}$, 95:4:1) followed by trituration in Et$_2$O. Title compound: ESI-MS: 602.0 [M+H]$^+$; t$_R$=4.01 min (System 1); TLC: R$_f$=0.38 (DCM/MeOH, 9:1).

Step 104.1: 5-(1,1-Dioxothiomorpholin-4-ylmethyl)-pyridin-2-ylamine

The title compound was prepared in analogy to the procedures described in Steps 100.1-100.2 but using thiomorpholine-1,1-dioxide in Step 100.2: 242.2 [M+H]$^+$; TLC: R$_f$=0.33 (DCM/MeOH, 9:1).

EXAMPLE 105

8-(2,6-Dichloro-3,5-dimethoxy-phenyl)-quinoxaline-5-carboxylic acid (5-piperazin-1-ylmethyl-pyridin-2-yl)-amide Intermediate 105 was prepared in analogy to the procedure described in Step 14.1 but using 5-[4-(4-methoxy-benzyl)-piperazin-1-ylmethyl]-pyridin-2-ylamine (Step 105.1) and stirring the reaction mixture for 72 h at rt: ESI-MS: 673.0 [M+H]$^+$; TLC: R$_f$=0.51 (DCM/MeOH, 9:1).

A mixture of intermediate 105 (200 mg, 0.3 mmol) and TFA (5 mL) was stirred for 2 h at 120° C. in a microwave apparatus. The reaction mixture was neutralized by addition of NaHCO$_3$, extracted with EtOAc. The organic layer was washed with brine, dried (Na$_2$SO$_4$), filtered and concentrated. The residue was purified by silica gel column chromatography (DCM/NH$_3^{aq}$, 99:1→DCM/MeOH/NH$_3^{aq}$, 95:4:1) followed by trituration in Et$_2$O to afford 100 mg of the title

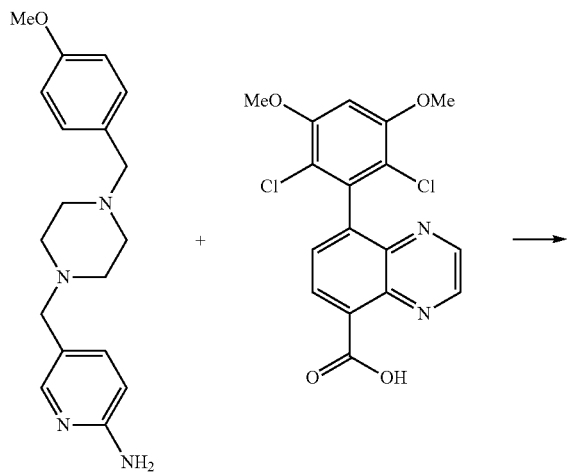

Step 105.1        Step 1.1

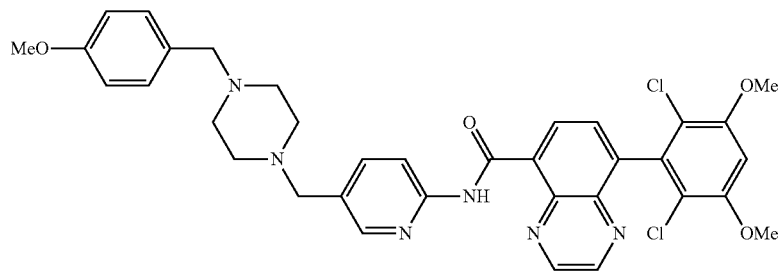

Intermediate 105

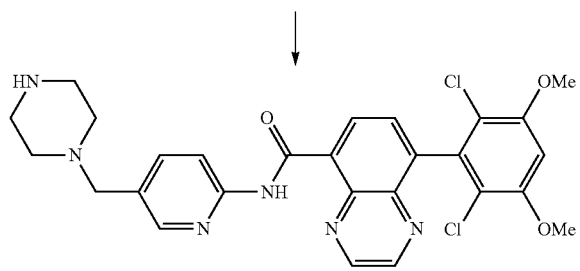

Example 105 compound as a yellow solid. Title compound: ESI-MS: 552.9/555.2 [M+H]$^+$; $t_R$=3.42 min (System 1); TLC: $R_f$=0.09 (DCM/MeOH, 9:1).

Step 105.1: 5-[4-(4-Methoxy-benzyl)-piperazin-1-ylmethyl]-pyridin-2-ylamine

The title compound was prepared in analogy to the procedures described in Steps 100.1-100.2 but using 1-(4-methoxybenzyl)piperazine in Step 100.2: 313.3 [M+H]$^+$.

EXAMPLE 106

8-(2,6-Dichloro-3,5-dimethoxy-phenyl)-quinoxaline-5-carboxylic acid {5-[4-(2-hydroxy-ethyl)-piperazin-1-ylmethyl]-pyridin-2-yl}-amide

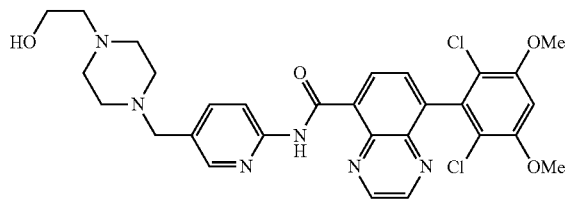 [SMILES: COc1cc(OC)c(Cl)c(-c2ccc(C(=O)Nc3ccc(CN4CCN(CCO)CC4)cn3)c3nccnc23)c1Cl]

2-Iodoethanol (26 µL, 0.33 mmol, 10 equiv) was added to a mixture of 8-(2,6-dichloro-3,5-dimethoxy-phenyl)-quinoxaline-5-carboxylic acid (5-piperazin-1-ylmethyl-pyridin-2-yl)-amide (Example 105) (18 mg, 0.033 mmol) in CH$_3$CN (1 mL), under an argon atmosphere. The reaction mixture was stirred for 14 h at rt, quenched by addition of a saturated aqueous solution of NaHCO$_3$ (50 mL) and extracted with EtOAc. The organic layer was washed with a saturated aqueous solution of NaHCO$_3$, dried (Na$_2$SO$_4$), filtered and concentrated. The residue was purified by silica gel column chromatography (DCM/NH$_3$$^{aq}$, 99:1→DCM/MeOH/NH$_3$$^{aq}$, 96:3:1) to afford 15 mg of the title compound as a yellow solid. Title compound: ESI-MS: 596.6/598.4 [M+H]$^+$; $t_R$=3.45 min (System 1); TLC: $R_f$=0.30 (DCM/MeOH, 9:1).

EXAMPLE 107

8-(2,6-Dichloro-3,5-dimethoxy-phenyl)-quinoxaline-5-carboxylic acid [5-(3,3,4-trimethyl-piperazin-1-ylmethyl)-pyridin-2-yl]-amide

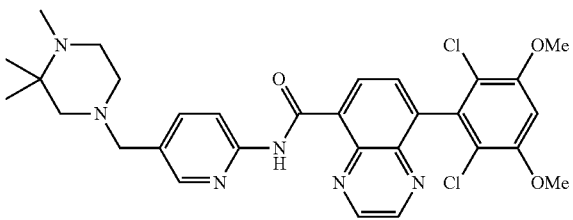 [SMILES: COc1cc(OC)c(Cl)c(-c2ccc(C(=O)Nc3ccc(CN4CCN(C)C(C)(C)C4)cn3)c3nccnc23)c1Cl]

The title compound was prepared in analogy to the procedure described in Step 14.1 but using 5-(3,3,4-trimethyl-piperazin-1-ylmethyl)-pyridin-2-ylamine (Step 107.1) and stirring the reaction mixture for 20 h at rt. The crude product was purified by silica gel column chromatography (DCM/NH$_3$$^{aq}$, 99:1→DCM/MeOH/NH$_3$$^{aq}$, 97:2:1) followed by trituration in Et$_2$O. Title compound: ESI-MS: 595.0/597.3 [M+H]$^+$; $t_R$=4.40 min (System 1); TLC: $R_f$=0.36 (DCM/MeOH, 9:1).

Step 107.1: 5-(3,3,4-Trimethyl-piperazin-1-ylmethyl)-pyridin-2-ylamine

The title compound was prepared in analogy to the procedures described in Steps 100.1-100.2 but using 1,2,2-trimethyl-piperazine (Step 107.2) in Step 100.2: 253.3 [M+H]$^+$; TLC: $R_f$=0.09 (DCM/MeOH, 9:1).

Step 107.2: 1,2,2-Trimethyl-piperazine

LiAlH$_4$ (1M in THF, 47 mL, 47 mmol, 1.5 equiv) was added to a solution of 3,3,4-trimethyl-piperazin-2-one (Step 107.3) (4.5 g, 32 mmol) in THF (50 mL) at 50° C., under an argon atmosphere. The resulting mixture was stirred for 2 h at 50° C., quenched by addition of acetone, filtered through a pad of celite and concentrated. The residue was purified by silica gel column chromatography (DCM/MeOH/NH$_3$$^{aq}$, 94:5:1) to afford 1.9 g of the title compound as a yellow oil. Title compound: ESI-MS: 129.1 [M+H]$^+$.

Step 107.3: 3,3,4-Trimethyl-piperazin-2-one

A mixture of ethyl-2-bromoisobutyrate (14.6 g, 74.9 mmol), ethylene diamine (33 mL, 487 mmol, 6.5 equiv) and potassium carbonate (11.4 g, 82.4 mmol, 1.1 equiv) in toluene (150 mL) was stirred for 22 h at reflux, cooled and filtered. The filtrate was concentrated and the residue triturated in Et$_2$O to afford 6.3 g of 3,3-dimethyl-piperazin-2-one as a white solid. Methyl iodide (4 mL, 64.0 mmol, 1.3 equiv) was added dropwise to a suspension of 3,3-dimethyl-piperazin-2-one (6.3 g, 49.2 mmol) and potassium carbonate (8.8 g, 64.0 mmol, 1.3 equiv) in DME (20 mL). The reaction mixture was heated to 45° C., stirred for 3 h, cooled and filtered, washing the filter cake with DME. The filtrate was concentrated and the residue triturated in DME to afford 2.8 g (batch 1) of the title compound as a white solid. The filtrate from the trituration was concentrated and the residue purified by silica gel column chromatography (DCM/MeOH, 9:1) to afford 1.75 g (batch 2) of the title compound as a white solid. Title compound: ESI-MS: 143.1 [M+H]$^+$; TLC: $R_f$=0.25 (DCM/MeOH, 9:1).

EXAMPLE 108

8-(2,6-Dichloro-3,5-dimethoxy-phenyl)-quinoxaline-5-carboxylic acid [5-(3,3,4-trimethyl-piperazin-1-ylmethyl)-pyridin-2-yl]-amide

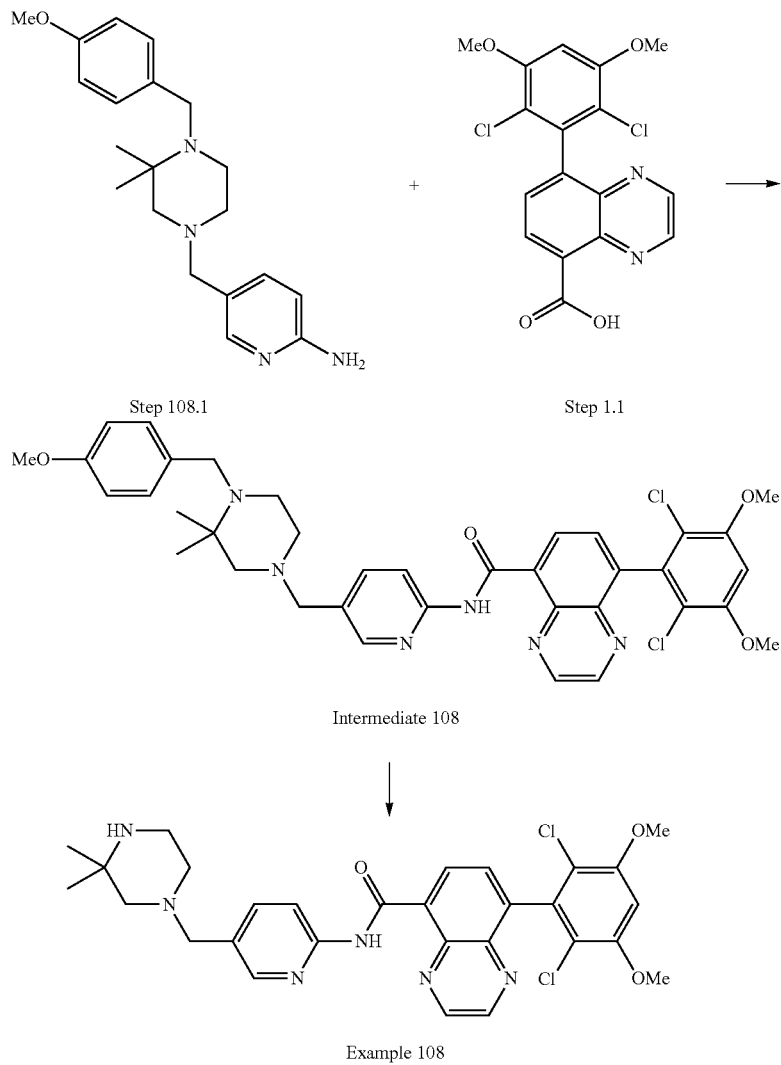

Intermediate 108 was prepared in analogy to the procedures described in Step 14.1 but using 5-[4-(4-methoxy-benzyl)-3,3-dimethyl-piperazin-1-ylmethyl]-pyridin-2-ylamine (Step 108.1) and stirring the reaction mixture for 20 h at rt: ESI-MS: 701.0 [M+H]$^+$; $t_R$=4.88 min (System 1);

The title compound was prepared in analogy to the procedure described in Example 105. Title compound: ESI-MS: 581.0/583.2 [M+H]$^+$; $t_R$=4.20 min (System 1); TLC: R$_f$=0.09 (DCM/MeOH, 9:1).

Step 108.1: 5-[4-(4-Methoxy-benzyl)-3,3-dimethyl-piperazin-1-ylmethyl]-pyridin-2-ylamine The title compound was prepared in analogy to the procedures described in Steps 100.1-100.2 but using 1-(4-methoxy-benzyl)-2,2-dimethyl-piperazine (Step 108.2) in Step 100.2: ESI-MS: 341.3 [M+H]$^+$; TLC: R$_f$=0.30 (DCM/MeOH, 9:1).

Step 108.2:
1-(4-Methoxy-benzyl)-2,2-dimethyl-piperazine

LiAlH$_4$ (1M in THF, 27.8 mL, 27.8 mmol, 1.5 equiv) was added to a solution of 4-(4-methoxy-benzyl)-3,3-dimethyl-piperazin-2-one (Step 108.3) (4.6 g, 18.5 mmol) in THF (100 mL) at 50° C., under an argon atmosphere. The resulting mixture was stirred for 2 h at 50° C., quenched by sequential addition of H$_2$O (1 mL), 1 N NaOH (1 mL) and H$_2$O (3 mL), filtered through a pad of celite and concentrated to afford 4.0 g of the title compound as a white solid: ESI-MS: 235.2 [M+H]$^+$.

Step 108.3:
4-(4-Methoxy-benzyl)-3,3-dimethyl-piperazin-2-one

A mixture of 3,3-dimethyl-piperazin-2-one (Step 108.4) (3.7 g, 28.9 mmol), 4-methoxybenzyl bromide (5.4 mL, 37.6 mmol, 1.3 equiv) and triethylamine (5.2 mL, 37.6 mmol, 1.3 equiv) in DCM (60 mL) was stirred for 48 h at rt. Additional 5.0 mL of 4-methoxybenzyl bromide were added and the mixture was stirred for 72 h at rt, then concentrated. The residue was diluted with DCM/saturated aqueous solution of NaHCO$_3$. The aqueous phase was separated and extracted with DCM. The organic phase was washed with H$_2$O and brine, dried (Na$_2$SO$_4$), filtered and concentrated. The residue was triturated in DCM to provide 3.95 g of the title compound as a white solid: ESI-MS: 249.2 [M+H]$^+$; TLC: R$_f$=0.16 (Hex/EtOAc, 2:3).

Step 108.4: 3,3-Dimethyl-piperazin-2-one

A solution of ethyl-2-bromoisobutyrate (24 mL, 161 mmol) in toluene (150 mL) was added to a mixture of ethylene diamine (70 mL, 1046 mmol, 6.5 equiv) and potassium carbonate (24.4 g, 177 mmol, 1.1 equiv) in toluene (150 mL). The reaction mixture was heated for 20 h at 115° C., cooled and filtered. The filtrate was concentrated and the residue triturated in Et$_2$O to afford 14.2 g of the title compound as a yellow solid: ESI-MS: 129.1 [M+H]$^+$.

EXAMPLE 109

8-(2,6-Dichloro-3,5-dimethoxy-phenyl)-quinoxaline-5-carboxylic acid [5-(2,2-dimethyl-piperazin-1-ylmethyl)-pyridin-2-yl]-amide

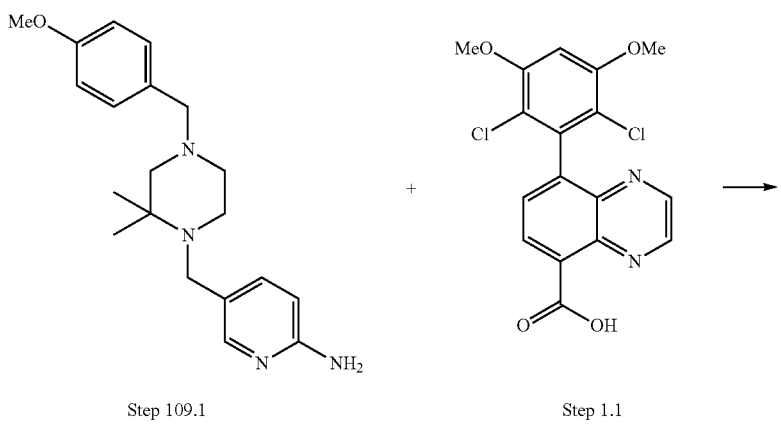

Step 109.1     Step 1.1

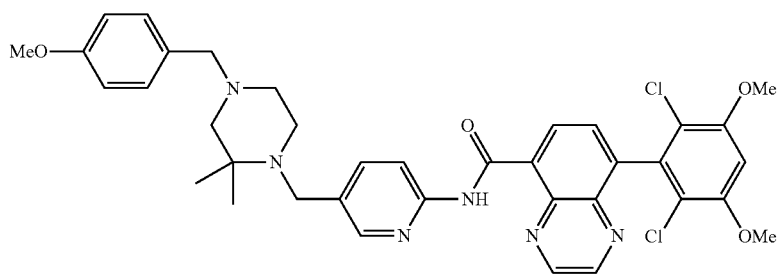

Intermediate 109

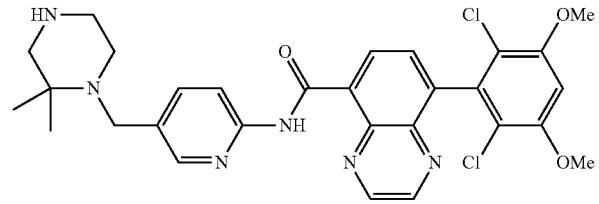

Example 109

Intermediate 109 was prepared in analogy to the procedure described in Step 14.1 but using 5-[4-(4-methoxy-benzyl)-2,2-dimethyl-piperazin-1-ylmethyl]-pyridin-2-ylamine (Step 109.1) and stirring the reaction mixture for 20 h at rt: ESI-MS: 701.0/583.2 [M+H]$^+$; TLC: R$_f$=0.40 (DCM/MeOH, 9:1).

The title compound was prepared in analogy to the procedure described in Example 105. Title compound: ESI-MS: 581.0/582.8 [M+H]$^+$; t$_R$=3.53 min (System 1); TLC: R$_f$=0.14 (DCM/MeOH, 9:1).

Step 109.1: 5-[4-(4-Methoxy-benzyl)-2,2-dimethyl-piperazin-1-ylmethyl]-pyridin-2-ylamine A mixture of {5-[4-(4-methoxy-benzyl)-2,2-dimethyl-piperazin-1-ylmethyl]-pyridin-2-yl}-carbamic acid tert-butyl ester (Step 109.2) (1.88 g, 4.3 mmol), a 4 N solution of HCl in dioxane (25 mL) and MeOH (25 mL) was stirred for 22 h at rt. The reaction mixture was allowed to cool, quenched by addition of a saturated aqueous solution of NaHCO$_3$ and extracted with DCM. The organic layer was washed with a saturated aqueous solution of NaHCO$_3$, dried (Na$_2$SO$_4$), filtered and concentrated to provide 1.5 g of the title compound as a brown solid: ESI-MS: 341.3 [M+H]$^+$;]$^+$; t$_R$=1.72 min (System 1).

Step 109.2: {5-[4-(4-Methoxy-benzyl)-2,2-dimethyl-piperazin-1-ylmethyl]-pyridin-2-yl}-carbamic acid tert-butyl ester A mixture of [5-(2,2-dimethyl-piperazin-1-ylmethyl)-pyridin-2-yl]carbamic acid tert-butyl ester (Step 109.3) (3.85 g, 12 mmol), 4-methoxybenzyl bromide (2.6 mL, 18 mmol, 1.5 equiv) and triethylamine (1.83 mL, 13.2 mmol, 1.1 equiv) in DCM (25 mL) was stirred for 16 h at rt and concentrated. The residue was purified by silica gel column chromatography (DCM DCM/MeOH, 97:3) to afford 1.88 g of the title compound as a white solid. Title compound: ESI-MS: 441.3 [M+H]$^+$; t$_R$=3.12 min (System 1).

Step 109.3: [5-(2,2-Dimethyl-piperazin-1-ylmethyl)-pyridin-2-yl]-carbamic acid tert-butyl ester LiAlH$_4$ (1M in THF, 78 mL, 78 mmol, 2 equiv) was added to a solution of [5-(2,2-dimethyl-3-oxo-piperazin-1-ylmethyl)-pyridin-2-yl]-carbamic acid tert-butyl ester (Step 109.4) (13 g, 39 mmol) in THF (150 mL) at 50° C., under an argon atmosphere. The resulting mixture was stirred for 3 h at 50° C., cooled to 0° C., quenched by addition of acetone, filtered through a pad of celite and the filtrate was concentrated. The residue was purified by silica gel column chromatography (DCM/MeOH/NH$_3^{aq}$, 97.5:1.5:1) to afford 7.25 g of the title compound as a white solid. Title compound: ESI-MS: 321.3 [M+H]$^+$; t$_R$=1.91 min (System 1); TLC: R$_f$=0.11 (DCM/MeOH, 9:1).

Step 109.4: [5-(2,2-Dimethyl-3-oxo-piperazin-1-ylmethyl)-pyridin-2-yl]-carbamic acid tert-butyl ester A mixture of intermediate 100.2 (Step 100.2) (18.4 g, 64 mmol), 3,3-dimethyl-piperazin-2-one (Step 108.4) (9 g, 70 mmol, 1.1 equiv) and Cs$_2$CO$_3$ (27.1 g, 83.2 mmol, 1.3 equiv) in DMF (75 ml) was stirred for 12 h at rt, quenched by addition of H$_2$O (500 mL) and filtered to afford 14.5 g of the title compound as an off-white solid. Title compound: ESI-MS: 335.2 [M+H]$^+$; t$_R$=2.22 min (System 1).

EXAMPLE 110

8-(2,6-Dichloro-3,5-dimethoxy-phenyl)-quinoxaline-5-carboxylic acid [5-(2,2,4-trimethyl-piperazin-1-ylmethyl)-pyridin-2-yl]-amide

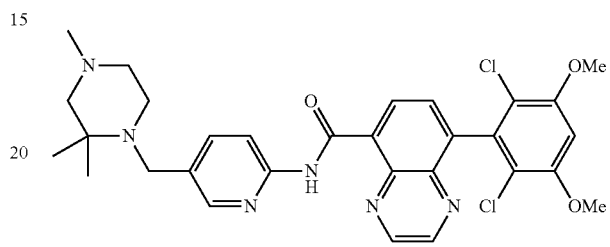

The title compound was prepared in analogy to the procedure described in Step 14.1 but using 5-[4-(4-methoxy-benzyl)-2,2-dimethyl-piperazin-1-ylmethyl]-pyridin-2-ylamine (Step 110.1) and stirring the reaction mixture for 20 h at rt. The crude product was purified by silica gel column chromatography (DCM/MeOH/NH$_3^{aq}$, 98:1:1) followed by trituration in Et$_2$O. Title compound: ESI-MS: 595.0/597.2 [M+H]$^+$; t$_R$=3.74 min (System 1); TLC: R$_f$=0.47 (DCM/MeOH, 9:1).

Step 110.1: 5-(2,2,4-Trimethyl-piperazin-1-ylmethyl)-pyridin-2-ylamine

A mixture of [5-(2,2,4-trimethyl-piperazin-1-ylmethyl)-pyridin-2-yl]-carbamic acid tert-butyl ester (Step 110.2) (1.94 g, 5.8 mmol), a 4 N solution of HCl in dioxane (20 mL) and MeOH (5 mL) was stirred for 12 h at rt and concentrated. The residue was purified by silica gel column chromatography (DCM/NH$_3^{aq}$, 99:1→DCM/MeOH/NH$_3^{aq}$, 95:4:1) to afford 1.02 g of the title compound as a white solid. Title compound: ESI-MS: 235.2 [M+H]$^+$; TLC: R$_f$=0.11 (DCM/MeOH, 9:1).

Step 110.2: [5-(2,2,4-Trimethyl-piperazin-1-ylmethyl)-pyridin-2-yl]-carbamic acid tert-butyl ester Methyl iodide (954 µL, 15.3 mmol, 1.3 equiv) was added dropwise to a suspension of [5-(2,2-dimethyl-piperazin-1-ylmethyl)-pyridin-2-yl]-carbamic acid tert-butyl ester (Step 109.3) (3.8 g, 11.8 mmol) and potassium carbonate (2.13 g, 15.4 mmol, 1.3 equiv) in DME (25 mL). The reaction mixture was heated to 50° C., stirred for 2 h, allowed to cool, quenched by addition of a H$_2$O and extracted with DCM. The organic layer was washed with a saturated aqueous solution of NaHCO$_3$, dried (Na$_2$SO$_4$), filtered and concentrated. The residue was purified by silica gel column chromatography (DCM/MeOH/NH$_3^{aq}$, 98:1:1) to afford 1.94 g of the title compound as an off-white solid. Title compound: ESI-MS: 335.3 [M+H]$^+$; TLC: R$_f$=0.31 (DCM/MeOH, 9:1).

EXAMPLE 111

8-(2,6-Dichloro-3,5-dimethoxy-phenyl)-quinoxaline-5-carboxylic acid (6-piperazin-1-ylmethyl-pyridin-3-yl)-amide

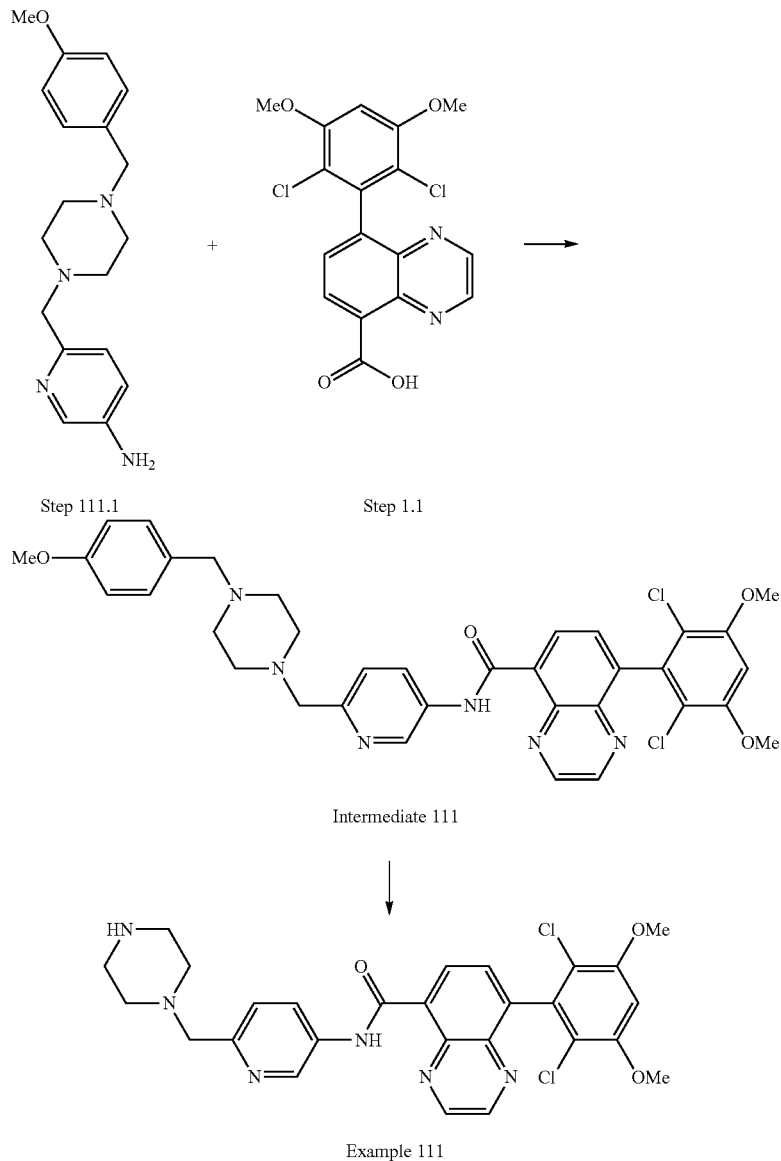

Intermediate 111 was prepared in analogy to the procedure described in Step 14.1 but using 6-[4-(4-methoxy-benzyl)-piperazin-1-ylmethyl]-pyridin-3-ylamine (Step 111.1) and stirring the reaction mixture for 14 h at rt: ESI-MS: 673.0 [M+H]$^+$; $t_R$=3.88 min (System 1). The title compound was prepared in analogy to the procedure described in Example 105 but stirring the reaction mixture for 1 h at 120° C.: ESI-MS: 553.0/554.8 [M+H]$^+$; $t_R$=3.34 min (System 1); TLC: R$_f$=0.05 (DCM/MeOH, 9:1).

Step 111.1: 6-[4-(4-Methoxy-benzyl)-piperazin-1-ylmethyl]-pyridin-3-ylamine

A suspension of 1-(4-methoxy-benzyl)-4-(5-nitro-pyridin-2-ylmethyl)-piperazine (Step 111.2) (0.635 g, 1.85 mmol) and Raney Nickel (0.150 g) in MeOH/THF (1:1, v/v; 50 mL) was stirred for 24 h at rt, under a hydrogen atmosphere. The mixture was filtered through a pad of celite and the filtrate was concentrated. The residue was purified by silica gel column chromatography (DCM/MeOH/NH$_3$$^{aq}$, 98:1:1) to afford 439 mg of the title compound as a white solid. Title compound: ESI-MS: 313.3 [M+H]$^+$; $t_R$=1.40 min (System 1); TLC: R$_f$=0.18 (DCM/MeOH, 9:1).

Step 111.2: 1-(4-Methoxy-benzyl)-4-(5-nitro-pyridin-2-ylmethyl)-piperazine

The title compound was prepared in analogy to the procedures described in Steps 39.1-39.2 but using 1-(4-methoxybenzyl)piperazine, 3 equiv of sodium triacetoxyborohydride and stirring the reaction mixture for 20 h at rt, in Step 39.2. Title compound: ESI-MS: 343.2 [M+H]$^+$; $t_R$=2.50 min (System 1); TLC: $R_f$=0.40 (DCM/MeOH, 9:1).

EXAMPLE 112

8-(2,6-Dichloro-3,5-dimethoxy-phenyl)-quinoxaline-5-carboxylic acid [6-(3,3-dimethyl-piperazin-1-ylmethyl)-pyridin-3-yl]-amide Intermediate 112 was prepared in analogy to the procedure described in Step 14.1 but using 6-[4-(4-methoxy-benzyl)-3,3-dimethyl-piperazin-1-ylmethyl]-pyridin-3-ylamine (Step 112.1) and stirring the reaction mixture for 3 h at rt: ESI-MS: 700.9 [M+H]$^+$; $t_R$=4.00 min (System 1); TLC: $R_f$=0.45 (DCM/MeOH, 9:1).

The title compound was prepared in analogy to the procedure described in Example 105 but stirring the reaction mixture for 1 h at 120° C.: ESI-MS: 581.0/583.2 [M+H]$^+$; $t_R$=3.47 min (System 1); TLC: $R_f$=0.11 (DCM/MeOH, 9:1).

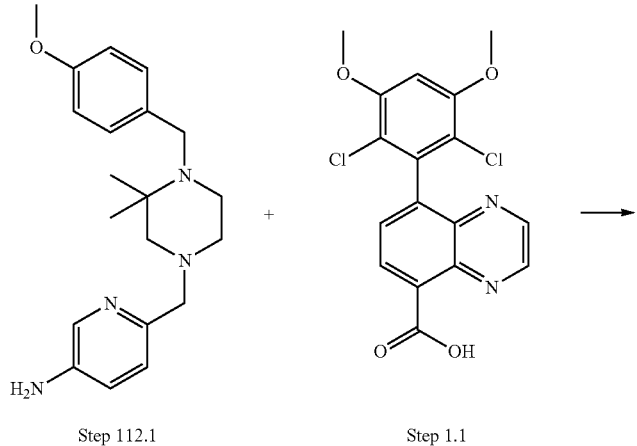

Step 112.1                Step 1.1

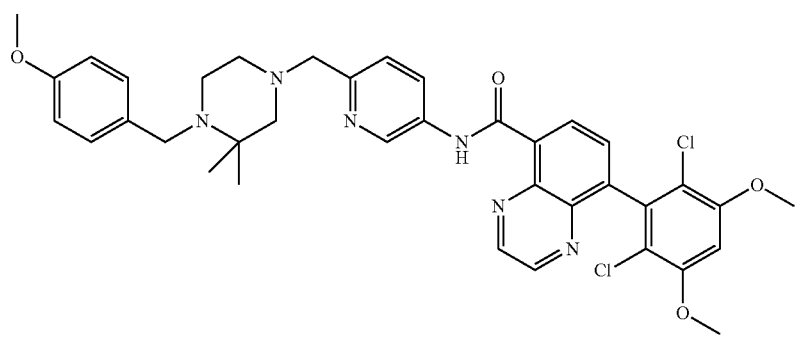

Intermediate 112

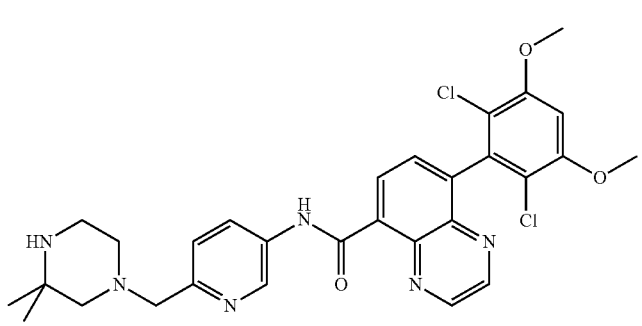

Example 112

Step 112.1: 6-[4-(4-Methoxy-benzyl)-3,3-dimethyl-piperazin-1-ylmethyl]-pyridin-3-ylamine A suspension of 1-(4-methoxy-benzyl)-2,2-dimethyl-4-(5-nitro-pyridin-2-ylmethyl)-piperazine (Step 112.2) (0.640 g, 1.72 mmol) and Raney Nickel (0.150 g) in MeOH/THF (1:1, v/v; 50 mL) was stirred for 20 h at rt, under a hydrogen atmosphere. The mixture was filtered through a pad of celite and the filtrate was concentrated. The residue was purified by silica gel column chromatography (DCM/NH$_3$$^{aq}$, 99:1→DCM/MeOH/NH$_3$$^{aq}$, 97:2:1) to afford 455 mg of the title compound as a yellow foam. Title compound: ESI-MS: 341.3 [M+H]$^+$; $t_R$=1.71 min (System 1); TLC: R$_f$=0.30 (DCM/MeOH, 9:1).

Step 112.2: 1-(4-Methoxy-benzyl)-2,2-dimethyl-4-(5-nitro-pyridin-2-ylmethyl)-piperazine A mixture of methanesulfonic acid 5-nitro-pyridin-2-ylmethyl ester (Step 112.3) (0.5 g, 2.16 mmol), 1-(4-methoxy-benzyl)-2,2-dimethyl-piperazine (Step 108.2) (0.655 g, 2.8 mmol, 1.3 equiv), cesium carbonate (0.845 g, 2.6 mmol, 1.2 equiv), and DMF (4 ml) was stirred for 5 h at rt, quenched by addition of a saturated aqueous solution of NaHCO$_3$ and extracted with EtOAc. The organic phase was washed with a saturated aqueous solution of NaHCO$_3$, dried (Na$_2$SO$_4$), filtered and concentrated. The residue was purified by by silica gel column chromatography (DCM DCM/MeOH, 99:1) to provide 0.642 g of the title compound as a red solid: ESI-MS: 371.2 [M+H]$^+$; $t_R$=3.18 min (System 1); TLC: R$_f$=0.44 (DCM/MeOH, 9:1).

Step 112.3: Methanesulfonic acid 5-nitro-pyridin-2-ylmethyl ester

Methanesulfonic anhydride (1.79 g, 10.3 mmol, 1.1 equiv) was added portionwise to a cold (5° C.) mixture of (5-nitro-pyridin-2-yl)-methanol (Step 112.4) (1.44 g, 9.4 mmol) and triethylamine (1.57 mL, 11.3 mmol, 1.2 equiv) in DCM (20 mL), under an argon atmosphere. The reaction mixture was allowed to stir for 0.5 h at 5° C., quenched with H$_2$O and extracted with DCM. The organic phase was washed with H$_2$O, dried (Na$_2$SO$_4$), filtered and concentrated to provide 2.16 g of the title compound as a brown solid: : ESI-MS: 231.1 [M−H]$^-$; $t_R$=2.85 min (System 1).

Step 112.4: (5-Nitro-pyridin-2-yl)-methanol

Diisobutylaluminium hydride (1 M in DCM, 41.6 mL, 41.6 mmol, 1.3 equiv) was added dropwise to a cold (−78° C.) solution of 5-nitro-pyridine-2-carboxylic acid ethyl ester (Step 39.4) (6.4 g, 32 mmol) in DCM (120 mL), under an argon atmosphere. The reaction mixture was allowed to warm to rt, quenched by addition of an aqueous solution of potassium sodium tartrate, diluted with DCM and H$_2$O, and filtered through a pad of celite. The filtrate was extracted several times with DCM. The organic phase was washed with brine, dried (Na$_2$SO$_4$), filtered and concentrated. The residue was purified by silica gel column chromatography (Hex/EtOAc, 9:1→1:1) to provide 1.44 g of the title compound: ESI-MS: 153.1 [M−H]$^-$.

EXAMPLE 113

8-(2,6-Dichloro-3,5-dimethoxy-phenyl)-quinoxaline-5-carboxylic acid [6-(3,3,4-trimethyl-piperazin-1-ylmethyl)-pyridin-3-yl]-amide

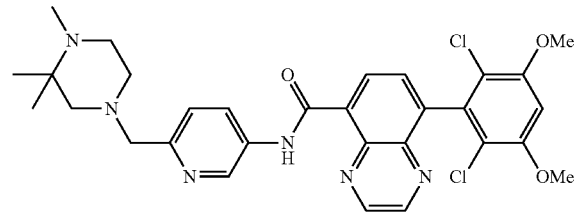 [SMILES: COc1cc(OC)c(Cl)c(-c2ccc(C(=O)Nc3ccc(CN4CCN(C)C(C)(C)C4)nc3)c3nccnc23)c1Cl]

Methyl iodide (15 μL, 0.24 mmol, 1.2 equiv) was added to a mixture of 8-(2,6-dichloro-3,5-dimethoxy-phenyl)-quinoxaline-5-carboxylic acid [6-(3,3-dimethyl-piperazin-1-ylmethyl)-pyridin-3-yl]-amide (Example 112) (115 mg, 0.2 mmol) and potassium carbonate (33 mg, 0.24 mmol, 1.2 equiv) in CH$_3$CN (4 mL). The reaction mixture was stirred for 72 h at rt, quenched by addition of a saturated aqueous solution of NaHCO$_3$ and extracted with EtOAc.

The organic layer was washed with a saturated aqueous solution of NaHCO$_3$, dried (Na$_2$SO$_4$), filtered and concentrated. The residue was purified by silica gel column chromatography (DCM/NH$_3$$^{aq}$, 99:1→DCM/MeOH/NH$_3$$^{aq}$, 96:3:1) followed by trituration id Et$_2$O to afford 27 mg of the title compound as a yellow solid. Title compound: ESI-MS: 595.1/596.6 [M+H]$^+$; $t_R$=3.54 min (System 1); TLC: R$_f$=0.17 (DCM/MeOH, 9:1).

EXAMPLE 114

8-(2,6-Dichloro-3,5-dimethoxy-phenyl)-quinoxaline-5-carboxylic acid [6-(2,2,4-trimethyl-piperazin-1-ylmethyl)-pyridin-3-yl]-amide

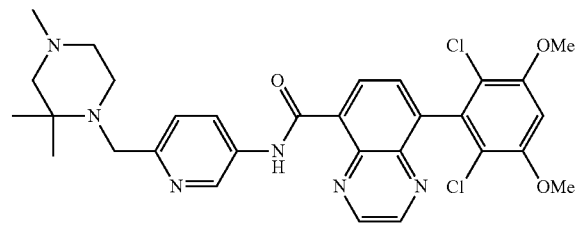 [SMILES: COc1cc(OC)c(Cl)c(-c2ccc(C(=O)Nc3ccc(CN4CCN(C)CC4(C)C)nc3)c3nccnc23)c1Cl]

The title compound was prepared in analogy to the procedure described in Step 14.1 but using 6-(2,2,4-trimethyl-piperazin-1-ylmethyl)-pyridin-3-ylamine (Step 114.1) and stirring the reaction mixture for 14 h at rt. ESI-MS: 595.1/597.2 [M+H]$^+$; $t_R$=3.52 min (System 1); TLC: R$_f$=0.37 (DCM/MeOH, 9:1).

Step 114.1: 6-(2,2,4-Trimethyl-piperazin-1-ylmethyl)-pyridin-3-ylamine

The title compound was prepared in analogy to the procedures described in Steps 112.1-112.2 but using 1,3,3-trimethyl-piperazine (Step 114.2) in Step 112.2: ESI-MS: 235.3 [M+H]$^+$; TLC: $R_f$=0.13 (DCM/MeOH, 9:1).

Step 114.2: 1,3,3-Trimethyl-piperazine

LiAlH$_4$ (1M in THF, 32.5 mL, 32.5 mmol, 1.5 equiv) was added to a solution of 3,3-dimethyl-2-oxo-piperazine-1-carboxylic acid tert-butyl ester (Step 114.3) (4.95 g, 21.7 mmol) in THF (100 mL) at 50° C., under an argon atmosphere. The resulting mixture was stirred for 3 h at 50° C., cooled to 0° C., quenched by addition of acetone and concentrated. The residue was purified by silica gel column chromatography (DCM/MeOH/NH$_3$$^{aq}$, 94:5:1) to afford 2 g of the title compound as a yellow oil. Title compound: ESI-MS: 129.1.

Step 114.3: 3,3-Dimethyl-2-oxo-piperazine-1-carboxylic acid tert-butyl ester

A solution of di-tert-butyl dicarbonate (9.3 g, 42.5 mmol, 1.1 equiv) in DCM (20 mL) was added dropwise to a solution of 3,3-dimethyl-piperazin-2-one (Step 108.4) (4.95 g, 38.7 mmol) and DMAP (457 mg, 3.9 mmol, 0.1 equiv) in DCM (20 mL) at rt, under an argon atmosphere. The reaction mixture was stirred for 20 h at rt, quenched by addition of a saturated aqueous solution of NaHCO$_3$ (100 mL) and extracted with DCM. The organic phase was washed with a saturated aqueous solution of NaHCO$_3$, dried (Na$_2$SO$_4$), filtered and concentrated. The residue was purified by silica gel column chromatography (DCM/MeOH/NH$_3$$^{aq}$, 98:1:1) to afford 4.97 g of the title compound as a colorless oil. Title compound: ESI-MS: 227.2 [M–H]$^-$; $t_R$=1.62 min (System 1).

EXAMPLE 115

8-(3,5-Dimethoxy-phenyl)-quinoxaline-5-carboxylic acid [5-(4-ethyl-piperazin-1-ylmethyl)-pyridin-2-yl]-amide

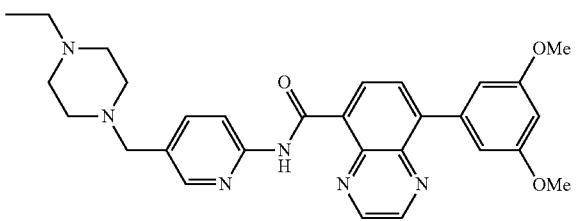 [SMILES: CCN1CCN(Cc2ccc(NC(=O)c3ccc(-c4cc(OC)cc(OC)c4)c4nccnc34)nc2)CC1]

Trimethyl aluminum (2 M in toluene, 0.37 mL, 0.74 mmol, 2.5 equiv) was added to a mixture of 8-(3,5-dimethoxy-phenyl)-quinoxaline-5-carboxylic acid ethyl ester (Step 115.1) (100 mg, 0.30 mmol) and 5-(4-ethyl-piperazin-1-ylmethyl)-pyridin-2-ylamine (Step 26.1; purified by column chromatography) (78 mg, 0.36 mmol, 1.2 equiv) in toluene (2 mL). The reaction mixture was stirred for 1 h at rt, heated to reflux, stirred for 3 h, allowed to cool, poured onto EtOAc and H$_2$O, and filtered through a pad of celite. The filtrate was extracted with EtOAc. The organic phase was washed with H$_2$O and brine, dried (Na$_2$SO$_4$), filtered and concentrated. The residue was purified by silica gel column chromatography (DCM/MeOH/NH$_3$$^{aq}$, 94:5:1) followed by reverse-phase preparative HPLC to afford 54 mg of the title compound as a pale yellow solid. Title compound: ESI-MS: 513.2 [M+H]$^+$; $t_R$=3.54 min (System 1); TLC: $R_f$=0.29 (DCM/MeOH/NH$_3$$^{aq}$, 94:5:1).

Step 115.1: 8-(3,5-Dimethoxy-phenyl)-quinoxaline-5-carboxylic acid ethyl ester

A mixture of 8-(3,5-dimethoxy-phenyl)-quinoxaline-5-carboxylic acid (Step 1.2) (10 g), H$_2$SO$_4$ conc. (3 mL) and EtOH (500 mL) was stirred at reflux for 7 h, allowed to cool and concentrated. The residue was diluted in EtOAc and a saturated aqueous solution of NaHCO$_3$. The aqueous phase was separated and extracted with EtOAc. The combined organic layers were washed with H$_2$O and brine, dried (Na$_2$SO$_4$), filtered and concentrated to afford 10.1 g of the title compound as a beige solid. Title compound: ESI-MS: 339.2 [M–H]$^-$; $t_R$=4.72 min (System 1).

EXAMPLE 116

8-(3,5-Dimethoxy-phenyl)-quinoxaline-5-carboxylic acid {5-[4-(4-methoxy-benzyl)-piperazin-1-ylmethyl]-pyridin-2-yl}-amide

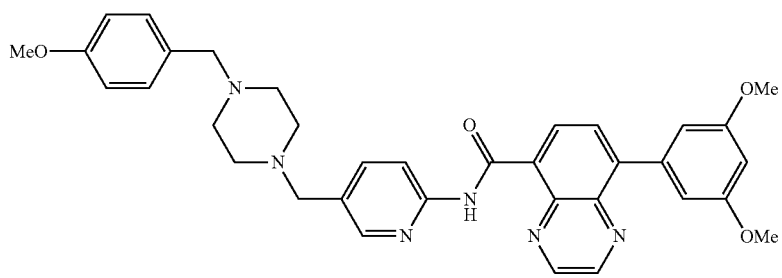 [SMILES: COc1ccc(CN2CCN(Cc3ccc(NC(=O)c4ccc(-c5cc(OC)cc(OC)c5)c5nccnc45)nc3)CC2)cc1]

The title compound was in analogy to the procedure described in Example 115 but using 5-[4-(4-methoxy-benzyl)-piperazin-1-ylmethyl]-pyridin-2-ylamine (Step 105.1). The residue was purified by silica gel column chromatography (DCM/MeOH/NH$_3^{aq}$, 94:5:1) to afford 54 mg of the title compound as a yellow foam. Title compound: ESI-MS: 605.1 [M+H]$^+$; t$_R$=3.98 min (System 1).

EXAMPLE 117

8-(3,5-Dimethoxy-phenyl)-quinoxaline-5-carboxylic acid {5-[4-(4-methoxy-benzyl)-piperazin-1-ylmethyl]-pyridin-2-yl}-amide

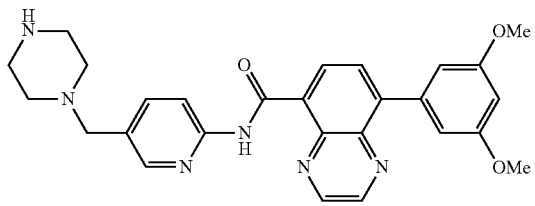 [SMILES: COc1cc(OC)cc(-c2ccc(C(=O)Nc3ccc(CN4CCNCC4)cn3)c3nccnc23)c1]

α-Chloroethyl chloroformate (19 µL, 0.17 mmol) was added to a cold (−78° C.) solution of 8-(3,5-dimethoxy-phenyl)-quinoxaline-5-carboxylic acid {5-[4-(4-methoxy-benzyl)-piperazin-1-ylmethyl]-pyridin-2-yl}-amide (Example 116) (103 mg, 0.17 mmol) in THF (2 mL). The reaction mixture was stirred for 1 h at −78° C., quenched by addition of MeOH and concentrated. The residue was dissolved in MeOH (5 mL), heated to reflux for 3 h, allowed to cool. The resulting solid was collected by filtration, diluted in in DCM and a saturated aqueous solution of NaHCO$_3$, and extracted with DCM. The organic phase was dried (Na$_2$SO$_4$), filtered and concentrated. The residue was purified by silica gel column chromatography (DCM/MeOH/NH$_3^{aq}$, 91.5:7.5:1) followed by trituration in Et$_2$O to afford 28 mg of the title compound as a white solid. Title compound: ESI-MS: 485.2 [M+H]$^+$; t$_R$=3.80 min (System 1); TLC: R$_f$=0.10 (DCM/MeOH/NH$_3^{aq}$, 91.5:7.5:1).

EXAMPLE 118

8-(2,6-Dichloro-3,5-dimethoxy-phenyl)-quinoxaline-5-carboxylic acid {5-[(carbamoylmethyl-methyl-amino)-methyl]-pyridin-2-yl}-amide

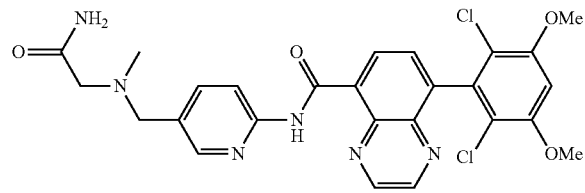 [SMILES: COc1cc(OC)c(Cl)c(-c2ccc(C(=O)Nc3ccc(CN(C)CC(N)=O)cn3)c3nccnc23)c1Cl]

The title compound was prepared in analogy to the procedure described in Step 14.1 but using 2-[(6-amino-pyridin-3-ylmethyl)-methyl-amino]-acetamide (Step 118.1) and stirring the reaction mixture for 14 h at rt. Title compound: ESI-MS: 555.0/556.8 [M+H]$^+$; t$_R$=3.72 min (System 1); TLC: R$_f$=0.40 (DCM/MeOH, 9:1).

Step 118.1: 2-[(6-Amino-pyridin-3-ylmethyl)-methyl-amino]-acetamide

The title compound was prepared in analogy to the procedures described in Steps 100.1-100.2 but using 2-(methylamino)-acetamide hydrochloride in Step 100.2: 195.1 [M+H]$^+$; TLC: R$_f$=0.12 (DCM/MeOH/NH$_3^{aq}$, 89:10:1).

EXAMPLE 119

8-(2,6-Dichloro-3,5-dimethoxy-phenyl)-quinoxaline-5-carboxylic acid {5-[(dimethylcarbamoylmethyl-methyl-amino)-methyl]-pyridin-2-yl}-amide

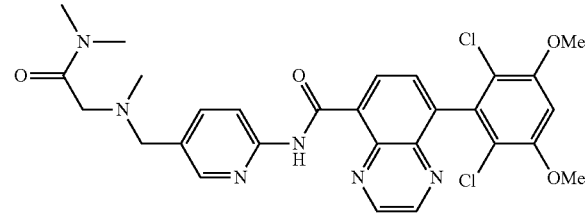 [SMILES: COc1cc(OC)c(Cl)c(-c2ccc(C(=O)Nc3ccc(CN(C)CC(=O)N(C)C)cn3)c3nccnc23)c1Cl]

The title compound was prepared in analogy to the procedure described in Step 14.1 but using 2-[(6-amino-pyridin-3-ylmethyl)-methyl-amino]-N,N-dimethyl-acetamide (Step 119.1) and stirring the reaction mixture for 72 h at rt. Title compound: ESI-MS: 583.0/585.2 [M+H]$^+$; t$_R$=4.02 min (System 1); TLC: R$_f$=0.36 (DCM/MeOH, 9:1).

Step 119.1: 2-[(6-Amino-pyridin-3-ylmethyl)-methyl-amino]-N,N-dimethyl-acetamide The title compound was prepared in analogy to the procedures described in Steps 100.1-100.2 but using N,N-dimethyl-2-(methylamino)-acetamide in Step 100.2: 223.2 [M+H]$^+$; TLC: R$_f$=0.31 (DCM/MeOH/NH$_3^{aq}$, 89:10:1).

EXAMPLE 120

8-(2,6-Dichloro-3,5-dimethoxy-phenyl)-quinoxaline-5-carboxylic acid (5-imidazol-1-ylmethyl-pyridin-2-yl)-amide

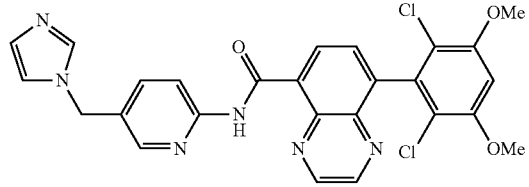 [SMILES: COc1cc(OC)c(Cl)c(-c2ccc(C(=O)Nc3ccc(Cn4ccnc4)cn3)c3nccnc23)c1Cl]

The title compound was prepared in analogy to the procedure described in Step 14.1 but using 5-imidazol-1-ylmethyl-pyridin-2-ylamine (Step 120.1) and stirring the reaction mixture for 20 h at rt. Title compound: ESI-MS: 535.0/536.8 [M+H]$^+$; $t_R$=4.00 min (System 1); TLC: $R_f$=0.35 (DCM/MeOH, 9:1).

Step 120.1:
5-Imidazol-1-ylmethyl-pyridin-2-ylamine

The title compound was prepared in analogy to the procedures described in Steps 100.1-100.2 but using imidazole in Step 100.2: 175.1 [M+H]$^+$; TLC: $R_f$=0.24 (DCM/MeOH, 9:1).

EXAMPLE 121

8-(2,6-Dichloro-3,5-dimethoxy-phenyl)-quinoxaline-5-carboxylic acid [1-(2-dimethylamino-ethyl)-1H-pyrrol-3-yl]-amide

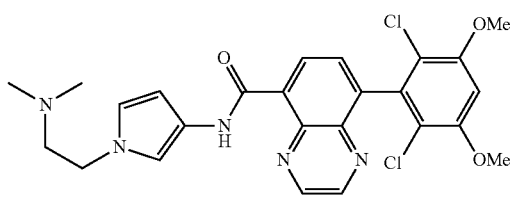 [SMILES: COc1cc(OC)c(Cl)c(-c2ccc(C(=O)Nc3ccn(CCN(C)C)c3)c3nccnc23)c1Cl]

The title compound was prepared in analogy to the procedure described in Step 14.1 but using 1-(2-dimethylamino-ethyl)-1H-pyrrol-3-ylamine (Step 121.1) and stirring the reaction mixture for 14 h at rt. Title compound: ESI-MS: 514.0/515.9 [M+H]$^+$; $t_R$=3.86 min (System 1); TLC: $R_f$=0.22 (DCM/MeOH, 9:1).

Step 121.1:
1-(2-Dimethylamino-ethyl)-1H-pyrrol-3-ylamine

A suspension of dimethyl-[2-(3-nitro-pyrrol-1-yl)-ethyl]-amine (Step 121.2) (650 mg, 3.55 mmol) and Raney Nickel (300 mg) in MeOH/THF (1:1, v/v; 150 mL) was stirred for 7 h at rt, under a hydrogen atmosphere. The mixture was filtered through a pad of celite and the filtrate was concentrated. The residue was purified by silica gel column chromatography (DCM/MeOH/NH$_3$$^{aq}$, 98:1:1→93:6:1) to afford 440 mg of the title compound as a red oil. Title compound: ESI-MS: 154.1 [M+H]$^+$; TLC: $R_f$=0.02 (DCM/MeOH, 9:1).

Step 121.2:
Dimethyl-[2-(3-nitro-pyrrol-1-yl)-ethyl]amine

A mixture of 3-nitropyrrole (500 mg, 4.46 mmol), cesium carbonate (3.63 g, 11.2 mmol, 2.5 equiv), 1-chloro-2-dimethylaminoethane (835 mg, 5.8 mmol, 1.3 equiv) and DMF (5 mL) was stirred for 16 h at rt. The reaction mixture was quenched by addition of a saturated aqueous solution of NaHCO$_3$ and extracted with DCM/MeOH (9:1, v/v). The organic phase was washed with a saturated aqueous solution of NaHCO$_3$, dried (Na$_2$SO$_4$), filtered and concentrated. The residue was purified by silica gel column chromatography (DCM DCM/MeOH, 97:3) to afford 656 mg of the title compound as a yellow oil. Title compound: ESI-MS: 184.1 [M+H]$^+$; TLC: $R_f$=0.38 (DCM/MeOH, 9:1).

EXAMPLE 122

8-(2,6-Dichloro-3,5-dimethoxy-phenyl)-2,3-dimethyl-quinoxaline-5-carboxylic acid [5-(4-methyl-piperazin-1-ylmethyl)-pyridin-2-yl]-amide

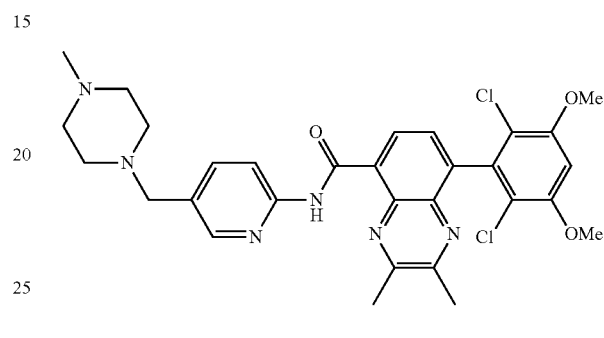

The title compound was prepared in analogy to the procedure described in Step 14.1 but using 8-(2,6-dichloro-3,5-dimethoxy-phenyl)-2,3-dimethyl-quinoxaline-5-carboxylic acid (Step 122.1), 5-(4-methyl-piperazin-1-ylmethyl)-pyridin-2-ylamine (Example 31; purified by silica gel column chromatography), and stirring the reaction mixture 18 h at rt. Title compound: ESI-MS: 595.0 [M+H]$^+$; $t_R$=3.86 min (System 1); TLC: $R_f$=0.15 (DCM/MeOH/NH$_3$$^{aq}$, 94:5:1).

Step 122.1: 8-(2,6-Dichloro-3,5-dimethoxy-phenyl)-2,3-dimethyl-quinoxaline-5-carboxylic acid The title compound was prepared in analogy to the procedures described in Steps 1.1-1.3 but using 5-bromo-8-(3,5-dimethoxy-phenyl)-2,3-dimethyl-quinoxaline (Step 122.2) in Step 1.3. Title compound: ESI-MS: 407.1/408.9 [M+H]$^+$.

Step 122.2: 5-Bromo-8-(3,5-dimethoxy-phenyl)-2,3-dimethyl-quinoxaline

A mixture of 4-bromo-3',5'-dimethoxy-biphenyl-2,3-diamine (Step 85.7) (3 g, 9.3 mmol) and 2,3-butanedione (1 mL, 11.1 mmol, 1.2 equiv) in EtOH (60 mL) was stirred at reflux for 2 h, allowed to cool to rt and stirred for 16 h. Additional 2,3-butanedione (0.4 ml) was added. The reaction mixture was stirred at reflux for 2 h, allowed to cool and concentrated to half of the initial volume. The resulting yellow precipitate was collected vacuum filtration providing 2.9 g of the title compound: ES-MS: 373.1/375.0 [M+H]$^+$; $t_R$=5.60 min (System 1).

EXAMPLE 123
8-(2,6-Dichloro-3,5-dimethoxy-phenyl)-2,3-dimethyl-quinoxaline-5-carboxylic acid (5-piperazin-1-ylmethyl-pyridin-2-yl)-amide
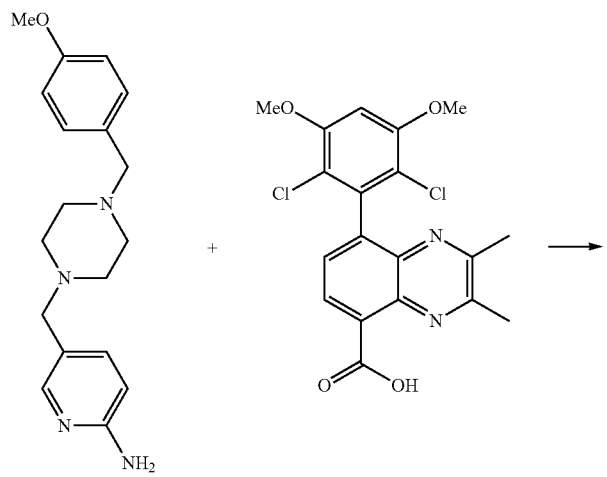
Step 105.1          Step 122.1
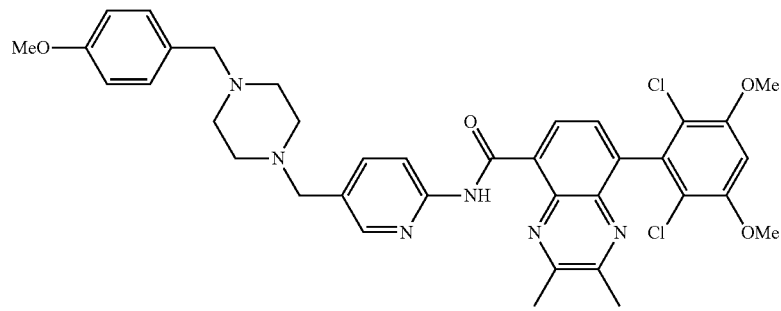
Intermediate 123
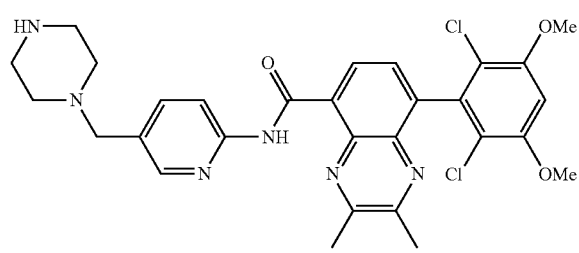
Example 123

Intermediate 123 was prepared in analogy to the procedure described in Step 14.1 but using 5-[4-(4-methoxy-benzyl)-piperazin-1-ylmethyl]-pyridin-2-ylamine (Step 105.1) and stirring the reaction mixture for 18 h at rt: ESI-MS: 701.0 [M+H]$^+$; TLC: R$_f$=0.54 (DCM/MeOH/NH$_3{}^{aq}$, 94:5:1).

The title compound was prepared in analogy to the procedure described in Example 105 but stirring the reaction mixture for 0.5 h at 120° C. in a microwave apparatus. Title compound: ESI-MS: 581.0/583.2 [M+H]$^+$; t$_R$=3.69 min (System 1); TLC: R$_f$=0.10 (DCM/MeOH/NH$_3{}^{aq}$, 91.5:7.5:1).

EXAMPLE 124

8-(2,6-Difluoro-3,5-dimethoxy-phenyl)-quinoxaline-5-carboxylic acid [5-(4-methyl-piperazin-1-ylmethyl)-pyridin-2-yl]-amide

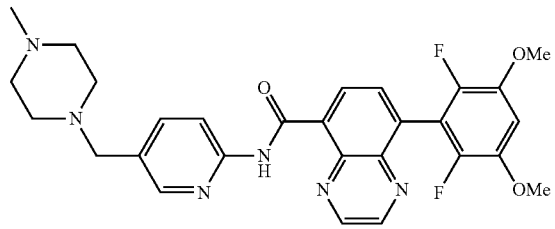 [SMILES: COc1cc(OC)c(F)c(-c2ccc(C(=O)Nc3ccc(CN4CCN(C)CC4)cn3)c3nccnc23)c1F]

The title compound was prepared in analogy to the procedure described in Example 115 but using 8-(2,6-difluoro-3,5-dimethoxy-phenyl)-quinoxaline-5-carboxylic acid ethyl ester (Step 124.1) and 5-(4-methyl-piperazin-1-ylmethyl)-pyridin-2-ylamine (Example 31; purified by silica gel column chromatography). Title compound: ESI-MS: 535.1 [M+H]$^+$; t$_R$=3.45 min (System 1); TLC: R$_f$=0.19 (DCM/MeOH/NH$_3{}^{aq}$, 94:5:1).

Step 124.1: 8-(2,6-Difluoro-3,5-dimethoxy-phenyl)-quinoxaline-5-carboxylic acid ethyl ester 2,6-dichloro-1-fluoropyridinium tetrafluoroborate (13.9 g, 54.6 mmol, 1.8 equiv) was added to a cold (−5° C.) solution of 8-(3,5-dimethoxy-phenyl)-quinoxaline-5-carboxylic acid ethyl ester (Step 115.1) (10.1 g, 29.9 mmol) in CH$_3$CN (100 mL). The reaction mixture was allowed to warm to rt overnight, cooled to 5° C. and quenched by addition of a saturated aqueous solution of NaHCO$_3$ (20 mL). The organic solvent was removed in vacuo and the residual layer was diluted in EtOAc and a saturated aqueous solution of NaHCO$_3$. The aqueous phase was separated and extracted with EtOAc. The combined organic layers were washed with H$_2$O and brine, dried (Na$_2$SO$_4$), filtered and concentrated. Several purifications by silica gel column chromatography (DCM/Hex/Et$_{20}$, 1:3:6) provide 2.93 g of the title compound as a white solid. Title compound: ESI-MS: 375.1 [M+H]$^+$; t$_R$=4.60 min (System 1); TLC: R$_f$=0.19 (DCM/Hex/Et$_{20}$, 1:3:6).

EXAMPLE 125

8-(2,6-Difluoro-3,5-dimethoxy-phenyl)-quinoxaline-5-carboxylic acid (5-piperazin-1-ylmethyl-pyridin-2-yl)-amide

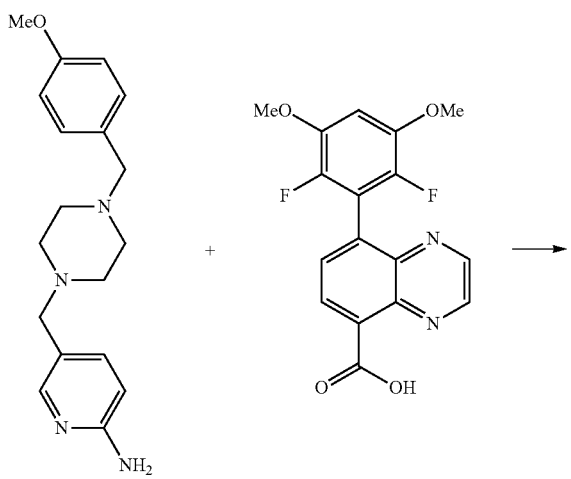

Step 105.1    Step 124.1

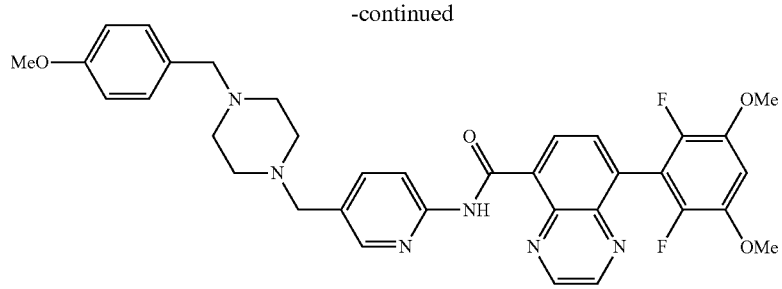

Intermediate 125

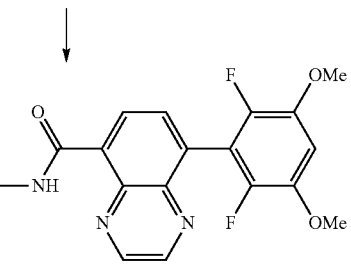

Example 125

Intermediate 125 was prepared in analogy to the procedure described in Example 115 but using 8-(2,6-difluoro-3,5-dimethoxy-phenyl)-quinoxaline-5-carboxylic acid ethyl ester (Step 124.1), 5-[4-(4-methoxy-benzyl)-piperazin-1-ylmethyl]-pyridin-2-ylamine (Step 105.1), 2 equiv of trimethyl aluminum, stirring the reaction mixture for 9 h at 80° C., pouring it onto a saturated aqueous solution of NaHCO$_3$ and DCM: ESI-MS: 641.0 [M+H]$^+$; TLC: R$_f$=0.61 (DCM/MeOH/NH$_3$$^{aq}$, 94:5:1).

The title compound was prepared in analogy to the procedure described in Example 105 but stirring the reaction mixture for 0.5 h at 120° C.: ESI-MS: 521.1 [M+H]$^+$; t$_R$=3.30 min (System 1); TLC: R$_f$=0.10 (DCM/MeOH/NH$_3$$^{aq}$, 91.5:7.5:1).

EXAMPLE 126

8-(2,6-Difluoro-3,5-dimethoxy-phenyl)-quinoxaline-5-carboxylic acid [5-(3,3,4-trimethyl-piperazin-1-ylmethyl)-pyridin-2-yl]-amide

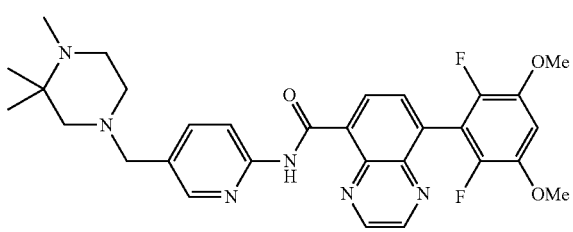 [SMILES: COc1cc(OC)c(F)c(-c2ccc(C(=O)Nc3ccc(CN4CCN(C)C(C)(C)C4)cn3)c3nccnc23)c1F]

The title compound was prepared in analogy to the procedure described in Example 115 but using 8-(2,6-difluoro-3,5-dimethoxy-phenyl)-quinoxaline-5-carboxylic acid ethyl ester (Step 124.1), 5-(3,3,4-trimethyl-piperazin-1-ylmethyl)-pyridin-2-ylamine (Step 107.1), stirring the reaction mixture for 15 min at reflux, pouring it onto a saturated aqueous solution of NaHCO$_3$ and DCM. Title compound: ESI-MS: 563.1 [M+H]$^+$; t$_R$=3.72 min (System 1); TLC: R$_f$=0.33 (DCM/MeOH/NH$_3$$^{aq}$, 94:5:1).

EXAMPLE 127

8-(2,6-Difluoro-3,5-dimethoxy-phenyl)-quinoxaline-5-carboxylic acid (4-dimethylaminomethyl-1H-imidazol-2-yl)-amide

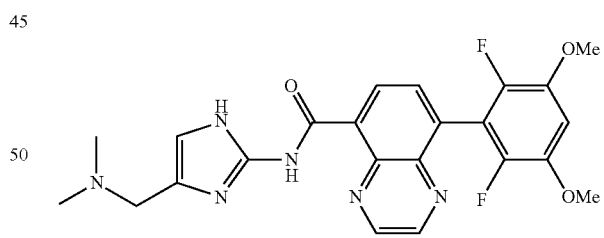

The title compound was prepared in analogy to the procedures described in Example 14 but using 8-(2,6-difluoro-3,5-dimethoxy-phenyl)-quinoxaline-5-carboxylic acid ethyl ester (Step 124.1), Raney nickel and MeOH/THF (1:1) instead of palladium on carbon and MeOH in Step 14.2, dimethyl-(2-nitro-1H-imidazol-4-ylmethyl)-amine (Step 22.1) instead of 2-nitroimidazole in Step 14.3. The title compound: ESI-MS: 469.1 [M+H]$^+$; t$_R$=3.15 min (System 1); TLC: R$_f$=0.22 (DCM/MeOH/NH$_3$$^{aq}$, 91.5:7.5:1).

EXAMPLE 128

8-(2,6-Difluoro-3,5-dimethoxy-phenyl)-quinoxaline-5-carboxylic acid [5-(2,2,4-trimethyl-piperazin-1-ylmethyl)-pyridin-2-yl]-amide

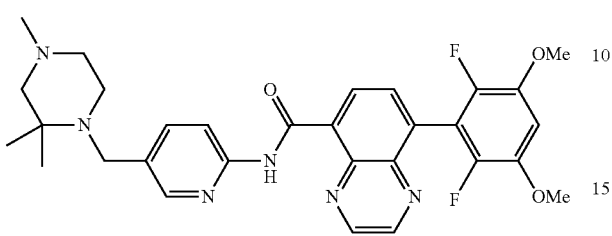

The title compound was prepared in analogy to the procedures described in Example 115 but using 8-(2,6-difluoro-3,5-dimethoxy-phenyl)-quinoxaline-5-carboxylic acid ethyl ester (Step 124.1), 5-(2,2,4-trimethyl-piperazin-1-ylmethyl)-pyridin-2-ylamine (Step 110.1), 1.5 equiv of trimethyl aluminum, stirring the reaction mixture for 6 h at 80° C. and pouring it onto a saturated aqueous solution of NaHCO$_3$ and DCM. Title compound: ESI-MS: 563.1 [M+H]$^+$; $t_R$=3.55 min (System 1); TLC: R$_f$=0.08 (DCM/MeOH, 95:5).

EXAMPLE 129

8-(2,6-Difluoro-3,5-dimethoxy-phenyl)-quinoxaline-5-carboxylic acid [5-(2,2-dimethyl-piperazin-1-ylmethyl)-pyridin-2-yl]-amide

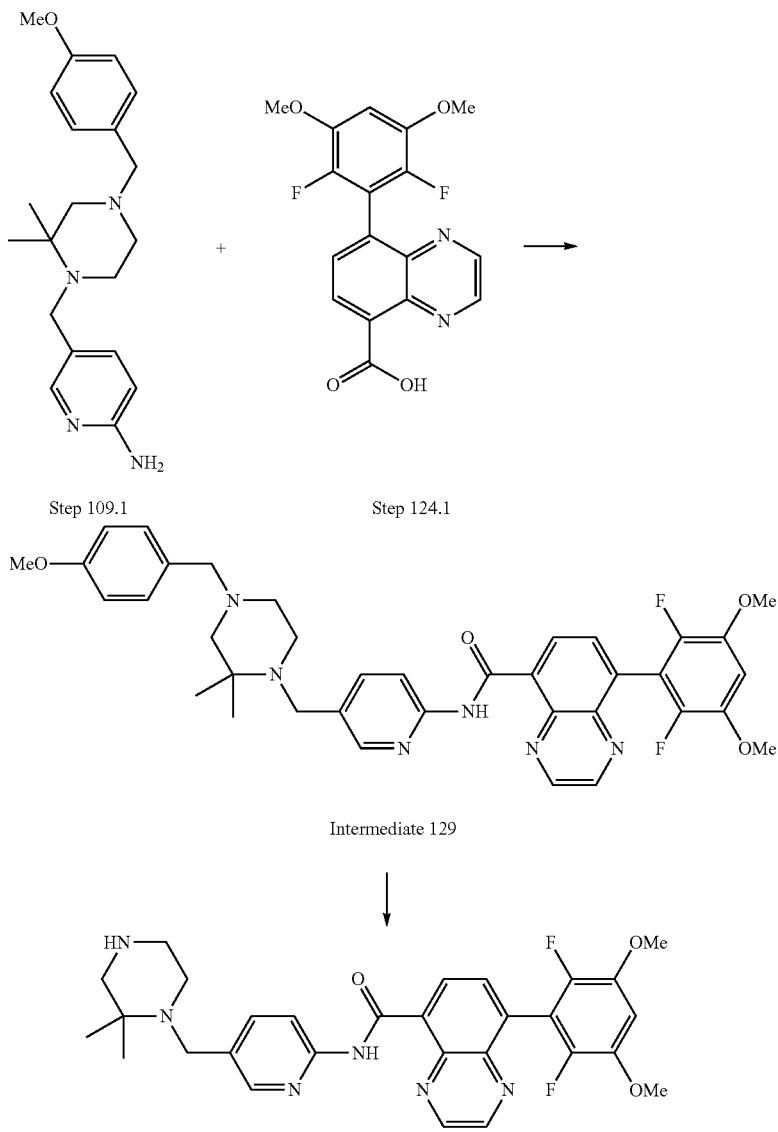

Example 129

Intermediate 129 was prepared in analogy to the procedure described in Example 115 but using 8-(2,6-difluoro-3,5-dimethoxy-phenyl)-quinoxaline-5-carboxylic acid ethyl ester (Step 124.1), 5-[4-(4-methoxy-benzyl)-2,2-dimethyl-piperazin-1-ylmethyl]-pyridin-2-ylamine (Step 109.1), 1.5 equiv of trimethyl aluminum, and stirring the reaction mixture for 5 h at 80° C.: ESI-MS: 669.0 [M+H]$^+$; TLC: R$_f$=0.24 (DCM/MeOH/NH$_3^{aq}$, 94:5:1).

The title compound was prepared in analogy to the procedure described in Example 105 but stirring the reaction mixture for 0.5 h at 120° C.: ESI-MS: 549.1 [M+H]$^+$; t$_R$=3.37 min (System 1); TLC: R$_f$=0.22 (DCM/MeOH/NH$_3^{aq}$, 91.5:7.5:1).

EXAMPLE 130

8-(2,6-Difluoro-3,5-dimethoxy-phenyl)-quinoxaline-5-carboxylic acid [5-(3,3-dimethyl-piperazin-1-ylmethyl)-pyridin-2-yl]-amide

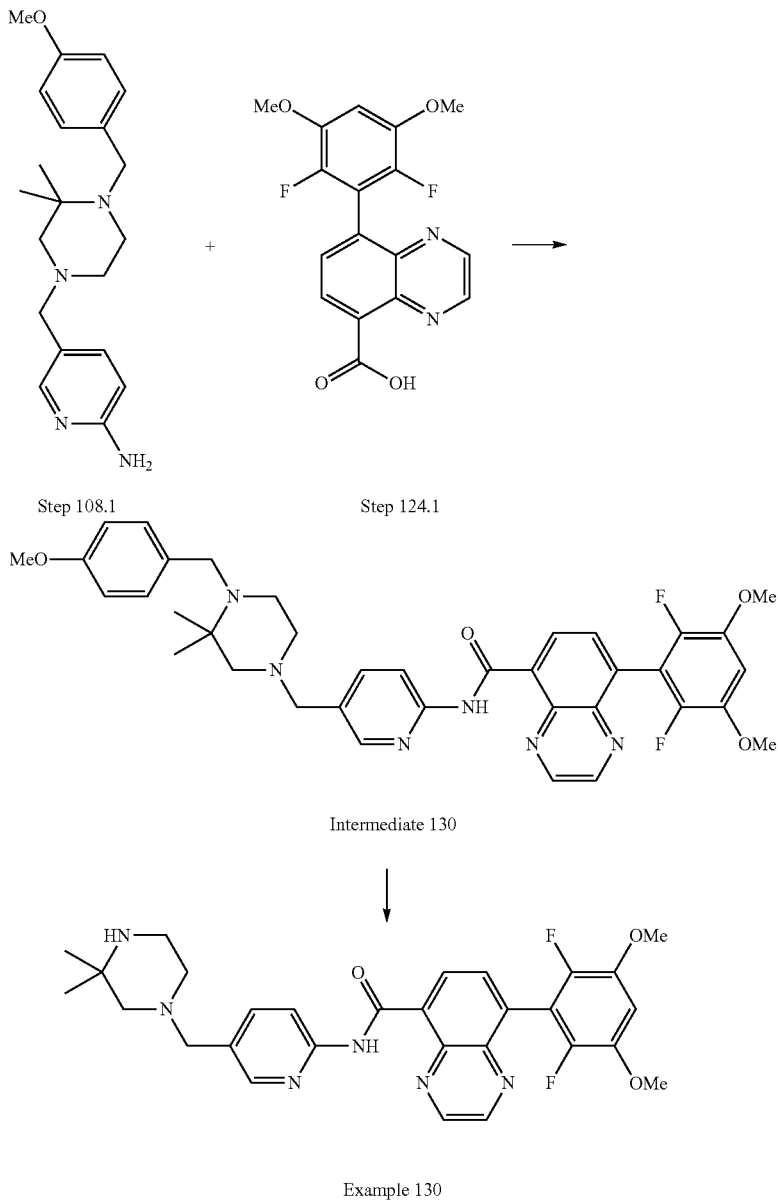

Intermediate 130 was prepared in analogy to the procedure described in in Example 115 but using 8-(2,6-difluoro-3,5-dimethoxy-phenyl)-quinoxaline-5-carboxylic acid ethyl ester (Step 124.1), 5-[4-(4-methoxy-benzyl)-3,3-dimethyl-piperazin-1-ylmethyl]-pyridin-2-ylamine (Step 108.1), 1.5 equiv of trimethyl aluminum, and stirring the reaction mixture for 5 h at 80° C.: ESI-MS: 669.0 [M+H]$^+$; t$_R$=4.26 min (System 1); TLC: R$_f$=0.13 (DCM/MeOH, 95:5).

The title compound was prepared in analogy to the procedure described in Example 105 but stirring the reaction mixture for 0.5 h at 120° C.: ESI-MS: 549.1 [M+H]⁺; t_R=3.55 min (System 1); TLC: R_f=0.11 (DCM/MeOH/NH_3^aq, 91.5:7.5:1).

EXAMPLE 131

8-(2,6-Difluoro-3,5-dimethoxy-phenyl)-quinoxaline-5-carboxylic acid [6-(2,2,4-trimethyl-piperazin-1-ylmethyl)-pyridin-3-yl]-amide

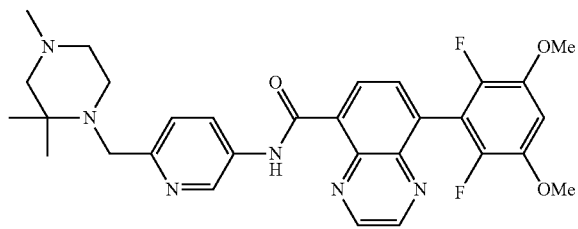 [SMILES: COc1cc(OC)c(F)c(-c2ccc(C(=O)Nc3ccc(CN4CCN(C)CC4(C)C)nc3)c3nccnc23)c1F]

The title compound was prepared in analogy to the procedures described in Example 115 but using 8-(2,6-difluoro-3,5-dimethoxy-phenyl)-quinoxaline-5-carboxylic acid ethyl ester (Step 124.1), 6-(2,2,4-trimethyl-piperazin-1-ylmethyl)-pyridin-3-ylamine (Step 114.1), 1.5 equiv of trimethyl aluminum, stirring the reaction mixture for 2 h at 80° C. and pouring it onto a saturated aqueous solution of NaHCO_3 and DCM. Title compound: ESI-MS: 563.2 [M+H]⁺; t_R=3.36 min (System 1); TLC: R_f=0.22 (DCM/MeOH/NH_3^aq, 94:5:1).

EXAMPLE 132

8-(2,6-Difluoro-3,5-dimethoxy-phenyl)-quinoxaline-5-carboxylic acid (6-piperazin-1-ylmethyl-pyridin-3-yl)-amide

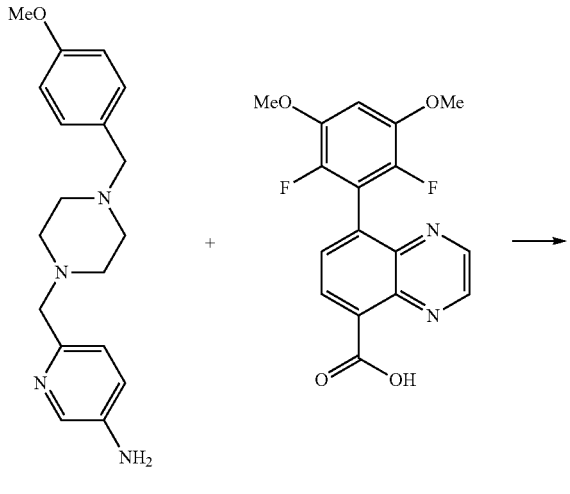

Step 111.1              Step 124.1

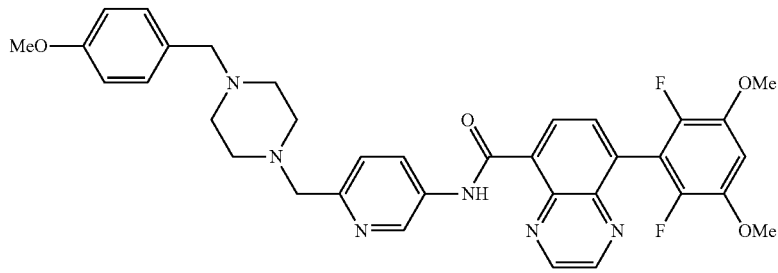

Intermediate 132

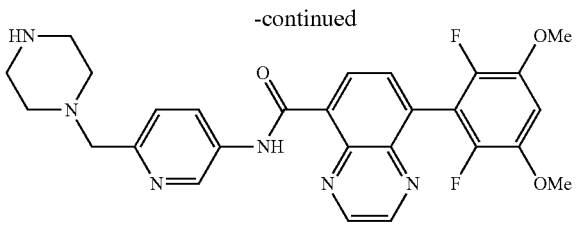

Example 132

Intermediate 132 was prepared in analogy to the procedure described in Example 115 but using 8-(2,6-difluoro-3,5-dimethoxy-phenyl)-quinoxaline-5-carboxylic acid ethyl ester (Step 124.1), 6-[4-(4-methoxy-benzyl)-piperazin-1-ylmethyl]-pyridin-3-ylamine (Step 111.1), 1.5 equiv of trimethyl aluminum, stirring the reaction mixture for 0.5 h at 80° C. and pouring it onto a saturated aqueous solution of NaHCO$_3$ and DCM: ESI-MS: 641.1 [M+H]$^+$; t$_R$=3.72 min (System 1); TLC: R$_f$=0.22 (DCM/MeOH/NH$_3$$^{aq}$, 94:5:1).

The title compound was prepared in analogy to the procedure described in Example 105 but stirring the reaction mixture for 0.5 h at 120° C.: ESI-MS: 521.1 [M+H]$^+$; t$_R$=3.21 min (System 1); TLC: R$_f$=0.06 (DCM/MeOH/NH$_3$$^{aq}$, 91.5:7.5:1).

EXAMPLE 133

8-(2,6-Difluoro-3,5-dimethoxy-phenyl)-quinoxaline-5-carboxylic acid [5-(3-oxo-piperazin-1-ylmethyl)-pyridin-2-yl]-amide

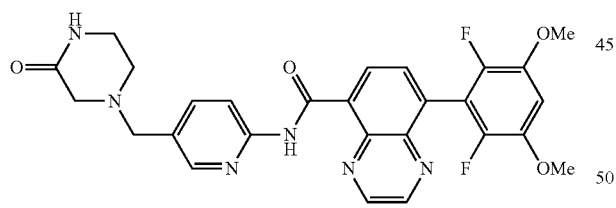

The title compound was prepared in analogy to the procedure described in Example 115 but using 8-(2,6-difluoro-3,5-dimethoxy-phenyl)-quinoxaline-5-carboxylic acid ethyl ester (Step 124.1), 4-(6-amino-pyridin-3-ylmethyl)-piperazin-2-one (Step 103.1), 1.5 equiv of trimethyl aluminum, stirring the reaction mixture for 7 h at 80° C. and pouring it onto a saturated aqueous solution of NaHCO$_3$ and DCM. The title compound: ESI-MS: 535.1 [M+H]$^+$; t$_R$=3.50 min (System 1); TLC: R$_f$=0.16 (DCM/MeOH/NH$_3$$^{aq}$, 94:5:1).

EXAMPLE 134

8-(2,6-Difluoro-3,5-dimethoxy-phenyl)-quinoxaline-5-carboxylic acid (5-{[(2-dimethylamino-ethyl)-methyl-amino]-methyl}-pyridin-2-yl)-amide

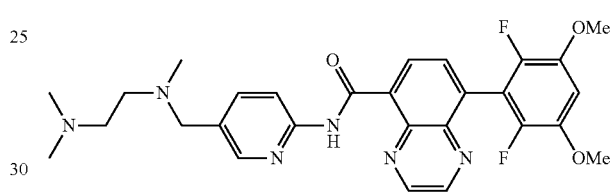

The title compound was prepared in analogy to the procedure described in Example 115 but using 8-(2,6-difluoro-3,5-dimethoxy-phenyl)-quinoxaline-5-carboxylic acid ethyl ester (Step 124.1), N-(6-amino-pyridin-3-ylmethyl)-N,N',N'-trimethyl-ethane-1,2-diamine (prepared as described in Example 26 but using N,N,N'-trimethyl-ethane-1,2-diamine in Step 26.2 and purified by column chromatography), 1.5 equiv of trimethyl aluminum, stirring the reaction mixture for 5 h at 80° C. and pouring it onto a saturated aqueous solution of NaHCO$_3$ and DCM. The title compound: ESI-MS: 537.1 [M+H]$^+$; t$_R$=3.31 min (System 1); TLC: R$_f$=0.13 (DCM/MeOH, 95:5).

EXAMPLE 135

8-(2,6-Difluoro-3,5-dimethoxy-phenyl)-quinoxaline-5-carboxylic acid (4-morpholin-4-ylmethyl-1H-imidazol-2-yl)-amide

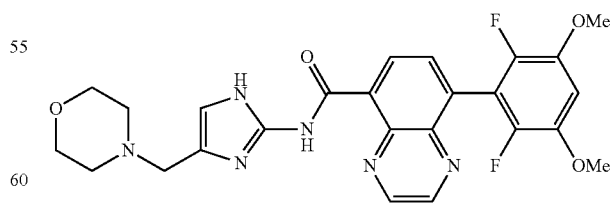

The title compound was prepared in analogy to the procedures described in Example 14 but stirring the reaction mixture for 2 h at 70° C. and using 8-(2,6-difluoro-3,5-dimethoxy-phenyl)-quinoxaline-5-carboxylic acid ethyl ester (Step 124.1). 4-(2-Nitro-1H-imidazol-4-ylmethyl)-

EXAMPLE 136

8-(2,6-Difluoro-3,5-dimethoxy-phenyl)-quinoxaline-5-carboxylic acid {5-[(carbamoylmethyl-methyl-amino)-methyl]-pyridin-2-yl}-amide

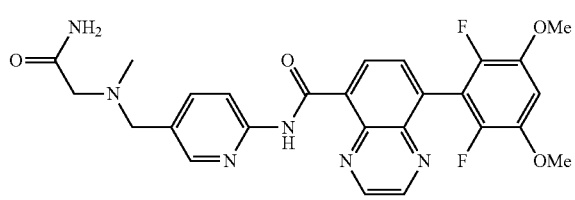 [SMILES: COc1cc(OC)c(F)c(-c2ccc(C(=O)Nc3ccc(CN(C)CC(N)=O)cn3)c3nccnc23)c1F]

The title compound was prepared in analogy to the procedure described in Example 115 but using 8-(2,6-difluoro-3,5-dimethoxy-phenyl)-quinoxaline-5-carboxylic acid ethyl ester (Step 124.1), 2-[(6-amino-pyridin-3-ylmethyl)-methyl-amino]-acetamide (Step 118.1), 2 equiv of trimethyl aluminum, stirring the reaction mixture for 22 h at 80° C. and pouring it onto a saturated aqueous solution of NaHCO$_3$ and DCM. The title compound: ESI-MS: 523.1 [M+H]$^+$; t$_R$=3.53 min (System 1); TLC: R$_f$=0.16 (DCM/MeOH/NH$_3$$^{aq}$, 94:5:1).

EXAMPLE 137

8-(2,6-Difluoro-3,5-dimethoxy-phenyl)-quinoxaline-5-carboxylic acid {5-[(dimethylcarbamoylmethyl-methyl-amino)-methyl]-pyridin-2-yl}-amide

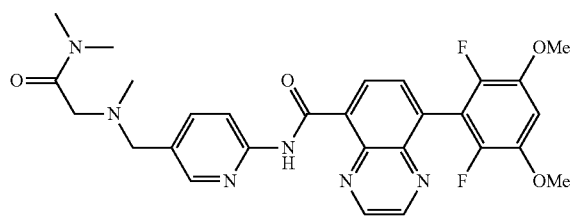 [SMILES: COc1cc(OC)c(F)c(-c2ccc(C(=O)Nc3ccc(CN(C)CC(=O)N(C)C)cn3)c3nccnc23)c1F]

The title compound was prepared in analogy to the procedure described in Example 115 but using 8-(2,6-difluoro-3,5-dimethoxy-phenyl)-quinoxaline-5-carboxylic acid ethyl ester (Step 124.1), 2-[(6-amino-pyridin-3-ylmethyl)-methyl-amino]-N,N-dimethyl-acetamide (Step 119.1), 2 equiv of trimethyl aluminum, stirring the reaction mixture for 6 h at 80° C. and pouring it onto a saturated aqueous solution of NaHCO$_3$ and DCM. The title compound: ESI-MS: 551.1 [M+H]$^+$; t$_R$=3.81 min (System 1); TLC: R$_f$=0.36 (DCM/MeOH/NH$_3$$^{aq}$, 94:5:1).

EXAMPLE 138

8-(2,6-Difluoro-3,5-dimethoxy-phenyl)-quinoxaline-5-carboxylic acid (5-imidazol-1-ylmethyl-pyridin-2-yl)-amide

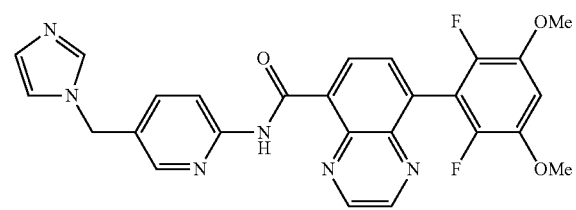 [SMILES: COc1cc(OC)c(F)c(-c2ccc(C(=O)Nc3ccc(Cn4ccnc4)cn3)c3nccnc23)c1F]

The title compound was prepared in analogy to the procedure described in Example 115 but using 8-(2,6-difluoro-3,5-dimethoxy-phenyl)-quinoxaline-5-carboxylic acid ethyl ester (Step 124.1), 5-imidazol-1-ylmethyl-pyridin-2-ylamine (Step 120.1), 2 equiv of trimethyl aluminum, stirring the reaction mixture for 3 h at 80° C. and pouring it onto a saturated aqueous solution of NaHCO$_3$ and DCM. The title compound: ESI-MS: 503.1 [M+H]$^+$; t$_R$=3.76 min (System 1); TLC: R$_f$=0.47 (DCM/MeOH, 9:1).

EXAMPLE 139

8-(2,6-Difluoro-3,5-dimethoxy-phenyl)-quinoxaline-5-carboxylic acid [1-(2-dimethylamino-ethyl)-1H-pyrrol-3-yl]-amide

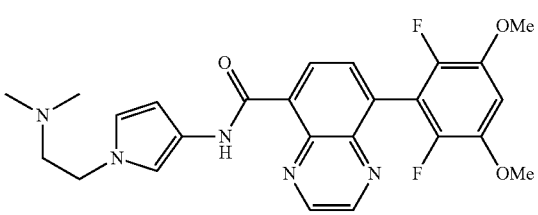 [SMILES: COc1cc(OC)c(F)c(-c2ccc(C(=O)Nc3ccn(CCN(C)C)c3)c3nccnc23)c1F]

The title compound was prepared in analogy to the procedure described in Step 14.1 but using 8-(2,6-difluoro-3,5-dimethoxy-phenyl)-quinoxaline-5-carboxylic acid ethyl ester (Step 124.1), 1-(2-dimethylamino-ethyl)-1H-pyrrol-3-ylamine (Step 121.1) and stirring the reaction mixture for 14

EXAMPLE 140

8-(2,6-Difluoro-3,5-dimethoxy-phenyl)-quinoxaline-5-carboxylic acid [5-(1,1-dioxo-thiomorpholin-4-ylmethyl)-pyridin-2-yl]-amide

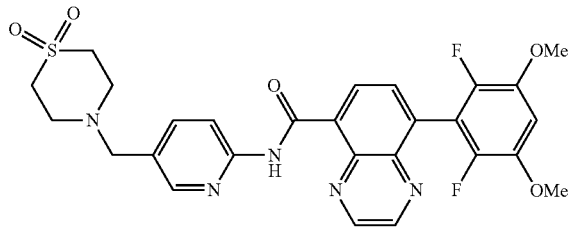 [SMILES: COc1cc(OC)c(F)c(-c2ccc(C(=O)Nc3ccc(CN4CCS(=O)(=O)CC4)cn3)c3nccnc23)c1F]

The title compound was prepared in analogy to the procedure described in Example 115 but using 8-(2,6-difluoro-3,5-dimethoxy-phenyl)-quinoxaline-5-carboxylic acid ethyl ester (Step 124.1), 5-(1,1-dioxothiomorpholin-4-ylmethyl)-pyridin-2-ylamine (Step 104.1), 2 equiv of trimethyl aluminum, stirring the reaction mixture for 6 h at 80° C. and pouring it onto a saturated aqueous solution of NaHCO$_3$ and DCM. Title compound: ESI-MS: 570.0 [M+H]$^+$; $t_R$=3.86 min (System 1); TLC: $R_f$=0.10 (DCM/MeOH/NH$_3$$^{aq}$, 94:5:1).

EXAMPLE 141

8-(2,6-Difluoro-3,5-dimethoxy-phenyl)-quinoxaline-5-carboxylic acid [4-(4-methyl-piperazin-1-ylmethyl)-1H-imidazol-2-yl]-amide

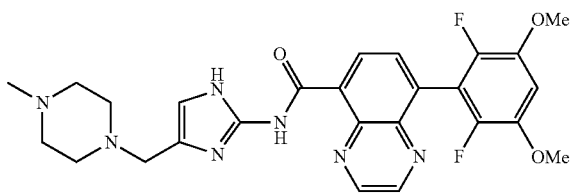 [SMILES: COc1cc(OC)c(F)c(-c2ccc(C(=O)Nc3nc(CN4CCN(C)CC4)c[nH]3)c3nccnc23)c1F]

The title compound was prepared in analogy to the procedures described in Example 14 but using 8-(2,6-difluoro-3,5-dimethoxy-phenyl)-quinoxaline-5-carboxylic acid ethyl ester (Step 124.1), Raney nickel and MeOH/THF (1:1) instead of palladium on carbon and MeOH in Step 14.2, and 1-methyl-4-(2-nitro-1H-imidazol-4-ylmethyl)-piperazine (Step 20.1) instead of 2-nitroimidazole in Step 14.3. Title compound: ESI-MS: 524.1 [M+H]$^+$; $t_R$=3.03 min (System 1); TLC: $R_f$=0.22 (DCM/MeOH/NH$_3$$^{aq}$, 94:5:1).

EXAMPLE 142

8-(2,6-Difluoro-3,5-dimethoxy-phenyl)-quinoxaline-5-carboxylic acid [4-(3-oxo-piperazin-1-ylmethyl)-1H-imidazol-2-yl]-amide

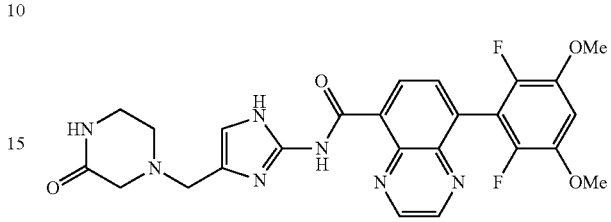

The title compound was prepared in analogy to the procedures described in Example 14 but using 8-(2,6-difluoro-3,5-dimethoxy-phenyl)-quinoxaline-5-carboxylic acid ethyl ester (Step 124.1), Raney nickel and MeOH/THF (1:1) instead of palladium on carbon and MeOH in Step 14.2, and 4-(2-nitro-1H-imidazol-4-ylmethyl)-piperazin-2-one (Step 142.1) instead of 2-nitroimidazole in Step 14.3. Title compound: ESI-MS: 524.1 [M+H]$^+$; $t_R$=3.10 min (System 1); TLC: $R_f$=0.23 (DCM/MeOH, 9:1).

Step 142.1: 4-(2-Nitro-1H-imidazol-4-ylmethyl)-piperazin-2-one

The title compound was prepared in analogy to the procedures described in Step 18.1 but using piperazin-2-one instead of diethyl amine, and it was obtained as an impure sample which was used without further purification.

EXAMPLE 143

8-(2-Fluoro-3,5-dimethoxy-phenyl)-quinoxaline-5-carboxylic acid [5-(4-methyl-piperazin-1-ylmethyl)-pyridin-2-yl]-amide

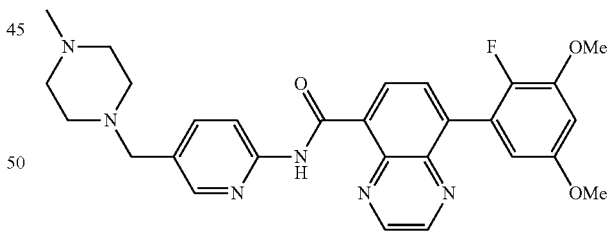

The title compound was prepared in analogy to the procedure described in Example 115 but using 8-(2-fluoro-3,5-dimethoxy-phenyl)quinoxaline-5-carboxylic acid ethyl ester (Step 143.1), 5-(4-methyl-piperazin-1-ylmethyl)-pyridin-2-ylamine (Example 31; purified by silica gel column chromatography), and stirring the reaction mixture for 1 h at reflux. Title compound: ESI-MS: 517.1 [M+H]$^+$; $t_R$=3.37 min (System 1); TLC: $R_f$=0.11 (DCM/MeOH/NH$_3$$^{aq}$, 94:5:1).

Step 143.1: 8-(2-Fluoro-3,5-dimethoxy-phenyl)-quinoxaline-5-carboxylic acid ethyl ester SelectFluor (105 mg, 0.30 mmol) was added to a cold (−5° C.) solution of 8-(3,5-dimethoxy-phenyl)-quinoxaline-5-carboxylic acid ethyl ester (Step 115.1) (100 mg, 0.30 mmol) in CH₃CN (2 mL), under an argon atmosphere. The reaction mixture was allowed to warm to rt over 6 h and stirred at that temperature for additional 12 h and diluted in EtOAc and a saturated aqueous solution of NaHCO₃. The aqueous phase was separated and extracted with EtOAc. The combined organic layers were washed with H₂O and brine, dried (Na₂SO₄), filtered and concentrated. The residue was purified by silica gel column chromatography (Hex/EtOAc, 3:2) to provide 50 mg of the title compound as an off-white solid. Title compound: ESI-MS: 357.2 [M+H]⁺; $t_R$=4.58 min (System 1); TLC: $R_f$=0.24 (Hex/EtOAc, 3:2).

EXAMPLE 144

8-(2-Chloro-6-fluoro-3,5-dimethoxy-phenyl)-quinoxaline-5-carboxylic acid [5-(4-methyl-piperazin-1-ylmethyl)-pyridin-2-yl]-amide

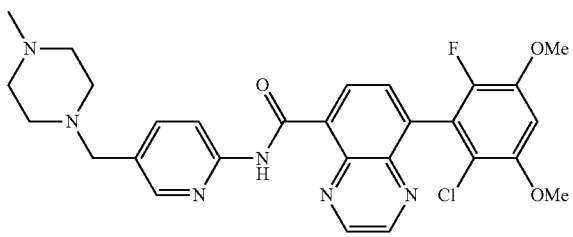 [SMILES: COc1cc(OC)c(Cl)c(-c2ccc(C(=O)Nc3ccc(CN4CCN(C)CC4)cn3)c3nccnc23)c1F]

The title compound was prepared in analogy to the procedure described in Example 115 but using 8-(2-chloro-6-fluoro-3,5-dimethoxy-phenyl)-quinoxaline-5-carboxylic acid ethyl ester (Step 144.1), 5-(4-methyl-piperazin-1-ylmethyl)-pyridin-2-ylamine (Example 31; purified by silica gel column chromatography), 2 equiv of trimethyl aluminum, stirring the reaction mixture for 4 h at 80° C., pouring it onto a saturated aqueous solution of NaHCO₃ and DCM. Title compound: ESI-MS: 551.1 [M+H]⁺; $t_R$=3.50 min (System 1); TLC: $R_f$=0.20 (DCM/MeOH/NH₃$^{aq}$, 94:5:1).

Step 144.1: 8-(2-Chloro-6-fluoro-3,5-dimethoxy-phenyl)-quinoxaline-5-carboxylic acid ethyl ester Sulfuryl chloride (0.35 mL, 4.33 mmol, 1.1 equiv) in CH₃CN (10 mL) was added dropwise to a cold (−30° C.) solution of 8-(2,6-difluoro-3,5-dimethoxy-phenyl)-quinoxaline-5-carboxylic acid ethyl ester (Step 143.1) (1.4 g, 3.93 mmol) in CH₃CN (40 mL). The reaction mixture was quenched by addition of a saturated solution of NaHCO₃, allowed to warm to rt and concentrated. The residue was diluted in EtOAc and a saturated solution of NaHCO₃. The aqueous phase was separated and extracted with EtOAc. The combined organic layers were washed with H₂O and brine, dried (Na₂SO₄), filtered and concentrated. The residue was purified by silica gel column chromatography (Hex/EtOAc, 3:2) to provide 1.27 g of the title compound as a white solid. Title compound: ESI-MS: 391.1 [M+H]⁺; $t_R$=4.71 min (System 1); TLC: $R_f$=0.12 (Hex/EtOAc, 3:2).

EXAMPLE 145

8-(2-Chloro-6-fluoro-3,5-dimethoxy-phenyl)-quinoxaline-5-carboxylic acid [5-(4-ethyl-piperazin-1-ylmethyl)-pyridin-2-yl]-amide

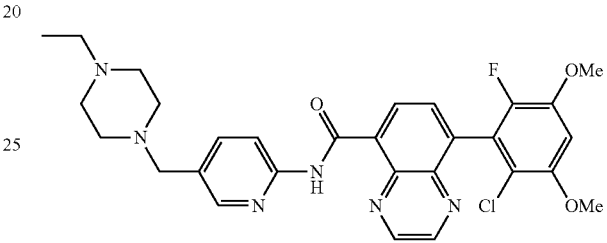

The title compound was prepared in analogy to the procedure described in Example 115 but using 8-(2-chloro-6-fluoro-3,5-dimethoxy-phenyl)-quinoxaline-5-carboxylic acid ethyl ester (Step 144.1), 5-(4-ethyl-piperazin-1-ylmethyl)-pyridin-2-ylamine (Example 26.1; purified by silica gel column chromatography), 2 equiv of trimethyl aluminum, stirring the reaction mixture for 7 h at 80° C., pouring it onto a saturated aqueous solution of NaHCO₃ and DCM. Title compound: ESI-MS: 564.8 [M+H]⁺; $t_R$=3.57 min (System 1); TLC: $R_f$=0.25 (DCM/MeOH/NH₃$^{aq}$, 94:5:1).

EXAMPLE 146

8-(2-Chloro-6-fluoro-3,5-dimethoxy-phenyl)-quinoxaline-5-carboxylic acid (5-piperazin-1-ylmethyl-pyridin-2-yl)-amide

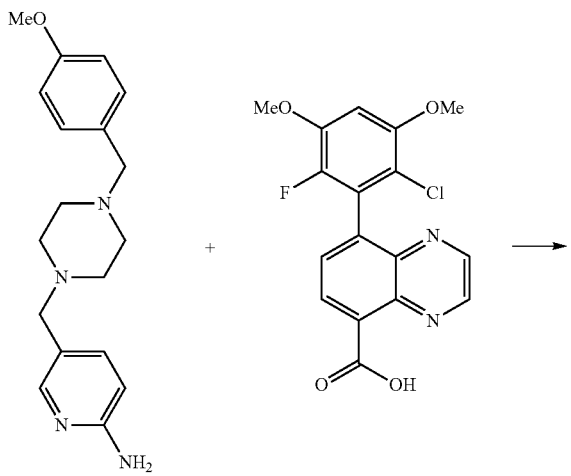

Step 105.1                    Step 144.1

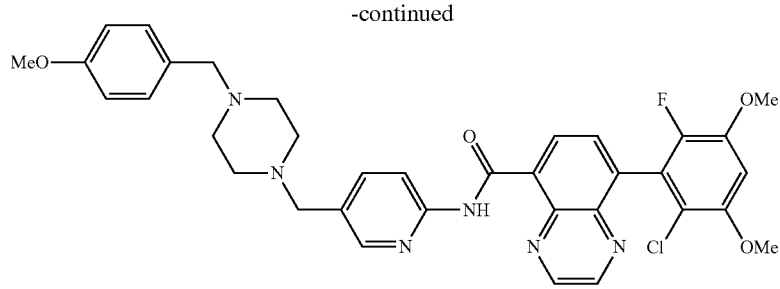

Intermediate 146

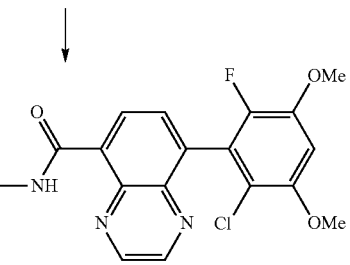

Example 146

Intermediate 146 was prepared in analogy to the procedure described in in Example 115 but using 8-(2-chloro-6-fluoro-3,5-dimethoxy-phenyl)-quinoxaline-5-carboxylic acid ethyl ester (Step 144.1), 5-[4-(4-methoxy-benzyl)-piperazin-1-yl-methyl]-pyridin-2-ylamine (Step 105.1), 2 equiv of trimethyl aluminum, stirring the reaction mixture for 4 h at 80° C., pouring it onto a saturated aqueous solution of NaHCO$_3$ and DCM: ESI-MS: 657.0 [M+H]$^+$; TLC: R$_f$=0.58 (DCM/MeOH/NH$_3$$^{aq}$, 94:5:1).

The title compound was prepared in analogy to the procedure described in Example 105 but stirring the reaction mixture for 0.5 h at 120° C.: ESI-MS: 537.0 [M+H]$^+$; t$_R$=3.38 min (System 1); TLC: R$_f$=0.05 (DCM/MeOH/NH$_3$$^{aq}$, 91.5:7.5:1).

EXAMPLE 147

8-(2-Chloro-6-fluoro-3,5-dimethoxy-phenyl)-quinoxaline-5-carboxylic acid [5-(3-oxo-piperazin-1-ylmethyl)-pyridin-2-yl]-amide

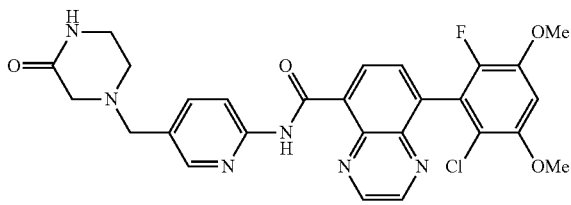

The title compound was prepared in analogy to the procedure described in Example 115 but using 8-(2-chloro-6-fluoro-3,5-dimethoxy-phenyl)-quinoxaline-5-carboxylic acid ethyl ester (Step 144.1), 4-(6-amino-pyridin-3-ylmethyl)-piperazin-2-one (Step 103.1), 2 equiv of trimethyl aluminum, stirring the reaction mixture for 6 h at 80° C., pouring it onto a saturated aqueous solution of NaHCO$_3$ and DCM.

The title compound: ESI-MS: 551.0 [M+H]$^+$; t$_R$=3.59 min (System 1); TLC: R$_f$=0.13 (DCM/MeOH/NH$_3$$^{aq}$, 94:5:1).

EXAMPLE 148

8-(2-Chloro-6-fluoro-3,5-dimethoxy-phenyl)-quinoxaline-5-carboxylic acid (5-{[(2-dimethylamino-ethyl)-methyl-amino]-methyl}-pyridin-2-yl)-amide

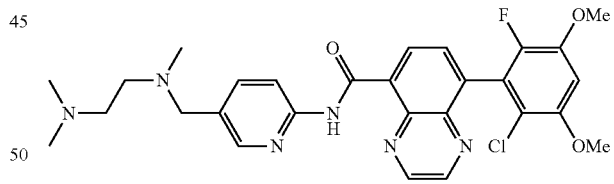

The title compound was prepared in analogy to the procedure described in Example 115 but using 8-(2-chloro-6-fluoro-3,5-dimethoxy-phenyl)-quinoxaline-5-carboxylic acid ethyl ester (Step 144.1), N-(6-amino-pyridin-3-ylmethyl)-N,N',N'-trimethyl-ethane-1,2-diamine (prepared as described in Example 26 but using N,N,N'-trimethyl-ethane-1,2-diamine in Step 26.2 and purified by column chromatography), 2 equiv of trimethyl aluminum, stirring the reaction mixture for 5 h at 80° C., pouring it onto a saturated aqueous solution of NaHCO$_3$ and DCM. The title compound: ESI- MS: 553.1 [M+H]$^+$; $t_R$=3.43 min (System 1); TLC: $R_f$=0.06 (DCM/MeOH/NH$_3$$^{aq}$, 94:5:1).

EXAMPLE 149

8-(2-Chloro-6-fluoro-3,5-dimethoxy-phenyl)-quinoxaline-5-carboxylic acid {5-[(dimethylcarbamoyl-methyl-methyl-amino)-methyl]-pyridin-2-yl}-amide

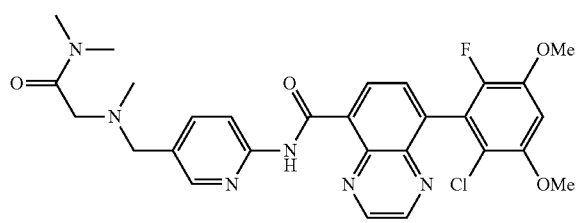 [SMILES: COc1cc(OC)c(Cl)c(-c2ccc(C(=O)Nc3ccc(CN(C)CC(=O)N(C)C)cn3)c3nccnc23)c1F]

The title compound was prepared in analogy to the procedure described in Step 14.1 but using 8-(2-chloro-6-fluoro-3,5-dimethoxy-phenyl)-quinoxaline-5-carboxylic acid ethyl ester (Step 144.1), 2-[(6-amino-pyridin-3-ylmethyl)-methyl-amino]-N,N-dimethyl-acetamide (Step 119.1), stirring the reaction mixture for 72 h at rt. The title compound: ESI-MS: 583.0 [M+H]$^+$; $t_R$=4.02 min (System 1); TLC: $R_f$=0.36 (DCM/MeOH, 9:1).

EXAMPLE 150

8-(2-Chloro-6-fluoro-3,5-dimethoxy-phenyl)-quinoxaline-5-carboxylic acid {5-[(carbamoylmethyl-methyl-amino)-methyl]-pyridin-2-yl}-amide

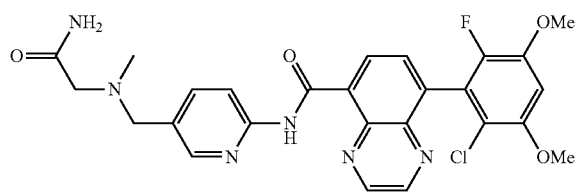

The title compound was prepared in analogy to the procedure described in Example 115 but using 8-(2-chloro-6-fluoro-3,5-dimethoxy-phenyl)-quinoxaline-5-carboxylic acid ethyl ester (Step 144.1), 2-[(6-amino-pyridin-3-ylmethyl)-methyl-amino]-acetamide (Step 118.1), 2 equiv of trimethyl aluminum, stirring the reaction mixture for 6 h at 80° C. and pouring it onto a saturated aqueous solution of NaHCO$_3$ and DCM. The title compound: ESI-MS: 539.0 [M+H]$^+$; $t_R$=3.61 min (System 1); TLC: $R_f$=0.49 (DCM/MeOH/NH$_3$$^{aq}$, 9:1).

EXAMPLE 151

8-(2-Chloro-6-fluoro-3,5-dimethoxy-phenyl)-quinoxaline-5-carboxylic acid (5-imidazol-1-ylmethyl-pyridin-2-yl)-amide

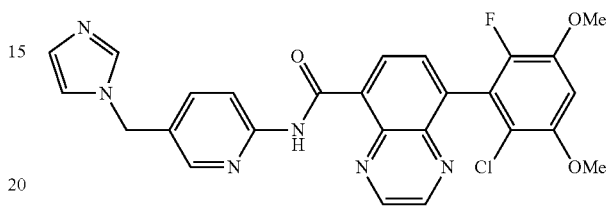

The title compound was prepared in analogy to the procedure described in Example 115 but using 8-(2-chloro-6-fluoro-3,5-dimethoxy-phenyl)-quinoxaline-5-carboxylic acid ethyl ester (Step 144.1), 5-imidazol-1-ylmethyl-pyridin-2-ylamine (Step 120.1), 2 equiv of trimethyl aluminum, stirring the reaction mixture for 3 h at 80° C. and pouring it onto a saturated aqueous solution of NaHCO$_3$ and DCM. The title compound: ESI-MS: 519.0 [M+H]$^+$; $t_R$=3.86 min (System 1); TLC: $R_f$=0.40 (DCM/MeOH, 9:1).

EXAMPLE 152

8-(2-Chloro-6-fluoro-3,5-dimethoxy-phenyl)-quinoxaline-5-carboxylic acid [5-(1,1-dioxo-thiomorpholin-4-ylmethyl)-pyridin-2-yl]-amide

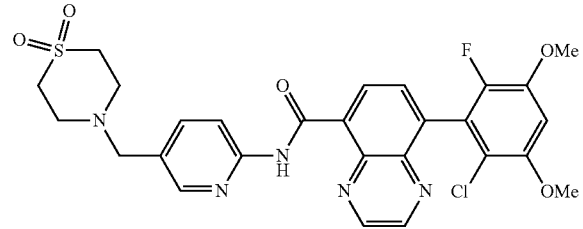 [SMILES: COc1cc(OC)c(Cl)c(-c2ccc(C(=O)Nc3ccc(CN4CCS(=O)(=O)CC4)cn3)c3nccnc23)c1F]

The title compound was prepared in analogy to the procedure described in Example 115 but using 8-(2-chloro-6-fluoro-3,5-dimethoxy-phenyl)-quinoxaline-5-carboxylic acid ethyl ester (Step 144.1), 5-(1,1-dioxothiomorpholin-4-ylmethyl)-pyridin-2-ylamine (Step 104.1), 2 equiv of trimethyl aluminum, stirring the reaction mixture for 6 h at 80° C., pouring it onto a saturated aqueous solution of NaHCO$_3$ and DCM. Title compound: ESI-MS: 585.9 [M+H]$^+$; $t_R$=3.96 min (System 1); TLC: $R_f$=0.39 (DCM/MeOH/NH$_3{}^{aq}$, 94:5:1).

EXAMPLE 153

8-(2-Chloro-6-fluoro-3,5-dimethoxy-phenyl)-quinoxaline-5-carboxylic acid (4-dimethylaminomethyl-1H-imidazol-2-yl)-amide

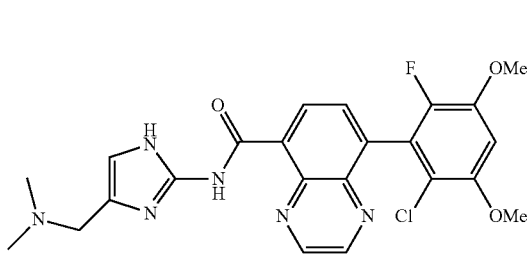 [SMILES: COc1cc(OC)c(Cl)c(-c2ccc(C(=O)Nc3nc(CN(C)C)c[nH]3)c3nccnc23)c1F]

The title compound was prepared in analogy to the procedures described in Example 14 but using 8-(2-chloro-6-fluoro-3,5-dimethoxy-phenyl)-quinoxaline-5-carboxylic acid ethyl ester (Step 144.1), Raney nickel and MeOH/THF (1:1) instead of palladium on carbon and MeOH in Step 14.2, and dimethyl-(2-nitro-1H-imidazol-4-ylmethyl)-amine (Step 22.1) instead of 2-nitroimidazole in Step 14.3. The title compound: ESI-MS: 485.1 [M+H]$^+$; $t_R$=3.24 min (System 1); TLC: $R_f$=0.20 (DCM/MeOH/NH$_3{}^{aq}$, 91.5:7.5:1).

EXAMPLE 154

8-(2-Chloro-6-fluoro-3,5-dimethoxy-phenyl)-quinoxaline-5-carboxylic acid [4-(4-methyl-piperazin-1-ylmethyl)-1H-imidazol-2-yl]-amide

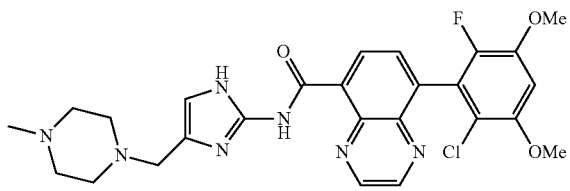 [SMILES: COc1cc(OC)c(Cl)c(-c2ccc(C(=O)Nc3nc(CN4CCN(C)CC4)c[nH]3)c3nccnc23)c1F]

The title compound was prepared in analogy to the procedures described in Example 14 but using 8-(2-chloro-6-fluoro-3,5-dimethoxy-phenyl)-quinoxaline-5-carboxylic acid ethyl ester (Step 144.1), Raney nickel and MeOH/THF (1:1) instead of palladium on carbon and MeOH in Step 14.2, and 1-methyl-4-(2-nitro-1H-imidazol-4-ylmethyl)-piperazine (Step 20.1) instead of 2-nitroimidazole in Step 14.3. Title compound: ESI-MS: 540.0 [M+H]$^+$; $t_R$=3.07 min (System 1); TLC: $R_f$=0.23 (DCM/MeOH/NH$_3{}^{aq}$, 94:5:1).

EXAMPLE 155

8-(2-Chloro-6-fluoro-3,5-dimethoxy-phenyl)-quinoxaline-5-carboxylic acid [4-(3-oxo-piperazin-1-ylmethyl)-1H-imidazol-2-yl]-amide

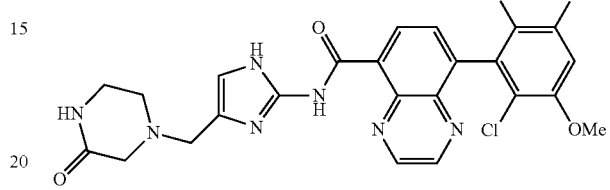

The title compound was prepared in analogy to the procedures described in Example 14 but using 8-(2-chloro-6-fluoro-3,5-dimethoxy-phenyl)-quinoxaline-5-carboxylic acid ethyl ester (Step 144.1), Raney nickel and MeOH/THF (1:1) instead of palladium on carbon and MeOH in Step 14.2, and 4-(2-nitro-1H-imidazol-4-ylmethyl)-piperazin-2-one (Step 142.1) instead of 2-nitroimidazole in Step 14.3. Title compound: ESI-MS: 540.0 [M+H]$^+$; $t_R$=3.18 min (System 1); TLC: $R_f$=0.18 (DCM/MeOH, 9:1).

EXAMPLE 156

8-(2,6-Dichloro-3,5-dimethoxy-phenyl)-quinoxaline-5-carboxylic acid [5-(4-benzyl-piperazin-1-ylmethyl)-pyridin-2-yl]-amide

The title compound was prepared in analogy to the procedure described in Step 14.1 but using 5-(4-benzyl-piperazin-1-ylmethyl)-pyridin-2-ylamine (Step 156.1) and stirring the reaction mixture for 72 h at rt. Title compound: ESI-MS: 643.0 [M+H]⁺; $t_R$=4.02 min (System 1); TLC: $R_f$=0.55 (DCM/MeOH, 9:1).

Step 156.1: 5-(4-Benzyl-piperazin-1-ylmethyl)-pyridin-2-ylamine

The title compound was prepared in analogy to the procedures described in Steps 100.1-100.2 but using 1-benzyl-piperazine in Step 100.2: ESI-MS: 283.2 [M+H]⁺.

EXAMPLE 157

8-(2,6-Difluoro-3,5-dimethoxy-phenyl)-quinoxaline-5-carboxylic acid {4-[(ethyl-methyl-amino)-methyl]-1H-imidazol-2-yl}-amide

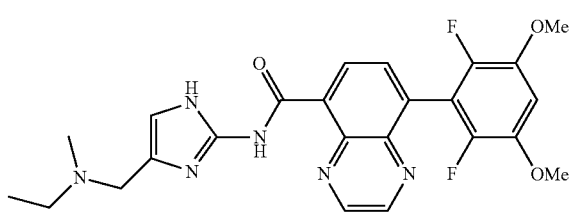 [SMILES: CCN(C)Cc1c[nH]c(NC(=O)c2ccc(-c3c(F)c(OC)cc(OC)c3F)c3nccnc23)n1]

The title compound was prepared in analogy to the procedures described in Example 14 but using 8-(2,6-difluoro-3,5-dimethoxy-phenyl)-quinoxaline-5-carboxylic acid ethyl ester (Step 124.1) and stirring the reaction mixture for 3 h at 70° C. Ethyl-methyl-(2-nitro-1H-imidazol-4-ylmethyl)-amine (Step 157.1) instead of 2-nitroimidazole was used in Step 14.3, and Raney nickel and MeOH/THF (1:1) instead of palladium on carbon and MeOH in Step 14.2. Title compound: ESI-MS: 483.9 [M+H]⁺; TLC: $R_f$=0.10 (DCM/MeOH, 9:1).

Step 157.1: Ethyl-methyl-(2-nitro-1H-imidazol-4-ylmethyl)-amine

The title compound was prepared in analogy to the procedure described in Step 18.1 but using 2 equivalents of 2-nitroimidazole, ethyl-methyl-amine instead of diethyl amine, and stirring the reaction mixture for 72 h at 82° C. The residue was purified by silica gel column chromatography (DCM/MeOH/NH₃$^{aq}$, 89:10:1, then 84:15:1) to afford an impure sample of the title compound which was used without further purification.

EXAMPLE 158

8-(2,6-Difluoro-3,5-dimethoxy-phenyl)-quinoxaline-5-carboxylic acid (4-diethylaminomethyl-1H-imidazol-2-yl)-amide

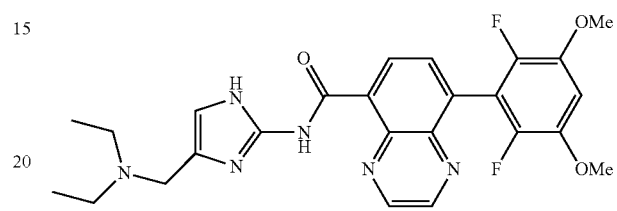

The title compound was prepared in analogy to the procedures described in Example 14 but stirring the reaction mixture at 70° C. for 7 h and using 8-(2,6-difluoro-3,5-dimethoxy-phenyl)-quinoxaline-5-carboxylic acid ethyl ester (Step 124.1). Diethyl-(2-nitro-1H-imidazol-4-ylmethyl)-amine (Step 18.1) instead of 2-nitroimidazole was used in Step 14.3, and Raney nickel and MeOH/THF (1:1) instead of palladium on carbon and MeOH in Step 14.2. Title compound: ESI-MS: 497.0 [M+H]⁺; $t_R$=3.36 min (System 1); TLC: $R_f$=0.18 (DCM/MeOH/NH₃$^{aq}$, 91.5:7.5:1).

EXAMPLE 159

5-(2,6-Dichloro-3,5-dimethoxy-phenyl)-quinoline-8-carboxylic acid [4-(4-ethyl-piperazin-1-yl)-phenyl]-amide

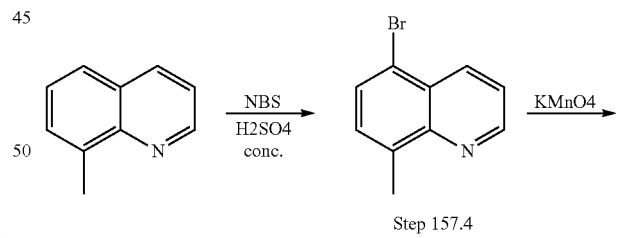

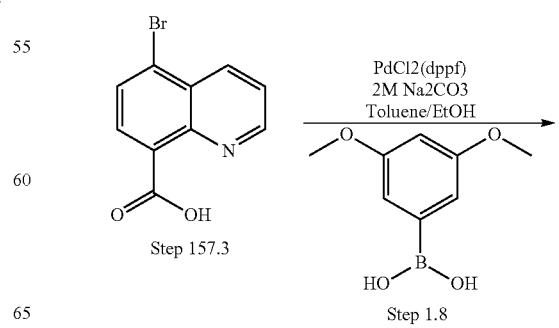

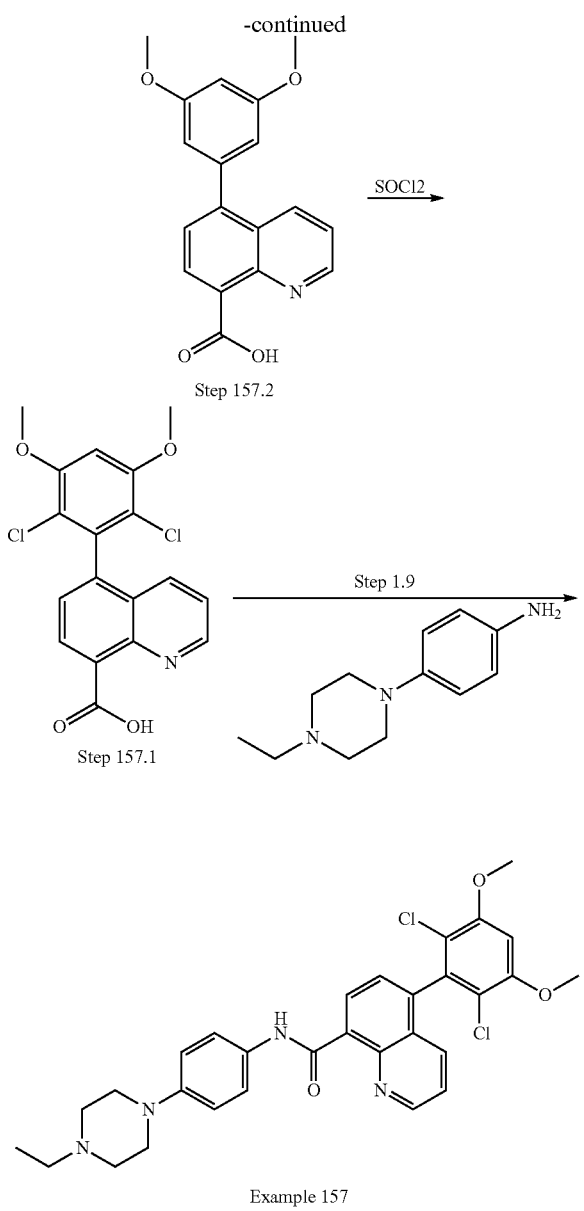

Example 157

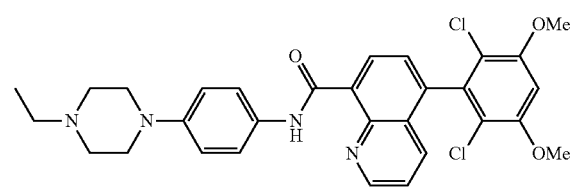 [SMILES: CCN1CCN(c2ccc(NC(=O)c3ccc(-c4c(Cl)c(OC)cc(OC)c4Cl)c4cccnc34)cc2)CC1]

A mixture of propylphosphonic anhydride (50% in DMF, 0.41 mL, 0.70 mmol, 2 equiv), 5-(2,6-dichloro-3,5-dimethoxy-phenyl)-quinoline-8-carboxylic acid (Step 159.1) (132 mg, 0.35 mmol), 4-(4-ethylpiperazin-1-yl)-aniline (Step 1.9) (79 mg, 0.39 mmol, 1.1 equiv), DMAP (3 mg), and Et$_3$N (0.49 mL, 3.5 mmol, 10 equiv) in DMF (3 mL), was stirred for 16 h at rt, under an argon atmosphere. The reaction mixture was diluted with EtOAc and H$_2$O. The aqueous layer was separated and extracted with EtOAc. The combined organic phase was washed with brine, dried (Na$_2$SO$_4$), filtered and concentrated. The residue was purified by trituration in EtOAc to afford the title compound as a yellow solid: ES-MS: 564.9/566.9 [M+H]$^+$; $t_R$=4.45 min (System 1).

Step 159.1: 5-(2,6-Dichloro-3,5-dimethoxy-phenyl)-quinoline-8-carboxylic acid

Sulfuryl chloride (0.1 mL, 1.19 mmol, 1.5 equiv) was added dropwise to a cold (5° C.) suspension of 5-(3,5-dimethoxy-phenyl)-quinoline-8-carboxylic acid (Step 159.2) (245 mg, 0.79 mmol) in CH$_3$CN (5 mL). The reaction mixture was stirred at 5° C. for 15 min, quenched by addition of H$_2$O (0.2 mL), and concentrated. Trituration of the residue in H$_2$O provided 270 mg of the title compound as a white solid: ESI-MS: 378.0/380.0 [M+H]$^+$; $t_R$=4.48 min (System 1).

Step 159.2: 5-(3,5-Dimethoxy-phenyl)-quinoline-8-carboxylic acid

A mixture of 3,5-dimethoxyphenylboronic acid (217 mg, 1.19 mmol, 1.2 equiv) (Step 1.8) in EtOH (0.5 mL) was added dropwise to a mixture of 5-bromo-quinoline-8-carboxylic acid (Step 159.3) (250 mg, 0.99 mmol), PdCl$_2$(dppf) (22 mg, 0.03 mmol, 0.03 equiv), Na$_2$CO$_3$ (2M solution in H$_2$O, 1 mL, 3.97 mmol, 4 equiv) in toluene (5 mL) at 105° C., under an argon atmosphere. The reaction mixture was stirred at 105° C. for 1 h, allowed to cool to rt, diluted with EtOAc and H$_2$O, basified by addition of a 2N aqueous solution of NaOH (2 mL), filtered through a pad of celite and the filtrate was extracted with EtOAc. The aqueous layer was separated and acidified to pH 5. The resulting precipitate was collected by vacuum filtration to provide 248 mg of the title compound as a white solid: ESI-MS:310.1 [M+H]$^+$; $t_R$=4.06 min (System 1).

Step 159.3: 5-Bromo-quinoline-8-carboxylic acid

A solution of potassium permanganate (18.2 g, 115.5 mmol, 2 equiv) in H$_2$O (200 mL) was added to a hot (110° C.) solution of 5-bromo-8-methyl-quinoline (Step 159.4) (12.8 g, 57.7 mmol) in pyridine (120 mL). The reaction mixture was stirred for 10 min at 110° C. and filtered while hot. The residue in the filter was washed with H$_2$O and pyridine. The filtrate was concentrated to remove pyridine, diluted with Et$_2$O and basified by addition of a 2 N aqueous solution of NaOH (20 mL). The aqueous layer was separated and made acidic (pH 3) by addition of a 2 N aqueous solution of HCl. The resulting precipitate was collected by vacuum filtration to provide 1.45 g of the title compound as a green solid: ESI-MS: 251.9/253.9 [M+H]$^+$; $t_R$=3.56 min (System 1).

Step 159.4: 5-Bromo-8-methyl-quinoline

NBS (13.7 g, 76.9 mmol, 1.1 equiv) was added portionwise to a cold (5° C.) solution of 8-methyl-quinoline (10 g, 69.9 mmol) in concentrated H$_2$SO$_4$ (150 mL). The reaction mixture was stirred for 18 h at 5° C., diluted in ice (300 mL) and basified by addition of an aqueous solution of NaOH (10% wt). The resulting white solid was collected by vacuum filtration, rinsed with water, and dissolved in DCM. The organic phase was washed with H$_2$O and brine, dried (Na$_2$SO$_4$), filtered and concentrated to afford 15.2 g of the title compound as a beige solid: ESI-MS: 221.9/223.9 [M+H]⁺; $t_R$=3.59 min (System 1).

EXAMPLE 160

5-(2,6-Dichloro-3,5-dimethoxy-phenyl)-quinoline-8-carboxylic acid (1-benzyl-1H-imidazol-2-yl)-amide

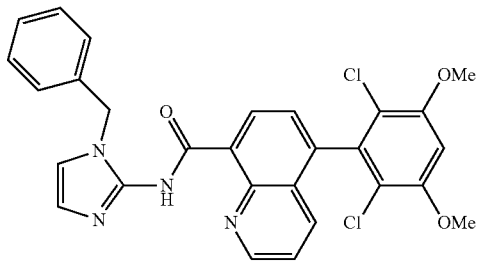 [SMILES: COc1cc(OC)c(Cl)c(-c2ccc(C(=O)Nc3nccn3Cc3ccccc3)c3ncccc23)c1Cl]

The title compound was prepared in analogy to the procedure described in Example 159 but using 1-benzyl-1H-imidazol-2-ylamine (Step 160.1). The title compound: ESI-MS: 532.9 [M+H]⁺; $t_R$=4.75 min (System 1).

Step 160.1: 1-Benzyl-1H-imidazol-2-ylamine

A suspension of 1-benzyl-2-nitro-1H-imidazole (Step 160.2) (410 mg, 1.16 mmol) and Raney nickel (40 mg) in MeOH (10 mL) was stirred for 3 h at rt, under a hydrogen atmosphere. The reaction mixture was filtered through a pad of celite and concentrated to afford 345 mg of the title compound as a brown solid: ESI-MS: 173.9 [M+H]⁺; $t_R$=2.02 min (System 1).

Step 160.2: 1-Benzyl-2-nitro-1H-imidazole

Benzyl chloride (1.8 mL, 15.4 mmol, 1.2 equiv) was added to a solution of 2-nitroimidazole (1.45 g, 12.8 mmol) and triethylamine (3.6 mL, 25.7 mmol, 2 equiv) in DCM (40 mL). The reaction mixture was stirred at reflux for 72 h, allowed to cool to rt, diluted with DCM, washed with H₂O and brine, dried (sodium sulfate), filtered and concentrated. The residue was purified by silica gel column chromatography (Hex/EtOAc, 7:3) to afford 1.31 g of the title compound as a white solid: ES-MS: 204.0 [M+H]⁺; $t_R$=3.72 min (System 1); TLC: $R_f$=0.22 (Hex/EtOAc, 7:3).

EXAMPLE 161

5-(2,6-Dichloro-3,5-dimethoxy-phenyl)-quinoline-8-carboxylic acid (1H-imidazol-2-yl)-amide

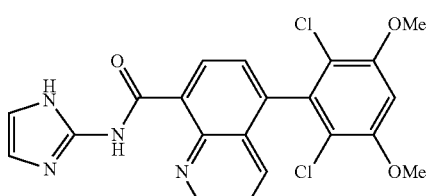

A suspension of 5-(2,6-dichloro-3,5-dimethoxy-phenyl)quinoline-8-carboxylic acid (1-benzyl-1H-imidazol-2-yl)-amide (Example 160) (100 mg, 1.16 mmol) and palladium hydroxyde (75 mg) in MeOH (5 mL) was stirred for 72 h at rt, under a hydrogen atmosphere. The reaction mixture was filtered through a pad of celite and concentrated. The residue was purified by silica gel column chromatography (Hex/EtOAc, 1:4) followed by trituration in Et₂O to provide 15 mg of the title compound as a yellow solid: ES-MS: 442.9 [M+H]⁺; $t_R$=4.05 min (System 1); TLC: $R_f$=0.08 (Hex/EtOAc, 1:4).

EXAMPLE 162

5-(2,6-Dichloro-3,5-dimethoxy-phenyl)-quinoline-8-carboxylic acid (3H-imidazol-4-yl)-amide

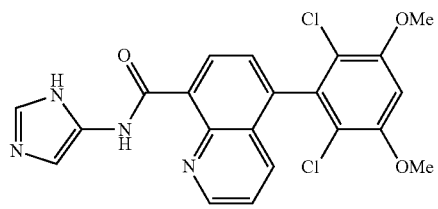 [SMILES: COc1cc(OC)c(Cl)c(-c2ccc(C(=O)Nc3cnc[nH]3)c3ncccc23)c1Cl]

The title compound was prepared in analogy to the procedures described in Example 14 but using 5-(2,6-dichloro-3,5-dimethoxy-phenyl)-quinoline-8-carboxylic acid (Step 159.1), stirring the reaction mixture for 3 h at 70° C., and using 4-nitro-imidazole instead of 2-nitroimidazole in Step 14.3. The title compound: ESI-MS: 442.9 [M+H]⁺; $t_R$=3.93 min (System 1); TLC: $R_f$=0.17 (DCM/MeOH/NH₃$^{aq}$, 94:5:1).

EXAMPLE 163

8-(2,6-Dichloro-3,5-dimethoxy-phenyl)-quinoxaline-5-carboxylic acid (4H-[1,2,4]triazol-3-yl)-amide

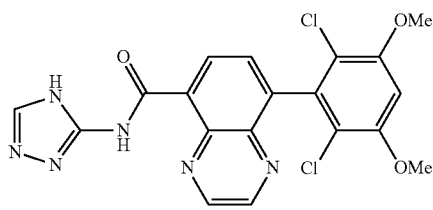 [SMILES: COc1cc(OC)c(Cl)c(-c2ccc(C(=O)Nc3nnc[nH]3)c3nccnc23)c1Cl]

The title compound was prepared in analogy to the procedures described in Example 14 but using 5-(2,6-dichloro-3,5-dimethoxy-phenyl)-quinoline-8-carboxylic acid (Step 159.1), stirring the reaction mixture for 4 h at 70° C., and using 3-nitro-1,2,4-triazole instead of 2-nitroimidazole in Step 14.3. The title compound: ESI-MS: 443.9 [M+H]$^+$; $t_R$=4.60 min (System 1); TLC: $R_f$=0.33 (DCM/MeOH/NH$_3^{aq}$, 94:5:1).

EXAMPLE 164

5-(2,6-Dichloro-3,5-dimethoxy-phenyl)-quinoline-8-carboxylic acid [5-(4-methyl-piperazin-1-ylmethyl)-pyridin-2-yl]-amide

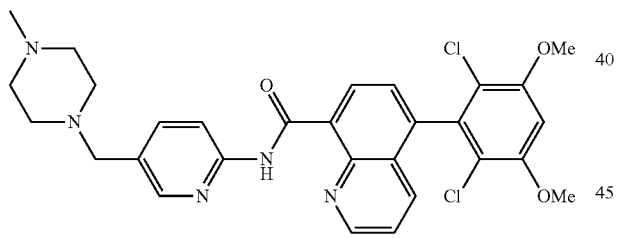

The title compound was prepared in analogy to the procedure described in Step 14.1 but using 5-(2,6-dichloro-3,5-dimethoxy-phenyl)-quinoline-8-carboxylic acid (Step 159.1), 5-(4-methyl-piperazin-1-ylmethyl)-pyridin-2-ylamine (Example 31; purified by silica gel column chromatography), and stirring the reaction mixture for 20 h at rt. Title compound: ESI-MS: 566.1 [M+H]$^+$; TLC: $R_f$=0.22 (DCM/MeOH, 9:1).

EXAMPLE 165

5-(2,6-Dichloro-3,5-dimethoxy-phenyl)-quinoline-8-carboxylic acid [5-(4-ethyl-piperazin-1-ylmethyl)-pyridin-2-yl]-amide

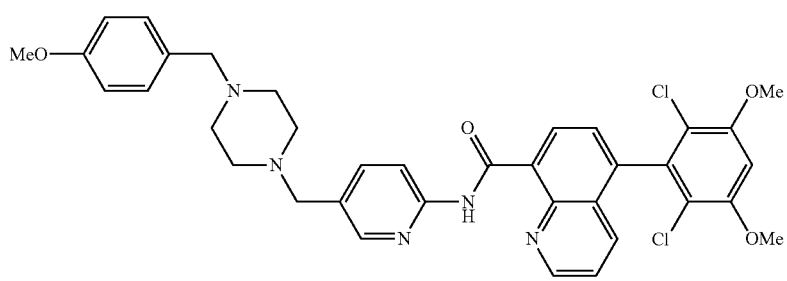 [SMILES: COc1ccc(CN2CCN(Cc3ccc(NC(=O)c4ccc(-c5c(Cl)c(OC)cc(OC)c5Cl)c5cccnc45)nc3)CC2)cc1]

The title compound was prepared in analogy to the procedure described in Step 14.1 but using 5-(2,6-dichloro-3,5-dimethoxy-phenyl)-quinoline-8-carboxylic acid (Step 159.1), 5-(4-ethyl-piperazin-1-ylmethyl)-pyridin-2-ylamine (Step 26.1; purified by silica gel column chromatography), and stirring the reaction mixture for 20 h at rt. Title compound: ESI-MS: 580.1 [M+H]$^+$; $t_R$=3.80 min (System 1); TLC: $R_f$=0.27 (DCM/MeOH/NH$_3^{aq}$, 94:5:1).

EXAMPLE 166

5-(2,6-Dichloro-3,5-dimethoxy-phenyl)-quinoline-8-carboxylic acid {5-1-[4-methoxy-benzyl)-piperazin-1-ylmethyl]-pyridin-2-yl}-amide The title compound was prepared in analogy to the procedure described in Step 14.1 but using 5-(2,6-dichloro-3,5-dimethoxy-phenyl)-quinoline-8-carboxylic acid (Step 159.1), 5-[4-(4-methoxy-benzyl)-piperazin-1-ylmethyl]-pyridin-2-ylamine (Step 105.1) and stirring the reaction mixture for 20 h at rt. Title compound: ESI-MS: 672.0 [M+H]$^+$; TLC: R$_f$=0.25 (DCM/MeOH, 9:1).

EXAMPLE 167

5-(2,6-Dichloro-3,5-dimethoxy-phenyl)-quinoline-8-carboxylic acid (5-piperazin-1-ylmethyl-pyridin-2-yl)-amide

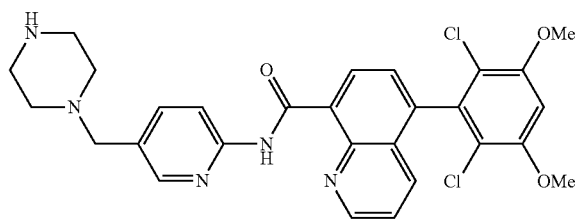 [SMILES: COc1cc(OC)c(Cl)c(-c2ccc(C(=O)Nc3ccc(CN4CCNCC4)cn3)c3ncccc23)c1Cl]

The title compound was prepared in analogy to the procedure described in Example 105 but using 5-(2,6-dichloro-3,5-dimethoxy-phenyl)-quinoline-8-carboxylic acid {5-[4-(4-methoxy-benzyl)-piperazin-1-ylmethyl]-pyridin-2-yl}-amide (Example 166) and stirring the reaction mixture for 1 h at 120° C. Title compound: ESI-MS: 552.1 [M+H]$^+$; TLC: R$_f$=0.12 (DCM/MeOH, 9:1).

EXAMPLE 168

5-(2,6-Dichloro-3,5-dimethoxy-phenyl)-quinoline-8-carboxylic acid [6-(4-methyl-piperazin-1-ylmethyl)-pyridin-3-yl]-amide

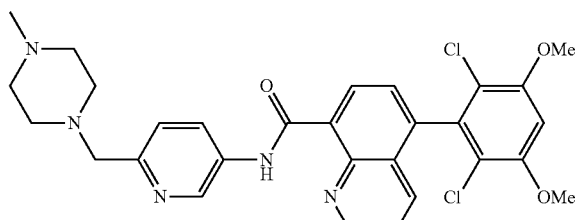

The title compound was prepared in analogy to the procedure described in Step 14.1 but using 5-(2,6-dichloro-3,5-dimethoxy-phenyl)-quinoline-8-carboxylic acid (Step 159.1), 6-(4-methyl-piperazin-1-ylmethyl)-pyridin-3-ylamine (Step 39.1), and stirring the reaction mixture for 3 h at rt. Title compound: ESI-MS: 566.0 [M+H]$^+$; t$_R$=3.64 min (System 1); TLC: R$_f$=0.24 (DCM/MeOH, 9:1).

EXAMPLE 169

5-(2,6-Dichloro-3,5-dimethoxy-phenyl)-quinoline-8-carboxylic acid [6-(4-ethyl-piperazin-1-ylmethyl)-pyridin-3-yl]-amide

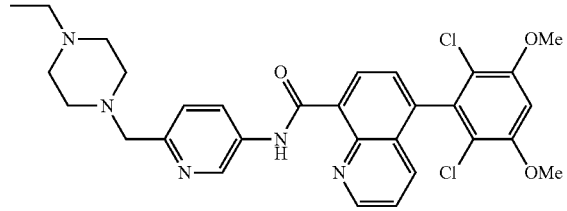 [SMILES: CCN1CCN(Cc2ccc(NC(=O)c3ccc(-c4c(Cl)c(OC)cc(OC)c4Cl)c4cccnc34)cn2)CC1]

The title compound was prepared in analogy to the procedure described in Step 14.1 but using 5-(2,6-dichloro-3,5-dimethoxy-phenyl)-quinoline-8-carboxylic acid (Step 159.1), 6-(4-ethyl-piperazin-1-ylmethyl)-pyridin-3-ylamine (prepared as described in Example 39 but using N-ethyl-piperazine in Step 39.2), and stirring the reaction mixture for 3 h at rt. Title compound: ESI-MS: 580.1 [M+H]$^+$; t$_R$=3.70 min (System 1); TLC: R$_f$=0.33 (DCM/MeOH, 9:1).

EXAMPLE 170

5-(2,6-Dichloro-3,5-dimethoxy-phenyl)-quinoline-8-carboxylic acid {6-[4-(4-methoxy-benzyl)-piperazin-1-ylmethyl]-pyridin-3-yl}-amide

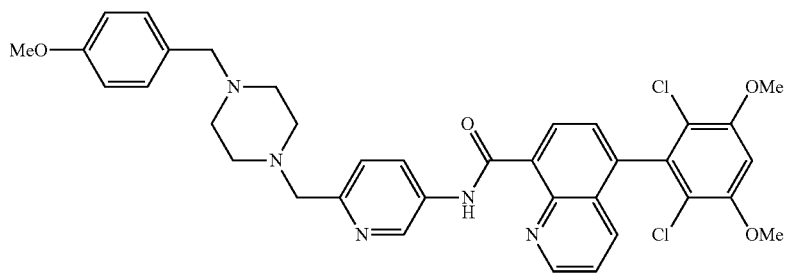 [SMILES: COc1ccc(CN2CCN(Cc3ccc(NC(=O)c4ccc(-c5c(Cl)c(OC)cc(OC)c5Cl)c5cccnc45)cn3)CC2)cc1]

The title compound was prepared in analogy to the procedure described in Step 14.1 but using 5-(2,6-dichloro-3,5-dimethoxy-phenyl)-quinoline-8-carboxylic acid (Step 159.1), 6-[4-(4-methoxy-benzyl)-piperazin-1-ylmethyl]-pyridin-3-ylamine (Step 111.1) and stirring the reaction mixture for 20 h at rt. Title compound: ESI-MS: 672.1 [M+H]$^+$; TLC: R$_f$=0.45 (DCM/MeOH, 9:1).

EXAMPLE 171

5-(2,6-Dichloro-3,5-dimethoxy-phenyl)-quinoline-8-carboxylic acid (6-piperazin-1-ylmethyl-pyridin-3-yl)-amide

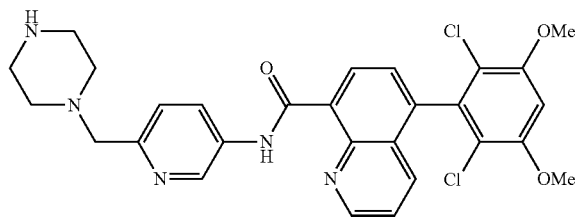 [SMILES: COc1cc(OC)c(Cl)c(-c2ccc(C(=O)Nc3ccc(CN4CCNCC4)nc3)c3ncccc23)c1Cl]

The title compound was prepared in analogy to the procedure described in Example 105 but using 5-(2,6-dichloro-3,5-dimethoxy-phenyl)-quinoline-8-carboxylic acid (6-piperazin-1-ylmethyl-pyridin-3-yl)-amide (Example 170) and stirring the reaction mixture for 1 h at 120° C. Title compound: ESI-MS: 552.0 [M+H]$^+$; t$_R$=3.57 min (System 1); TLC: R$_f$=0.12 (DCM/MeOH, 9:1).

EXAMPLE 172

5-(2,6-Dichloro-3,5-dimethoxy-phenyl)-quinoline-8-carboxylic acid (4-dimethylaminomethyl-1H-imidazol-2-yl)-amide

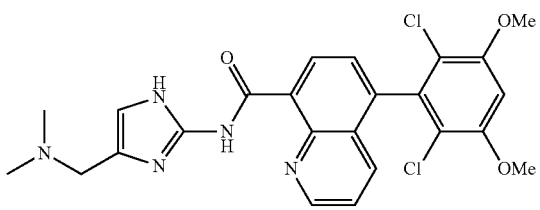 [SMILES: COc1cc(OC)c(Cl)c(-c2ccc(C(=O)Nc3nc(CN(C)C)c[nH]3)c3ncccc23)c1Cl]

The title compound was prepared in analogy to the procedures described in Example 14 but using 5-(2,6-dichloro-3,5-dimethoxy-phenyl)-quinoline-8-carboxylic acid (6-piperazin-1-ylmethyl-pyridin-3-yl)-amide (Example 170), dimethyl-(2-nitro-1H-imidazol-4-ylmethyl)-amine (Step 22.1) instead of 2-nitroimidazole in Step 14.3, and Raney nickel and MeOH/THF (1:1) instead of palladium on carbon and MeOH in Step 14.2. The title compound: ESI-MS: 500.0 [M+H]$^+$; t$_R$=3.50 min (System 1); TLC: R$_f$=0.20 (DCM/MeOH, 9:1).

EXAMPLE 173

5-(2,6-Dichloro-3,5-dimethoxy-phenyl)-quinoline-8-carboxylic acid (5-{[(2-dimethylamino-ethyl)-methyl-amino]-methyl}-pyridin-2-yl)-amide

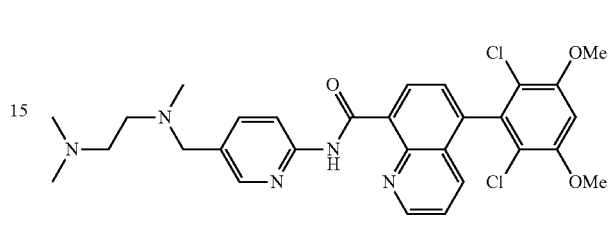

The title compound was prepared in analogy to the procedure described in Step 14.1 but using 5-(2,6-dichloro-3,5-dimethoxy-phenyl)-quinoline-8-carboxylic acid (6-piperazin-1-ylmethyl-pyridin-3-yl)-amide (Example 170), N-(6-amino-pyridin-3-ylmethyl)-N,N',N'-trimethyl-ethane-1,2-diamine (prepared as described in Example 26 but using N,N,N'-trimethyl-ethane-1,2-diamine in Step 26.2), and stirring the reaction mixture for 14 h at rt. Title compound: ESI-MS: 568.0 [M+H]$^+$; TLC: R$_f$=0.15 (DCM/MeOH, 9:1).

EXAMPLE 174

5-(2,6-Difluoro-3,5-dimethoxy-phenyl)-quinoline-8-carboxylic acid [5-(4-methyl-piperazin-1-ylmethyl)-pyridin-2-yl]-amide

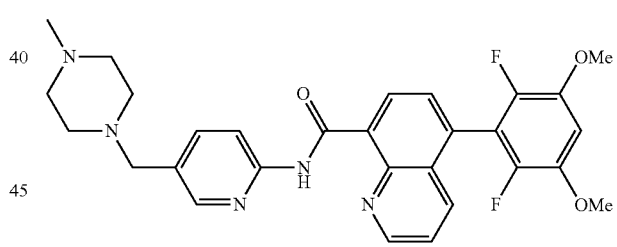

The title compound was prepared in analogy to the procedure described in Example 115 but using 5-(2,6-difluoro-3,5-dimethoxy-phenyl)-quinoline-8-carboxylic acid ethyl ester (Step 174.1), 5-(4-methyl-piperazin-1-ylmethyl)-pyridin-2-ylamine (Example 31; purified by silica gel column chromatography), 2 equiv of trimethyl aluminum, stirring the reaction mixture for 2 h at 80° C. Title compound: ESI-MS: 534.1 [M+H]$^+$; t$_R$=3.56 min (System 1); TLC: R$_f$=0.14 (DCM/MeOH/NH$_3^{aq}$, 94:5:1).

Step 174.1: 5-(2,6-Difluoro-3,5-dimethoxy-phenyl)-quinoline-8-carboxylic acid ethyl ester SelectFluor (2.04 g, 5.8 mmol, 2 equiv) was added to a cold (−5° C.) solution of 5-(3,5-dimethoxy-phenyl)-quinoline-8-carboxylic acid ethyl ester (Step 174.2) (970 mg, 2.9 mmol) in CH$_3$CN (40 mL), under an argon atmosphere. The reaction mixture was allowed to warm to rt, stirred at that temperature for 6 h, quenched by addition of a saturated aqueous solution of NaHCO₃, and concentrated. The residue was diluted in EtOAc and a saturated aqueous solution of NaHCO₃. The aqueous phase was separated and extracted with EtOAc. The combined organic layers were washed with H₂O and brine, dried (Na₂SO₄), filtered and concentrated. The residue was purified by silica gel column chromatography (Hex/EtOAc, 3:2) followed by trituration in Et₂O to provide 257 mg of the title compound: ESI-MS: 374.0 [M+H]⁺; $t_R$=3.81 min (System 1); TLC: $R_f$=0.13 (Hex/EtOAc, 3:2).

Step 174.2:
5-(3,5-Dimethoxy-phenyl)-quinoline-8-carboxylic acid ethyl ester

A mixture of 5-(3,5-dimethoxy-phenyl)-quinoline-8-carboxylic acid (Step 159.2) (2 g), H₂SO₄ conc. (0.6 mL) and EtOH (100 mL) was stirred at reflux for 30 h, allowed to cool and concentrated. The residue was diluted in EtOAc and a saturated aqueous solution of NaHCO₃. The aqueous phase was separated and extracted with EtOAc. The combined organic layers were washed with H₂O and brine, dried (Na₂SO₄), filtered and concentrated. The residue was purified by silica gel column chromatography (Hex/EtOAc, 3:2) to provide 1.77 g of the title compound as a white solid. Title compound: ESI-MS: 338.2 [M+H]⁺; $t_R$=3.81 min (System 1); TLC: $R_f$=0.29 (Hex/EtOAc, 3:2).

EXAMPLE 175

5-(2,6-Difluoro-3,5-dimethoxy-phenyl)-quinoline-8-carboxylic acid (4-d imethylaminomethyl-1H-imidazol-2-yl)-amide

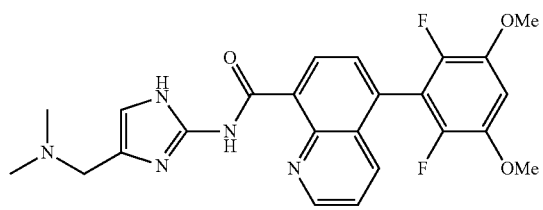

The title compound was prepared in analogy to the procedures described in Example 14 but using 8-(2,6-difluoro-3,5-dimethoxy-phenyl)-quinoxaline-5-carboxylic acid ethyl ester (Step 124.1), stirring the reaction mixture for 7 h at 70° C., and using dimethyl-(2-nitro-1H-imidazol-4-ylmethyl)-amine (Step 22.1) instead of 2-nitroimidazole in Step 14.3, and Raney nickel and MeOH/THF (1:1) instead of palladium on carbon and MeOH in Step 14.2. The title compound: ESI-MS: 468.1 [M+H]⁺; $t_R$=3.29 min (System 1); TLC: $R_f$=0.18 (DCM/MeOH/NH₃$^{aq}$, 91.5:7.5:1).

EXAMPLE 176

5-(2-Chloro-6-fluoro-3,5-dimethoxy-phenyl)-quinoline-8-carboxylic acid [5-(4-methyl-piperazin-1-ylmethyl)-pyridin-2-yl]-amide

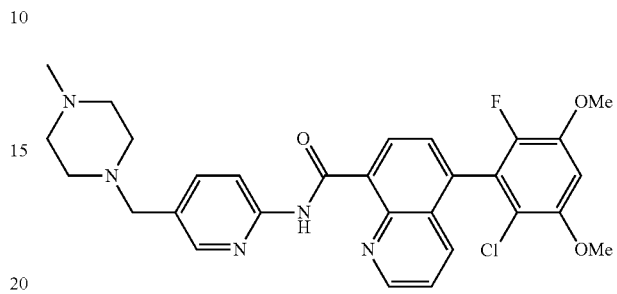

The title compound was prepared in analogy to the procedure described in Step 14.1 but using 5-(2-chloro-6-fluoro-3,5-dimethoxy-phenyl)-quinoline-8-carboxylic (Step 176.1), 5-(4-methyl-piperazin-1-ylmethyl)-pyridin-2-ylamine (Example 31; purified by silica gel column chromatography), and stirring the reaction mixture for 16 h at rt. Title compound: ESI-MS: 550.1 [M+H]⁺; TLC: $R_f$=0.20 (DCM/MeOH/NH₃$^{aq}$, 94:5:1).

Step 176.1: 5-(2-Chloro-6-fluoro-3,5-dimethoxy-phenyl)-quinoline-8-carboxylic acid A mixture of 5-(2-chloro-6-fluoro-3,5-dimethoxy-phenyl)-quinoline-8-carboxylic acid ethyl ester (Step 176.2) (235 mg, 0.60 mmol), a 2 N aqueous solution of LiOH (3 mL) and THF (3 mL) was stirred for 20 h at rt, diluted with H₂O and extracted with Et₂O. The aqueous layer was acidified to pH 4 by addition of a 2 N aqueous solution of HCl. The resulting white precipitate was collected by vacuum filtration providing 210 mg of the title compound: ESI-MS: 362.1 [M+H]⁺; $t_R$=4.24 min (System 1).

Step 176.2: 5-(2-Chloro-6-fluoro-3,5-dimethoxy-phenyl)-quinoline-8-carboxylicacid ethyl ester Sulfuryl chloride (75 μL, 0.93 mmol) was added dropwise to a cold (−20° C.) solution of 5-(2-fluoro-3,5-dimethoxy-phenyl)-quinoline-8-carboxylic acid ethyl ester (Step 176.3) (330 mg, 0.93 mmol) in CH₃CN (6 mL). The reaction mixture was stirred for 10 min at −20° C., quenched by addition of a saturated solution of NaHCO₃, and concentrated. The residue was diluted in EtOAc and a saturated solution of NaHCO₃. The aqueous phase was separated and extracted with EtOAc. The combined organic layers were washed with H₂O and brine, dried (Na₂SO₄), filtered and concentrated. The residue was purified by silica gel column chromatography (Hex/EtOAc, 3:2) to provide 240 mg of the title compound as a white solid. Title compound: ESI-MS: 390.1 [M+H]⁺; $t_R$=3.98 min (System 1); TLC: $R_f$=0.15 (Hex/EtOAc, 3:2).

Step 176.3: 5-(2-Fluoro-3,5-dimethoxy-phenyl)-quinoline-8-carboxylic acid ethyl ester SelectFluor (2.04 g, 5.8 mmol, 2 equiv) was added to a cold (−5° C.) solution of 5-(3,5-dimethoxy-phenyl)-quinoline-8-carboxylic acid ethyl ester (Step 174.2) (970 mg, 2.9 mmol)

in CH₃CN (40 mL), under an argon atmosphere. The reaction mixture was allowed to warm to rt, stirred at that temperature for 6 h, quenched by addition of a saturated aqueous solution of NaHCO₃, and concentrated. The residue was diluted in EtOAc and a saturated aqueous solution of NaHCO₃. The aqueous phase was separated and extracted with EtOAc. The combined organic layers were washed with H₂O and brine, dried (Na₂SO₄), filtered and concentrated. The residue was purified by silica gel column chromatography (Hex/EtOAc, 3:2) followed by trituration in Et₂O to provide 355 mg of the title compound: ESI-MS: 356.2 [M+H]⁺; $t_R$=3.80 min (System 1); TLC: $R_f$=0.18 (Hex/EtOAc, 3:2).

EXAMPLE 177

5-(2-Chloro-6-fluoro-3,5-dimethoxy-phenyl)-quinoline-8-carboxylic acid (4-dimethylaminomethyl-1H-imidazol-2-yl)-amide

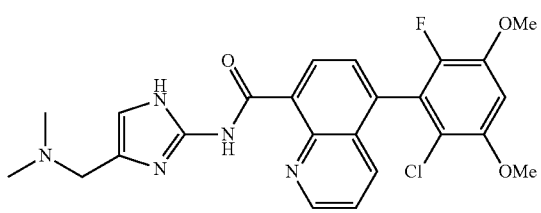 [SMILES: COc1cc(OC)c(Cl)c(-c2ccc(C(=O)Nc3nc(CN(C)C)c[nH]3)c3ncccc23)c1F]

The title compound was prepared in analogy to the procedures described in Example 14 but using 5-(2-chloro-6-fluoro-3,5-dimethoxy-phenyl)-quinoline-8-carboxylic (Step 176.1), stirring the reaction mixture for 8 h at 70° C., and using dimethyl-(2-nitro-1H-imidazol-4-ylmethyl)-amine (Step 22.1) instead of 2-nitroimidazole in Step 14.3, and Raney nickel and MeOH/THF (1:1) instead of palladium on carbon and MeOH in Step 14.2. The title compound: ESI-MS: 484.1 [M+H]⁺; $t_R$=3.39 min (System 1); TLC: $R_f$=0.15 (DCM/MeOH/NH₃$^{aq}$, 91.5:7.5:1).

EXAMPLE 178

5-(2-Chloro-6-fluoro-3,5-dimethoxy-phenyl)-quinoline-8-carboxylic acid [4-(4-methyl-piperazin-1-ylmethyl)-1H-imidazol-2-yl]-amide

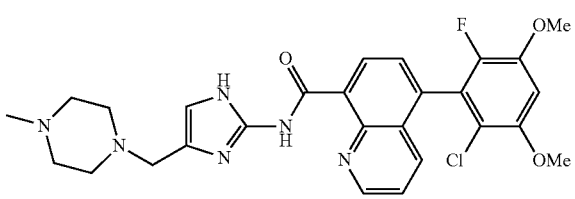 [SMILES: COc1cc(OC)c(Cl)c(-c2ccc(C(=O)Nc3nc(CN4CCN(C)CC4)c[nH]3)c3ncccc23)c1F]

The title compound was prepared in analogy to the procedures described in Example 14 but using 5-(2-chloro-6-fluoro-3,5-dimethoxy-phenyl)-quinoline-8-carboxylic (Step 176.1), stirring the reaction mixture for 8 h at 70° C., and using 1-methyl-4-(2-nitro-1H-imidazol-4-ylmethyl)-piperazine (Step 20.1) instead of 2-nitroimidazole in Step 14.3, and Raney nickel and MeOH/THF (1:1) instead of palladium on carbon and MeOH in Step 14.2. Title compound: ESI-MS: 539.1 [M+H]⁺; $t_R$=3.33 min (System 1); TLC: $R_f$=0.22 (DCM/MeOH/NH₃$^{aq}$, 94:5:1).

EXAMPLE 179

8-(2,6-Dichloro-3,5-dimethoxy-phenyl)-quinoxaline-5-carboxylic acid (4-formyl-1H-imidazol-2-yl)-amide

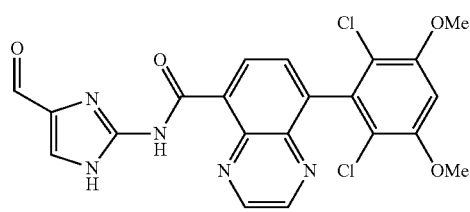 [SMILES: COc1cc(OC)c(Cl)c(-c2ccc(C(=O)Nc3nc(C=O)c[nH]3)c3nccnc23)c1Cl]

A mixture of 8-(2,6-dichloro-3,5-dimethoxy-phenyl)quinoxaline-5-carboxylic acid (300 mg, 0.791 mmol) (Step 179.1), 2-amino-4-diethoxymethyl-imidazole-1-carboxylic acid tert-butyl ester (226 mg, 0.791 mmol) (Step 179.8), TBTU (305 mg, 0.949 mmol, 1.2 equiv) and DIEA (409 mg, 3.17 mmol, 4 equiv) in DMF (6 mL) was stirred for 48 h at rt. After further addition of 2-amino-4-diethoxymethyl-imidazole-1-carboxylic acid tert-butyl ester (80 mg, 0.280 mmol) (Step 179.8), the reaction mixture was stirred for additional 72 h at rt, diluted with EtOAc/H₂O and extracted with EtOAc. The organic phase was washed with H₂O and brine, dried (Na₂SO₄), filtered and concentrated. The residue was purified by silica gel column chromatography (EtOAc/Hex, 1:1) to afford 470 mg of a mixture of products. Part of this mixture (280 mg) was dissolved in acetone (3 mL) and H₂O (2 mL) and treated with PPTS (10.9 mg). The reaction mixture was stirred for 7 h at rt, heated to 50° C., stirred for 20 h, allowed to cool to rt and diluted with EtOAc/H₂O. The resulting yellow precipitate was collected by vacuum filtration and dried to provide 128 mg of the title compound: ES-MS: 472 [M+H]+; $t_R$=4.16 min (System 1).

Step 179.1: 8-(2,6-Dichloro-3,5-dimethoxy-phenyl)-quinoxaline-5-carboxylic acid

Sulfuryl chloride (1.7 mL, 21.3 mmol, 2 equiv) was added dropwise to a cold (5° C.) suspension of 8-(3,5-dimethoxy-phenyl)-quinoxaline-5-carboxylic acid (Step 179.2) (3.3 g, 10.6 mmol) in CH₃CN (30 mL). The reaction mixture was stirred at 5° C. for 2 h, quenched by addition of H₂O, and concentrated. Trituration of the residue in H₂O provided 4.0 g of the title compound as a white solid: ESI-MS: 379 [M+H]⁺; $t_R$=4.54 min (System 1).

Step 179.2: 8-(3,5-Dimethoxy-phenyl)-quinoxaline-5-carboxylic acid

KOH (6.0 g, 107 mmol, 10 equiv) was added to 8-(3,5-dimethoxy-phenyl)-quinoxaline-5-carbonitrile (Step 179.3) (3.12 g, 10.7 mmol) in ethylene glycol (30 mL). The reaction mixture was stirred at 150° C. for 3 h (a solution was obtained), allowed to cool to rt, diluted with Et₂O/H₂O, and extracted with Et₂O. The aqueous phase was acidified to pH 5 by addition of HCl. Vacuum filtration of the resulting suspension afforded 3.3 g of the title compound as a yellow solid: ESI-MS: 311 [M+H]$^+$; $t_R$=4.34 min (System 1).

Step 179.3: 8-(3,5-Dimethoxy-phenyl)-quinoxaline-5-carbonitrile

A mixture of 5-bromo-8-(3,5-dimethoxy-phenyl)-quinoxaline (Step 179.4) (4.54 g, 13.2 mmol) and CuCN (1.54 g, 17.1 mmol, 1.3 equiv) in NMP (50 mL) was stirred for 2 h at 180° C., under an argon atmosphere. The reaction mixture was allowed to cool to rt, diluted with EtOAc/(10% aqueous solution of ethylenediamine) (150 mL), and filtered to afford 1.19 g (batch 1) of the title compound as a yellow solid. The filtrate was extracted with DCM. The organic phase was washed with $H_2O$ and brine, dried ($Na_2SO_4$), filtered and concentrated. The residue was triturated in EtOAc to provide 2.31 g (batch 2) of the title compound: ESI-MS: 292 [M+H]$^+$; $t_R$=4.53 min (System 1).

Step 179.4: 5-Bromo-8-(3,5-dimethoxy-phenyl)-quinoxaline

A mixture of 3,5-dimethoxyphenylboronic acid (3.38 g, 18.6 mmol) in EtOH (15 mL) was added dropwise to a mixture of 5,8-dibromo-quinoxaline (Step 179.5) (10.7 g, 37.1 mmol, 2 equiv), PdCl$_2$(dppf) (530 mg, 0.7 mmol, 0.03 equiv), Na$_2$CO$_3$ (2 M solution in H$_2$O, 37 mL, 74.3 mmol, 4 equiv) in toluene (100 mL) at 105° C., under an argon atmosphere. The reaction mixture was stirred at 105° C. for 2 h, allowed to cool to rt, diluted with EtOAc and H$_2$O, filtered through a pad of celite and extracted with EtOAc. The organic phase was washed with H$_2$O and brine, dried (Na$_2$SO$_4$), filtered and concentrated in vacuo. The crude product was purified by trituration in DCM, followed by silica gel column chromatography (Hex/EtOAc, 4:1) to afford 4.54 g of the title compound as a yellow solid: ES-MS: 345 [M+H]$^+$; $t_R$=5.13 min (System 1); $R_f$=0.17 (Hex/EtOAc, 4:1).

Step 179.5: 5,8-Dibromo-quinoxaline

A 40% aqueous solution of glyoxal (8.8 M, 6.3 mL, 55.1 mmol, 1.3 equiv) was added to a suspension of 3,6-dibromo-benzene-1,2-diamine (Step 179.6) (11.3 g, 42.4 mmol) in EtOH (280 mL). The reaction mixture was heated to reflux for 3 h and allowed to cool to rt overnight. Vacuum filtration of the reaction mixture afforded 9.7 g of the title compound as a yellow solid: APCI-MS: 286/288/291 [M–1]$^-$; $t_R$=4.40 min (System 1).

Step 179.6: 3,6-Dibromo-benzene-1,2-diamine

NaBH$_4$ (26 g, 680 mmol, 10 equiv) was added portionwise (2 h) to a vigorously stirred suspension of 4,7-dibromo-benzo[1,2,5]thiadiazole (Step 179.7) (20 g, 68.0 mmol) in EtOH (400 mL), under a nitrogen atmosphere and keeping the internal temperature below 15° C. The reaction mixture was allowed to warm to 30° C., stirred for 1 h, cooled to 5° C., quenched by addition of H$_2$O (50 mL), and concentrated. The residue was diluted with Et$_2$O/H$_2$O. The resulting suspension was filtered and the filtrate extracted with Et$_2$O. The organic phase was washed with H$_2$O and brine, dried (Na$_2$SO$_4$), filtered and concentrated. The residue was triturated in hexane to provide 12 g of the title compound as a white solid: ESI-MS: 263/265/267 [M–H]$^-$; $t_R$=4.20 min (System 1).

Step 179.7: 4,7-Dibromo-benzo[1,2,5]thiadiazole

Bromine (18.6 mL, 265 mmol, 1.2 equiv) was added to a refluxing solution of 1,2,5-benzothiazole (30 g, 220 mmol) in HBr (48% in H$_2$O, 150 mL). The reaction mixture was stirred for 4 h at reflux and allowed to cool to rt. The resulting solid was collected by vacuum filtration, washed with H$_2$O, dried under vacuum, and triturated in MeOH to afford 63 g of the title compound as an off-white solid: $^1$H NMR (400 MHz, DMSO-d6) δ(ppm): 8.00 (s, 2H); $t_R$=5.05 min (System 1).

Step 179.8: 2-Amino-4-diethoxymethyl-imidazole-1-carboxylic acid tert-butyl ester A mixture of 3-bromo-1,1-diethoxy-propan-2-one (21.3 g, 95 mmol) (Step 179.9) and N-tert-butoxycarbonylguanidine (45.3 g, 284 mmol, 3 equiv) (Step 179.10) was stirred at 50° C. for 8 h. The reaction mixture was concentrated, diluted in EtOAc/H$_2$O and extracted with EtOAc. The organic phase was washed with water and brine, dried (Na$_2$SO$_4$) and concentrated. The residue was purified by silica gel column chromatography (DCM/EtOAc, 3:7) followed by trituration in Et$_2$O to afford 11.3 g of the title compound as a white solid: ES-MS: 286 [M+H]$^+$; $R_f$=0.34 (DCM/EtOAc, 3:7).

Step 179.9: 3-Bromo-1,1-diethoxy-propan-2-one

Copper (II) bromide (159 g, 711 mmol, 2.1 equiv) was added to a mechanically stirred solution of pyruvic aldehyde dimethyl acetal (40 g, 339 mmol) in EtOAc (1.5 L) at rt. The reaction mixture was heated to reflux, stirred for 3 h, cooled to rt, quenched by addition of a saturated aqueous solution of NaHCO$_3$ (500 mL), stirred for 30 min and filtered through a pad of celite. The filtrate was extracted with EtOAc and the combined organic extracts were washed with H$_2$O and brine, dried (Na$_2$SO$_4$), filtered and concentrated. The residue was purified by distillation to afford 22.4 g of the title compound as a yellow oil: ES-MS: 223/225 [M+H]$^+$; bp: 80° C./40 mmbar.

Step 179.10: N-tert-Butoxycarbonylguanidine

Guanidine hydrochloride (175 g, 1833 mmol, 4 equiv) was added to a solution of NaOH (147 g, 3666 mmol, 8 equiv) in H$_2$O (360 mL), portionwise and keeping the internal temperature around 0° C. tert-Butoxycarbonyl anhydride (100 g, 458 mmol) in acetone (1.5 L) was then added over 2 h and the reaction mixture was allowed to warm to rt over 14 h. The acetone was removed under vacuum and the resulting aqueous mixture was extracted with EtOAc. The organic phase was washed with H$_2$O and brine, dried (Na$_2$SO$_4$), filtered and concentrated to afford 61.6 g of the title compound as a white solid: ES-MS: 160 [M+H]$^+$.

EXAMPLE 180

8-(2,6-Dichloro-3,5-dimethoxy-phenyl)-quinoxaline-5-carboxylic acid (4-{[(2-dimethylamino-ethyl)-methyl-amino]-methyl}-1H-imidazol-2-yl)-amide

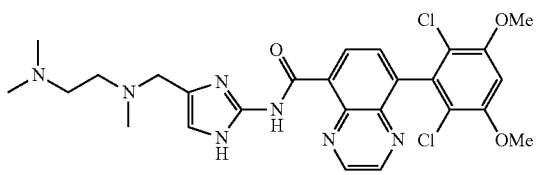 [SMILES: COc1cc(OC)c(Cl)c(-c2ccc(C(=O)Nc3nc(CN(C)CCN(C)C)c[nH]3)c3nccnc23)c1Cl]

Sodium triacetoxyborohydride (168 mg, 0.794 mmol, 3 equiv) was added to a suspension of 8-(2,6-dichloro-3,5-dimethoxy-phenyl)-quinoxaline-5-carboxylic acid (4-formyl-1H-imidazol-2-yl)-amide (125 mg, 0.265 mmol) (Example 179) and N,N,N'-trimethylethylenediamine (81 mg, 0.792 mmol, 3 equiv) in DCM (4 mL) at rt, under an argon atmosphere. The reaction mixture was stirred for 18 h at rt, diluted in DCM/H$_2$O and extracted with DCM. The organic phase was washed with H$_2$O and brine, dried (Na$_2$SO$_4$), filtered and concentrated. The residue was purified by silica gel column chromatography (DCM/MeOH/NH$_3{}^{aq}$, 94:5:1) followed by trituration in Et$_2$O to afford 88 mg of the title compound as a yellow solid: ES-MS: 558 [M+H]+; $t_R$=3.14 min (System 1); TLC: R$_f$=0.05 (DCM/MeOH/NH$_3{}^{aq}$, 94:5:1).

EXAMPLE 181

8-(2,6-Dichloro-3,5-dimethoxy-phenyl)-quinoxaline-5-carboxylic acid {4-[(2,2,2-trifluoro-ethylamino)-methyl]-1H-imidazol-2-yl}-amide

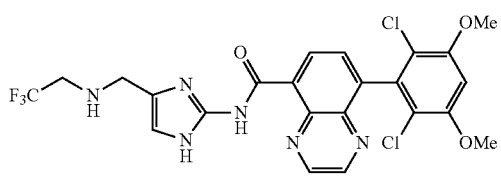 [SMILES: COc1cc(OC)c(Cl)c(-c2ccc(C(=O)Nc3nc(CNCC(F)(F)F)c[nH]3)c3nccnc23)c1Cl]

Sodium triacetoxyborohydride (101 mg, 0.476 mmol, 3 equiv) was added to a suspension of 8-(2,6-dichloro-3,5-dimethoxy-phenyl)-quinoxaline-5-carboxylic acid (4-formyl-1H-imidazol-2-yl)-amide (75 mg, 0.159 mmol) and trifluoroethylamine (15 µl, 0.188 mmol), 1.18 equiv) in DCM (3 mL) at rt, under an argon atmosphere. The reaction mixture was stirred for 18 h at rt, quenched by addition of H$_2$O and extracted with DCM. The organic phase was washed with a saturated aqueous solution of NaHCO$_3$, dried (Na$_2$SO$_4$), filtered and concentrated. The residue was purified by silica gel column chromatography (DCM/MeOH/NH$_3{}^{aq}$, 98:1:1) followed by trituration in Et$_2$O to afford 55 mg of the title compound as a yellow solid: ES-MS: 555 [M+H]+; $t_R$=3.78 min (System 1); TLC: R$_f$=0.55 (DCM/MeOH, 9:1).

EXAMPLE 182

8-(2,6-Dichloro-3,5-dimethoxy-phenyl)-quinoxaline-5-carboxylic acid {4-[(cyanomethyl-methyl-amino)-methyl]-1H-imidazol-2-yl}-amide

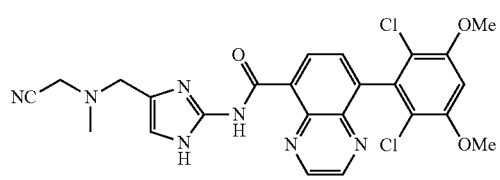 [SMILES: COc1cc(OC)c(Cl)c(-c2ccc(C(=O)Nc3nc(CN(C)CC#N)c[nH]3)c3nccnc23)c1Cl]

The title compound was prepared in analogy to the procedure described in Example 181 but using ethylaminoacetonitrile hydrochloride instead of trifluoroethylamine. Title compound: ES-MS: 526/528 [M+H]+; $t_R$=3.88 min (System 1); TLC: R$_f$=0.24 (DCM/MeOH, 9:1).

EXAMPLE 183

8-(2,6-Dichloro-3,5-dimethoxy-phenyl)-quinoxaline-5-carboxylic acid [4-(3-cyano-azetidin-1-ylmethyl)-1H-imidazol-2-yl]-amide

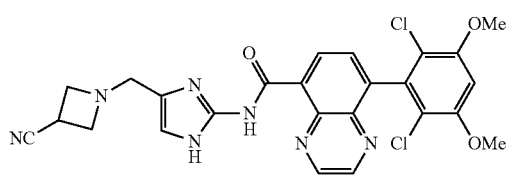 [SMILES: COc1cc(OC)c(Cl)c(-c2ccc(C(=O)Nc3nc(CN4CC(C#N)C4)c[nH]3)c3nccnc23)c1Cl]

The title compound was prepared in analogy to the procedure described in Example 181 but using ethylaminoacetonitrile hydrochloride instead of trifluoroethylamine. Title compound: ES-MS: 538/540 [M+H]+; $t_R$=3.49 min (System 1); TLC: R$_f$=0.48 (DCM/MeOH, 9:1).

EXAMPLE 184

8-(2,6-Dichloro-3,5-dimethoxy-phenyl)-quinoxaline-5-carboxylic acid [4-(3,3-difluoro-azetidin-1-ylmethyl)-1H-imidazol-2-yl]-amide

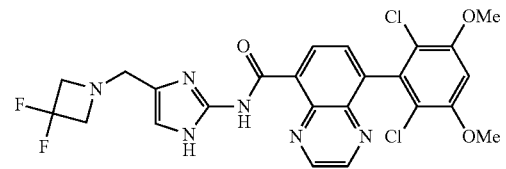 [SMILES: COc1cc(OC)c(Cl)c(-c2ccc(C(=O)Nc3nc(CN4CC(F)(F)C4)c[nH]3)c3nccnc23)c1Cl]

The title compound was prepared in analogy to the procedure described in Example 180 but using 3,3-difluoroazetidine hydrochloride (1.2 equiv) instead of N,N,N'-trimethylethylenediamine and stirring the reaction mixture for 72 h at rt. Title compound: ES-MS: 549/551 [M+H]+; $t_R$=3.65 min (System 1); TLC: R$_f$=0.55 (DCM/MeOH/NH$_3{}^{aq}$, 91.5:7.5:1).

EXAMPLE 185

8-(2,6-Difluoro-3,5-dimethoxy-phenyl)-quinoxaline-5-carboxylic acid (4-formyl-1H-imidazol-2-yl)-amide

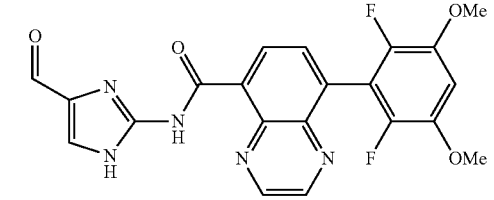 [SMILES: COc1cc(OC)c(F)c(-c2ccc(C(=O)Nc3nc(C=O)c[nH]3)c3nccnc23)c1F]

A mixture of 8-(2,6-difluoro-3,5-dimethoxy-phenyl)-quinoxaline-5-carboxylic acid (200 mg, 0.578 mmol) (Step 185.1), 2-amino-4-diethoxymethyl-imidazole-1-carboxylic acid tert-butyl ester (198 mg, 0.693 mmol, 1.2 equiv) (Step 179.8), TBTU (223 mg, 0.693 mmol, 1.2 equiv), DIEA (74.7 mg, 0.578 mmol) in DMF (4 mL) was stirred for 18 h at rt. The reaction mixture was diluted in EtOAc/$H_2O$ and extracted with EtOAc. The organic phase was washed with $H_2O$ and brine, dried ($Na_2SO_4$), filtered and concentrated. The resulting yellow foam (405 mg) was dissolved in acetone (5 mL) and $H_2O$ (3 mL) and treated with PPTS (30 mg). The reaction mixture was heated to 50° C., stirred for 2 h, allowed to cool to rt and diluted with EtOAc/$H_2O$. The resulting yellow precipitate was collected by vacuum filtration and dried to provide 174 mg of the title compound: ES-MS: 440 [M+H]+; $t_R$=3.89 min (System 1).

Step 185.1: 8-(2,6-Difluoro-3,5-dimethoxy-phenyl)-quinoxaline-5-carboxylic acid A mixture of 8-(2,6-difluoro-3,5-dimethoxy-phenyl)-quinoxaline-5-carboxylic acid ethyl ester (885 mg, 2.37 mmol) (Step 185.2), a 2N aqueous solution of LiOH (8 mL) and THF (8 mL) was stirred for 16 h at rt. THF was removed under vacuum. The resulting mixture was diluted with $Et_2O/H_2O$. The aqueous layer was separated and extracted with $Et_2O$. The aqueous layer was acidified to pH 6 by addition of a 2N aqueous solution of HCl. The resulting yellow precipitate was collected by vacuum filtration and dried to provide 701 mg of the title compound: ESI-MS: 347 [M+H]+; $t_R$=3.16 min (System 1)

Step 185.2: 8-(2,6-Difluoro-3,5-dimethoxy-phenyl)-quinoxaline-5-carboxylic acid ethyl ester 2,6-dichloro-1-fluoropyridinium tetrafluoroborate (13.9 g, 54.6 mmol, 1.8 equiv) was added to a cold (−5° C.) solution of 8-(3,5-dimethoxy-phenyl)-quinoxaline-5-carboxylic acid ethyl ester (Step 185.3) (10.1 g, 29.9 mmol) in $CH_3CN$ (100 mL). The reaction mixture was allowed to warm to rt overnight, cooled to 5° C. and quenched by addition of a saturated aqueous solution of $NaHCO_3$ (20 mL). The organic solvent was removed in vacuo and the residual layer was diluted in EtOAc and a saturated aqueous solution of $NaHCO_3$. The aqueous phase was separated and extracted with EtOAc. The combined organic layers were washed with $H_2O$ and brine, dried ($Na_2SO_4$), filtered and concentrated. Several purifications by silica gel column chromatography (DCM/Hex/$Et_2O$, 1:3:6) provide 2.93 g of the title compound as a white solid. Title compound: ESI-MS: 375 [M+H]+; $t_R$=4.60 min (System 1); TLC: $R_f$=0.19 (DCM/Hex/$Et_2O$, 1:3:6).

Step 185.3: 8-(3,5-Dimethoxy-phenyl)-quinoxaline-5-carboxylic acid ethyl ester A mixture of 8-(3,5-dimethoxy-phenyl)-quinoxaline-5-carboxylic acid (Step 179.2) (10 g), $H_2SO_4$ conc. (3 mL) and EtOH (500 mL) was stirred at reflux for 7 h, allowed to cool and concentrated. The residue was diluted in EtOAc and a saturated aqueous solution of $NaHCO_3$. The aqueous phase was separated and extracted with EtOAc. The combined organic layers were washed with $H_2O$ and brine, dried ($Na_2SO_4$), filtered and concentrated to afford 10.1 g of the title compound as a beige solid. Title compound: ESI-MS: 339 [M−H]−; $t_R$=4.72 min (System 1).

EXAMPLE 186

8-(2,6-Difluoro-3,5-dimethoxy-phenyl)-quinoxaline-5-carboxylic acid (4-methylaminomethyl-1H-imidazol-2-yl)-amide

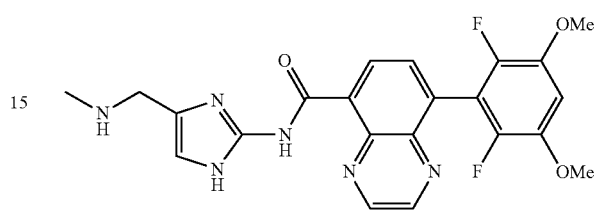

Sodium triacetoxyborohydride (72.4 mg, 0.341 mmol, 1.5 equiv) was added to a suspension of 8-(2,6-difluoro-3,5-dimethoxy-phenyl)-quinoxaline-5-carboxylic acid (4-formyl-1H-imidazol-2-yl)-amide (100 mg, 0.228 mmol) (Example 185) and methylamine (40% wt in $H_2O$, 40 μL, 0.455 mmol, 2 equiv) in DCM (4 mL) at rt, under an argon atmosphere. The reaction mixture was stirred for 4 h at rt. After further addition of sodium triacetoxyborohydride (72.4 mg, 0.341 mmol, 1.5 equiv), the reaction mixture was stirred for additional 16 h at rt. Then, methylamine (50 μL) and sodium triacetoxyborohydride (150 mg) were added. The reaction mixture was stirred for 4 h at rt, diluted with EtOAc/saturated aqueous solution of $NaHCO_3$ and extracted with DCM. The organic phase was dried ($Na_2SO_4$), filtered and concentrated.

The residue was purified by silica gel column chromatography (DCM/MeOH/$NH_3^{aq}$, 91.5:7.5:1) to afford 41 mg of the title compound as a yellow solid: ES-MS: 455 [M+H]+; $t_R$=3.00 min (System 1); TLC: $R_f$=0.10 (DCM/MeOH/$NH_3^{aq}$, 91.5:7.5:1).

EXAMPLE 187

8-(2,6-Difluoro-3,5-dimethoxy-phenyl)-quinoxaline-5-carboxylic acid (4-N,N-dimethyl-N-oxidyl-aminomethyl-1H-imidazol-2-yl)-amide

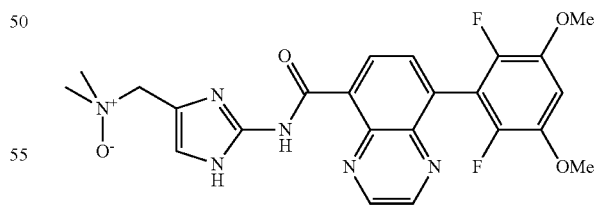

A mixture of 8-(2,6-difluoro-3,5-dimethoxy-phenyl)-quinoxaline-5-carboxylic acid (4-dimethylaminomethyl-1H-imidazol-2-yl)-amide (30 mg, 0.64 mmol) (Step 187.1) and mCPBA (20.1 g, 0.064 mmol) was stirred for 30 min at 5° C., diluted with DCM/saturated aqueous solution of $NaHCO_3$ and extracted with DCM/MeOH (9:1, v/v). The organic phase was dried ($Na_2SO_4$), filtered and concentrated. The residue was purified by silica gel column chromatography (DCM/MeOH/$NH_3^{aq}$, 89:10:1) to afford 20 mg of the title compound as a yellow solid: ES-MS: 485 [M+H]+; $t_R$=3.21 min (System 1); TLC: $R_f$=0.05 (DCM/MeOH/NH$_3^{aq}$, 89:10:1).

Step 187.1: 8-(2,6-Difluoro-3,5-dimethoxy-phenyl)-quinoxaline-5-carboxylic acid (4-dimethylaminomethyl-1H-imidazol-2-yl)-amide The title compound was prepared in analogy to the procedure described in Example 180 but using dimethylamine hydrochloride (1.5 equiv) instead of N,N,N'-trimethylethylenediamine and 8-(2,6-difluoro-3,5-dimethoxy-phenyl)-quinoxaline-5-carboxylic acid (4-formyl-1H-imidazol-2-yl)-amide (Example 7). Title compound: ES-MS: 469 [M+H]+; $t_R$=3.14 min (System 1); TLC: $R_f$=0.22 (DCM/MeOH/NH$_3^{aq}$, 91.5:7.5:1).

$^1$H NMR data for selected examples are provided in the following table:

| Example | $^1$H NMR Data (400 MHz, DMSO-d6) |
|---|---|
| 81 | δ(ppm): 2.11 (s, 6 H), 2.14 (s, 3 H), 2.30-2.46 (m, 4 H), 3.49 (s, 2 H), 3.98 (s, 6 H), 7.05 (s, 1 H), 7.80 (d, J = 8.4 Hz, 1 H), 7.93 (d, J = 7.8 Hz, 1 H), 8.29 (s, 1 H), 8.35 (d, J = 8.2 Hz, 1 H), 8.76 (d, J = 7.4 Hz, 1 H), 9.06 (s, 1 H), 9.19 (s, 1 H), 12.70 (s, 1 H) |
| 92 | δ(ppm): 0.96 (t, J = 7.23 Hz, 3 H), 2.28 (q, J = 7.43 Hz, 2 H), 2.30-2.60 (m, 8 H), 3.47 (s, 2 H), 3.92 (s, 6 H), 7.15 (t, J = 8.41 Hz, 1 H), 7.80 (dd, J = 8.60, 2.35 Hz, 1 H), 8.11 (d, J = 7.82 Hz, 1 H), 8.29 (d, J = 1.56 Hz, 1 H), 8.35 (d, J = 8.60 Hz, 1 H), 8.71 (d, J = 7.82 Hz, 1 H), 9.10 (d, J = 1.56 Hz, 1 H), 9.20 (d, J = 1.96 Hz, 1 H), 12.59 (s, 1 H) |
| 122 | δ(ppm): 2.15 (s, 3 H), 2.20-2.58 (m, 8 H), 2.59 (s, 3 H), 2.84 (s, 3 H), 3.47 (s, 2 H), 3.98 (s, 6 H), 7.04 (s, 1 H), 7.75 (d, J = 7.82 Hz, 1 H), 7.79 (d, J = 8.60 Hz, 1 H), 8.32 (s, 1 H), 8.35 (d, J = 8.60 Hz, 1 H), 8.70 (d, J = 7.82 Hz, 1 H), 13.43 (s, 1 H) |
| 127 | δ(ppm): 2.14 (s, 6 H), 3.32 (s, 2 H), 3.92 (s, 6 H), 6.67 (br s, 1 H), 7.15 (t, J = 8.41 Hz, 1 H), 8.10 (d, J = 7.82 Hz, 1 H), 8.62 (d, J = 7.43 Hz, 1 H), 9.10 (s, 1 H), 9.18 (s, 1 H) |
| 135 | δ(ppm): 2.38 (br s, 4 H), 3.31 (s, 2 H), 3.55 (br s, 4 H), 3.92 (s, 6 H), 6.74 (br s, 1 H), 7.15 (t, J = 8.41 Hz, 1 H), 8.10 (d, J = 7.43 Hz, 1 H), 8.64 (br. s., 1 H), 9.10 (s, 1 H), 9.19 (br s, 1 H), 11.77 (br s, 1 H), 12.68 (br s, 1 H) |
| 141 | δ(ppm): 2.12 (s, 3 H), 2.20-2.50 (m, 8 H), 3.32 (s, 2 H), 3.92 (s, 6 H), 6.69 (br s, 1 H), 7.15 (t, J = 8.41 Hz, 1 H), 8.10 (d, J = 7.43 Hz, 1 H), 8.63 (d, J = 7.04 Hz, 1 H), 9.10 (s, 1 H), 9.19 (s, 1 H) |
| 142 | δ(ppm): 2.58 (br s, 2 H), 2.94 (s, 2 H), 3.13 (br s, 2 H), 3.41 (br s, 2 H), 3.92 (s, 6 H), 6.79 (br s, 1 H), 7.15 (t, J = 8.4 Hz, 1 H), 7.71 (br s, 1 H), 8.10 (d, J = 7.8 Hz, 1 H), 8.63 (d, J = 5.5 Hz, 1 H), 9.10 (s, 1 H), 9.19 (br s, 1 H), 11.81 (br s, 1 H), 12.68 (br s, 1 H) |
| 145 | δ(ppm): 0.96 (t, J = 7.0 Hz, 3 H), 1.90-2.70 (m, 10 H), 3.47 (s, 2 H) 3.95 (br s, 6 H), 7.10 (d, J = 7.8 Hz, 1 H), 7.80 (d, J = 8.2 Hz, 1 H), 8.02 (d, J = 7.8 Hz, 1 H), 8.28 (s, 1 H), 8.34 (d, J = 8.6 Hz, 1 H), 8.73 (d, J = 7.4 Hz, 1 H), 9.07 (s, 1 H), 9.19 (s, 1 H), 12.64 (s, 1 H) |
| 152 | δ(ppm): 2.70-3.20 (m, 8 H), 3.70 (s, 2 H), 3.95 (d, J = 3.13 Hz, 6 H), 7.10 (d, J = 7.82 Hz, 1 H), 7.86 (d, J = 8.60 Hz, 1 H), 8.02 (d, J = 7.43 Hz, 1 H), 8.25-8.48 (m, 2 H), 8.72 (d, J = 7.43 Hz, 1 H), 9.07 (s, 1 H), 9.19 (s, 1 H), 12.65 (s, 1 H) |
| 155 | δ(ppm): 2.58 (br s, 2 H), 2.94 (s, 2 H), 3.13 (br s, 2 H), 3.42 (br s, 2 H), 3.95 (s, 6 H), 6.79 (br s, 1 H), 7.10 (d, J = 7.8 Hz, 1 H), 7.70 (br s, 1 H), 8.02 (d, J = 7.4 Hz, 1 H,) 8.64 (br s, 1 H), 9.07 (s, 1 H), 9.18 (s, 1 H), 11.81 (br s, 1 H), 12.71 (br s, 1 H) |
| 157 | δ(ppm): 1.00 (t, J = 7.2 Hz, 3 H), 2.13 (s, 3 H), 2.38 (q, J = 7.0 Hz, 2 H), 3.39 (br s, 2 H), 3.92 (s, 6 H), 6.68 (br s, 1 H), 7.15 (t, J = 8.2 Hz, 1 H), 8.10 (d, J = 7.8 Hz, 1 H), 8.63 (d, J = 7.4 Hz, 1 H), 9.10 (s, 1 H), 9.18 (s, 1 H) |
| 158 | δ(ppm): 0.98 (t, J = 7.04 Hz, 6 H), 2.36-2.57 (m, 4 H), 3.46 (br s, 2 H), 3.92 (s, 6 H), 6.68 (br s, 1 H), 7.15 (t, J = 8.21 Hz, 1 H), 8.09 (d, J = 7.43 Hz, 1 H), 8.62 (d, J = 7.43 Hz, 1 H), 9.09 (s, 1 H), 9.18 (s, 1 H) |
| 177 | $^1$H NMR (600 MHz) δ(ppm): 2.20 (br s, 6 H), 3.45 (br s, 2 H), 3.99 (s, 6 H), 6.75 (br s, 1 H), 7.19 (d, J = 7.9 Hz, 1 H), 7.75 (dd, J = 8.3, 4.0 Hz, 1 H), 7.82 (d, J = 7.7 Hz, 1 H), 8.03 (d, J = 8.5 Hz, 1 H), 8.80 (br s, 1 H), 9.22 (br s, 1 H), 11.77 (br s, 1 H), 13.88 (br s, 1 H) |
| 178 | $^1$H NMR (600 Mz) δ(ppm): 2.16 (s, 3 H), 2.33-2.49 (m, 8 H), 3.34 (br s, 2 H), 3.99 (d, J = 5.0 Hz, 6 H), 6.74 (br s, 1 H), 7.19 (d, J = 7.9 Hz, 1 H), 7.75 (dd, J = 8.5, 4.2 Hz, 1 H), 7.82 (d, J = 7.5 Hz, 1 H), 8.03 (d, J = 8.3 Hz, 1 H), 8.80 (d, J = 7.7 Hz, 1 H), 9.23 (br s, 1 H), 11.76 (br s, 1 H), 13.86 (br s, 1 H) |
| 180 | δ(ppm): 2.07-2.23 (m, 9 H), 2.32-2.39 (m, 2 H), 2.39-2.46 (m, 2 H), 3.42 (br s, 2 H), 3.98 (s, 6 H), 6.67 (br s, 1 H), 7.06 (s, 1 H), 7.92 (d, J = 7.43 Hz, 1 H), 8.67 (d, J = 7.82 Hz, 1 H), 9.05 (d, J = 1.56 Hz, 1 H), 9.16 (d, J = 1.56 Hz, 1 H) |
| 183 | δ(ppm): 3.30-4.20 (m, 13 H), 6.72 (br s, 1 H), 7.06 (s, 1 H), 7.92 (d, J = 7.8 Hz, 1 H), 8.67 (d, J = 6.6 Hz, 1 H), 9.05 (s, 1 H), 9.16 (s, 1 H), 11.77 (br s, 1 H), 12.73 (br s, 1 H) |
| 186 | δ(ppm): 2.25 (s, 3 H), 3.52 (br s, 2 H), 3.92 (s, 6 H), 6.65 (br s, 1 H), 7.15 (t, J = 8.21 Hz, 1 H), 8.10 (d, J = 7.43 Hz, 1 H), 8.63 (d, J = 7.43 Hz, 1 H), 9.09 (s, 1 H), 9.17 (s, 1 H) | br: broad; s: singlet; d: doublet; t: triplet; q: quartet; Hz: Hertz; ppm: part per million The $^1$H-NMR spectra were measured on either a Varian Mercury 400 spectrometer or a Bruker Avance 600 spectrometer.

EXAMPLE 188

Pharmaceutical Formulations

EXAMPLE 188.1

Soft Capsules 5000 soft gelatin capsules, each comprising as active ingredient 0.05 g of any one of the compounds of formula (I) mentioned in any one of the preceding Examples are prepared as follows: 250 g pulverized active ingredient is suspended in 2 liters Lauroglykol* (propylene glycol laurate, Gattefossé S.A., Saint Priest, France) and ground in a wet pulverizer to produce a particle size of about 1 to 3 μm. 0.419 g portions of the mixture are then introduced into soft gelatin capsules using a capsule-filling machine.

EXAMPLE 188.2

Tablets

Tablets, comprising, as active ingredient 100 mg of any one of the compounds of formula (I) mentioned in any one of the preceding Examples are prepared with the following composition according to standard procedures.

| | |
|---|---|
| compound (I) | 100 mg |
| crystalline lactose | 240 mg |
| Avicel | 80 mg |
| PVPPXL | 20 mg |
| Aerosil | 2 mg |
| magnesium stearate | 5 mg |

The active ingredient is mixed with the carrier materials and compressed by means of a tabletting machine (Korsch EKO, stamp diameter 10 mm). Avicel® is microcrystalline cellulose (FMC, Philadelphia, USA). PVPPXL is polyvinylpolypyrrolidone, cross-linked (BASF, Germany). Aerosil® is silicon dioxide (Degussa, Germany).

EXAMPLE 189

Protein Kinase Activities Assays

Selected compounds of formula (I) are assayed to measure their capacity to inhibit protein kinases as described herein.

EXAMPLE 189.1

Protein Kinase Activities Measured by a Radiometric Assay Generic Assay Set-Up

Enzyme activities were measured by mixing 10 μL of a 3-fold concentrated compound solution or control with 10 μL of the corresponding substrate mixture (peptidic substrate, ATP and [γ$^{33}$P]ATP). The reactions were initiated by addition of 10 μL of a 3-fold concentrated solution of the respective enzyme in assay buffer. The final concentrations of the assay components were as following: (FGFR-3-K650E) 10 ng of GST-FGR-3-K650E, 20 mM Tris-HCl, pH 7.5, 3 mM MnCl$_2$, 3 mM MgCl$_2$, 1 mM DTT, 250 μg/mL PEG 20'000, 2 μg/mL poly(EY) 4:1, 1% DMSO and 0.5 μM ATP (γ-[$^{33}$P]-ATP 0.1 μCi), (KDR) 15 ng of GST-KDR, 20 mM Tris-HCl, pH 7.5, 1.0 mM MnCl$_2$, 10 mM MgCl$_2$, 1 mM DTT, 10 μM Na$_3$VO$_4$, 250 μg/mL PEG 20'000, 8.0 μg/mL poly(Glu,Tyr) 4:1, 1% DMSO and 8.0 μM ATP (γ-[$^{33}$P]-ATP 0.1 μCi), (PDGFR-beta) 30 ng of GST-Xa-PDGF-beta, 20 mM Tris-HCl, pH 7.5, 10 mM MnCl$_2$, 3.0 mM MgCl$_2$, 1 mM DTT, 10 μM Na$_3$VO$_4$, 250 μg/mL PEG 20'000, 3.0 μg/mL poly(Glu,Tyr) 4:1, 1% DMSO and 1.0 μM ATP (γ-[$^{33}$P]-ATP 0.1 μCi), (RET) 15 ng of GST-Ret, 20 mM Tris-HCl, pH 7.5, 1.0 mM MnCl$_2$, 10 mM MgCl$_2$, 1 mM DTT, 3.0 μg/mL poly(Glu,Tyr) 4:1, 1% DMSO and 2.0 μM ATP (γ-[$^{33}$P]-ATP 0.1 μCi.

Filter binding (FB) method: FB assays were carried out in 96-well plates at room temperature for 10 min in a finial volume of 30 μL including the components as indicated in section above. The enzymatic reactions were stopped by the addition of 20 μL of 125 mM EDTA and the incorporation of $^{33}$P into the poly-peptidic substrates were quantified as following: 30 μL of the stopped reaction mixture were transferred onto Immobilon-PVDF membranes previously soaked for 5 min with methanol, rinsed with water, soaked for 5 min with 0.5% H$_3$PO$_4$ and mounted on vacuum manifold with disconnected vacuum source. After spotting, vacuum was connected and each well rinsed with 200 μL 0.5% H$_3$PO$_4$. Free membranes were removed and washed 4 times on a shaker with 1% H$_3$PO$_4$ and once with ethanol. Membranes were dried and overlaid with addition of 10 μL/well of a scintillation fluid. The plates were eventually sealed and counted in a microplate scintillation counter. IC$_{50}$ values were calculated by linear regression analysis of the percentage inhibition of the compound.

EXAMPLE 189.2

Protein Kinase Activities Measured by the LanthaScreen TR-FRET Method Generic Assay Set-Up The assay has been run at room temperature on a liquid handling robot. To the assay plates containing 50 mL compound or control solutions, 4.5 μL of solution A (50 mM Tris-HCl pH7.4, 2.0 m MDTT, 0.05% Tween20, 0.02 mM Na$_3$VO$_4$) including a generic concentration of 2.0 μM ATP was added per well, followed by 4.5 μL of solution B (0.5% BSA) including a generic concentration of 50 nM poly(EAY) to give 9.05 μL of a reaction volume with final concentrations of 2.0 μM ATP, 50 nM poly(EAY), 25 mM Tris-HCl pH7.4, 1.0 mM DTT, 0.025% Tween20, 0.01 mM Na$_3$VO$_4$, 0.025% BSA as well as specific concentration of the respective enzyme and individual concentrations of divalent cations: (FGFR-3-K650E) 0.2 nM GST-FGR-3-K650E, 3.0 mM MgCl$_2$, (KIT) 36.6 nM GST-KIT, 10 mM MnCl$_2$, (RET) 0.11 nM GST-Xa-RET, 1.0 mM MnCl$_2$, 10 mM MgCl$_2$, (LCK) 3.3 nM His-LCK, 10 mM MnCl$_2$. (KDR) 0.38 nM GST-KDR, 10 mM MgCl$_2$, 1.0 mM MnCl$_2$, (PDGFaV561D) 4.4 nM GST-PDGFRaV561D, 10 mM MnCl$_2$. After 1 hour of incubation the kinase reactions have been stopped by the addition of 4.5 μL of stop solution D (48 mM EDTA, 0.08% CH$_3$COONa, 0.04% NP-40) immediately followed by 4.5 μL of solution A including the Tb-labeled P-20 antibody to detect phosphorylated poly(EAY) by TR-FRET (Time-Resolved Fluorescence Resonance Energy Transfer). The total detection volume of 18.05 μL included the following components: 1.0 mM ATP, 25 nM poly(EAY), half the concentrations of individual enzymes and divalent cations as indicated above and 12 mM EDTA, 0.43 μg/mL Tb-PY20 antibody (2.85 nM), 25 mM Tris-HCl pH7.4, 1.0 mMDTT, 0.025% Tween20, 0.01 mM Na$_3$VO$_4$, 0.01 mM Na$_3$VO$_4$, 0.025%, 0.02% CH$_3$COONa, 0.01% NP-40). After an incubation time of 45 min in the dark, the plates were transferred into a fluorescence reader for counting. The effect of compound on the enzymatic activity was obtained from the linear progress curves and determined from one reading (end point measurement).

EXAMPLE 189.3

Protein Kinase Activities Measured by the Microfluidic Caliper Method (I) Generic Assay Set-Up The assay was prepared and incubated on a liquid handling robot system using 384 well plates. To the assay plates containing 50 nL compound or control solutions, 4.5 µL of solution A consisting of the peptide substrate and ATP in assay buffer were added. The reactions were initiated by adding 4.5 µL of solution B consisting of the respective kinase in assay buffer. The reactions were incubated for 1 hour at 30° C. in a final reaction volume of 9.05 µL. Based on a generic assay buffer (50 mM HEPES pH7.5, 1 mM DTT, 0.02% Tween20, 0.02% BSA), the following components were added: (cAbl) 16 nM His-cAbl, 5 µM peptide substrate (FITC-Ahx-EAIYAAPFAKKK-CONH2), 10 mM MgCl$_2$, 10 µM ATP. After incubation, the kinase reactions were stopped by the addition of 16 µL of stop solution (100 mM HEPES, 5% DMSO, 0.1% Coating reagent, 10 mM EDTA, 0.015% Brij 35). Subsequently, the assay plates were transferred to a Caliper LabChip3000 reader and the unphosphorylated substrate and the phosphorylated product were separated and quantitated in a microfluidic chip. From these data the turnover of the kinase reactions and the effects of the compounds were calculated.

EXAMPLE 189.4

Protein Kinase Activities Measured by the Microfluidic Caliper Method (II) Generic Assay Set-Up The assay was prepared and incubated on a liquid handling robot system using 384 well plates. To the assay plates containing 50 nL compound or control solutions, 4.5 µL of solution A consisting of the peptide substrate and ATP in assay buffer were added. The reactions were initiated by adding 4.5 µL of solution B consisting of the respective kinase in assay buffer. The reactions were incubated for 1 hour at 30° C. in a final reaction volume of 9.05 µL. Based on a generic assay buffer (50 mM HEPES pH7.5, 1 mM DTT, 0.02% Tween20, 0.02% BSA), the following components were added: (cAbl-T315I) 2.4 nM His-cAbl-T315I, 5 µM peptide substrate (FITC-Ahx-EAIYAAPFAKKK-CONH2), 10 mM MgCl$_2$, 10 µM ATP. After incubation, the kinase reactions were stopped by the addition of 16 µL of stop solution (100 mM HEPES, 5% DMSO, 0.1% Coating reagent, 10 mM EDTA, 0.015% Brij 35). Subsequently, the assay plates were transfered to a Caliper LabChip3000 reader and the unphosphorylated substrate and the phosphorylated product were separated and quantitated in a microfluidic chip. From these data the turnover of the kinase reactions and the effects of the compounds were calculated. Compounds of formula (I) are assayed to measure their capacity to inhibit FGFR3 kinase as described above.

Results are provided in the following table:

| rating | example no. |
| --- | --- |
| Excellent (IC50 < 0.1 µM) | 1, 5, 6, 8-14, 18-23, 25-27, 31, 33, 34, 37, 39-43, 81, 88, 89, 92-95, 100-103, 105-109, 118-120, 122-138, 140, 141, 143-154, 159, 161, 164, 167, 172, 174-178 |
| Good (0.1 < IC50 < 0.5 µM) | 38, 85, 90, 91, 104, 111-114, 139, 162, 165, 168, 169, 173 |
| Moderate (0.5 µM < IC50 < 50 µM) | 2-4, 7, 17, 24, 45-51, 56-62, 65, 67-70, 72, 75-80, 82, 83, 86, 87, 97-99, 115, 117, 121, 160, 163, 171 |

Selected results for specific compounds are provided in the following table:

| Example | FGFR3 IC$_{50}$ (nM) |
| --- | --- |
| 2 | 530* |
| 3 | >10000* |
| 4 | 1300* |
| 6 | 74* |
| 10 | 58* |
| 11 | 31* |
| 17 | >10000* |
| 20 | 16* |
| 22 | 10* |
| 24 | 530* |
| 25 | 41* |
| 31 | 22* |
| 34 | 54* |
| 38 | 270 |
| 43 | 87 |
| 56 | 1200* |
| 58 | 700* |
| 62 | 8100* |
| 69 | >10000* |
| 77 | >10000 |
| 82 | 605 |
| 83 | 945 |
| 85 | 210 |
| 86 | 2550 |
| 91 | 485 |
| 93 | 7* |
| 95 | 42 |
| 97 | 875 |
| 98 | 1050 |
| 99 | >10000 |
| 106 | 20 |
| 112 | 139 |
| 122 | 14 |
| 124 | 10 |
| 127 | 16 |
| 135 | 11 |
| 136 | 11 |
| 139 | 265 |
| 143 | 44 |
| 144 | 7 |
| 152 | 32 |
| 153 | 11 |
| 154 | 9 |
| 155 | 12 |
| 167 | 99 |
| 172 | 70 |
| 173 | 245 |
| 174 | 16 |
| 175 | 9 |
| 176 | 51 |
| 177 | 10 |

IC$_{50}$ values are the average IC$_{50}$ values of 2 independent measurements.
*Single value.

Further, selected compounds of formula (I) are assayed to measure their capacity to inhibit other kinases, such as KDR, cKIT, PDGF-R, LCK, cABL, RET as described above. Results are provided in the following table:

| Enzyme | KDR | cKIT | PDGF-R | LCK | cABL | RET |
|---|---|---|---|---|---|---|
| IC50 (µM) range | 0.003-50 | 0.240-50 | 0.100-50 | 0.170-50 | 0.010-50 | 0.390-50 |

What is claimed is:

1. A method for the treatment of cancer of the bladder comprising the step of administering to a subject in need thereof a therapeutically effective amount of a compound selected from the group consisting of:

8-(2,6-Dichloro-3,5-dimethoxy-phenyl)-quinoxaline-5-carboxylic acid (4-dimethylaminomethyl-1H-imidazol-2-yl)-amide of formula

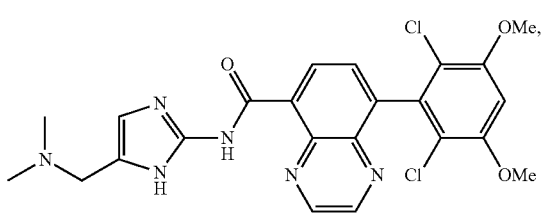

8-(2,6-Difluoro-3,5-dimethoxy-phenyl)-quinoxaline-5-carboxylic acid (4-dimethylaminomethyl-1H-imidazol-2-yl)-amide of formula

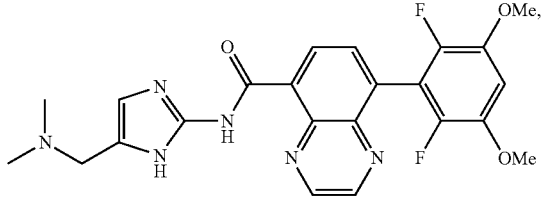 [SMILES: COc1cc(OC)c(F)c(-c2ccc(C(=O)Nc3ncc(CN(C)C)[nH]3)c3nccnc23)c1F]

8-(2,6-Dichloro-3,5-dimethoxy-phenyl)-quinoxaline-5-carboxylic acid [5-(4-ethyl-piperazin-1-ylmethyl)-pyridin-2-yl]-amide of formula

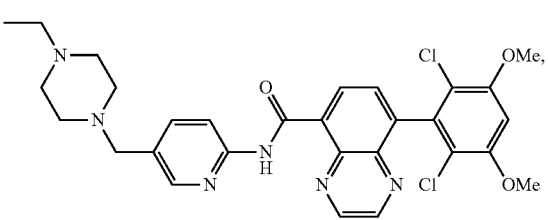 [SMILES: CCN1CCN(Cc2ccc(NC(=O)c3ccc(-c4c(Cl)c(OC)cc(OC)c4Cl)c4nccnc34)nc2)CC1]

8-(2,6-Difluoro-3,5-dimethoxy-phenyl)-quinoxaline-5-carboxylic acid [5-(4-ethyl-piperazin-1-ylmethyl)-pyridin-2-yl]-amide of formula

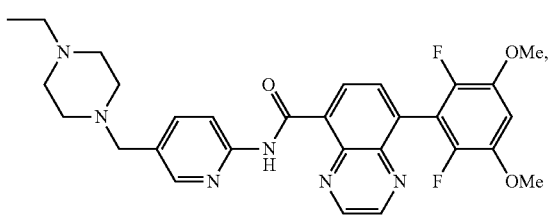 [SMILES: CCN1CCN(Cc2ccc(NC(=O)c3ccc(-c4c(F)c(OC)cc(OC)c4F)c4nccnc34)nc2)CC1]

8-(2-Chloro-6-fluoro-3,5-dimethoxy-phenyl)-quinoxaline-5-carboxylic acid [5-(4-methyl-piperazin-1-ylmethyl)-pyridin-2-yl]-amide of formula

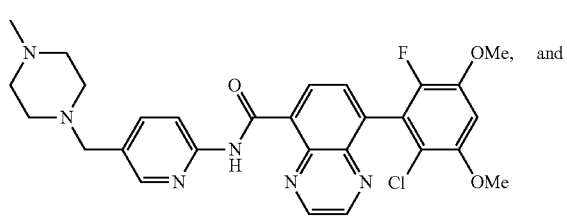 [SMILES: COc1cc(OC)c(Cl)c(-c2ccc(C(=O)Nc3ccc(CN4CCN(C)CC4)cn3)c3nccnc23)c1F]

8-(2-Chloro-6-fluoro-3,5-dimethoxy-phenyl)-quinoxaline-5-carboxylic acid (5-piperazin-1-ylmethyl-pyridin-2-yl)-amide of formula

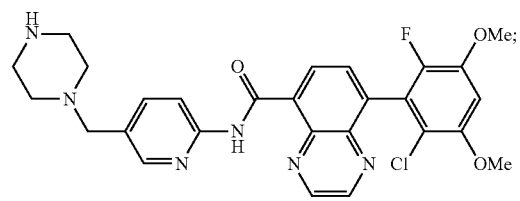 [SMILES: COc1cc(OC)c(Cl)c(-c2ccc(C(=O)Nc3ccc(CN4CCNCC4)cn3)c3nccnc23)c1F]

or a pharmaceutically acceptable salt thereof.

2. The method according to claim 1 wherein the compound is 8-(2,6-Dichloro-3,5-dimethoxy-phenyl)-quinoxaline-5-carboxylic acid (4-dimethylaminomethyl-1H-imidazol-2-yl)-amide of formula

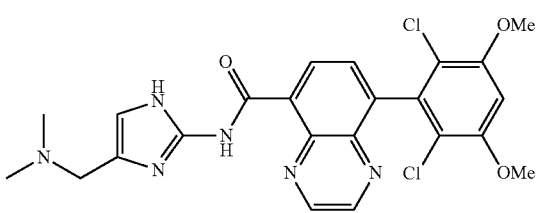 [SMILES: COc1cc(OC)c(Cl)c(-c2ccc(C(=O)Nc3nc(CN(C)C)c[nH]3)c3nccnc23)c1Cl]

or a pharmaceutically acceptable salt thereof.

3. The method according to claim 1 wherein the compound is 8-(2,6-Difluoro-3,5-dimethoxy-phenyl)-quinoxaline-5-carboxylic acid (4-dimethylaminomethyl-1H-imidazol-2-yl)-amide of formula

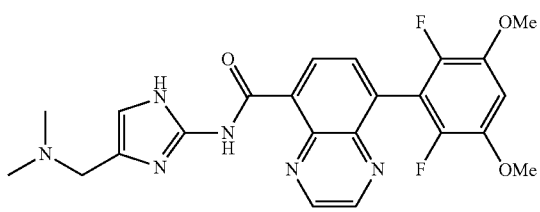 [SMILES: COc1cc(OC)c(F)c(-c2ccc(C(=O)Nc3nc(CN(C)C)c[nH]3)c3nccnc23)c1F]

or a pharmaceutically acceptable salt thereof.

4. The method according to claim 1 wherein the compound is 8-(2,6-Dichloro-3,5-dimethoxy-phenyl)-quinoxaline-5-carboxylic acid [5-(4-ethyl-piperazin-1-ylmethyl)-pyridin-2-yl]-amide of formula

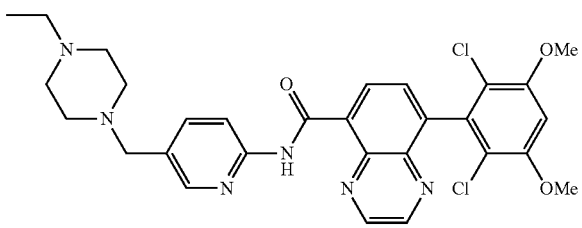

or a pharmaceutically acceptable salt thereof.

5. The method according to claim 1 wherein the compound is 8-(2,6-Difluoro-3,5-dimethoxy-phenyl)-quinoxaline-5-carboxylic acid [5-(4-ethyl-piperazin-1-ylmethyl)-pyridin-2-yl]-amide of formula

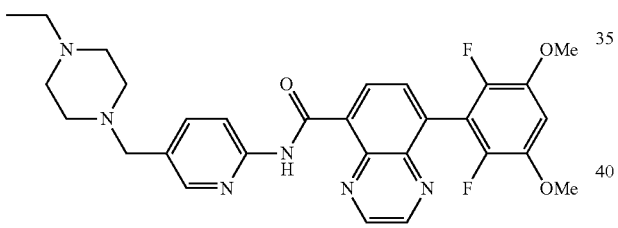

or a pharmaceutically acceptable salt thereof.

6. The method according to claim 1 wherein the compound is 8-(2-Chloro-6-fluoro-3,5-dimethoxy-phenyl)-quinoxaline-5-carboxylic acid [5-(4-methyl-piperazin-1-ylmethyl)-pyridin-2-yl]-amide of formula

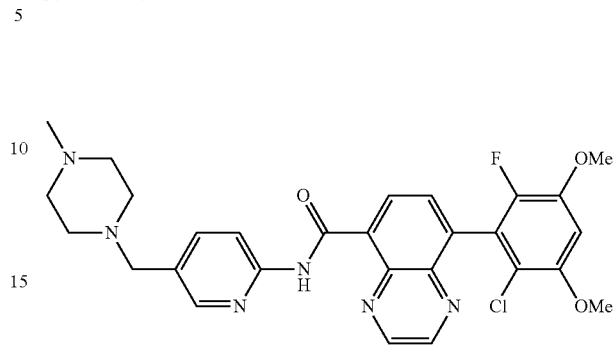

or a pharmaceutically acceptable salt thereof.

7. The method according to claim 1 wherein the compound is 8-(2-Chloro-6-fluoro-3,5-dimethoxy-phenyl)-quinoxaline-5-carboxylic acid (5-piperazin-1-ylmethyl-pyridin-2-yl)-amide of formula

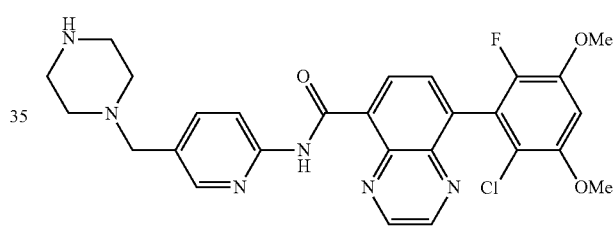

or a pharmaceutically acceptable salt thereof.

\* \* \* \* \*